US012161696B2

(12) United States Patent
Dumont et al.

(10) Patent No.: US 12,161,696 B2
(45) Date of Patent: Dec. 10, 2024

(54) METHODS OF TREATING HEMOPHILIC ARTHROPATHY USING CHIMERIC CLOTTING FACTORS

(71) Applicant: BIOVERATIV THERAPEUTICS INC., Waltham, MA (US)

(72) Inventors: Jennifer Dumont, Waltham, MA (US); Nisha Jain, Waltham, MA (US); Desilu Glazebrook, Waltham, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 500 days.

(21) Appl. No.: 16/463,748

(22) PCT Filed: Dec. 1, 2017

(86) PCT No.: PCT/US2017/064302
§ 371 (c)(1),
(2) Date: May 23, 2019

(87) PCT Pub. No.: WO2018/102743
PCT Pub. Date: Jun. 7, 2018

(65) Prior Publication Data
US 2019/0381149 A1  Dec. 19, 2019

Related U.S. Application Data

(60) Provisional application No. 62/558,793, filed on Sep. 14, 2017, provisional application No. 62/550,488, filed on Aug. 25, 2017, provisional application No. 62/529,896, filed on Jul. 7, 2017, provisional application No. 62/429,509, filed on Dec. 2, 2016.

(51) Int. Cl.
*A61K 38/37* (2006.01)
*A61K 38/48* (2006.01)
*A61P 7/04* (2006.01)
*A61P 19/02* (2006.01)

(52) U.S. Cl.
CPC .......... *A61K 38/37* (2013.01); *A61K 38/4846* (2013.01); *A61P 7/04* (2018.01); *A61P 19/02* (2018.01)

(58) Field of Classification Search
None
See application file for complete search history.

(56) References Cited

U.S. PATENT DOCUMENTS

| 836,805 A | 11/1906 | Dozier |
| 3,992,518 A | 11/1976 | Chien et al. |
| 4,088,864 A | 5/1978 | Theeuwes et al. |
| 4,179,337 A | 12/1979 | Davis et al. |
| 4,200,098 A | 4/1980 | Ayer et al. |
| 4,200,984 A | 5/1980 | Fink |
| 4,215,051 A | 7/1980 | Schroeder et al. |
| 4,235,881 A | 11/1980 | Cort |
| 4,284,444 A | 8/1981 | Bernstein et al. |
| 4,398,908 A | 8/1983 | Siposs |
| 4,435,173 A | 3/1984 | Siposs et al. |
| 4,456,591 A | 6/1984 | Thomas |
| 4,542,025 A | 9/1985 | Tice et al. |
| 4,599,311 A | 7/1986 | Kawasaki |
| 4,683,195 A | 7/1987 | Mullis et al. |
| 4,683,202 A | 7/1987 | Mullis |
| 4,684,479 A | 8/1987 | D'Arrigo |
| 4,704,362 A | 11/1987 | Itakura et al. |
| 4,713,339 A | 12/1987 | Levinson et al. |
| 4,757,006 A | 7/1988 | Toole et al. |
| 4,770,999 A | 9/1988 | Kaufman et al. |
| 4,784,950 A | 11/1988 | Hagen et al. |
| 4,800,159 A | 1/1989 | Mullis et al. |
| 4,845,075 A | 7/1989 | Murray et al. |
| 4,861,800 A | 8/1989 | Buyske |
| 4,868,112 A | 9/1989 | Toole, Jr. |
| 4,870,008 A | 9/1989 | Brake |
| 4,882,279 A | 11/1989 | Cregg |
| 4,897,268 A | 1/1990 | Tice et al. |
| 4,931,373 A | 6/1990 | Kawasaki et al. |
| 4,933,185 A | 6/1990 | Wheatley et al. |
| 4,965,188 A | 10/1990 | Mullis et al. |
| 4,965,199 A | 10/1990 | Capon et al. |
| 4,970,300 A | 11/1990 | Fulton et al. |
| 4,976,696 A | 12/1990 | Sanderson et al. |
| 4,988,337 A | 1/1991 | Ito |
| 4,994,371 A | 2/1991 | Davie et al. |

(Continued)

FOREIGN PATENT DOCUMENTS

| AU | 609829 B2 | 5/1991 |
| AU | 2016213822 B2 | 8/2017 |

(Continued)

OTHER PUBLICATIONS

Smith, Kenneth GC, and Menna R. Clatworthy. Nature Reviews Immunology 10.5 (2010): 328-343 (Year: 2010).*
Knobe, Karin, and Erik Berntorp. Journal of comorbidity vol. 1 51-59. Dec. 27, 2011 (Year: 2011).*
Bhat, Vikas, et al. American journal of hematology 90.11 (2015): 1027-1035 (Year: 2015).*
Lobet, Sébastien, Cedric Hermans, and Catherine Lambert. Journal of blood medicine 5 (2014): 207 (Year: 2014).*

(Continued)

*Primary Examiner* — Michael Szperka
*Assistant Examiner* — Lia E Taylor
(74) *Attorney, Agent, or Firm* — LATHROP GPM LLP; James H. Velema, Esq.

(57) ABSTRACT

The present disclosure provides methods treating reversible hemophilic arthropathy of a joint in a human having hemophilia comprising administering to the human an effective amount of a chimeric protein or composition comprising a clotting factor and an Fc region.

17 Claims, 35 Drawing Sheets

(56) References Cited

U.S. PATENT DOCUMENTS

| | | |
|---|---|---|
| 5,004,803 A | 4/1991 | Kaufman et al. |
| 5,004,804 A | 4/1991 | Kuo et al. |
| 5,017,378 A | 5/1991 | Turner et al. |
| 5,037,743 A | 8/1991 | Welch et al. |
| 5,089,474 A | 2/1992 | Castro et al. |
| 5,112,950 A | 5/1992 | Meulien et al. |
| 5,171,844 A | 12/1992 | van Ooyen et al. |
| 5,186,938 A | 2/1993 | Sablotsky et al. |
| 5,198,349 A | 3/1993 | Kaufman |
| 5,215,680 A | 6/1993 | D'Arrigo |
| 5,223,409 A | 6/1993 | Ladner et al. |
| 5,250,421 A | 10/1993 | Kaufman et al. |
| 5,270,176 A | 12/1993 | Dorschug et al. |
| 5,298,022 A | 3/1994 | Bernardi |
| 5,318,540 A | 6/1994 | Athayde et al. |
| 5,364,771 A | 11/1994 | Lollar et al. |
| 5,364,934 A | 11/1994 | Drayna et al. |
| 5,407,609 A | 4/1995 | Tice et al. |
| 5,422,260 A | 6/1995 | Kaufman et al. |
| 5,424,199 A | 6/1995 | Goeddel et al. |
| 5,492,534 A | 2/1996 | Athayde et al. |
| 5,534,617 A | 7/1996 | Cunningham et al. |
| 5,543,502 A | 8/1996 | Nordfang et al. |
| 5,554,730 A | 9/1996 | Woiszwillo et al. |
| 5,573,776 A | 11/1996 | Harrison et al. |
| 5,576,291 A | 11/1996 | Curtis et al. |
| 5,578,709 A | 11/1996 | Woiszwillo |
| 5,595,886 A | 1/1997 | Chapman et al. |
| 5,599,907 A | 2/1997 | Anderson et al. |
| 5,610,278 A | 3/1997 | Nordfang et al. |
| 5,643,575 A | 7/1997 | Martinez et al. |
| 5,648,260 A | 7/1997 | Winter et al. |
| 5,658,570 A | 8/1997 | Newman et al. |
| 5,660,848 A | 8/1997 | Moo-Young |
| 5,693,499 A | 12/1997 | Yonemura et al. |
| 5,712,122 A | 1/1998 | Boime et al. |
| 5,736,137 A | 4/1998 | Anderson et al. |
| 5,739,277 A | 4/1998 | Presta et al. |
| 5,756,115 A | 5/1998 | Moo-Young et al. |
| 5,789,203 A | 8/1998 | Chapman et al. |
| 5,833,982 A | 11/1998 | Berkner et al. |
| 5,834,250 A | 11/1998 | Wells et al. |
| 5,837,679 A | 11/1998 | Wolf et al. |
| 5,846,951 A | 12/1998 | Gregoriadis |
| 5,859,204 A | 1/1999 | Lollar |
| 5,869,046 A | 2/1999 | Presta et al. |
| 5,874,104 A | 2/1999 | Adler-Moore et al. |
| 5,916,588 A | 6/1999 | Popescu et al. |
| 5,919,766 A | 7/1999 | Osterberg et al. |
| 5,942,252 A | 8/1999 | Tice et al. |
| 5,965,156 A | 10/1999 | Proffitt et al. |
| 5,972,885 A | 10/1999 | Spira et al. |
| 5,981,216 A | 11/1999 | Kenten et al. |
| 5,981,719 A | 11/1999 | Woiszwillo et al. |
| 6,005,082 A | 12/1999 | Smeds |
| 6,024,983 A | 2/2000 | Tice et al. |
| 6,030,613 A | 2/2000 | Blumberg et al. |
| 6,037,452 A | 3/2000 | Minamino et al. |
| 6,043,094 A | 3/2000 | Martin et al. |
| 6,048,720 A | 4/2000 | Dalborg et al. |
| 6,056,973 A | 5/2000 | Allen et al. |
| 6,060,447 A | 5/2000 | Chapman et al. |
| 6,086,875 A | 7/2000 | Blumberg et al. |
| 6,090,925 A | 7/2000 | Woiszwillo et al. |
| 6,096,871 A | 8/2000 | Presta et al. |
| 6,110,498 A | 8/2000 | Rudnic et al. |
| 6,121,022 A | 9/2000 | Presta et al. |
| 6,126,966 A | 10/2000 | Abra et al. |
| 6,159,730 A | 12/2000 | Reff |
| 6,183,770 B1 | 2/2001 | Muchin et al. |
| 6,193,980 B1 | 2/2001 | Efstathiou et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,254,573 B1 | 7/2001 | Haim et al. |
| 6,268,053 B1 | 7/2001 | Woiszwillo et al. |
| 6,277,375 B1 | 8/2001 | Ward |
| 6,284,276 B1 | 9/2001 | Rudnic et al. |
| 6,294,170 B1 | 9/2001 | Boone et al. |
| 6,294,191 B1 | 9/2001 | Meers et al. |
| 6,294,201 B1 | 9/2001 | Kettelhoit et al. |
| 6,303,148 B1 | 10/2001 | Hennink et al. |
| 6,309,370 B1 | 10/2001 | Haim et al. |
| 6,310,183 B1 | 10/2001 | Johannessen et al. |
| 6,316,024 B1 | 11/2001 | Allen et al. |
| 6,316,226 B1 | 11/2001 | Van Ooyen et al. |
| 6,329,186 B1 | 12/2001 | Nielsen et al. |
| 6,346,513 B1 | 2/2002 | Van Ooyen et al. |
| 6,352,716 B1 | 3/2002 | Janoff et al. |
| 6,352,721 B1 | 3/2002 | Faour |
| 6,358,703 B1 | 3/2002 | Cho et al. |
| 6,361,796 B1 | 3/2002 | Rudnic et al. |
| 6,376,463 B1 | 4/2002 | Lollar |
| 6,395,302 B1 | 5/2002 | Hennink et al. |
| 6,406,632 B1 | 6/2002 | Safir et al. |
| 6,406,713 B1 | 6/2002 | Janoff et al. |
| 6,413,777 B1 | 7/2002 | Reff et al. |
| 6,458,387 B1 | 10/2002 | Scott et al. |
| 6,458,563 B1 | 10/2002 | Lollar |
| 6,485,726 B1 | 11/2002 | Blumberg et al. |
| 6,514,532 B2 | 2/2003 | Rudnic et al. |
| 6,517,859 B1 | 2/2003 | Tice et al. |
| 6,528,624 B1 | 3/2003 | Idusogie et al. |
| 6,530,648 B2 | 3/2003 | Leu et al. |
| 6,534,090 B2 | 3/2003 | Puthli et al. |
| 6,538,124 B1 | 3/2003 | Idusogie et al. |
| 6,572,585 B2 | 6/2003 | Choi |
| 6,669,961 B2 | 12/2003 | Kim et al. |
| 6,686,179 B2 | 2/2004 | Fleer et al. |
| 6,696,245 B2 | 2/2004 | Winter et al. |
| 6,713,086 B2 | 3/2004 | Qiu et al. |
| 6,715,485 B1 | 4/2004 | Djupesland |
| 6,733,753 B2 | 5/2004 | Boone et al. |
| 6,737,056 B1 | 5/2004 | Presta |
| 6,743,211 B1 | 6/2004 | Prausnitz et al. |
| 6,759,057 B1 | 7/2004 | Weiner et al. |
| 6,770,744 B2 | 8/2004 | Lollar |
| 6,814,979 B2 | 11/2004 | Rudnic et al. |
| 6,818,439 B1 | 11/2004 | Jolly et al. |
| 6,821,505 B2 | 11/2004 | Ward |
| 6,833,352 B2 | 12/2004 | Johannessen et al. |
| 6,838,093 B2 | 1/2005 | Flanner et al. |
| 6,887,852 B1 | 5/2005 | Paik et al. |
| 6,890,918 B2 | 5/2005 | Burnside et al. |
| 6,905,688 B2 | 6/2005 | Rosen et al. |
| 6,911,323 B2 | 6/2005 | Persson et al. |
| 6,919,311 B2 | 7/2005 | Lenting et al. |
| 6,945,952 B2 | 9/2005 | Kwon |
| 6,960,657 B2 | 11/2005 | Persson et al. |
| 6,998,253 B1 | 2/2006 | Presta et al. |
| 7,026,524 B2 | 4/2006 | Persson et al. |
| 7,041,635 B2 | 5/2006 | Kim et al. |
| 7,045,318 B2 | 5/2006 | Balance |
| 7,083,784 B2 | 8/2006 | Dall'acqua et al. |
| 7,091,321 B2 | 8/2006 | Gillies et al. |
| 7,125,841 B2 | 10/2006 | Sheehan |
| 7,138,505 B1 | 11/2006 | Kuo et al. |
| 7,176,288 B2 | 2/2007 | Persson et al. |
| 7,199,223 B2 | 4/2007 | Bossard et al. |
| 7,211,559 B2 | 5/2007 | Saenko et al. |
| 7,276,475 B2 | 10/2007 | Defrees et al. |
| 7,276,593 B2 | 10/2007 | Vernet et al. |
| 7,294,513 B2 | 11/2007 | Wyatt |
| 7,317,091 B2 | 1/2008 | Lazar et al. |
| 7,329,640 B2 | 2/2008 | Vlasuk |
| 7,348,004 B2 | 3/2008 | Peters et al. |
| 7,381,408 B2 | 6/2008 | Mezo et al. |
| 7,404,956 B2 | 7/2008 | Peters et al. |
| 7,413,537 B2 | 8/2008 | Ladner et al. |
| 7,414,022 B2 | 8/2008 | Pedersen et al. |
| 7,442,778 B2 | 10/2008 | Gegg et al. |
| 7,452,967 B2 | 11/2008 | Bertin |
| 7,507,406 B2 | 3/2009 | Gillies et al. |

(56) References Cited

U.S. PATENT DOCUMENTS

| | | |
|---|---|---|
| 7,511,024 B2 | 3/2009 | Pedersen et al. |
| 7,514,257 B2 | 4/2009 | Lee et al. |
| 7,528,242 B2 | 5/2009 | Anderson et al. |
| 7,560,107 B2 | 7/2009 | Lollar |
| 7,566,565 B2 * | 7/2009 | Peters ............ C12Y 304/21022 435/325 |
| 7,566,701 B2 | 7/2009 | Diener et al. |
| 7,592,010 B2 | 9/2009 | Rosen et al. |
| 7,620,601 B2 | 11/2009 | Miyawaki et al. |
| 7,632,921 B2 | 12/2009 | Pan et al. |
| 7,645,860 B2 | 1/2010 | Turecek et al. |
| 7,683,158 B2 | 3/2010 | Siekmann et al. |
| 7,700,733 B2 | 4/2010 | Haaning et al. |
| 7,700,734 B2 | 4/2010 | Lin et al. |
| 7,786,070 B2 | 8/2010 | Johannessen et al. |
| 7,790,415 B2 | 9/2010 | Gillies et al. |
| 7,820,162 B2 | 10/2010 | Mezo et al. |
| 7,846,445 B2 | 12/2010 | Schellenberger et al. |
| 7,846,455 B2 | 12/2010 | Collins et al. |
| 7,855,279 B2 | 12/2010 | Schellenberger et al. |
| 7,862,820 B2 * | 1/2011 | Peters ..................... A61P 31/00 424/179.1 |
| 7,884,075 B2 | 2/2011 | Scheiflinger et al. |
| 7,939,632 B2 | 5/2011 | Metzner et al. |
| 8,021,880 B2 * | 9/2011 | Peters ............ C12Y 304/21022 435/325 |
| 8,329,182 B2 * | 12/2012 | Peters ..................... A61P 31/18 424/178.1 |
| 8,357,779 B2 | 1/2013 | Scheiflinger et al. |
| 8,367,805 B2 | 2/2013 | Chamberlain et al. |
| 8,492,530 B2 | 7/2013 | Schellenberger et al. |
| 8,563,521 B2 | 10/2013 | Skerra et al. |
| 8,575,104 B2 | 11/2013 | Weimer et al. |
| 8,673,860 B2 | 3/2014 | Schellenberger et al. |
| 8,680,050 B2 | 3/2014 | Schellenberger et al. |
| 8,703,717 B2 | 4/2014 | Schellenberger et al. |
| 8,716,448 B2 | 5/2014 | Schellenberger et al. |
| 8,754,194 B2 | 6/2014 | Schulte et al. |
| 8,835,388 B2 | 9/2014 | Scheiflinger et al. |
| 8,932,830 B2 * | 1/2015 | Peters .................. C07K 14/565 435/69.7 |
| 8,933,197 B2 | 1/2015 | Stemmer et al. |
| 9,050,318 B2 | 6/2015 | Dumont et al. |
| 9,107,902 B2 | 8/2015 | Kronthaler |
| 9,168,312 B2 | 10/2015 | Schellenberger et al. |
| 9,233,145 B2 * | 1/2016 | Pierce ............... A61K 38/4846 |
| 9,241,978 B2 | 1/2016 | Dumont et al. |
| 9,376,672 B2 | 6/2016 | Schellenberger et al. |
| 9,458,223 B2 | 10/2016 | Schulte et al. |
| 9,486,507 B2 * | 11/2016 | Thorn ....................... A61P 7/04 |
| 9,623,091 B2 * | 4/2017 | Pierce ............... A61K 39/39533 |
| 9,629,903 B2 * | 4/2017 | Pierce ........................ C12N 9/96 |
| 9,670,475 B2 * | 6/2017 | Pierce .................... C07K 16/18 |
| 9,675,676 B2 * | 6/2017 | Pierce .................... C12N 9/644 |
| 9,867,873 B2 * | 1/2018 | Pierce .................... A61K 9/0019 |
| 9,878,017 B2 | 1/2018 | Metzner et al. |
| 9,956,269 B2 | 5/2018 | Horn et al. |
| 9,958,572 B2 | 5/2018 | Chang et al. |
| 10,138,291 B2 | 11/2018 | Chaabra et al. |
| 10,325,687 B2 * | 6/2019 | Jiang .................... C07K 14/755 |
| 10,370,430 B2 | 8/2019 | Kulman |
| 10,391,152 B2 * | 8/2019 | Jiang ................. A61K 38/4846 |
| 10,421,798 B2 | 9/2019 | Schellenberger et al. |
| 10,537,616 B2 | 1/2020 | Horn et al. |
| 10,548,954 B2 * | 2/2020 | Pierce ............... A61K 39/3955 |
| 10,561,714 B2 * | 2/2020 | Pierce ........................ C12N 9/96 |
| 10,568,943 B2 * | 2/2020 | Pierce ............... A61K 39/3955 |
| 10,584,147 B2 * | 3/2020 | Thorn .................... C07K 14/00 |
| 10,588,949 B2 * | 3/2020 | Brader .................... A61M 5/19 |
| 10,772,942 B2 * | 9/2020 | Thome .................. A61K 9/0019 |
| 10,786,554 B2 | 9/2020 | Maloney et al. |
| 10,881,717 B2 | 1/2021 | Horn et al. |
| 10,898,554 B1 * | 1/2021 | Pierce ....................... A61P 7/04 |
| 10,927,362 B2 * | 2/2021 | Salas .................... C07K 16/28 |
| 11,091,534 B2 | 8/2021 | Chhabra et al. |
| 11,192,936 B2 | 12/2021 | Chhabra et al. |
| 11,225,650 B2 | 1/2022 | Pierce et al. |
| 11,266,720 B2 | 3/2022 | Dumont et al. |
| 11,370,827 B2 | 6/2022 | Chaabra et al. |
| 2002/0019036 A1 | 2/2002 | Schwarz et al. |
| 2002/0042079 A1 | 4/2002 | Simon et al. |
| 2002/0150881 A1 | 10/2002 | Ladner et al. |
| 2003/0049689 A1 | 3/2003 | Edwards et al. |
| 2003/0065787 A1 | 4/2003 | Osafune et al. |
| 2003/0069395 A1 | 4/2003 | Sato et al. |
| 2003/0143697 A1 | 7/2003 | Stahl et al. |
| 2003/0181381 A1 | 9/2003 | Himmelspach et al. |
| 2003/0190740 A1 | 10/2003 | Altman |
| 2003/0199444 A1 | 10/2003 | Knudsen et al. |
| 2003/0228309 A1 | 12/2003 | Salcedo et al. |
| 2003/0235536 A1 | 12/2003 | Blumberg et al. |
| 2004/0029207 A1 | 2/2004 | Marnett et al. |
| 2004/0043446 A1 | 3/2004 | Defrees et al. |
| 2004/0101740 A1 | 5/2004 | Sanders |
| 2004/0106118 A1 | 6/2004 | Kolmar et al. |
| 2004/0147436 A1 | 7/2004 | Kim et al. |
| 2004/0192599 A1 | 9/2004 | Schuh et al. |
| 2004/0203107 A1 | 10/2004 | Murray |
| 2004/0259780 A1 | 12/2004 | Glasebrook et al. |
| 2005/0042721 A1 | 2/2005 | Fang et al. |
| 2005/0048512 A1 | 3/2005 | Kolkman et al. |
| 2005/0100990 A1 | 5/2005 | Saenko et al. |
| 2005/0118136 A1 | 6/2005 | Leung et al. |
| 2005/0123997 A1 | 6/2005 | Lollar |
| 2005/0147618 A1 | 7/2005 | Rivera et al. |
| 2005/0260194 A1 | 11/2005 | Peters et al. |
| 2005/0260605 A1 | 11/2005 | Punnonen et al. |
| 2005/0266533 A1 | 12/2005 | Ballance et al. |
| 2005/0287153 A1 | 12/2005 | Dennis |
| 2006/0026719 A1 | 2/2006 | Kieliszewski et al. |
| 2006/0040856 A1 | 2/2006 | Defrees et al. |
| 2006/0074199 A1 | 4/2006 | Hirata et al. |
| 2006/0084113 A1 | 4/2006 | Ladner et al. |
| 2006/0115876 A1 | 6/2006 | Pan et al. |
| 2006/0122376 A1 | 6/2006 | Chapman et al. |
| 2006/0159675 A1 | 7/2006 | Jiao et al. |
| 2006/0160948 A1 | 7/2006 | Scheiflinger et al. |
| 2006/0205036 A1 | 9/2006 | Ostergaard et al. |
| 2006/0211621 A1 | 9/2006 | Knudsen et al. |
| 2006/0287220 A1 | 12/2006 | Li et al. |
| 2006/0293232 A1 | 12/2006 | Levy et al. |
| 2006/0293238 A1 | 12/2006 | Kaufman et al. |
| 2007/0021494 A1 | 1/2007 | Taveras et al. |
| 2007/0048282 A1 | 3/2007 | Rosen et al. |
| 2007/0161087 A1 | 7/2007 | Glaesner et al. |
| 2007/0191272 A1 | 8/2007 | Stemmer et al. |
| 2007/0191597 A1 | 8/2007 | Jain et al. |
| 2007/0203058 A1 | 8/2007 | Lau et al. |
| 2007/0212703 A1 | 9/2007 | Stemmer et al. |
| 2007/0231329 A1 | 10/2007 | Lazar et al. |
| 2007/0237237 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0244301 A1 | 10/2007 | Siekmann et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0033413 A1 | 2/2008 | Inochkin et al. |
| 2008/0039341 A1 | 2/2008 | Schellenberger et al. |
| 2008/0057056 A1 | 3/2008 | Lazar et al. |
| 2008/0146782 A1 | 6/2008 | Defrees et al. |
| 2008/0153751 A1 | 6/2008 | Rosen et al. |
| 2008/0161243 A1 | 7/2008 | Rosen et al. |
| 2008/0167219 A1 | 7/2008 | Lin et al. |
| 2008/0167238 A1 | 7/2008 | Rosen et al. |
| 2008/0176288 A1 | 7/2008 | Leung et al. |
| 2008/0193441 A1 | 8/2008 | Trown et al. |
| 2008/0194481 A1 | 8/2008 | Rosen et al. |
| 2008/0214462 A1 | 9/2008 | Dockal et al. |
| 2008/0227691 A1 | 9/2008 | Ostergaard et al. |
| 2008/0233100 A1 | 9/2008 | Chen et al. |
| 2008/0234193 A1 | 9/2008 | Bossard et al. |

(56) References Cited

U.S. PATENT DOCUMENTS

| | | |
|---|---|---|
| 2008/0255040 A1 | 10/2008 | Defrees |
| 2008/0260755 A1 | 10/2008 | Metzner et al. |
| 2008/0261877 A1 | 10/2008 | Ballance et al. |
| 2008/0269125 A1 | 10/2008 | Ballance et al. |
| 2008/0286808 A1 | 11/2008 | Schellenberger et al. |
| 2008/0312157 A1 | 12/2008 | Levy et al. |
| 2009/0011992 A1 | 1/2009 | Olsen et al. |
| 2009/0042787 A1 | 2/2009 | Metzner et al. |
| 2009/0058322 A1 | 3/2009 | Toma et al. |
| 2009/0060862 A1 | 3/2009 | Chang et al. |
| 2009/0087411 A1 | 4/2009 | Fares et al. |
| 2009/0092582 A1 | 4/2009 | Bogin et al. |
| 2009/0099031 A1 | 4/2009 | Stemmer et al. |
| 2009/0117104 A1 | 5/2009 | Baker et al. |
| 2009/0118185 A1 | 5/2009 | Fay et al. |
| 2009/0169553 A1 | 7/2009 | Day |
| 2009/0192076 A1 | 7/2009 | Matthiessen et al. |
| 2009/0247459 A1 | 10/2009 | Schwarz et al. |
| 2009/0250598 A1 | 10/2009 | Hamada et al. |
| 2009/0263380 A1 | 10/2009 | Gilles et al. |
| 2010/0022445 A1 | 1/2010 | Scheiflinger et al. |
| 2010/0081187 A1 | 4/2010 | Griffith et al. |
| 2010/0081615 A1 | 4/2010 | Pan et al. |
| 2010/0120664 A1 | 5/2010 | Schulte et al. |
| 2010/0130427 A1 | 5/2010 | Bossard et al. |
| 2010/0143326 A1 | 6/2010 | Rischel et al. |
| 2010/0189682 A1 | 7/2010 | Schellenberger et al. |
| 2010/0239554 A1 | 9/2010 | Schellenberger et al. |
| 2010/0260706 A1 | 10/2010 | Bogin et al. |
| 2010/0285021 A1 | 11/2010 | Jacquemin et al. |
| 2010/0292130 A1 | 11/2010 | Skerra et al. |
| 2010/0183556 A1 | 12/2010 | Choi et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0069164 A1 | 3/2011 | Satoshi et al. |
| 2011/0077199 A1 | 3/2011 | Schellenberger et al. |
| 2011/0124656 A1 | 5/2011 | Hauser et al. |
| 2011/0151433 A1 | 6/2011 | Schellenberger et al. |
| 2011/0172146 A1 | 7/2011 | Schellenberger et al. |
| 2011/0183907 A1 | 7/2011 | Weimer et al. |
| 2011/0263595 A1 | 10/2011 | Zhang et al. |
| 2011/0286988 A1 | 11/2011 | Jiang et al. |
| 2011/0287041 A1 | 11/2011 | Carrico et al. |
| 2011/0287517 A1 | 11/2011 | Steward et al. |
| 2011/0288005 A1 | 11/2011 | Silverman et al. |
| 2011/0312881 A1 | 12/2011 | Silverman et al. |
| 2012/0065077 A1 | 3/2012 | Astermark et al. |
| 2012/0121706 A1 | 5/2012 | Kuliopulos et al. |
| 2012/0142593 A1 | 6/2012 | Zhao et al. |
| 2012/0178691 A1 | 7/2012 | Schellenberger et al. |
| 2012/0220011 A1 | 8/2012 | Schellenberger et al. |
| 2012/0230947 A1 | 9/2012 | Schellenberger et al. |
| 2012/0263701 A1 | 10/2012 | Schellenberger et al. |
| 2012/0263703 A1 | 10/2012 | Schellenberger et al. |
| 2012/0289468 A1 | 11/2012 | Barnett |
| 2012/0308641 A1 | 12/2012 | Arruda et al. |
| 2013/0001799 A1 | 1/2013 | Chang et al. |
| 2013/0017997 A1 | 1/2013 | Schellenberger et al. |
| 2013/0039884 A1 | 2/2013 | Bogin et al. |
| 2013/0108629 A1 | 5/2013 | Dumont et al. |
| 2013/0165389 A1 | 6/2013 | Schellenberger et al. |
| 2013/0171138 A1 | 7/2013 | Peters et al. |
| 2013/0171175 A1* | 7/2013 | Pierce .............. A61K 39/395 424/179.1 |
| 2013/0172274 A1 | 7/2013 | Chilkoti |
| 2013/0183280 A1 | 7/2013 | Oestergaard et al. |
| 2013/0274194 A1 | 10/2013 | Dumont et al. |
| 2014/0018297 A1 | 1/2014 | Bolt et al. |
| 2014/0050693 A1 | 2/2014 | Skerra et al. |
| 2014/0072561 A1 | 3/2014 | Weimer et al. |
| 2014/0186327 A1 | 7/2014 | Schellenberger et al. |
| 2014/0273096 A1 | 9/2014 | Schulte et al. |
| 2014/0294821 A1 | 10/2014 | Dumont et al. |
| 2014/0301974 A1 | 10/2014 | Schellenberger et al. |
| 2014/0308280 A1 | 10/2014 | Maloney et al. |
| 2014/0328819 A1 | 11/2014 | Schellenberger et al. |
| 2014/0356326 A1 | 12/2014 | Schellenberger et al. |
| 2014/0370035 A1 | 12/2014 | Jiang et al. |
| 2014/0371136 A1 | 12/2014 | Schellenberger et al. |
| 2015/0023959 A1 | 1/2015 | Chhabra et al. |
| 2015/0038421 A1 | 2/2015 | Schellenberger et al. |
| 2015/0158929 A1 | 6/2015 | Schellenberger et al. |
| 2015/0175503 A1 | 6/2015 | Marks et al. |
| 2015/0252345 A1 | 9/2015 | Pierce et al. |
| 2015/0259431 A1 | 9/2015 | Stemmer et al. |
| 2015/0266943 A1 | 9/2015 | Chhabra et al. |
| 2015/0328819 A1 | 11/2015 | Tom et al. |
| 2015/0344862 A1 | 12/2015 | Schellenberger et al. |
| 2016/0115467 A1 | 4/2016 | Salas |
| 2016/0199454 A1 | 7/2016 | Liu et al. |
| 2016/0199455 A1 | 7/2016 | Dumont et al. |
| 2016/0200794 A1 | 7/2016 | Metzner et al. |
| 2016/0229903 A1 | 8/2016 | Chhabra et al. |
| 2016/0251408 A1 | 9/2016 | Chhabra et al. |
| 2016/0306945 A1 | 10/2016 | Jiang |
| 2016/0355568 A1 | 12/2016 | Kulman |
| 2016/0376344 A1 | 12/2016 | Schellenberger et al. |
| 2017/0073393 A1 | 3/2017 | Chhabra et al. |
| 2017/0152300 A1 | 6/2017 | Wilson et al. |
| 2017/0209546 A1 | 7/2017 | Schmidbauer et al. |
| 2018/0002684 A1 | 1/2018 | Pierce et al. |
| 2018/0051067 A1 | 2/2018 | Moses et al. |
| 2018/0161402 A1 | 6/2018 | Schulte et al. |
| 2018/0185455 A1 | 7/2018 | Kannicht et al. |
| 2018/0207244 A1 | 7/2018 | Pierce et al. |
| 2018/0228879 A1 | 8/2018 | Pierce et al. |
| 2019/0169267 A1 | 6/2019 | Chhabra et al. |
| 2019/0262429 A1 | 8/2019 | Dumont et al. |
| 2019/0315835 A1 | 10/2019 | Schellenberger et al. |
| 2019/0375822 A1 | 12/2019 | Chhabra et al. |
| 2019/0381149 A1 | 12/2019 | Dumont et al. |
| 2020/0087379 A1 | 3/2020 | Schellenberger et al. |
| 2020/0095567 A1 | 3/2020 | Metzner et al. |
| 2020/0261554 A1 | 8/2020 | Brader |
| 2021/0008178 A1 | 1/2021 | Pierce et al. |
| 2021/0032616 A1 | 2/2021 | Liu et al. |
| 2021/0069307 A1 | 3/2021 | Thome et al. |
| 2022/0056108 A1 | 2/2022 | Chhabra et al. |
| 2022/0064622 A1 | 3/2022 | Pierce et al. |
| 2022/0106383 A1 | 4/2022 | Chhabra et al. |
| 2022/0265780 A1 | 8/2022 | Dumont et al. |
| 2022/0275057 A1 | 9/2022 | Chhabra et al. |
| 2023/0011438 A1 | 1/2023 | Chhabra et al. |
| 2023/0019286 A1 | 1/2023 | Schellenberger et al. |
| 2023/0322900 A1 | 10/2023 | Schellenberger et al. |
| 2024/0083875 A1 | 3/2024 | Chhabra et al. |

FOREIGN PATENT DOCUMENTS

| | | |
|---|---|---|
| BR | 112015000267 A2 | 3/2018 |
| CA | 2728012 A1 | 12/2009 |
| CA | 2780542 A1 | 5/2011 |
| CA | 2804280 A1 | 1/2012 |
| CL | 2011001856 A1 | 3/2011 |
| CN | 1761684 A | 4/2006 |
| CN | 1863556 A | 11/2006 |
| CN | 1871252 A | 11/2006 |
| CN | 101190945 A | 6/2008 |
| CN | 101743309 A | 6/2010 |
| CN | 102076855 A | 5/2011 |
| CN | 102348715 A | 2/2012 |
| CN | 102648212 A | 8/2012 |
| CN | 102741422 A | 10/2012 |
| CN | 103796670 A | 5/2014 |
| CN | 104271150 A | 1/2015 |
| CN | 104411716 A | 3/2015 |
| CN | 104487452 A | 4/2015 |
| CN | 104661674 A | 5/2015 |
| CN | 106456718 A | 2/2017 |
| EA | 200501756 A1 | 8/2006 |
| EA | 201590198 A1 | 6/2015 |
| EA | 201792485 A2 | 8/2018 |
| EP | 0154316 A2 | 9/1985 |

(56) References Cited

FOREIGN PATENT DOCUMENTS

| | | |
|---|---|---|
| EP | 0184438 A3 | 1/1988 |
| EP | 0272277 A1 | 6/1988 |
| EP | 0244234 A3 | 10/1988 |
| EP | 0295597 A2 | 12/1988 |
| EP | 0238023 A3 | 2/1989 |
| EP | 0272277 B1 | 9/1993 |
| EP | 0401384 B1 | 3/1996 |
| EP | 1444986 A1 | 8/2004 |
| EP | 1203014 B1 | 10/2004 |
| EP | 0506757 B2 | 10/2005 |
| EP | 1252192 B1 | 8/2006 |
| EP | 1935430 A1 | 6/2008 |
| EP | 2173890 A1 | 4/2010 |
| EP | 2256135 A1 | 12/2010 |
| EP | 2371856 A2 | 10/2011 |
| EP | 2506868 A2 | 10/2012 |
| EP | 2032607 B1 | 1/2014 |
| EP | 2796145 A1 | 10/2014 |
| EP | 2804623 A1 | 11/2014 |
| EP | 2814840 A1 | 12/2014 |
| EP | 2882450 A2 | 6/2015 |
| EP | 3013358 A1 | 5/2016 |
| EP | 3091997 A1 | 11/2016 |
| EP | 3326643 A1 | 5/2018 |
| EP | 3505179 A1 | 7/2019 |
| EP | 3548066 A1 | 10/2019 |
| EP | 3564260 A1 | 11/2019 |
| EP | 3674410 A1 | 7/2020 |
| EP | 3793588 A1 | 3/2021 |
| JP | 2006-518985 A | 8/2006 |
| JP | 2007-500744 A | 1/2007 |
| JP | 2008-508871 A | 3/2008 |
| JP | 2008-520208 A | 6/2008 |
| JP | 2008-524117 A | 7/2008 |
| JP | 2008-525491 A | 7/2008 |
| JP | 2009-505964 A | 2/2009 |
| JP | 2009-534392 A | 9/2009 |
| JP | 2010-512768 A | 4/2010 |
| JP | 2010-531135 A | 9/2010 |
| JP | 2011-503101 A | 1/2011 |
| JP | 2011-519898 A | 7/2011 |
| JP | 2011-525363 A | 9/2011 |
| JP | 2011-526151 A | 10/2011 |
| JP | 2011-528562 A | 11/2011 |
| JP | 2013-510581 A | 3/2013 |
| JP | 2013-512678 A | 4/2013 |
| JP | 2013-525363 A | 6/2013 |
| JP | 2013-534427 A | 9/2013 |
| JP | 2015-527882 A | 9/2015 |
| JP | 2016-519670 A | 7/2016 |
| JP | 63-85410 B2 | 8/2016 |
| JP | 2016-523919 A | 8/2016 |
| JP | 60-62459 B2 | 12/2016 |
| JP | 2017-503509 A | 2/2017 |
| JP | 2020-115424 A | 7/2020 |
| TW | 201605889 A | 2/2016 |
| WO | WO 1987/004187 A1 | 7/1987 |
| WO | WO 1988/000831 A1 | 2/1988 |
| WO | WO 1988/003558 A1 | 5/1988 |
| WO | WO 1988/007089 A1 | 9/1988 |
| WO | WO 1988/007220 A1 | 9/1988 |
| WO | WO 1988/008035 A1 | 10/1988 |
| WO | WO 1989/009051 A1 | 10/1989 |
| WO | WO 1991/009122 A1 | 6/1991 |
| WO | WO 1992/010576 A1 | 6/1992 |
| WO | WO 1992/016221 A1 | 10/1992 |
| WO | WO 1993/020093 A1 | 10/1993 |
| WO | WO 1994/011503 A2 | 5/1994 |
| WO | WO 1995/034326 A1 | 12/1995 |
| WO | WO 1996/014339 A1 | 5/1996 |
| WO | WO 1997/033552 A1 | 9/1997 |
| WO | WO 1998/005787 A1 | 2/1998 |
| WO | WO 1998/022577 A1 | 5/1998 |
| WO | WO 1998/023289 A1 | 6/1998 |
| WO | WO 1998/052976 A1 | 11/1998 |
| WO | WO 1999/041383 A1 | 8/1999 |
| WO | WO 1999/049901 A1 | 10/1999 |
| WO | WO 1999/051642 A1 | 10/1999 |
| WO | WO 1999/058572 A1 | 11/1999 |
| WO | WO 2000/003317 A1 | 1/2000 |
| WO | WO 2000/009560 A2 | 2/2000 |
| WO | WO 2000/032767 A1 | 6/2000 |
| WO | WO 2000/042072 A2 | 7/2000 |
| WO | WO 2001/007072 A1 | 2/2001 |
| WO | WO 2001/187922 A2 | 11/2001 |
| WO | WO 2002/044215 A2 | 6/2002 |
| WO | WO 2002/060919 A2 | 8/2002 |
| WO | WO 2002/040544 A3 | 10/2002 |
| WO | WO 2002/077036 A2 | 10/2002 |
| WO | WO 2002/079232 A2 | 10/2002 |
| WO | WO 2003/020764 A2 | 3/2003 |
| WO | WO 2003/074569 A2 | 9/2003 |
| WO | WO 2003/077834 A2 | 9/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/044859 A1 | 5/2004 |
| WO | WO 2004/063351 A2 | 7/2004 |
| WO | WO 2004/067566 A1 | 8/2004 |
| WO | WO 2004/074455 A2 | 9/2004 |
| WO | WO 2004/076484 A1 | 10/2004 |
| WO | WO 2004/099249 A2 | 11/2004 |
| WO | WO 2004/101739 A2 | 11/2004 |
| WO | WO 2004/101740 A2 | 11/2004 |
| WO | WO 2005/001025 A2 | 1/2005 |
| WO | WO 2005/016455 A2 | 2/2005 |
| WO | WO 2005/025499 A2 | 3/2005 |
| WO | WO 2005/040217 A2 | 5/2005 |
| WO | WO 2005/047327 A2 | 5/2005 |
| WO | WO 2005/069845 A2 | 8/2005 |
| WO | WO 2005/070963 A1 | 8/2005 |
| WO | WO 2005/077981 A2 | 8/2005 |
| WO | WO 2005/092925 A2 | 10/2005 |
| WO | WO 2005/123780 A2 | 11/2005 |
| WO | WO 2006/015879 A1 | 2/2006 |
| WO | WO 2006/019447 A1 | 2/2006 |
| WO | WO 2006/047350 A2 | 5/2006 |
| WO | WO 2006/053299 A2 | 5/2006 |
| WO | WO 2006/071801 A2 | 7/2006 |
| WO | WO 2006/074199 A1 | 7/2006 |
| WO | WO 2006/085967 A2 | 8/2006 |
| WO | WO 2006/127040 A2 | 11/2006 |
| WO | WO 2006/081249 A3 | 2/2007 |
| WO | WO 2007/015107 A2 | 2/2007 |
| WO | WO 2007/021494 A2 | 2/2007 |
| WO | WO 2007/073486 A2 | 6/2007 |
| WO | WO 2007/090584 A1 | 8/2007 |
| WO | WO 2007/103455 A2 | 9/2007 |
| WO | WO 2007/103515 A2 | 9/2007 |
| WO | WO 2007/124090 A2 | 11/2007 |
| WO | WO 2007/144173 A1 | 12/2007 |
| WO | WO 2007/149406 A2 | 12/2007 |
| WO | WO 2008/033413 A2 | 3/2008 |
| WO | WO 2008/049931 A1 | 5/2008 |
| WO | WO 2008/057683 A2 | 5/2008 |
| WO | WO 2008/077616 A1 | 7/2008 |
| WO | WO 2008/118507 A2 | 10/2008 |
| WO | WO 2008/151258 A2 | 12/2008 |
| WO | WO 2008/155134 A1 | 12/2008 |
| WO | WO 2009/023270 A2 | 2/2009 |
| WO | WO 2009/051717 A2 | 4/2009 |
| WO | WO 2009/023270 A3 | 5/2009 |
| WO | WO 2009/058322 A1 | 5/2009 |
| WO | WO 2009/062100 A1 | 5/2009 |
| WO | WO 2009/130198 A2 | 10/2009 |
| WO | WO 2009/135888 A2 | 11/2009 |
| WO | WO 2009/137254 A1 | 11/2009 |
| WO | WO 2009/140015 A2 | 11/2009 |
| WO | WO 2009/149303 A1 | 12/2009 |
| WO | WO 2009/156137 A1 | 12/2009 |
| WO | WO 2009/158511 A1 | 12/2009 |
| WO | WO 2010/009122 A1 | 1/2010 |
| WO | WO 2010/010051 A1 | 1/2010 |
| WO | WO 2010/060081 A1 | 5/2010 |

(56) References Cited

FOREIGN PATENT DOCUMENTS

| | | |
|---|---|---|
| WO | WO 2010/062768 A1 | 6/2010 |
| WO | WO 2010/091122 A1 | 8/2010 |
| WO | WO 2010/111414 A1 | 9/2010 |
| WO | WO 2010/133834 A2 | 11/2010 |
| WO | WO 2010/144502 A2 | 12/2010 |
| WO | WO 2010/144508 A1 | 12/2010 |
| WO | WO 2011/020866 A2 | 2/2011 |
| WO | WO 2011/028228 A1 | 3/2011 |
| WO | WO 2011/028229 A1 | 3/2011 |
| WO | WO 2011/028344 A2 | 3/2011 |
| WO | WO 2011/041770 A1 | 4/2011 |
| WO | WO 2011/043568 A2 | 4/2011 |
| WO | WO 2011/060242 A2 | 5/2011 |
| WO | WO 2011/069164 A2 | 6/2011 |
| WO | WO 2011/084808 A2 | 7/2011 |
| WO | WO 2011/101242 A1 | 8/2011 |
| WO | WO 2011/101267 A1 | 8/2011 |
| WO | WO 2011/101284 A1 | 8/2011 |
| WO | WO 2011/123813 A2 | 10/2011 |
| WO | WO 2011/133637 A2 | 10/2011 |
| WO | WO 2012/006623 A1 | 1/2012 |
| WO | WO 2012/006624 A2 | 1/2012 |
| WO | WO 2012/006633 A1 | 1/2012 |
| WO | WO 2012/006635 A1 | 1/2012 |
| WO | WO 2012/007324 A2 | 1/2012 |
| WO | WO 2012/170969 A2 | 12/2012 |
| WO | WO 2013/009627 A2 | 1/2013 |
| WO | WO 2013/083858 A1 | 6/2013 |
| WO | WO 2013/106786 A2 | 7/2013 |
| WO | WO 2013/106787 A1 | 7/2013 |
| WO | WO 2013/106789 A1 | 7/2013 |
| WO | WO 2013/122617 A1 | 8/2013 |
| WO | WO 2013/123457 A1 | 8/2013 |
| WO | WO 2013/160005 A1 | 10/2013 |
| WO | WO 2013/189827 A2 | 12/2013 |
| WO | WO 2014/011819 A2 | 1/2014 |
| WO | WO 2014/052490 A1 | 4/2014 |
| WO | WO 2014/070953 A1 | 5/2014 |
| WO | WO 2014/101287 A1 | 7/2014 |
| WO | WO-2014144549 A1 * | 9/2014 ............ A61K 47/10 |
| WO | WO 2014/173873 A1 | 10/2014 |
| WO | WO 2014/194282 A2 | 12/2014 |
| WO | WO 2014/198699 A2 | 12/2014 |
| WO | WO 2014/210448 A1 | 12/2014 |
| WO | WO 2014/210547 A1 | 12/2014 |
| WO | WO 2014/210558 A1 | 12/2014 |
| WO | WO 2015/021423 A2 | 2/2015 |
| WO | WO 2015/023891 A2 | 2/2015 |
| WO | WO 2015/106052 A1 | 7/2015 |
| WO | WO 2015/185758 A2 | 12/2015 |
| WO | WO 2016/025764 A2 | 2/2016 |
| WO | WO 2017/024060 A1 | 2/2017 |
| WO | WO 2017/117630 A1 | 7/2017 |
| WO | WO 2017/117631 A1 | 7/2017 |
| WO | WO 2017/222337 A1 | 12/2017 |
| WO | WO 2018/087271 A1 | 5/2018 |
| WO | WO 2018/102743 A1 | 6/2018 |
| WO | WO 2019/222682 A1 | 11/2019 |
| WO | WO 2021/257899 A1 | 12/2021 |

OTHER PUBLICATIONS

Ng, W. H., et al. "Role of imaging in management of hemophilic patients." American Journal of Roentgenology 184.5 (2005): 1619-1623 (Year: 2005).*

Arnold, William D., and M. W. Hilgartner. "Hemophilic arthropathy. Current concepts of pathogenesis and management." JBJS 59.3 (1977): 287-305 (Year: 1977).*

Polyanskaya et al., "Modern Concepts of the Pathogenesis of Hemophilic Arthropathy", Issues of Hematology/Oncology and Immunopathology in Pediatrics, 2015, 14(3): 5-12, including English abstract.

Groomes et al., "Reduction of Factor VIII Inhibitor Titers During Immune Tolerance Induction with Recombinant Factor VIII-Fc Fusion Protein: Use of Eloctate for ITI in HA With inhibitor", Pediatric Blood and Cancer, vol. 63, No. 5, Jan. 6, 2016.

International Preliminary Report on Patentability in related PCT Application No. PCT/US2017/064302, dated Jun. 4, 2019 (7 pages).

International Search Report and Written Opinion in related PCT Application No. PCT/US2017/064302, dated Mar. 28, 2018 (10 pages).

Kerlin et al., "Long-Term Efficacy of rFVIIIFc Prophylaxis in Pediatric, Adolescent, and Adult Subjects with Target Joints and Severe Hemophilia A", Blood, vol. 126, No. 23, Dec. 2012; 57th Annual Meeting of the American-Society-of-Hematology; Orlando, FL, USA, Dec. 5-8, 2015 (Abstract).

Krishnamoorthy et al., "Recombinant factor VIII Fc (rFVIIIFc) fusion protein reduces immunogenicity and induces tolerance in hemophilia A mice", Cellular Immunology, vol. 301, Dec. 29, 2015.

Malec et al., "Immune Tolerance Induction Using Rfviiifc (Eloctate)", Blood, vol. 126, No. 23, Dec. 2015 (Abstract).

Young et al., "Recombinant factor VIII Fc fusion protein for the prevention and treatment of bleeding in children with severe hemophilia A", Journal of Thrombosis and Haemostasis, vol. 13, No. 6, Apr. 23, 2015, pp. 967-977.

Peters et al., "Biochemical and Functional Characterization of a Recombinant Monomeric Factor VIII-Fc Fusion Protein", Journ. of Thrombosis and Haemostasis, Jan. 2013, 11: 132-141.

Rodriguez-Merchan, "Haemophilic synovitis: basic concepts", Haemophilia, 2007, 13(Suppl 3): 1-3.

Rodriguez-Merchan, et al., "General principals and indications of synoviorthesis (medical synovectomy) in haemophilia", Haemophilia, 2001, 7(Suppl 2): 6-10.

Bai, et al. (May 17, 2005) "Recombinant Granulocyte Colony-Stimulating Factor-Transferrin Fusion Protein as An Oral Myelopoietic Agent", Proceedings of the National Academy of Sciences of the United States of America, vol. 102, No. 20, pp. 7292-7296.

Benhar, et al. (Dec. 1994) "Cloning, Expression and Characterization of The Fv Fragments of The Anti-Carbohydrate mAbs B1 and B5 as Single-Chain Immunotoxins", Protein Engineering, Design and Selection, vol. 7, No. 12, pp. 1509-1515.

Blanchette et al., Definitions in hemophilia: communication from the SSC of the ISTH, J Thromb Haemost., 2014, 12(11): 1935-1939.

Bovenschen, et al. (2005) "LDL Receptor Cooperates with LDL Receptor-Related Protein in Regulating Plasma Levels of Coagulation Factor VIII In vivo", Blood, vol. 106, pp. 906-912.

Bovenschen, Niels (2010) "LDL Receptor Polymorphisms Revisited", Blood, vol. 116, No. 25, pp. 5439-5440.

Brandsma, et al. (Mar.-Apr. 2011) "Recombinant Human Transferrin: Beyond Iron Binding and Transport", Biotechnology Advances, vol. 29, No. 2, pp. 230-238.

Cameron, et al. (Feb. 1998) "The Canine Factor VIII cDNA and 5' Flanking Sequence", Journal of Thrombosis and Haemostasis, vol. 79, No. 2, pp. 317-322.

Capon, et al. (Feb. 9, 1989) "Designing CD4 Immunoadhesins for AIDS Therapy", Nature, vol. 337, No. 6207, pp. 525-531.

Choo, et al. (1982) "Molecular Cloning Of The Gene For Human Anti-Haemophilic Factor IX", Nature, vol. 299, No. 5879, pp. 178-180.

Clinicaltrials.gov, NCT01027364, Study of Recombinant Factor IX Fc Fusion Protein (rFIXFc) in Subjects with Hemophilia B, Dec. 7, 2009.

Clinicaltrials.gov, NCT01181128, Study to Evaluate the Safety, Pharmacokinetics and Efficacy of Recombinant Factor VIII Fc Fusion Protein (rFVIIIFc) in Previously Treated Subjects With Severe Hemophilia A, Aug. 13, 2010.

Clinicaltrials.gov, NCT01425723, Long-Term Safety and Efficacy of Recombinant Human Coagulation Factor IX Fusion Protein (rFIXFc) in the Prevention and Treatment of Bleeding Episodes in Previously Treated Subjects with Hemophilia B, Aug. 30, 2011.

Clinicaltrials.gov, NCT01454739, Long-Term Safety and Efficacy of rFVIIIFc in the Prevention and Treatment of Bleeding Episodes in Previously Treated Participants With Hemophilia A (Aspire), Oct. 19, 2011.

Clinicaltrials.gov, NCT01458106, Study to Evaluate the Safety, Efficacy, and Pharmacokinetics of Recombinant Coagulation Factor

(56) References Cited

OTHER PUBLICATIONS

VIII Fc Fusion Protein (rFVIIIFc) in Previously Treated Pediatric Subjects With Hemophilia A (Kids Along), Oct. 24, 2011.
Cutler, et al. (2002) "The Identification and Classification Of 41 Novel Mutations in The Factor VIII Gene (F8c)", Human Mutation, vol. 19, No. 3, pp. 274-278.
Dennis, et al. (Sep. 20, 2002) "Albumin Binding as a General Strategy for Improving the Pharmacokinetics of Proteins", Journal of Biological Chemistry, vol. 277, No. 38, pp. 35035-35043.
Dobeli, et al., "Role of the Carboxy-Terminal Sequence on the Biological Activity of Human Immune Interferon (IFN-y)", Journal of Biotechnology, vol. 7, No. 3, pp. 199-216. (1988).
Eaton, et al. (Dec. 1986) "Construction and Characterization of An Active Factor VIII Variant Lacking the Central One-Third of The Molecule", Biochemistry, vol. 25, No. 26, pp. 8343-8347.
Fair, et al. (1984) "Human Hepatoma Cells Secrete Single Chain Factor X, Prothrombin, And Antithrombin III", Blood, vol. 64, No. 1, pp. 194-204.
Feldman et al., "Tailored Prophylaxis in Severe Hemophilia A: Interim Results From the First 5 Years of the Canadian Hemophilia Primary Prophylaxis Study," J Thromb Haemost 4:1228-1236, 2006.
Fischer et al., "Prophylaxis in real life scenarios", Haemophilia 20(Suppl 4): 106-113 (2014).
Gayle, et al., "Identification Of Regions In Interleukin-1 Alpha Important For Activity", Journal of Biological Chemistry, vol. 268, No. 29, pp. 22105-22111. (Oct. 15, 1993).
GenBank (Jan. 14, 1995) "Human Transferrin mRNA, Complete cds", GenBank Accession No. M12530.1.
GenBank (May 7, 1993) "Transferrin [human, liver, mRNA, 2347 nt]", Accession No. S95936.1, accessed at http://www.ncbi.nlm.nih.gov/nuccore/S95936, 2 pages.
Genbank Database (Jul. 16, 2001) "Homo Sapiens Transferrin (TF), mRNA", GenBank accession No. XM039845.
Genbank Database (Jul. 16, 2001) "Homo Sapiens Transferrin (TF), mRNA", GenBank accession No. XM039847.
Genbank Database (Mar. 29, 2016) "Homo sapiens von Willebrand Factor (VWF), mRNA", NCBI Reference Sequence: NM_000552.3.
Genbank Database (Mar. 29, 2016) "Von Willebrand Factor Preproprotein [Homo sapiens]", NCBI Reference Sequence: NP_000543.2.
Genbank Database (May 13, 2002) "Homo Sapiens Transferrin (TF), mRNA", GenBank accession No. XM002793.
Genbank Database (May 25, 2014) "Homo Sapiens Transferrin (TF), Transcript Variant 1, mRNA", Accession No. NM001063.3.
Guo et al., "Contrast Clinical Efficiency Evaluation of Children and Adult Patients with Severe Hemophilia A Prevention and Treatment of Low Dose", Heilongjiang Medical Journal, Aug. 2020, 44(8): 1043-1044.
Hilgartner, "Current treatment of hemophilic arthropathy", Current Opinion in Pediatrics, Feb. 2002, 14(1): 46-49.
Ho, et al. (Apr. 15, 1989) "Site-Directed Mutagenesis by Overlap Extension Using the Polymerase Chain Reaction", Gene, vol. 77, No. 1, pp. 51-59.
Hoeben, et al. (1990) "Expression of Functional Factor Viii in Primary Human Skin Fibroblasts After Retrovirus-Mediated Gene Transfer", Journal of Biological Chemistry, vol. 265, No. 13, pp. 7318-7323.
Holt, L.J., et al., "Anti-Serum Albumin Domain Antibodies for Extending the Half-lives of Short Lived Drugs," Protein Engineering, Design and Selection 21(5):283-288, Oxford University Press, England (May 2008).
Horton, et al. (1993) "Gene Splicing by Overlap Extension", Methods in Enzymology, vol. 217, pp. 270-279.
Kasuda, et al. (Aug. 2008) "Establishment of Embryonic Stem Cells Secreting Human Factor VIII for Cell-Based Treatment of Hemophilia A", Journal of Thrombosis and Haemostasis, vol. 6, No. 8, pp. 1352-1359.

Kavakli et al., "Once-weekly prophylactic treatment vs. on-demand treatment with nonacog alfa in patients with moderately severe to severe haemophilia B", Haemophilia 22(3/4): 381-88 (2016).
Khayat, "Once-weekly prophylactic dosing of recombinant factor IX improves adherence in hemophilia B", J Blood Med., Nov. 30, 2016, 7: 275-282.
Kim, et al. (Sep. 2010) "Transferrin Fusion Technology: A Novel Approach to Prolonging Biological Half-Life of Insulinotropic Peptides", Journal of Pharmacology and Experimental Therapeutics, vol. 334, No. 3, pp. 682-692.
Kobayashi, et al. (Feb. 2002) "FcRn-Mediated Transcytosis of Immunoglobulin G in Human Renal Proximal Tubular Epithelial Cells", American Journal of Physiology-Renal Physiology, vol. 282, No. 2, pp. F358-F365.
Kraulis, et al. (Jan. 8, 1996) "The Serum Albumin-Binding Domain of Streptococcal Protein G Is A Three-Helical Bundle: A Heteronuclear NMR Study", FEBS Letters, vol. 378, Issue 2, pp. 190-194.
Kurachi, et al. (1982) "Isolation and Characterization of A cDNA Coding for Human Factor IX", Proceedings of the National Academy of Sciences, pp. 6461-6464.
Langner, et al. (Apr. 1988) "Synthesis of Biologically Active Deletion Mutants of Human Factor VIII:C", Behring Institute Mitteilungen, No. 82, pp. 16-25.
Larrick, et al. (1989) "Rapid Cloning of Rearranged Immunoglobulin Genes from Human Hybridoma Cells using Mixed Primers and the Polymerase Chain Reaction", Biochemical and Biophysical Research Communications, vol. 160, No. 3, pp. 1250-1256.
Lenting, et al. (May 2010) "The Disappearing Act of Factor VIII", Haemophilia, vol. 16, No. 102, pp. 6-15.
Li, et al. (May 2002) "The Role of The Transferrin-Transferrin-Receptor System in Drug Delivery and Targeting", Trends in Pharmacological Sciences, vol. 23, No. 5, pp. 206-209.
Linhult, et al. (Feb. 2002) "Mutational Analysis of The Interaction Between Albumin-Binding Domain from Streptococcal Protein G and Human Serum Albumin", Protein Science, vol. 11, No. 2, pp. 206-213.
Liu et al., "NF-kB Signaling Regulates Functional Expression of the MHC Class I-Related Neonatal Fc Receptor for IgG via Intronic Binding Sequences," J Immunol 179(5):2999-3011, 2007.
Mahlangu et al. "Phase 3 study of recombinant factor VIII Fc fusion protein in severe hemophilia A", Blood. Jan. 16, 2014; 123(3): 317-325.
Malec, et al. (Nov. 2016) "Extended Half-Life Factor Vill for Immune Tolerance Induction in Haemophilia", Haemophilia, vol. 22, Issue 6, pp. e552-e554.
Malik, et al. (Sep. 1992) "Polyethylene Glycol (PEG)-Modified Granulocyte-Macrophage Colony-Stimulating Factor (GM-CSF) With Conserved Biological Activity", Experimental Hematology, vol. 20, No. 8, pp. 1028-1035.
Mannucci, et al., "The Hemophilias—From Royal Genes to Gene Therapy", New England Journal of Medicine, vol. 344, No. 23, pp. 1773-1779. (Jun. 1, 2001).
Martinelli, et al. (2010) "Polymorphisms at LDLR Locus May Be Associated with Coronary Artery Disease Through Modulation of Coagulation Factor VIII Activity and Independently from Lipid Profile", Blood, vol. 116, pp. 5688-5697.
Mei, et al. (Jul. 15, 2010) "Rational Design of a Fully Active, Long-Acting PEGylated Factor VIII for Hemophilia A Treatment", Blood, vol. 116, No. 2, pp. 270-279.
Meulien, et al. (1988) "A New Recombinant Procoagulant Protein Derived from the cDNA Encoding Human Factor Viii", Protein Engineering, Design and Selection, vol. 2, No. 4, pp. 301-306.
Miao, et al. (May 1, 2004) "Bioengineering of Coagulation Factor VIII for Improved Secretion", Blood, vol. 103, No. 9, pp. 3412-3419.
Muller, et al. (Aug. 2007) "Recombinant Bispecific Antibodies for Cellular Cancer Immunotherapy", Current opinion in molecular therapeutics, vol. 9, No. 4, pp. 319-326.
Nimmerjahn, Chapter 5, Molecular and Cellular Pathways Involved in the Anti-inflammatory Activity of IgG, Molecular Mechanisms of Antibody Activity, 2013, pp. 113-138.

(56) References Cited

OTHER PUBLICATIONS

Nolan et al., "Long-term safety and efficacy of recombinant factor VIII Fc fusion protein (rFVIIIFc) in subjects with haemophilia A", Haemophilia, Jan. 2016, 22(1): 72-80.
Oymak et al., "The effectiveness of tools for monitoring hemophilic arthropathy", J Pediatr Hematol Oncol. 2015;37(2): e80-85.
Pasi et al., "Long-term safety and efficacy of extended-interval prophylaxis with recombinant factor IX Fc fusion protein (rFIXFc) in subjects with haemophilia B", Thromb Haemost., Feb. 28, 2017, 117(3): 508-518, ePublished Dec. 22, 2016.
Peyvandi, et al. (Jul. 2006) "Genetic Diagnosis of Haemophilia and Other Inherited Bleeding Disorders", Haemophilia, vol. 12, Suppl 3, pp. 82-89.
Pipe, et al. (2011) "Functional Factor VIII Made with Von Willebrand Factor at High Levels in Transgenic Milk", Journal of Thrombosis and Haemostasis, vol. 9, No. 11, pp. 2235-2242.
Powell, et al., "Phase 3 Study of Recombinant Factor IX Fc Fusion Protein in Hemophilia B", NEJM, Dec. 12, 2013, 369: 2313-2323.
Powell, J., et al., "Switching to recombinant factor IX Fc fusion protein prophylaxis results in fewer infusions, decreased factor IX consumption and lower bleeding rates," British Journal of Haematology 168: 113-123 (2015).
Powell, J.S., et al., "Long-Acting Recombinant Factor IX Fc Fusion Protein (rFIXFc) for Perioperative Management of Subjects with Haemophilia B in the Phase 3 B-Long Study," British Journal of Haematology, 168: 124-134 (2015).
Ragni, et al., "Use of Recombinant Factor IX in Subjects with Haemophilia B Undergoing Surgery", Haemophilia, vol. 8, No. 2, Blackwell Science, pp. 91-97. (Mar. 2002).
Roth, et al. (1993) "Expression of Polysialic Acid in Human Tumors and Its Significance for Tumor Growth", Polysialic Acid: From Microbes to Man, pp. 335-348.
Ruberti, et al. (Jul. 12, 1994) "The Use of The Race Method to Clone Hybridoma cDNA When V Region Primers Fail", Journal of Immunological Methods, vol. 173, No. 1, pp. 33-39.
Sarver, et al. (Dec. 1987) "Stable Expression of Recombinant Factor Viii Molecules Using a Bovine Papillomavirus Vector", DNA, vol. 6, No. 6, pp. 553-564.
Schmidt et al., "Structure-function relationships in factor IX and factor IXa", Trends Cardiovasc Med, 2003, 13(1): 39-45.
Simioni, et al. (Oct. 22, 2009) "X-Linked Thrombophilia with a Mutant Factor IX (Factor IX Padua)", The New England Journal of Medicine, vol. 361, No. 17, pp. 1671-1675.
Simpson et al., "Management of joint bleeding in hemophilia", Expert Rev Hematol., 2012, 5(4): 459-468.
Sommermeyer, et al. (1987) "Klinisch Verwendete Hydroxyethylstärke: Physikalischchemische Charakterisierung", Krankenhauspharmazie, vol. 8, No. 8, Deutscher Apotheker Verlag, Birkenwaldstr, Germany, pp. 271-278.
Story, et al., "A Major Histocompatibility Complex Class I-like Fc Receptor Cloned from Human Placenta: Possible Role in Transfer of Immunoglobulin G from Mother to Fetus", Journal of Experimental Medicine, vol. 180, No. 6, pp. 2377-2381. (Dec. 1, 1994).
Toole, et al. (Aug. 1986) "A Large Region (Approximately Equal To 95 kDa) of Human Factor VIII Is Dispensable for in Vitro Procoagulant Activity", Proceedings of the National Academy of Sciences, vol. 83, No. 16, pp. 5939-5942.
Trakymiene et al., "Utility of the Haemophilia Joint Health Score in study of episodically treated boys with severe haemophilia A and B in Lithuania", Haemophilia 16(3) :479-486 (2010).
Trussel, et al. (Dec. 2009) "New Strategy for The Extension of The Serum Half-Life of Antibody Fragments", Bioconjugate Chemistry, vol. 20, No. 12, pp. 2286-2292.
Wang, et al. (Nov. 7, 2011) "Receptor-Mediated Activation of a Proinsulin-Transferrin Fusion Protein in Hepatoma Cells", Journal of Controlled Release, vol. 155, No. 3, pp. 386-392.
Weidler, et al. (May 1991) "Pharmacokinetic Parameters as Criteria for Clinical Use of Hydroxyethyl Starch Preparations", Arzneimittelforschung/Drug Research, vol. 41, No. 5, pp. 494-498.

WFH (World Federation of Hemophilia), "Hemophilia Joint Health Score (HJHS) 2.1," Feb. 7, 2011, available at https://elearning.wfh.org/resource/hemophilia-joint-health-score-hjhs/.
WFH (World Federation of Hemophilia), Guidelines for the Management of Hemophilia: Knowledge and Expertise in Coagulation Laboratory Testing, 2nd Edition, World Federation of Hemophilia, 2012, 80 pages.
Wyrwich et al., "Changes in health-related quality of life with treatment of longer-acting clotting factors: results in the A-LONG and B-LONG clinical studies", Haemophilia, Nov. 2016, 22(6): 866-872.
VV-TMF-68870: Model Patient Information Sheet and Informed Consent Form for Clinical Trial Identifier No. 9HB01EXT, dated Jul. 18, 2011, pp. 1-9.
VV-TMF-68872: Model Patient Information Sheet and Informed Consent Form for Clinical Trial Identifier No. 9HB01EXT, dated Jul. 18, 2011, pp. 1-8.
VV-TMF-68874: Model Patient Information Sheet and Informed Consent Form for Clinical Trial Identifier No. 9HB01EXT, dated Jul. 18, 2011, pp. 1-10.
"Report of Expert Meeting on FVIII Products and Inhibitor Development", European Medicines Agency, (Feb. 28, 2006-Mar. 2, 2006), 32 Pages.
(Dec. 12, 2014) "Approval Letter—NovoSeven", U.S. Food and Drug Administration, Department of Health and Human Services, FDA Reference No. 96- 0597, accessed at http://www.fda.gov/BiologicsBloodVaccines/BloodBloodProducts/ApprovedProducts/LicensedProductsBLAs/FractionatedPlasmaProducts/ucm056916.htm#, 2 Pages.
Abraham et al. Outcome of Immune Tolerance Induction Using an Extended Half-Life Clotting Factor Concentrate—Recombinant Factor VIII Fc (Eloctate T'•')—a Report from India. Blood. 2018:132(S1):2494.
Abstracts, Haemophilia, Jul. 11, 2016, 22 (Suppl. 4): 3-138, Konkle et al. "Dosing regimens before and following long-term treatment with recombinant factor VIII Fc fusion protein (rFVIIIFc) in adults and adolescents with severe hemophilia A".
Ackerman, et al. (1997) "Ion Channels-Basic Science and Clinical Disease", the New England Journal of Medicine, vol. 336, No. 22, pp. 1575-1586.
Adams, et al. (1998) "Increased Affinity Leads to Improved Selective Tumor Delivery of Single-Chain Fv Antibodies", Cancer Research, vol. 58, No. 3, pp. 485-490.
Adams, et al. (2001) "High Affinity Restricts the Localization and Tumor Penetration of Single-Chain Fv Antibody Molecules", Cancer Research, vol. 61, No. 12, pp. 4750-4755.
Advate, United States Prescribing Information [USPI], May 2015, Baxter International Inc., The most recent version is available at: http://www.shirecontent.com/PI/PDFs/ADVATE_USA_ENG.pdf.
Adynovate, United States Prescribing Information [USPI], Dec. 2016, Baxalta US Inc., The most recent version is available at: http://www.shirecontent.com/PI/PDFs/ADYNOVATE_USA_ENG.pdf.
Agarwal et al., Retroviral gene therapy with an immunoglobulin-antigen fusion construct protects from experimental autoimmune uveitis, J Clin Invest., 2000, 106(2): 245-252.
Agersoe, et al. (Jul. 2011) "Prolonged effect of N8-Gp In Haemophilia a Dogs Supports Less Frequent Dosing", Journal of Thrombosis and Haemostasis, vol. 9, Supplement 2, P-MO-181, Isth Meeting, International Society on Thrombosis and Haemostasis, United States.
Ahmad, et al. (May 1, 2004) "ASA View: Database and tool for Solvent Accessibility Representation in Proteins", BMC Bioinformatics, vol. 5, No. 51, pp. 1-5.
Ahnstrom et al., "A 6-year follow-up of dosing, coagulation factor levels and bleedings in relation to joint status in the prophylactic treatment of haemophilia", Haemophilia, Nov. 2004, 10(6): 689-697.
Alam, et al. (1998) "Expression and Purification of a Mutant Human Growth Hormone That Is Resistant to Proteolytic Cleavage by Thrombin, Plasmin and Human Plasma In Vitro", Journal of Biotechnology, vol. 65, No. 2-3, Elsevier Science Publishers, Netherlands, pp. 183-190.

(56) References Cited

OTHER PUBLICATIONS

Alber, et al. (1982) "Nucleotide Sequence of the Triose Phosphate Isomerase Gene of Saccharomyces Cerevisiae", Journal of Molecular and Applied Genetics, vol. 1.5, pp. 419-434.
Aledort et al., A longitudinal study of orthopaedic outcomes for severe factor-VIII-deficient haemophiliacs, The Orthopaedic Outcome Study Group, J Intern Med. 1994, 236(4): 391-399.
Aleman et al., "Recombinant FVIIIFc-VWF-XTEN (BIVV001) promotes normal fibrin formation, structure and stability", International Society on Thrombosis and Haemostasis (ISTH) Congress, Jul. 8-13, 2017, Berlin Germany, 1 page.
Algiman, et al. (1992) "Natural Antibodies to Factor VIII (Anti-Hemophilic Factor) In Healthy Individuals", Proceedings of the National Academy of Sciences, vol. 89, No. 9, pp. 3795-3799.
Altuviiio [package insert], Waltham, MA: Bioverativ Therapeutics Inc., 2023.
Alvarez, et al. (Jan. 30, 2003) "Improving Protein Pharmacokinetics by Genetic Fusion to Simple Amino Acid Sequences", Journal of Biological Chemistry, vol. 279, No. 5, pp. 3375-3381.
Amin, et al. (2004) "Construction of Stabilized Proteins by Combinatorial Consensus Mutagenesis", Protein Engineering, Design & Selection: PEDS, vol. 17, No. 11, pp. 787-793.
Amunix, "Bioverativ announces FDA acceptance of IND Application for BIVV001 a novel, long-acting FVIII hemophilia therapeutic utilizing Amunix XTEN® half-life extension technology", Jun. 14, 2017, retrieved from: https://www.amunix.com/newsroom/press-releases/2017/061417, 2 pages.
Amy et al., Hemophilia A, in Transfusion Medicine and Hemostasis (2nd Ed.) 2013, Clinical and Laboratory Aspects, Chapter 106, pp. 699-704.
Ansong, et al. (2006) "Epitope Mapping Factor VIII A2 Domain by Affinity-Directed Mass Spectrometry: Residues 497-510 and 584-593 Comprise a Discontinuous Epitope for the Monoclonal Antibody R8B 12", Journal of Thrombosis and Haemostasis, vol. 4, No. 4, pp. 842-847.
Antcheva (2001) "Proteins of Circularly Permuted Sequence Present within the Same Organism: The Major Serine Proteinase inhibitor from Capsicum Annuum Seeds", Protein Science, vol. 10, No. 11, pp. 2280-2290.
Appa, R, et al. (Aug. 2010) "Investigating Clearance Mechanisms for Recombinant Activated Factor VII in a Perfused Liver Model", Journal of Thrombosis and Haemostasis, vol. 104, No. 2, pp. 243-251.
Araki, et al. (1990) "Four Disulfide Bonds' Allocation of Na+, K+-ATPase Inhibitor (SPAI)", Biochemical and Biophysical Research Communications, vol. 172, No. 1, pp. 42-46.
Arap, et al. (2002) "Steps Toward Mapping the Human Vasculature by Phage Display", Nature Medicine, vol. 8, No. 2, pp. 121-127.
Armour, et al. (Aug. 1999) "Recombinant Human IgG Molecules Lacking Fcgamma Receptor I Binding and Monocyte Triggering Activities", European Journal of Immunology, vol. 29, No. 8, pp. 2613-2624.
Arnau, et al. (Jul. 2006) "Current Strategies for the Use of Affinity Tags and Tag Removal for the Purification of Recombinant Proteins", Protein Expression and Purification, vol. 48, No. 1, pp. 1-13.
Arndt, et al. (1998) "Factors Influencing the Dimer to Monomer Transition of an Antibody Single-Chain Fv Fragment", Biochemistry, vol. 37, p. 12918-12926.
Arnold et al., "Hemophilic Arthropathy—Current Concepts of Pathogenesis and Management," The Journal of Bone & Joint Surgery, Apr. 1977, vol. 59, Issue 3, pp. 287-305.
Arruda, et al. (Jan. 1, 2001) "Posttranslational Modifications of Recombinant Myotube-Synthesized Human Factor Ix", Blood, vol. 97, No. 1, pp. 130-138.
Ashkenazi, et al., "Immunoadhesins", International Reviews of Immunology, vol. 10, Issue 2-3, Harwood Academic Publishers GmbH, United States, pp. 219-227, Jan. 1, 1993.
Assadi-Porter, et al. (2000) "Sweetness Determinant Sites of Brazzein, a Small, Heat-Stable, Sweet-Tasting Protein", Archives of Biochemistry and Biophysics, vol. 376, No. 2, pp. 259-265.

Aster, et al. (Apr. 13, 1999) "the Folding and Structural Integrity of the First LIN-12 Module of Human Notch1 Are Calcium-Dependent", Biochemistry, vol. 38, No. 15, pp. 4736-4742.
Astermark et al., The Malmo International Brother Study (MIBS), Genetic defects and inhibitor development in siblings with severe hemophilia A, Haematologica, 2005, 90(7): 924-931.
Astermark, et al. (Dec. 1, 2006) "Polymorphisms in the TNFA Gene and the Risk of Inhibitor Development in Patients with Hemophilia A", Hemostasis, Thrombosis, and Vascular Biology, Blood, vol. 108, No. 12, pp. 3739-3745.
Aznar et al., Haemophilia in Spain, Haemophilia, 2009, 15(3): 665-675.
Bachmann, et al. (1995) "T Helper Cell-Independent Neutralizing B Cell Response Against Vesicular Stomatitis Virus: Role of Antigen Patterns in B Cell Induction", European Journal of Immunology, vol. 25, No. 12, pp. 3445-3451.
Bailon, et al. (2001) "Rational Design of a Potent, Long-Lasting form of Interferon: a 40 kDa Branched Polyethylene Glycol-Conjugated Interferon α-2a for the Treatment of Hepatitis C", Bioconjugate Chemistry, vol. 12, No. 2, pp. 195-202.
Bajaj, et al. (1993) "Human Factor IX and Factor IXa", Methods in Enzymology, vol. 222, pp. 96-128.
Baneyx, et al. (2004) "Recombinant Protein Folding and Misfolding in *Escherichia Coli*", Nature Biotechnology, vol. 22, No. 11, pp. 1399-1408.
Baron, et al. (1990) "From Cloning to a Commercial Realization: Human Alpha Interferon", Critical Reviews in Biotechnology, vol. 10, No. 3, pp. 179-190.
Barrowcliffe, et al. (Jun. 2002) "Coagulation and Chromogenic Assays of Factor VIII Activity: General Aspects, Standardization, and Recommendations", Seminars in Thrombosis and Hemostasis, vol. 28, No. 3, pp. 247-256.
Barta, et al. (2002) "Repeats with Variations: Accelerated Evolution of the Pin2 Family of Proteinase Inhibitors", Trends in Genetics, vol. 18, No. 12, pp. 600-603.
Baskin et al., Management of occlusion and thrombosis associated with longterm indwelling central venous catheters, Lancet. 2009, 374(9684): 159-169.
Bateman, et al. (1998) "Granulins: The Structure and Function of An Emerging Family of Growth Factors, ", the Journal of Endocrinology, vol. 158, No. 2, pp. 145-151.
Batorova et al., "Expert opinion on current and future prophylaxis therapies aimed at improving protection for people with hemophilia A", Journal of Medicine and Life, Apr. 4, 2022, 15(4): 570-578.
Batsuli et al. Immune tolerance Induction in paediatric patients with haemophilia A and inhibitors receiving emicizumab prophylaxis. Haemophilia. 2019;25(5):789-796.
Baxevanis et al., Evidence for distinct epitopes on human IgG with T cell proliferative and suppressor function, Eur J Immunol., 1986, 16(8): 1013-1016.
Beissinger, et al. (1998) "How Chaperones Fold Proteins", Biological Chemistry, vol. 379, No. 3, pp. 245-259.
Belaaouaj, et al. (2000) "Matrix Metalloproteinases Cleave Tissue Factor Pathway Inhibitor Effects on Coagulation", Journal of Biological Chemistry, vol. 275, No. 35, pp. 27123-27128.
Belew, et al. (1994) "Purification of Recombinant Human Granulocyte-Macrophage Colony-Stimulating Factor from the Inclusion Bodies Produced by Transformed *Escherichia Coli*Cells", Journal of Chromatography A, vol. 679, No. 1, pp. 67-83.
Bensch, et al. (1995) "Hbd-1: A Novel Beta-Defensin from Human Plasma", FEBS Letters, vol. 368, No. 2, pp. 331-335.
Berger, et al. (1993) "Phoenix Mutagenesis: one-Step Reassembly of Multiply Cleaved Plasmids with Mixtures of Mutant and Wild-Type Fragments", Analytical Biochemistry, vol. 214, No. 2, pp. 571-579.
Berkner, et al., "Expression of Recombinant Vitamin K-Dependent Proteins in Mammalian Cells: Factors IX and VII", Methods in Enzymology, vol. 222, Academic Press, United States, pp. 450-477, Jan. 1, 1993.
Berntorp et al., Consensus perspectives on prophylactic therapy for haemophilia: summary statement, Haemophilia, 2003, 9(Suppl 1): 1-4.

(56) References Cited

OTHER PUBLICATIONS

Berntorp et al., Modern treatment of haemophilia, Bull World Health Organ., 1995, 73(5): 691-701.

Berntrop et al., "dosing regimens, FVIII levels and estimated haemostatic protection with special focus on rFVIIIFc", Haemophilia, May 2016, 22(3): 389-396.

Beste, et al. (1999) "Small Antibody-like Proteins with Prescribed Ligand Specificities Derived from the Lipocalin Fold", Proceedings of the National Academy of Sciences, vol. 96, No. 5, pp. 1898-1903.

Bhagunde et al., "A Population Pharmacokinetic (PopPK) Model to Characterize Efanesoctocog Alfa (BIVV001) Factor Viii (FVIII) Activity Levels in Patients With Severe Hemophilia A", Abstract, HTRS Mar. 10-12, 2023, Orlando, Florida.

Bhagunde et al., "A Population Pharmacokinetic (PopPK) Model to Characterize Efanesoctocog Alfa (BIVV001) Factor Viii (FVIII) Activity Levels in Patients with Severe Hemophilia A", Abstract, Blood, Nov. 15, 2022, 140 (Supplement 1): 8449-8450.

Bhagunde et al., "A Population Pharmacokinetic (PopPK) Model to Characterize Efanesoctocog Alfa (BIVV001) Factor Viii (FVIII) Activity Levels in Patients with Severe Hemophilia A", Poster, Blood, Nov. 15, 2022.

Bhagunde et al., "A Repeated Time to Event (RTTE) Model to Characterize Bleed Risk in Patients with Severe Hemophilia A Treated with Efanesoctocog Alfa", Abstract, 16th Annual Congress of the European Association for Haemophilia and Allied Disorders, Feb. 7-10, 2023.

Bhagunde et al., "A Repeated Time to Event (RTTE) Model to Characterize Bleed Risk in Patients with Severe Hemophilia A Treated with Efanesoctocog Alfa", Poster, 16th Annual Congress of the European Association for Haemophilia and Allied Disorders, Feb. 7-10, 2023.

Bhagunde et al., "A Population Pharmacokinetic (PopPK) Model to Characterize Efanesoctocog Alfa (BIVV001) Factor Viii (FVIII) Activity Levels in Patients With Severe Hemophilia", Poster, HTRS Mar. 10-12, 2023, Orlando, Florida.

Bharmal et al., Validation of an abbreviated Treatment Satisfaction Questionnaire for Medication (TSQM-9) among patients on antihypertensive medications, 2009, Health Qual Life Outcomes, 7: 36.

Bhat et al., "Vascular Remodeling Underlies Rebleeding in Hemophilic Arthropathy," American Journal of Hematology, Nov. 2015, vol. 90, No. 11, pp. 1027-1035.

Bi, et al., "Targeted Disruption of The Mouse Factor VIII Gene Produces A Model of Haemophilia A", Nature Genetics, vol. 10, No. 1, pp. 119-121, May 1, 1995.

Bihoreau et al., "Structural and functional characterization of Factor VIII-VII, a new recombinant Factor VIII lacking most of the B-domain", Biochem. J. Vol. 277, 1991, pp. 23-31.

Binz, et al. (2005) "Engineering Novel Binding Proteins from Nonimmunoglobulin Domains", Nature Biotechnology, vol. 23, No. 10, pp. 1257-1268.

Bioverativ Investor Day, Jan. 6, 2017.

Bioverativ Therapeutics Inc., "A Phase 1, Open-Label, Single-Site, Safety, Tolerability, and Pharmacokinetics Study of Repeat Doses of BIVV001", Investigator and Sponsor's Agreement and Brochure, Protocol No. 242HA102, EudraCT No. 2018-001535-51, Final, Version 3.0, Oct. 25, 2018.

Bioverativ Therapeutics Inc., "A Phase 1, Open-Label, Single-Site, Safety, Tolerability, and Pharmacokinetics Study of Repeat Doses of BIVV001", Patient Information Sheet and Informed Consent Form, Protocol No. 242HA101, Final Form for Bulgaria, Version 2.0, Nov. 15, 2018.

Bioverativ, a Sanofi company, "A Phase 3 Open-label Interventional Study of Intravenous Recombinant Coagulation Factor VIII Fc-von Willebrand Factor-XTEN Fusion Protein, Efanesoctocog Alfa (BIVV001), in Patients With Severe Hemophilia A (XTEND-1)", Study Record, NCT04161495, May 24, 2023.

Bioverativ, a Sanofi company, "A Phase 3 Open-Label, Multicenter Study of the Safety, Efficacy, and Pharmacokinetics of Intravenous Recombinant Coagulation Factor VIII Fc-von Willebrand Factor-XTEN Fusion Protein (rFVIIIFc-VWF-XTEN; BIVV001) in Previously Treated Patients >12 Years of Age With Severe Hemophilia A", Amended Clinical Trial Protocol 05, Protocol No. EFC16293, Version No. 1, Aug. 20, 2021.

Bioverativ, a Sanofi company, "A Phase 3 Open-Label, Multicenter Study of the Safety, Efficacy, and Pharmacokinetics of Intravenous Recombinant Coagulation Factor VIII Fc-von Willebrand Factor-XTEN Fusion Protein (rFVIIIFc-VWF-XTEN; BIVV001) in Previously Treated Patients >12 Years of Age With Severe Hemophilia A", Statistical Analysis Plan, NCT04161495, Protocol No. EFC16293, EudraCT: 2019-002023-15, Version No. 8.0, Jun. 16, 2020.

Bioverativ, a Sanofi company, "A Safety, Tolerability, and Pharmacokinetics Study of a Single Intravenous Injection of Recombinant Coagulation Factor VIII Fc - Von Willebrand Factor—XTEN Fusion Protein (rFVIIIFc-VWF-XTEN) (BIVV001) in Previously Treated Adults With Severe Hemophilia A (Exten-A)", Study Record, Protocol No. 242HA101, Apr. 19, 2022.

Bioverativ, Summary Basis for Regulatory Action of ALTUVIIIO, Feb. 21, 2023.

Bird, et al. (Oct. 21, 1988) "Single-Chain Antigen-Binding Proteins", Science, vol. 242, No. 4877, pp. 423-426.

Bitonti, et al., "Pulmonary Administration of Therapeutic Proteins using an Immunoglobulin Transport Pathway", Advanced Drug Delivery Reviews, vol. 58, Issues 9-10, pp. 1106-1118, Oct. 31, 2006.

Bittner, et al. (1998) "Recombinant Human Erythropoietin (rhEPO) Loaded Poly (Lactide-Co—Glycolide) Microspheres: influence of the Encapsulation Technique and Polymer Purity on Micro Sphere Characteristics", European Journal of Pharmaceutics and Biopharmaceutics vol. 45, No. 3, pp. 295-305.

Bjoern, S., et al. (Sep. 1986) "Activation of Coagulation Factor VII to VIIa", Research Disclosure, vol. 269, pp. 564-565.

Bjorkman, et al. (Nov. 1, 2001) "Pharmacokinetics of Coagulation Factors: Clinical Relevance for Patients with Haemophilia", Clinical Pharmacokinetics, vol. 40, No. 11, Adis International Ltd., New Zealand, pp. 815-832.

Blanchette et al., Plasma and albumin-free recombinant factor VIII: pharmacokinetics, efficacy, and safety in previously treated pediatric patients. J Thromb Haemost. 2008;6(8): 1319-26.

Blanchette, et al. (2004) "Principles of Transmucosal Delivery of therapeutic Agents", Biomedicine & Pharmacotherapy, vol. 58, No. 3, pp. 142-151.

Blanchette, et al., "A Survey of Factor Prophylaxis in the Canadian Haemophilia A Population", Haemophilia, vol. 10, Issue 6, Blackwell Publishing, England, pp. 679-683, Nov. 1, 2004.

Bloch, et al. (1998) "1H NMR Structure of An Antifungal Gannna-Thionin Protein Sialpha1: Similarity to Scorpion toxins", Proteins, vol. 32, No. 3, pp. 334-349.

Blumberg, Tolerogenic properties of the Fc portion of IgG and its relevance to the treatment and management of hemophilia. Blood. 2018;131(20):2205-2214.

Bobrow, R. S. (2005) "Excess Factor VIII: A Common Cause of Hypercoagulability", American Board of Family Medicine, United States, pp. 147-149.

Bodenmuller, et al. (1986) "the Neuropeptide Head Activator Loses Its Biological Acitivity by Dimerization", the EMBO Journal vol. 5, No. 8, pp. 1825-1829.

Boder, et al. (Sep. 26, 2000) "Directed Evolution of Antibody Fragments with Monovalent Femtomolar Antigen-Binding Affinity", Proceedings of the National Academy of Sciences, vol. 97, No. 20, pp. 10701-10705.

Borel et al., Prevention of Murine Lupus Nephritis by Carrier-Dependent Induction of Immunologic Tolerance to Denatured DNA, Science, 1973, 182(4107): 76-78.

Boshart, et al. (1985) "A Very Strong Enhancer Is Located Upstream of An Immediate Early Gene of Human Cytomegalovirus", Cell, vol. 41, No. 2, pp. 521-530.

Briet, et al. (1994) "High Titer Inhibitors in Severe Haemophilia A: A Meta-Analysis Based on Eight Long-term Follow-up Studies concerning Inhibitors Associated with Crude or Intermediate Purity Factor VIII Products", Journal of Thrombosis and Haemostasis, vol. 72, No. 1, pp. 162-164.

(56) References Cited

OTHER PUBLICATIONS

Brinkhous, et al., "Preclinical Pharmacology of Albumin-Free B-Domain Deleted Recombinant Factor VIII", Seminars in Thrombosis and Hemostasis, Thieme Medical Publishers, vol. 28, No. 3, pp. 269-272, Jun. 1, 2002.
Brooks, et al. (Oct. 2002) "Evolution of Amino Acid Frequencies in Proteins Over Deep Time: Inferred order of Introduction of Amino Acids into the Genetic Code", Molecular Biology and Evolution, vol. 19, No. 10, pp. 1645-1655.
Brutlag, et al., "Improved Sensitivity of Biological Sequence Database Searches", Computer Applications in the Biosciences: CABIOS, vol. 6, No. 3, pp. 237-245, Aug. 1, 1990.
Buchner, J. (1996) "Supervising the Fold: Functional Principles of Molecular Chaperones", F ASEB Journal, vol. 10, No. 1, pp. 10-19.
Bulaj, et al. (2003) "Efficient Oxidative Folding of Conotoxins and the Radiation of Venomous Cone Snails", Proceedings of the National Academy of Sciences of the United States of America, vol. 100, Supplement 2, pp. 14562-14568.
Bullinger et al., Pilot testing of the 'Haemo-QoL' quality of life questionnaire for haemophiliac children in six European countries. Haemophilia, Mar. 8, 2002, Suppl 2: 47-54.
Burmeister, et al. (Nov. 24, 1994) "Crystal Structure of the Complex of Rat Neonatal Fc Receptor with Fc", Nature, vol. 372, No. 6504, pp. 379-383.
Buscaglia, et al. (1999) "Tandem Amino Acid Repeats from Trypanosoma Cruzi Shed Antigens Increase the Half-Life of Proteins in Blood", Blood, vol. 93, No. 6, pp. 2025-2032.
Byetta United States Prescribing Information [USPI], Feb. 2015, AstraZeneca Pharmaceuticals LP. The most recent version is available at: https://www.azpicentral.com/byetta/pi_byetta.pdf.
Calabrese, et al. (2004) "Crystal Structure of Phenylalanine Ammonia Lyase: Multiple Helix Dipoles Implicated in Catalysis", Biochemistry, vol. 43, No. 36, pp. 11403-11416.
Caliceti, et al. (1999) "Biopharmaceutical Properties of Uricase Conjugated to Neutral and Amphiphilic Polymers", Bioconjugate Chemistry, vol. 10, No. 4, pp. 638-646.
Caliceti, et al. (2003) "Pharmacokinetic and Biodistribution Properties of Poly (Ethylene Glycol)-Protein Conjugates", Advanced Drug Delivery Reviews, vol. 55, No. 10, pp. 1261-1277.
Calvete, et al. (2000) "Disulphide-Bond Pattern and Molecular Modelling of the Dimeric Disintegrin Emf-10, A Potent and Selective integrin Alpha5Beta1 Antagonist from Eristocophis Macmahoni Venom", the Biochemical Journal, vol. 345, Part 3, pp. 573-581.
Calvete, et al. (2003) "Snake Venom Disintegrins: Novel Dimeric Disintegrins and Structural Diversification by Disulphide Bond Engineering", the Biochemical Journal, vol. 372, Part 3, pp. 725-734.
Calvete, et al. (2005) "Snake Venom Disintegrins: Evolution of Structure and Function", Toxicon, vol. 45, No. 8, pp. 1063-1074.
Cao, et al. (2006) "Development of a Compact Anti-Baff Antibody in *Escherichia Coli*", Applied Microbiology and Biotechnology, vol. 73, No. 1, pp. 151-157.
Carcao et al., Inhibitors in Hemophilia: a primer. 5 ed: World Federation of Hemophilia; 2018.
Carcao M, et al. Real-world data of immune tolerance induction using recombinant factor VIII Fc fusion protein in patients with severe haemophilia A with inhibitors at high risk for immune tolerance induction failure: A follow-up retrospective analysis. Haemophilia. 2020: 27(1):19-25.
Carcao M, et al. The changing face of immune tolerance induction in haemophilia A with the advent of emicizumab. Haemophilia. 2019:25(4): 676-684.
Carcao M, et al., Recombinant factor VIII Fc fusion protein for immune tolerance induction in patients with severe haemophilia A with inhibitors-A retrospective analysis, Haemophilia, 2018, 24(2): 245-252.
Carlsson et al., "Pain, deperssion and anxiety in people with haemophilia from three Nordic countries: Cross-sectional survey data from the Mind study", Haemophilia, 2022, 28: 557-567.
Carlsson et al., On-demand vs. prophylactic treatment for severe haemophilia in Norway and Sweden: differences in treatment characteristics and outcome, Haemophilia, 2003,9(5): 555-566.
Carpenter et al. Increased prevalence of inhibitors in Hispanic patients with severe haemophilia A enrolled in the Universal Data Collection database. Haemophilia. 2012;18(3):e260-5.
Carr, et al. (1994) "Solution Structure of a Trefoil-Motif-Containing Cell Growth Factor, Porcine Spasmolytic Protein", Proceedings of the National Academy of Sciences of the United States of America, vol. 91, No. 6, pp. 2206-2210.
Castor, et al. (1994) "Septic Cutaneous Lesions Caused by Mycobacterium Malmoense in A Patient with Hairy Cell Leukemia", European Journal of Clinical Microbiology & infectious Diseases, vol. 13, No. 2, pp. 145-148.
Cella et al., The Patient-Reported Outcomes Measurement Information System (PROMIS): Progress of an NIH Roadmap Cooperative Group During Its First Two Years, Medical Care, 45(5 Suppl 1), 2007, S3-S11.
Centers for Disease Control and Prevention (CDC), Summary Report of UDC Activity National, Patient Demographics (Hemophilia) 2017. Available at: https://www2a.cdc.gov/ncbddd/htcweb/UDC_Report/UDC_Report.asp.
Chamow at al., Immunoadhesins: principles and applications, Trends Biotechnol., 1996, 14(2): 52-60.
Chang, et al. (1978) "Phenotypic Expression in *E. Coli* of A DNA Sequence Coding for Mouse Dihydrofolate Reductase", Nature, vol. 275, No. 5681, pp. 617-624.
Chang, et al., "Replacing the First Epidermal Growth Factor-like Domain of Factor IX with That of Factor VII Enhances Activity In Vitro and in Canine Hemophilia B", The Journal of Clinical Investigation, vol. 100, No. 4, The American Society for Clinical Investigation, Inc., pp. 886-892, Aug. 15, 1997.
Chaudhury, et al., "Albumin Binding to FcRn: Distinct from the FcRn-IgG Interaction", Biochemistry, vol. 45, No. 15, pp. 4983-4990, Apr. 18, 2006.
Chen et al., "Fusion protein linkers: Property, design and functionality", Advanced Drug Delivery Reviews, Oct. 2013, 65(10): 1357-1369.
Chen, et al. (1991) "Crystal Structure of a Bovine Neurophysin li Dipeptide Complex at 2", Proceedings of the National Academy of Sciences of the United States of America vol. 88, No. 10, pp. 4240-4244.
Chen, et al. (1993) "Site-Directed Mutations in a Highly Conserved Region of Bacillus Thuringiensis Delta-Endotoxin Affect inhibition of Short Circuit Current Across Bombyx Mori Midguts", Proceedings of the National Academy of Sciences of the United States of America vol. 90, No. 19, pp. 9041-9045.
Chen, et al. (2006) "Expression, Purification, and in Vitro Refolding of a Humanized Single-Chain Fv Antibody Against Human Ctla4 (Cd152)", Protein Expression and Purification, vol. 46, No. 2, pp. 495-502.
Chhabra et al., "BIVV001, a new class of factor VIII replacement for hemophilia A that is independent of von Willebrand factor in primates and mice", Blood, Apr. 23, 2020, 135(17): 1484-1496.
Chhabra et al., Application of in silico antigenicity prediction methods to avoid neo-epitopes during the designing of BIIB073, a next-generation long-acting recombinant Factor VIII (rFVIII) molecule, Haemophilia, 2016, 22(Suppl 4): 18.
Chirino, et al. (2004) "Minimizing the Immunogenicity of Protein therapeutics", Drug Discovery Today, vol. 9, No. 2, pp. 82-90.
Cho, et al. (Nov. 22, 1994) "Polysialic Acid Engineering: Synthesis of Polysialylated Neoglycosphingolipids by Using the Polysialyltransferase From Neuroinvasive *Escherichia Coli*K1", Proceedings of the National Academy of Sciences of the United States of America, vol. 91, No. 24, pp. 11427-11431.
Chong, et al. (2001) "Determination of Disulfide Bond assignments and NGlycosylation Sites of the Human Gastrointestinal Carcinoma Antigen Ga733-2 (Co17-1A, EGP, Ks1-4, KSA, and Ep-Cam)", The Journal of Biological Chemistry, vol. 276, No. 8, pp. 5804-5813.
Chong, et al. (2002) "Disulfide Bond Assignments of Secreted Frizzled-Related Protein-1 Provide Insights About Frizzled Homology and Netrin Modules", the Journal of Biological Chemistry, vol. 277, No. 7, pp. 5134-5144.

(56) References Cited

OTHER PUBLICATIONS

Chou, et al. (1974) "Prediction of Protein Conformation", Biochemistry, vol. 13, No. 2, pp. 222-245.
Chowdary et al., "Managing surgery in hemophilia with recombinant factor VIII Fc and factor IX Fc: Data on safety and effectiveness from phase 3 pivotal studies", Res Pract Thromb Haemost., Jul. 2022, 6(5): E12760, 1-15.
Chowdhury, et al. (1999) "Improving Antibody Affinity by Mimicking Somatic Hypermutation In Vitro", Nature Biotechnology, vol. 17, No. 6, pp. 568-572.
Christmann, et al. (1999) "The Cystine Knot of a Squash-Type Protease Inhibitor as A Structural Scaffold for *Escherichia Coli*Cell Surface Display of Conformationally Constrained Peptides", Protein Engineering, vol. 12, No. 9, pp. 797-806.
Clark, et al. (1996) "Long-Acting Growth Hormones Produced by Conjugation with Polyethylene Glycol", Journal of Biological Chemistry, vol. 271, No. 36, p. 21969-21977.
Clark, et al. (1996) "Recombinant Human Growth Hormone (GH)-Binding Protein Enhances the Growth-Promoting Activity of Human GH in the Rat", Endocrinology, vol. 137, No. 10, pp. 4308-4315.
Cleland, et al. (2001) "Emerging Protein Delivery Methods", Current Opinion in Biotechnology, vol. 12, No. 2, pp. 212-219.
Cleland, et al. (2009) "An Extended Half-life Exenatide Construct for Weekly Administration in the Treatment of Diabetes Mellitus", Diabetes, vol. 58, pp. A511-A512.
Clinicaltrials.Gov, (Apr. 13, 2018) Bioverativ Therapeutics, Inc., NCT03205163, Statistical Analysis Plan: Protocol Title: A Phase 1/2a, Open-Label, Dose-Escalation Study to Determine the Safety, Tolerability, and Pharmacokinetics of a Single Intravenous Injection of rFVIIIFc-VWF-XTEN (BIVV001) in Previously Treated Adults With Severe Hemophilia A, Protocol No. 242HA101, Version 1.0 dated Apr. 13, 2018, based on Protocol Version 6.0, dated Jan. 2, 2018.
Clinicaltrials.Gov, (Apr. 7, 2023) "A Safety, Tolerability, and Pharmacokinetics Study of a Single Intravenous Injection of Recombinant Coagulation Factor VIII Fc—Von Willebrand Factor—XTEN Fusion Protein (rFVIIIFc-VWF-XTEN) (BIVV001) in Previously Treated Adults with Severe Hemophilia A (Exten-A)", Study Details, ClinicalTrials.gov Identifier: NCT03205163, https://clinicaltrials.gov/archive/NCT03205163.
Clinicaltrials.Gov, (Dec. 4, 2009) "Study of Recombinant Factor VIII Fc Fusion Protein (rFVIIIFc) in Subjects with Severe Hemophilia A", ClinicalTrials.gov Identifier: NCT01027377, 3 Pages.
Clinicaltrials.Gov, (Feb. 23, 2023) "A Phase 3, Open-label Interventional Study of an Intravenous Recombinant Coagulation Factor VIII Fc-von Willebrand Factor-XTEN Fusion Protein, Efanesoctocog Alfa (BIVV001), in Patients with Severe Hemophilia (XTEND-1)", History of Changes, ClinicalTrials.gov Identifier: NCT04161495, https://clinicaltrials.gov/archive/NCT04161495.
Clinicaltrials.Gov, (Jan. 4, 2018) Bioverativ Therapeutics, Inc., NCT03205163, Protocol Title: A Phase 1/2a, Open-Label, Dose-Escalation Study to Determine the Safety, Tolerability, and Pharmacokinetics of a Single Intravenous Injection of rFVIIIFc-VWF-XTEN (BIVV001) in Previously Treated Adults With Severe Hemophilia A, Protocol No. 242HA 101, Phase of Development: 1/2a, Eudra CT No. 2017-001140-34, Version 6.0.
Clinicaltrials.Gov, (Jan. 23, 2023) "Safety, Efficacy and PK of BIVV 001 in Pediatric Patients with Hemophilia A (XTEND-Kids)", Study Details, ClinicalTrials.gov Identifier: NCT04759131, https://clinicaltrials.gov/archive/NCT04759131.
Clinicaltrials.Gov, (Jan. 23, 2023) "Safety, Efficacy and PK of BIVV 001 in Pediatric Patients with Hemophilia A (XTEND-Kids)", Tabular View, ClinicalTrials.gov Identifier: NCT04759131, https://clinicaltrials.gov/archive/NCT04759131.
Clinicaltrials.Gov, (Jul. 19, 2022) "A Phase 3, Open-label Interventional Study of an Intravenous Recombinant Coagulation Factor VIII Fc-von Willebrand Factor-XTEN Fusion Protein, Efanesoctocog Alfa (BIVV001), in Patients with Severe Hemophilia (XTEND-1)", Tabular View, ClinicalTrials.gov Identifier: NCT04161495, https://clinicaltrials.gov/archive/NCT04161495.

Coia, et al. (1997) "Use of Mutator Cells as a Means for increasing Production Levels of a Recombinant Antibody Directed Against Hepatitis B", Gene, vol. 201, No. 1-2, pp. 203-209.
Collen, et al. (Oct. 10, 2000) "Polyethylene Glycol-Derivatized Cysteine-Substitution Variants of Recombinant Staphylokinase for Single-Bolus Treatment of Acute Myocardial Infarction", Circulation, vol. 102, Issue 15, pp. 1766-1772.
Collins et al., Break-through bleeding in relation to predicted factor VIII levels in patients receiving prophylactic treatment for severe hemophilia A, J Thromb Haemost, 2009, Mar,7(3): 413-420.
Collins et al., Factor Vill requirement to maintain a target plasma level in the prophylactic treatment of severe hemophilia A: influences of variance in pharmacokinetics and treatment regimens, J Thromb Haemost., 2009, 8(2): 269- 275.
Collins et al., Recombinant long-acting glycoPEGylated factor IX in hemophilia B: a multinational randomized phase 3 trial, Blood, 2014, 124(26): 3880-3886.
Collins, "Personalized prophylaxis", Haemophilia, 2012, 18(Suppl. 4): 131-135.
Conticello, et al. (Feb. 2001) "Mechanisms for Evolving Hypervariability: The Case of Conopeptides", Molecular Biology and Evolution, Oxford University Press, United States, vol. 18, Issue 2, pp. 120-131.
Coppola, et al. (Feb. 2012) "Prophylaxis in Children with Hemophilia: Evidence-Based Achievements, Old and New Challenges", Seminars in Thrombosis and Hemostasis, vol. 38, No. 1, pp. 79-94.
Corisdeo, et al. (Apr. 2004) "Functional Expression and Display of An Antibody Fab Fragment in *Escherichia Coli*: Study of Vector Designs and Culture Conditions", Protein Expression and Purification, vol. 34, Issue 2, pp. 270-279.
Corsaro, et al. (1981) "Enhancing the Efficiency of DNA-Mediated Gene Transfer in Mammalian Cells", Somatic Cell Genetics, vol. 7, No. 5, pp. 603-616.
Counts, et al. (Sep. 1978) "Disulfide Bonds and the Quaternary Structure of Factor VIII/von Willebrand Factor", Journal of Clinical Investigation, vol. 62, No. 3, pp. 702-709.
Coyle et al., Phase 1 study of BAY 94-9027, a PEGylated B-domain- deleted recombinant factor VIII with an extended half-life, in subjects with hemophilia A, J Thromb Haemost., 2014, 12(4): 488-496.
Craik, et al. (Dec. 17, 1999) "Plant cyclotides: A Unique Family of Cyclic and Knotted Proteins that Defines the Cyclic Cystine Knot Structural Motif", Journal of Molecular Biology, vol. 294, Issue 5, Dec. 17, 1999, pp. 1327-1336.
Crameri, et al. (Apr. 1996) "Improved Green Fluorescent Protein by Molecular Evolution Using DNA Shuffling", Nature Biotechnology, vol. 14, No. 3, pp. 315-319.
Cull, et al. (Mar. 1, 1992) "Screening for Receptor Ligands Using Large Libraries of Peptides Linked to the C Terminus of the Lac Repressor", Proceedings of the National Academy of Sciences, vol. 89, No. 5, pp. 1865-1869.
Daley, et al. (Apr. 30, 2002) "Structure and Dynamics of a Beta-Helical Antifreeze Protein", Biochemistry, vol. 41, No. 17, pp. 5515-5525.
Daniel, et al. (May 1991) "Screening for Potassium Channel Modulators by a High Through-Put 86-Rubidium Efflux Assay in a 96-Well Microtiter Plate", Journal of Pharmacological Methods, vol. 25, Issue 3, pp. 185-193.
Danner, et al. (Nov. 6, 2001) "T7 Phage Display: A Novel Genetic Selection System for Cloning RNA-Binding Proteins From cDNA Libraries", Proceedings of the National Academy of Sciences of the United States of America, vol. 98, No. 23, pp. 12954-12959.
D'Aquino, et al. (Jun. 1996) "the Magnitude of the Backbone Conformational Entropy Change in Protein Folding", Proteins, vol. 25, Issue 2, pp. 143-156.
Darby et al., The incidence of factor VIII and factor IX inhibitors in the hemophilia population of the UK and their effect on subsequent mortality, 1977-99, J Thromb Haemost., 2004, 2(7): 1047-1054.
Database Geneseq [Online] (Sep. 8, 2020) "dTDP-4-dehydrorhamnose reductase [Entomomonas moraniae]", GenBank Accession No. AZS50750.1.

(56) References Cited

OTHER PUBLICATIONS

Dattani, et al. (1996) "An Investigation into the Lability of the Bioactivity of Human Growth Hormone Using the ESTA Bioassay", Hormone Research, vol. 46, No. 2, pp. 64-73.
Dauplais, et al. (Feb. 14, 1997) "on the Convergent Evolution of Animal Toxins", the Journal of Biological Chemistry, vol. 272, No. 7, pp. 4302-4309.
Davidson, M. W. (2009) "Engineered Fluorescent Proteins: Innovations and Applications", Nature Methods, vol. 6, No. 10, pp. 713-717.
De Boer, et al. (1983) "the Tac Promoter: A Functional Hybrid Derived from the Trp and Lac Promoters", Proceedings of the National Academy of Sciences, vol. 80, No. 1, pp. 21-25.
De Groot et al., Activation of natural regulatory T cells by IgG Fc-derived peptide "Tregitopes", Blood, 2008, 112: 3303-3311.
De Kruif, et al. (Apr. 21, 1995) "Selection and Application of Human Single Chain Fv Antibody Fragments from A Semi-Synthetic Phage Antibody Display Library with Designed CDR3 Regions", Journal of Molecular Biology, vol. 248, No. 1, pp. 97-105.
De, et al. (1994) "Crystal Structure of a Disulfide-Linked" Trefoil" Motif Found in a Large Family of Putative Growth Factors", Proceedings of the National Academy of Sciences, vol. 91, No. 3, pp. 1084-1088.
Decision to Grant Received for European Patent Application No. 10835255.0, mailed on Oct. 19, 2017, 3 Pages.
Decision to Grant Received for European Patent Application No. 17194648.6, mailed on Mar. 12, 2021, 3 Pages.
Deckert, et al. (2000) "Pharmacokinetics and Microdistribution of Polyethylene Glycol-Modified Humanized A33 Antibody Targeting Colon Cancer Xenografts", International Journal of Cancer, vol. 87, No. 3, pp. 382-390.
Delgado, et al. (1992) "The Uses and Properties of PEG-Linked Proteins", Critical Reviews in therapeutic Drug Carrier Systems, vol. 9, No. 3-4, pp. 249-304.
Delignat et al., "Immunoprotective effect of von Willebrand factor towards therapeutic factor VIII in experimental haemophilia A", Haemophilia, Mar. 2012, 18(2): 248-254.
Demers et al., "Efanesoctocog alfa elicits functional clot formation that is indistinguishable to that of recombinant factor VIII", Journal of Thrombosis and Haemostasis, Jul. 20, 2022,(7): 1674-1583.
Demers et al., "rFVIIIFc-VWF-XTEN (BIVV001) demonstrates comparable efficacy to recombinant human FVIII in mice by acute bleeding and intravital microscopy models", International Society on Thrombosis and Haemostasis (ISTH) Congress, Jul. 8-13, 2017, Berlin, Germany, 1 page.
Den Uijl et al., "Analysis of low frequency bleeding data: the association of joint bleeds according to baseline FVIII activity levels". Haemophilia, Jan. 2011, 17(1): 41-44.
Den Uijl et al., Clinical severity of hemophilia A: does the classification of the 1950s still stand?, Hemophilia, 17: 849-853.
Denoto, et al. (1981) "Human Growth Hormone DNA Sequence and mRNA Structure: Possible Alternative Splicing", Nucleic Acids Research, vol. 9, No. 15, pp. 3719-3730.
Der Maur, et al. (2002) "Direct in Vivo Screening of intrabody Libraries Constructed on A Highly Stable Single-Chain Framework", The Journal of Biological Chemistry, vol. 277, No. 47, pp. 45075-45085.
Desplancq, et al. (1994) "Multimerization Behaviour of Single Chain Fv Variants for the Tumour-Binding Antibody B72.3,", Protein Engineering, vol. 7, No. 8, pp. 1027-1033.
Dhalluin, et al. (2005) "Structural and Biophysical Characterization of the 40 kDa Peg-Interferon-a2a and Its Individual Positional Isomers", Bioconjugate Chemistry, vol. 16, No. 3, pp. 504-517.
Di Lullo, et al. (2002) "Mapping the Ligand-Binding Sites and Disease-associated Mutations on the Most Abundant Protein in the Human, Type I Collagen", the Journal of Biological Chemistry, vol. 277, No. 6, pp. 4223-4231.
Di Michele et al., "Severe and moderate haemophilia A and B in US females". Haemophilia, Feb. 2014, 20: 136-143.

Diaz-Collier, et al. (1994) "Refold and Characterization of Recombinant Tissue Factor Pathway Inhibitor Expressed in *Escherichia Coli*", Thrombosis and Haemostasis, vol. 71, No. 03, pp. 339-346.
Dietrich, et al. (2003) "ABC of Oral Bioavailability: Transporters as Gatekeepers in the Gut", Gut, vol. 52, No. 12, pp. 1788-1795.
Ding et al., Multivalent antiviral XTEN-peptide conjugates with long in vivo half-life and enhanced solubility, Bioconjugate Chem., 2014, 25: 1351-1359.
Dolezal, et al. (2000) "ScFv Multimers of the Anti-Neuraminidase Antibody Nc10: Shortening of the Linker in Single-Chain Fv Fragment assembled in V(L) to V(H) orientation Drives the formation of Dimers, Trimers, Tetramers and Higher Molecular Mass Multimers", Protein Engineering, vol. 13, No. 8, pp. 565-574.
Donath et al., "Characterization of des-(741-1668)-factor VIII. A single-chain factor VIII variant with a fusion site susceptible to proteolysis by thrombin and factor Xa", Biochem J., 1995, vol. 312, pp. 49-55.
Dooley, et al. (1998) "Stabilization of Antibody Fragments in Adverse Environments", Biotechnology and Applied Biochemistry, vol. 28, Part 1, pp. 77-83.
Doyle, et al. (1996) "Crystal Structures of a Complexed and Peptide-Free Membrane Protein-Binding Domain: Molecular Basis of Peptide Recognition by PDZ", Cell, vol. 85, No. 7, pp. 1067-1076.
Drager et al., "Paper: Recombinant FVIIIFc-VWF-XTEN Demonstrates Significant Bioavailability Following Subcutaneous Administration in Hemophilia A Mice", Blood, vol. 126, Issue 23, Dec. 7, 2015.
Duan et al., "Recombinant factor VIII Fc fusion protein engages monocytes via Fc and FVIII domains to reduce monocyte differentiation into osteoclasts", Frontier in Hematology, Nov. 3, 2022, 1-13.
Dufton, M. J. (1984) "Classification of Elapid Snake Neurotoxins and Cytotoxins According to Chain Length: Evolutionary Implications", Journal of Molecular Evolution, vol. 20, No. 2, pp. 128-134.
Dumont et al., Prolonged activity of a recombinant factor VIII-Fc fusion protein in hemophilia A mice and dogs, Blood, Mar. 29, 2012, 119(13): 3024-3030.
Dumont, et al., "Delivery of an Erythropoietin-Fc Fusion Protein by Inhalation in Humans Through an Immunoglobulin Transport Pathway", Journal of Aerosol Medicine, vol. 18, No. 3, pp. 294-303, Sep. 23, 2005.
Dumont, et al., "Factor VIII-Fc Fusion Protein Shows Extended Half-Life and Hemostatic Activity in Hemophilia A Dogs", Abstract 545, Blood, vol. 114, No. 22, 51st Annual Meeting of the American Society of Hematology, 1 Page, Nov. 20, 2009.
Dumont, Ja., "Monomeric Fc Fusions: Impact on Pharmacokinetic and Biological Activity of Protein Therapeutics", BioDrugs, vol. 20, No. 3, pp. 151-160, May 1, 2006.
Dumont, The Evolving Science of Fc Fusion Proteins for the Treatment of Hemophilia, 2nd Fc Receptor & IgG Targeted Therapies Summit, Apr. 27, 2022, Boston, MA.
Dumoulin, et al. (Mar. 2002) "Single-Domain Antibody Fragments with High Conformational Stability", Protein Science, vol. 11, No. 3, pp. 500-515.
Dutton, et al. (2002) "A New Level of Conotoxin Diversity, A Non-Native Disulfide Bond Connectivity in Alpha-Conotoxin AuIB Reduces Structural Definition But increases Biological Activity", The Journal of Biological Chemistry, vol. 277, No. 50, p. 48849-48857.
Dyson, et al. (2004) "Production of Soluble Mammalian Proteins in *Escherichia Coli*: Identification of Protein Features That Correlate with Successful Expression," BMC Biotechnology 4:32, American Society for Biochemistry and Molecular Biology, United States, BMC Biotechnology, vol. 4, No. 32.
Ellis, et al. (1994) "Valid and Invalid Implementations of GOR Secondary Structure Predictions", Computer Applications in Biosciences, vol. 10, No. 3, pp. 341-348.
Ellis, et al., "Treatment of Chronic Plaque Psoriasis by Selective Targeting of Memory Effector T Lymphocytes", The New England Journal of Medicine, vol. 345, No. 4, Massachusetts Medical Society, pp. 248-255, Jul. 26, 2001.

(56) References Cited

OTHER PUBLICATIONS

Eloctate United States Prescribing Information [USPI], Jan. 2017, Biogen Inc., The most recent version is available at: https://www.eloctate.com/pdfs/full-prescribing-information.pdf.
Engels, et al. (Jun. 1989) "Gene Synthesis", Angewandte Chemie International Edition, vol. 28, No. 6, pp. 716-734.
English language Abstract of European Patent Publication No. EP0295597 A2, European Patent office, Espacenet database-worldwide, Dec. 21, 1988.
European Medicines Agency (EMA), Committee for Medicinal Products for Human Use (CHMP), Guideline on the clinical investigation of recombinant and human plasma-derived factor VIII products, London, Jul. 21, 2011., EMA/CHMP/BPWP/144533/2009 rev. 1, Available from: http://www.ema.europa.eu/docs/en_GB/document_library/Scientificguideline/2011/08/WC500109692.pdf.
European Medicines Agency. Elocta (rFVIIIFc) Summary of Product Characteristics. https://www.ema.europa.eu/en/ documents/product-information/elocta-epar-product-information_ en.pdf. Published 2019. Accessed May 2020.
European Search Report and opinion for European Application No. 08795371, mailed on Jan. 27, 2011.
Extended European Search report received for European Application No. 13735649.9, mailed on Nov. 3, 2015.
Extended European Search Report received for European Application No. 13816031.2, mailed on May 20, 2016, 7 Pages.
Extended European Search Report received for European Application No. 19210390.1, mailed on May 27, 2020, 11 Pages.
Extended European Search report received for European Application No. 22181403.1, mailed on Mar. 31, 2023.
Extended European Search Report received for European Patent Application No. 06804210, mailed on Feb. 4, 2010.
Extended European Search Report received for European Patent Application No. 07752549.1, dated Mar. 5, 2009.
Extended European Search Report received for European Patent Application No. 07752636.6, mailed on Mar. 26, 2009.
Extended European Search Report received for European Patent Application No. 10835255.0, mailed on Jun. 20, 2013, 8 Pages.
Extended European Search Report received for European Patent Application No. 12868427.1, mailed on Jan. 29, 2016.
Extended European Search Report received for European Patent Application No. 14817900.5, mailed on Feb. 21, 2017.
Extended European Search Report received for European Patent Application No. 15735473.9, mailed on Jun. 26, 2017.
Extended European Search Report received for European Patent Application No. 17194648.6, mailed on Apr. 4, 2018, 6 Pages.
Extended European Search Report received for European Patent Application No. 18211179.9, mailed on Mar. 22, 2019.
Extended European Search Report received for European Patent Application No. 19165518.2, mailed on Oct. 7, 2019.
Extended European Search Report received for European Patent Application No. 23179872.9 mailed on Sep. 28, 2023.
Fajloun, et al. (2000) "Maurotoxin Versus Pi1/Hstx1 Scorpion Toxins", the Journal of Biological Chemistry, vol. 275, No. 50, American Society for Biochemistry and Molecular Biology, pp. 39394-39402.
Fang, et al. (2007) "the Protein Structure and Effect of Factor VIII", Thrombosis Research, vol. 119, No. 1, pp. 1-13.
Fares, F. A. (1992) "Design of a Long-Acting Follitropin Agonist by Fusing the C-Terminal Sequence of the Chorionic Gonadotropin Beta Subunit to the Follitropin Beta Subunit", Proceedings of the National Academy of Sciences, vol. 89, No. 10, pp. 4304-4308.
Fay, Philip J., "Factor VIII Structure and Function", International Journal of Hematology, vol. 83, No. 2, pp. 103-108, Feb. 1, 2006.
FDA, Bla Approval Letter ALTUVIIIO to Bioverativ Therapeutics, Inc., Feb. 22, 2023.
Felici, et al. (1991) "Selection of Antibody Ligands from a Large Library of Oligopeptides Expressed on a Multivalent Exposition Vector", Journal of Molecular Biology, vol. 222, No. 2, pp. 301-310.

Final Office Action Received for U.S. Appl. No. 13/513,424, mailed on Oct. 1, 2014, 17 Pages.
Fisher, et al. (2006) "Genetic Selection for Protein Solubility Enabled by the Folding Quality Control Feature of the Twin-Arginine Translocation Pathway", Protein Science, vol. 15, No. 3, pp. 449-458.
Fisher, et al., "Treatment of Septic Shock with the Tumor Necrosis Factor Receptor: Fc Fusion Protein", The New England Journal of Medicine, vol. 334, No. 26, Massachusetts Medical Society, United States, pp. 1697-1702, Jun. 27, 1996.
Fitzgerald, et al. (1995) "Interchangeability of Caenorhabditis Elegans DSL Proteins and Intrinsic Signalling Activity of their Extracellular Domains In Vivo", Development, vol. 121, No. 12, pp. 4275-4282.
Fraczkiewicz, et al. (1998) "Exact and Efficient Analytical Calculation of the Accessible Surface Areas and their Gradients for Macromolecules", Journal of Computational Chemistry, vol. 19, pp. 319-333.
Frampton, Efmoroctocog alfa: A Review in Haemophilia A. Drugs, 2016, Abstract, 76: 1281-1291.
Francis, G E. (1992) "Protein Modification and Fusion Proteins", Focus on Growth Factors, vol. 3, No. 2, Mediscript, England, pp. 4-10.
Franz, T. J. (1975) "Percutaneous Absorption on the Relevance of in Vitro Data", Journal of Investigative Dermatology, vol. 64, No. 3, pp. 190-195.
Fraternale et al., Polarization and Repolarization of Macrophages, J Clin Cell Immunol, 2015, 6(2): 1-10.
Frenal, et al. (2004) "Exploring Structural Features of the interaction Between the Scorpion toxincnerg1 and ERG K+ Channels", Proteins, vol. 56, No. 2, pp. 367-375.
Friend, et al. (Dec. 15, 1999) "Phase I Study of An Engineered Aglycosylated Humanized Cd3 Antibody in Renal Transplant Rejection1", Transplantation, vol. 68, Issue 11, pp. 1632-1637.
Fulcher, et al. (1985) "Localization of Human Factor FVIII Inhibitor Epitopes to Two Polypeptide Fragments", Proceedings of the National Academy of Sciences, vol. 82, No. 22, pp. 7728-7732.
Gamez, et al. (2005) "Development of Pegylated forms of Recombinant Rhodosporidium Toruloides Phenylalanine Ammonia-Lyase for the Treatment of Classical Phenylketonuria", The Journal of the American Society of Gene, Therapy 11, No. 6, pp. 986-989.
Garnier, et al. (1996) "GOR Method for Predicting Protein Secondary Structure from Amino Acid Sequence", Methods in Enzymology. vol. 266, Academic Press, pp. 540-553.
Geething, et al. (2010) "Gcg-XTEN: An Improved Glucagon Capable of Preventing Hypoglycemia without Increasing Baseline Blood Glucose", Plos One, vol. 5, No. 4, e10175 Page.
GenBank (Jun. 11, 2015) "Hypothetical Protein TRAVEDRAFT_138159", EIW63862.1, Trametes versicolor FP-10 1664 SS1. Available at URL: http://www.ncbi.nlm.nih.gov/protein/392570690?report=genbank&log$=protalign&bla st_rank=1&RID=3ERSOM7501R, 3 Pages.
Genbank Database (Jan. 14, 1995) "Transferrin Precursor [Homo sapiens]", Accession No. AAA61140.1, accessed at http://www.ncbi.nlm.nih.gov/protein/AAA61140.1, 1 Page.
GeneBank (2008) "Homo Sapiens Coagulation Factor VIII, Procoagulant Component (F8), Transcript Variant 1, mRNA", Accession No. NM_000132.3, accessed at http://www.ncbi.nlm.nih.gov/nuccore/NM_000132.3, 12 Pages.
George, et al. (2003) "An Analysis of Protein Domain Linkers: their Classification and Role in Protein Folding", Protein Engineering Design, vol. 15, No. 11, pp. 871-879.
Ghetie, et al., "Multiple Roles for The Major Histocompatibility Complex Class I-Related Receptor FcRn", Annual Review of Immunology, vol. 18, pp. 739-766., Jan. 1, 2000.
Giangrande et al., Clinical evaluation of glycoPEGylated recombinant FVIII: Efficacy and safety in severe haemophilia A., Thromb Haemost., Jan. 26, 2017,117(2): 252-261.
Gilkes, et al. (1991) "Domains in Microbial Beta-1, 4-Glycanases: Sequence Conservation, Function, and Enzyme Families", Microbiological Reviews, vol. 55, No. 2, pp. 303-315.

(56) References Cited

OTHER PUBLICATIONS

Gilles, et al. (1993) "Anti-Factor VIII Antibodies of Hemophiliac Patients Are Frequently Directed Towards Nonfunctional Determinants and Do Not Exhibit Isotypic Restriction", Blood, vol. 82, No. 8, pp. 2452-2461.
Gitschier, et al. (Nov. 22-28, 1984) "Characterization of the Human Factor VIII Gene", Nature, vol. 312, No. 5992, pp. 326-330.
Gleeson, et al. (1986) "Transformation of the Methylotrophic Yeast Hansenula Polymorpha", Microbiology. vol. 132, No. 12, pp. 3459-3465.
Goeddel, et al. (1980) "Synthesis of Human Fibroblast Interferon by *E. Coli*", Nucleic Acids Research, vol. 8, No. 18, pp. 4057-4074.
Goeddel, et al. (Oct. 18, 1979) "Direct Expression in *Escherichia Coli* of a DNA Sequence Coding for Human Growth Hormone", Nature, vol. 281, No. 5732, pp. 544-548.
Gomez-Duarte, et al. (1995) "Expression of Fragment C of Tetanus Toxin Fused to A Carboxyl-Terminal Fragment of Diphtheria toxin in Salmonella Typhi CVD 908 Vaccine Strain", Vaccine, vol. 13, No. 16, pp. 1596-1602.
Goudemand, et al. (Oct. 2005) "Pharmacokinetic Studies on Wilfactin®, a von Willebrand Factor Concentrate with a Low Factor VIII Content Treated with Three Virus-Inactivation/Removal Methods", Journal of Thrombosis and Haemostasis, vol. 3, No. 10, pp. 2219-2227.
Gouw et al., Treatment characteristics and the risk of inhibitor development: a multicenter cohort study among previously untreated patients with severe hemophilia A, J Thromb Haemost., 2007, 5(7): 1383-1390.
Gouw, et al. (Nov. 2009) "the Multifactorial Etiology of Inhibitor Development in Hemophilia: Genetics and Environment", Seminars in Thrombosis and Hemostasis, vol. 35, No. 8, pp. 723-734.
Graff, et al. (2003) "theoretical Analysis of Antibody Targeting of Tumor Spheroids: Importance of Dosage for Penetration, and Affinity for Retention", Cancer Research, vol. 63, No. 6, pp. 1288-1296.
Graham, et al. (Apr. 1, 1973) "a New Technique for the Assay of Infectivity of Human Adenovirus 5 DNA", Virology, vol. 52, No. 2, pp. 456-467.
Graham, et al. (Jul. 1, 1977) "Characteristics of a Human Cell Line Transformed by DNA From Human Adenovirus Type 5", Journal of General Virology, vol. 36, No. 1, pp. 59-72.
Graham, et al., "Canine Hemophilia: Observations on the Course, the Clotting Anomaly", and the Effect of Blood Transfusions, Journal of Experimental Medicine, vol. 90, No. 2, pp. 97-111, Aug. 1, 1949.
Graw et al., Haemophilia A: from mutation analysis to new therapies, Nat Rev Genet. 2005, 6(6): 488-501.
Gray, et al. (1988) "Peptide Toxins from Venomous Conus Snails", Annual Review of Biochemistry, vol. 57, pp. 665-700.
Greenwald, et al. (2003) "Effective Drug Delivery by PEGylated Drug Conjugates", Advanced Drug Delivery Reviews, vol. 55, No. 2, pp. 217-250.
Gringeri et al., A randomized clinical trial of prophylaxis in children with hemophilia A (the ESPRIT Study), J Thromb Haemost., 2011, 9(4): 700-710.
Gruppo, et al. (May 2003) "Comparative Effectiveness of Full-Length and B-Domain Deleted Factor VIII for Prophylaxis-a Meta-Analysis", Haemophilia, vol. 9, No. 3, pp. 251-260.
Guncar, et al. (1999) "Crystal Structure of MHC Class li-associated P41 li Fragment Bound to Cathepsin L Reveals the Structural Basis for Differentiation Between Cathepsins L and S", The EMBO Journal, vol. 18, No. 4, pp. 793-803.
Guo, et al. (2005) "Crystal Structure of the Cysteine-Rich Secretory Protein Stecrisp Reveals That the Cysteine-Rich Domain Has A K + Channel inhibitor-Like Fold", The Journal of Biological Chemistry, vol. 280, No. 13, pp. 12405-12412.
Gupta et al., Regulation of immune responses to protein therapeutics by transplacental induction of T cell tolerance, Sci Transl Med., 2015, 7(275): 275ra21.

Gupta, et al. (2004) "Classification of Disulfide Patterns and Its Relationship to Protein Structure and Function", Protein Science: A Publication of the Protein Society, vol. 13, No. 8, pp. 2045-2058.
Gustafsson, et al. (2004) "Codon Bias and Heterologous Protein Expression", Trends in Biotechnology, vol. 22, No. 7, pp. 346-353.
Haberichter et al., "Regulated Release of VWF and FVIII and the Biologic Implications", Pediatric Blood Cancer, May 2006, 46(5): 547-553.
Hacker et al., "Barriers to compliance with prophylaxis therapy in haemophilia", Haemophilia, 2001 7: 392-396.
Hamers-Casterman, et al. (Jun. 3, 1993) "Naturally Occurring Antibodies Devoid of Light Chains", Nature, vol. 363, No. 6428, pp. 446-448.
Hammer, J. (1995) "New Methods to Predict MHC-Binding Sequences within Protein Antigens", Current Opinion in Immunology, vol. 7, No. 2, pp. 263-269.
Harlow, et al. (1988) "Cell Staining", Cold Spring Harbor Laboratory, pp. 359-420.
Harris, et al. (2000) "Rapid and General Profiling of Protease Specificity by Using Combinatorial Fluorogenic Substrate Libraries", Proceedings of the National Academy of Sciences, vol. 97, No. 14, pp. 7754-7759.
Harris, et al. (2003) "Effect of Pegylation on Pharmaceuticals", Nature Reviews Drug Discovery, vol. 2, No. 3, pp. 214-221.
Hay et al. The principal results of the International Immune Tolerance Study: a randomized dose comparison. Blood. 2012:119(6):1335-1344.
Healey, et al. (Dec. 1, 1996) "The cDNA and Derived Amino Acid Sequence of Porcine Factor VIII", Blood, vol. 88, No. 11, pp. 4209-4214.
Hedner, et al. (1983) "Use of Human Factor Vlla in The Treatment of Two Hemophilia a Patients with High-Titer inhibitors", The Journal of Clinical Investigation vol. 71, No. 6, pp. 1836-1841.
Hedner, U. (2000) "NovoSeven® as a Universal Haemostatic Agent", Blood Coagulation & Fibrinolysis II, Supplement 1, pp. S107-S111.
Heinz et al. (Nov. 2009) "Factor VIII-eGFP Fusion Proteins with Preserved Functional Activity for the Analysis of the Early Secretory Pathway of Factor VIII", Thrombosis and Haemostasis, vol. 102, No. 5, pp. 925-935.
Hennighausen et al., "Mouse Whey Acidic Protein is A Novel Member of the Family of Four-Disulfide Core' Proteins", Nucleic Acids Research, Apr. 1982, vol. 10, No. 8, pp. 2677-2684.
Hermans et al. Recombinant factor VIII Fc for the treatment of haemophilia A. Eur J Haematot 2021;106(6):745-761.
Hermans et al., Pharmacokinetics in routine haemophilia clinical practice: rationale and modalities—a practical review, Therapeutic Advances in Hematology, 2020, 11: 1-15.
Hermeling, et al. (2004) "Structure-Immunogenicity Relationships of therapeutic Proteins", Pharmaceutical Research, vol. 21, No. 6, pp. 897-903.
Higgins, et al. (1995) "Characterization of Mutant forms of Recombinant Human Properdin Lacking NPL177 Single Thrombospondin Type I Repeats", Journal of Immunology, vol. 155, No. 12, pp. 5777-5785.
Higgins, et al. (1995) "Polyclonal and Clonal Analysis of Human Cd4+ T-Lymphocyte Responses to Nut Extracts", Immunology, vol. 84, No. 1, pp. 91-97.
Hill, et al. (2000) "Conotoxin Tviia, A Novel Peptide from the Venom of Conus Tulipa 1", European NPL178 Journal of Biochemistry/FEBS, vol. 267, No. 15, pp. 4642-4648.
Hinds, et al. (2005) "PEGylated insulin in PLGA Microparticles. in Vivo and in Vitro Analysis", Journal of Controlled Release, vol. 104, No. 3, pp. 447-460.
Hirel, et al. (1989) "Extent of N-Terminal Methionine Excision from Escherichia Coli Proteins is Governed by the Side-Chain Length of the Penultimate Amino Acid", Proceedings of the National Academy of Sciences of the United States of America, vol. 86, No. 21, pp. 8247-8251.
Hogg, P. J. (2003) "Disulfide Bonds as Switches for Protein Function", Trends in Biochemical Sciences, vol. 28, No. 4, pp. 210-214.

(56) References Cited

OTHER PUBLICATIONS

Holevinsky, et al. (1994) "ATP-Sensitive K+ Channel Opener Acts as A Potent Cl- Channel inhibitor in Vascular Smooth Muscle Cells", The Journal of Membrane Biology 137, No. 1, pp. 59-70.
Hopp, et al. (1981) "Prediction of Protein Antigenic Determinants from Amino Acid Sequences", Proceedings of the National Academy of Sciences, vol. 78, No. 6, pp. 3824-3828.
Horvais et al., "rFVIII-Fc in severe haemophilia A: The incentive switch in case of high risk of joint bleedings", Eur J Clin Invest., Oct. 2022, 52(10): e13824, 11 pages.
HSU, et al. (2000) "Vaccination Against Gonadotropin-Releasing Hormone (GnRH) Using toxin Receptor-Binding Domain-Conjugated GnRH Repeats", Cancer Research, vol. 60, No. 14, pp. 3701-3705.
Hubbard, et al. (May 2013) "Recommendations on The Potency Labelling of Factor VIII and Factor IX Concentrates.", Journal of thrombosis and Haemostasis, vol. 11, Issue 5, pp. 988-989.
Hudson, et al. (1999) "High Avidity ScFv Multimers; Diabodies and Triabodies", Journal of Immunological Methods, vol. 231, No. 1-2, pp. 177-189.
Hugli, T. E. (1990) "Structure and Function of C3A Anaphylatoxin", Current topics in Microbiology and Immunology, vol. 153, pp. 181-208. Hugli, T. E. (1990) "Structure and Function of C3A Anaphylatoxin", Current topics in Microbiology and Immunology, vol. 153, pp. 181-208.
Huston, et al. (Aug. 1988) "Protein Engineering of Antibody Binding Sites: Recovery of Specific Activity in an Anti-Digoxin Single-Chain Fv Analogue Produced in *Escherichia coli*", Proceedings of the National Academy of Sciences of the United States of America, vol. 85, No. 16, pp. 5879-5883.
Intention to Grant Received for European Patent Application No. 10835255.0, mailed on Jun. 8, 2017, 6 Pages.
Intention to Grant Received for European Patent Application No. 17194648.6, mailed on Oct. 28, 2020, 6 Pages.
International Search Report and Written Opinion received for PCT Patent Application No. PCT/US2006/037713, mailed on Jan. 17, 2008.
International Search Report and Written Opinion received for PCT Patent Application No. PCT/US2007/005857, mailed on Sep. 26, 2007.
International Search Report and Written Opinion received for PCT Patent Application No. PCT/US2007/005952, mailed on Dec. 26, 2007.
International Search Report and Written Opinion received for PCT Patent Application No. PCT/US2008/009787, mailed on Mar. 16, 2009.
International Search Report and Written Opinion received for PCT Patent Application No. PCT/US2010/002147, mailed on Dec. 20, 2010.
International Search Report and Written Opinion received for PCT Patent Application No. PCT/US2010/002148, mailed on Dec. 1, 2010.
International Search Report and Written Opinion received for PCT Patent Application No. PCT/US2010/023106, mailed on Apr. 20, 2010.
International Search Report and Written Opinion received for PCT Patent Application No. PCT/US2010/037855, mailed on Oct. 29, 2010.
International Search Report and Written Opinion received for PCT Patent Application No. PCT/US2010/059136, mailed on Jun. 2, 2011, 11 Pages.
International Search Report and Written Opinion received for PCT Patent Application No. PCT/US2010/061590, mailed on Jul. 12, 2011.
International Search Report and Written Opinion received for PCT Patent Application No. PCT/US2011/043568, mailed on Nov. 25, 2011.
International Search Report and Written Opinion received for PCT Patent Application No. PCT/US2011/048517, mailed on Mar. 14, 2012.
International Search Report and Written Opinion received for PCT Patent Application No. PCT/US2012/046326, mailed on Jan. 25, 2013.
International Search Report and Written Opinion received for PCT Patent Application No. PCT/US2013/021330, mailed on Apr. 29, 2013.
International Search Report and Written Opinion received for PCT Patent Application No. PCT/US2013/026521, mailed on Apr. 24, 2013.
International Search Report and Written Opinion received for PCT Patent Application No. PCT/US2013/049989, mailed on Dec. 16, 2013.
International Search Report and Written Opinion received for PCT Patent Application No. PCT/US2014/040370, mailed on Jan. 9, 2015.
International Search Report and Written Opinion received for PCT Patent Application No. PCT/US2014/044718, mailed on Nov. 4, 2014.
International Search Report and Written Opinion received for PCT Patent Application No. PCT/US2014/044731, mailed on Nov. 4, 2014.
International Search Report and Written Opinion received for PCT Patent Application No. PCT/US2014/051144, mailed on Feb. 10, 2015.
International Search Report and Written Opinion received for PCT Patent Application No. PCT/US2015/010738, mailed on May 15, 2015.
International Search Report and Written Opinion received for PCT Patent Application No. PCT/US2019/032956 mailed Oct. 4, 2019.
International Search Report and Written Opinion received for PCT Patent Application No. PCT/US2021/037926, mailed on Nov. 9, 2021.
Irani et al., Molecular properties of human IgG subclasses and their implications for designing therapeutic monoclonal antibodies against infectious diseases, Mol Immunol., 2015, 67: 171-182.
Israel, et al. (Sep. 1997) "Expression of the Neonatal Fc Receptor, FcRn, on Human Intestinal Epithelial Cells", Immunology, vol. 92, No. 1, pp. 69-74.
Iwasaki, et al. (1997) "Solution Structure of Midkine, a New Heparin-Binding Growth Factor", the EMBO Journal, vol. 16, No. 23, pp. 6936-6946.
Jackson, et al. (2007) "The Characterization of Paclitaxel-Loaded Micro Spheres Manufactured from Blends of Poly (Lactic-Co-Glycolic Acid) (PLGA) and Low Molecular Weight Diblock Copolymers", International Journal of Pharmaceutics, vol. 342, No. 1-2, pp. 6-17.
Jacquemin, et al. (2000) "A Human Antibody Directed to The Factor VIII C1 Domain inhibits Factor VIII Cofactor Activity and Binding to Von Willebrand Factor", Blood, vol. 95, No. 1, pp. 156-163.
Janbain M, Pipe S. What is the role of an extended half-life product in immune tolerance induction in a patient with severe hemophilia A and high-titer inhibitors? Hematology Am Soc Hematol Educ Program. 2016;2016(1):648-649.
Jazayeri et al., Half-Life Extension by Fusion to the Fc Region, Therapeutic Proteins: Strategies to Modulate Their Plasma Half-Live, Wiley-VCH Verlag Gmbh & Co., KGaA, 2012, pp. 157-188.
Jenkins et al., Elevated factor VIII levels and risk of venous thrombosis, Brit J Haematology. 2012, 157: 653-663.
Jimenez-Yuste et al., Achieving and maintaining an optimal trough level for prophylaxis in haemophilia: the past, the present and the future, Blood Transfus., 2014, 12: 314-319.
JIVI [package insert], Whippany, NJ: Bayer HealthCare LLC, 2018.
Johansson, et al. (2007) "Modifications Increasing the Efficacy of Recombinant Vaccines; Marked Increase in Antibody Titers with Moderately Repetitive Variants of a Therapeutic Allergy Vaccine", Vaccine, vol. 25, No. 9, pp. 1676-1682.
Jonassen, et al. (1995) "Finding Flexible Patterns in Unaligned Protein Sequences", Protein Science, vol. 4, No. 8, pp. 1587-1595.
Jones, et al. (1997) "Determination of Tumor Necrosis Factor Binding Protein Disulfide Structure: Deviation of the Fourth Domain Structure from the TNFR/NGFR Family Cysteine-Rich Region Signature", Biochemistry, vol. 36, No. 48, pp. 14914-14923.

(56) References Cited

OTHER PUBLICATIONS

Jones, et al. (May 29, 1986) "Replacing the Complementarity-Determining Regions in a Human Antibody with Those from a Mouse", Nature, vol. 321, No. 6069, pp. 522-525.
Jonsson, et al. (1993) "Quantitative Sequence-Activity Models (QSAM)—Tools for Sequence Design", Nucleic Acids Research, vol. 21, No. 3, pp. 733-739.
Joosten, et al. (2011) "A Series of PDB Related Databases for Everyday Needs", Nucleic Acids D Research, vol. 39, pp. D411-D419.
Jung, et al. (1997) "Improving In Vivo Folding and Stability of a Single-Chain Fv Antibody Fragment by Loop Grafting", Protein Engineering, vol. 10, No. 8, pp. 959-966.
Kabsch, et al. (1983) "Dictionary of Protein Secondary Structure: Pattern Recognition of Hydrogen-Bonded and Geometrical Features", Biopolymers, vol. 22, No. 12, pp. 2577-2637.
Kamal (Jul. 2007) "How to Interpret and Pursue an Abnormal Prothrombin Time, Activated Partial Thromboplastin Time, and Bleeding Time in Adults", Mayo Clinic Proceedings, vol. 87, No. 7, pp. 863-874.
Kamikubo, et al. (2004) "Disulfide Bonding Arrangements in Active forms of the Somatomedin B Domain of Human Vitronectin", Biochemistry, vol. 43, No. 21, pp. 6519-6534.
Kasper, Ck, et al. (Nov. 15, 1975) "Proceedings: A More Uniform Measurement of Factor VIII Inhibitors", Thrombosis et diathesis haemorrhagica, vol. 34, No. 2, 612 Page.
Katragadda et al., "Population pharmacokinetic (PK) analysis of bivv001 (rFVIIIFc-VWF-xten), a new class of factor VIII (FVIII) replacement", Research and Practice in Thrombosis and Haemostasis, Jul. 2020, 4(Suppl 1): 474.
Kaufman, et al. (1982) "Amplification and Expression of Sequences Cotransfected with a Modular Dihydrofolate Reductase Complementary DNA Gene", Journal of Molecular Biology, vol. 159, No. 4, pp. 601-621.
Kaufman, et al. (1982) "Construction of a Modular Dihydrofolate Reductase cDNA Gene: Analysis of Signals Utilized for Efficient Expression", Molecular and Cellular Biology, vol. 2, No. 11, pp. 1304-1319.
Kavakli et al., Prophylaxis vs. on-demand treatment with BAY 81-8973, a full-length plasma protein-free recombinant factor VIII product: results from a randomized trial (Leopold II), J Thromb Haemost., Mar. 13, 2015, 13(3): 360-369.
Kay, et al. (1993) "An M13 Phage Library Displaying Random 38-Amino-Acid Peptides as a Source of Novel Sequences with Affinity to Selected Targets", Gene, vol. 128, No. 1, pp. 59-65.
Kazatchkine, et al. (1980) "Circulating Immune Complexes Containing Anti-VIII Antibodies in Multi-Transfused Patients with Haemophilia A", American Journal of Clinical and Experimental Immunology, vol. 39, No. 2, pp. 315-320.
Kelly, et al. (2003) "Isolation of a Colon Tumor Specific Binding Peptide Using Phage Display Selection", Neoplasia, vol. 5, No. 5, pp. 437-444.
Kemball-Cook, et al. (1998) "the factor VIII Structure and Mutation Resource Site: HAMSTERS Version 4", Nucleic Acids Research, vol. 26, No. 1, pp. 216-219.
Khan, et al. (1998) "Solubilization of Recombinant Ovine Growth Hormone with Retention of Native-Like Secondary Structure and Its Refolding from the Inclusion Bodies of *Escherichia Coli*", Biotechnology Progress, vol. 14, No. 5, pp. 722-728.
Kim, et al. (1995) "Three-Dimensional Solution Structure of the Calcium Channel Antagonist Omega-Agatoxin Iva: Consensus Molecular Folding of Calcium Channel Blockers", Journal of Molecular Biology, vol. 250, No. 5, pp. 659-671.
Kimble, et al. (1997) "the Lin-12/Notch Signaling Pathway and Its Regulation", Annual Review of Cell and Developmental Biology, pp. 333-361.
Kingdon et al., An adventure in biotechnology: the development of haemophilia A therapeutics from whole blood transfusion to recombinant DNA to gene therapy, Biotechnol Appl Biochem., 2002, 35(Pt 2): 141-148.
Kisiel, et al. (1983) "Enzymological Aspects of Blood Coagulation", Behring Institute Mitteilungen, vol. 73, pp. 29-42.
Kissel, et al. (2002) "Aba-Triblock Copolymers from Biodegradable Polyester A-Blocks and Hydrophilic Poly (Ethylene Oxide) B-Blocks as a Candidate for In Situ forming Hydrogel Delivery Systems for Proteins", Advanced Drug Delivery Reviews, vol. 54, No. 1, pp. 99-134.
Kis-Toth et al. Recombinant factor VIII Fc fusion protein drives regulatory macrophage polarization. Blood Adv. 2018;2(21):2904-2916.
Kis-Toth, et al., Recombinant Factor Viii Fc Fusion Protein Exhibits Immunomodulatory Effects On Antigen-Presenting Cells, 9th BIC Int'l Conference Presentation, 2017.
Klamroth al., Results from a phase 3, randomize, multicenter study of rurioctocog alfa pegol PK-guided prophylaxis targeting 2 FVIII trough levels in patients with severe hemophilia A (propel study), Poster P255 presented at: European Association for Haemophilia and Allied Disorders (EAHAD), Feb. 6-9, 2019, Prague, Czech Republic.
Klamroth et al., "Perioperative Management with Efanesoctocog Alfa in Patients with Hemophilia A in the Phase 3 XTEND-1 Study", Abstract, Haemophilia, 87-88.
Klamroth et al., "Perioperative Management with Efanesoctocog Alfa in Patients with Hemophilia A in the Phase 3 XTEND-1 Study", Poster, 16th Annual Congress of the European Association for Haemophilia and Allied Disorders, Feb. 7-10, 2023.
Klitgaard, et al. (2008) "Overview of the Human Pharmacokinetics of Recombinant Activated Factor VII", British Journal of Clinical Pharmacology, vol. 65, No. 1, pp. 3-11.
Knobe et al., "Haemophilia and Joint Disease: Pathophysiology, Evaluation, and Management," Journal of Comorbidity, Dec. 27, 2011, vol. 1, pp. 51-59.
Kochendoerfer, G. "Chemical and Biological Properties of Polymer-Modified Proteins", Expert Opinion on Biological therapy, vol. 3, No. 8, pp. 1253-1261.
KOGENATE [package insert], Whippany, NJ: Bayer HealthCare LLC, 2016.
Kohn, et al. (2004) "Random-Coil Behavior and the Dimensions of Chemically Unfolded Proteins", Proceedings of the National Academy of Sciences, vol. 101, No. 34, p. 12491-14296.
Koide, et al. (1998) "the Fibronectin Type III Domain as a Scaffold for Novel Binding Proteins", Journal of Molecular Biology, vol. 284, No. 4, pp. 1141-1151.
Konig, et al. (Sep. 1, 1998) "Use of an Albumin-Binding Domain for the Selective Immobilisation of Recombinant Capture Antibody Fragments on ELISA Plates", Journal of Immunological Methods, vol. 218, No. 1-2, pp. 73-83.
Konigs C, et al. Final results of PUPs A-LONG study: evaluating safety and efficacy of rFVIIIFc in previously untreated patients with haemophilia A. Res Pract Thromb Haemost. 2020;4 S1:8 (Abstract OC 03.02).
Konigs C, et al. Final Results of ReITIrate—A Prospective Study of Rescue Immune Tolerance Induction (ITI) with Recombinant Factor VIII Fc (rFVIIIFc) in Patients Who Have Failed Previous ITI Attempts. Poster PB0522 presented at the International Society on Thrombosis and Haemostasis (ISTH) 2021 Virtual Congress, Jul. 17-21, 2021, Philadelphia, Pa, USA.
Konigs et al., "First study of extended half-life rFVIIIFc in previously untreated patients with hemophilia A: PUPs A-LONG final results", Blood, Jun. 30, 2022, 139(26): 3699-3707.
Konkle et al. "BIVV001 Fusion Protein as Factor VIII Replacement Therapy for Hemophilia A", NEJM, 2020, 383: 1018-1027.
Konkle et al., "BIVV001: The First Investigational Factor VIII Therapy to Break Through the VWF Ceiling in Hemophilia A, with Potential for Extended Protection for One Week or Longer", Blood, Amer Soc of Hematology US, Nov. 29, 2018, 132: 636.
Konkle et al., "Pegylated, full-length, recombinant factor VIII for prophylactic and on-demand treatment of severe hemophilia A", Blood, Aug. 2015, 126(9): 1078- 1085.
Korea Hemophilia Foundation, Posting dated Apr. 22, 2013 (no English translation available).

(56) References Cited

OTHER PUBLICATIONS

Kornblatt, et al. (1980) "Cross-Linking of Cytochrome Oxidase Subunits with Difluorodinitrobenzene", Canadian Journal of Biochemistry, vol. 58, No. 3, pp. 219-224.

Kortt, et al. (1997) "Single-Chain Fv Fragments of Anti-Neuraminidase Antibody Nc10 Containing Five—and Ten-Residue Linkers Form Dimers and with Zero- Residue Linker a Trimer", Protein Engineering, vol. 10, No. 4, pp. 423-433.

Kou, et al. (2007) "Preparation and Characterization of Recombinant Protein ScFv(Cd11C)-Trp2 for Tumor therapy from inclusion Bodies in *Escherichia Coli*", Protein Expression and Purification, vol. 52, No. 1, pp. 131-138.

Kratzner, et al. (2005) "Structure of Ecballium Elaterium Trypsin inhibitor li (EETI-li): A Rigid Molecular Scaffold", Acta Crystallographica, vol. 61, Part 9, pp. 1255-1262.

Krishnamoorthy et al., Recombinant factor VIII Fc (rFVIIIFc) fusion protein reduces immunogenicity and induces tolerance in hemophilia A mice, Cell Immunol., 2016, 301: 30-39.

Krishnan et al., "Thrombin cleavage analysis of a novel antihaemophilic factor variant, factor VIII ΔIII", Eur. J. Biochem. Vol. 195, 1991, pp. 637-644.

Kristensen, et al. (1998) "Proteolytic Selection for Protein Folding Using Filamentous Bacteriophages", Folding & Design, vol. 3, No. 5, pp. 321-328.

Kronek et al., Biocompatibility and Immunocompatibility Assessment of Poly(2-Oxazolines), in Andrade et al. eds Practical Applications in Biomedical Engineering 2013.

Kubetzko, et al. (Nov. 1, 2005) "Protein PEGylation Decreases Observed Target Association Rates Via A Dual Blocking Mechanism", Molecular Pharmacology vol. 68, No. 5, The American Society for Pharmacology and Experimental Therapeutics, United States, pp. 1439-1454.

Kulkarni et al. Improved hemostasis and joint health over time in a subset of patients who did not reach optimal hemostatic control in the first year of recombinant factor VIII Fc fusion protein (rFVIIIFc) therapy. Research and Practice in Thrombosis and Haemostasis. 2019;3(S1):262.

Kulkarni et al., "Clinical Development of Efanesoctocog Alfa (BIV001), A New Class of Factor Viii (FVIII) Replacement Therapy Designed to Provide High Sustained Factor Activity", Abstract, THSNA 2022 Summit Abstract Proceedings, American Journal of Hematology, E601-E61.

Kulkarni et al., "Clinical Development of Efanesoctocog Alfa (BIV001), A New Class of Factor VIII (FVIII) Replacement Therapy Designed to Provide High Sustained Factor Activity", Poster, THSNA 2022 Summit of North America, Aug. 16-18, 2022.

Kulman, et al. (2007) "A Versatile System for Site-Specific Enzymatic Biotinylation and Regulated Expression of Proteins in Cultured Mammalian Cells", Protein Expression and Purification, vol. 52, No. 2, pp. 320-328.

Kwon, et al. (Feb. 2004) "Biodegradable Triblock Copolymer Microspheres Based on thermosensitive Sol-Gel Transition", Pharmaceutical Research, vol. 21, Issue 2, pp. 339-343.

Lacroix-Desmazes et al., Fc-fusion technology beyond half-life extension—review of potential immunomodulatory and anti-inflammatory effects of rFVIIIFc in haemophilia A, Wfh 2022 World Congress, Montreal and virtual, May 8-11, 2022.

Lambert et al., "Practical aspects of extended half-life products for the treatment of haemophilia", Therapeutic Advances in Hematology, 2018; 295-308.

Lane, et al. (Jan. 3, 2006) "Influence of Post-Emulsification Drying Processes on the Microencapsulation of Human Serum Albumin", International Journal of Pharmaceutics, vol. 307, No. 1, pp. 16-22.

Lapatto, et al. "X-ray Structure of Antistasin at 1.9 Å Resolution and Its Modelled Complex with Blood Coagulation Factor Xa", the EMBO Journal, Sep. 1997, vol. 16, No. 17, Wiley Blackwell, England, pp. 5151-5161.

Lauber, et al. (Apr. 18, 2003) "Homologous Proteins with Different Folds: The Three-Dimensional Structures of Domains 1 and 6 of the Multiple Kazal-Type inhibitor LEKTI", Journal of Molecular Biology, vol. 328, No. 1, pp. 205-219.

Lavigne-Lissalde, et al. (Oct. 2009) "Characteristics, mechanisms of action, and epitope mapping of anti-factor VIII antibodies", Clinical Reviews in Allergy & Immunology, vol. 37, No. 2, pp. 67-79.

Le Gall, et al. (Jun. 1999) "Di-, Tri- and Tetrameric Single Chain Fv Antibody Fragments Against Human Cd19: Effect of Valency on Cell Binding", FEBS letters, vol. 453, No. 1-2, pp. 164-168.

Lee et al. A crucial role for reactive oxygen species in RANKL-induced osteoclast differentiation. Blood. 2005;106(3):852-859.

Lee et al., Utilization patterns of coagulation factor consumption for patients with hemophilia, J Korean Med Sci., 2010, 31(1): 33-38.

Lee, et al. (Aug. 31, 2001) "Disorders of Coagulation", Pediatric Hematology Secrets, Weiner M.A. and Cario, M.S., eds., Hanley & Belfus, United States, pp. 47-52.

Lee, et al. (Dec. 1999) "Pharmacokinetics of Recombinant Factor VIII (Recombinate) Using One-Stage Clotting and Chromogenic Factor VIII Assay", Journal of Thrombosis and Haemostasis, vol. 82, No. 6, pp. 1644-1647.

Lee, et al. "A recombinant human G-CSF/GM-CSF fusion protein from E. coli showing colony stimulating activity on human bone marrow cells", Biotechnology Letters, Feb. 2003, vol. 25, No. 3, pp. 205-211.

Lee, Vincent H. (2001) "Mucosal Drug Delivery", Journal of the National Cancer Institute Monographs, vol. 29, pp. 41-44.

Lehtinen et al., "Surgical outcomes in patients with haemophilia A or B receiving extended half-life recombinant factor VIII and IX Fc fusion proteins: Real-world eperience in the Nordic countries", Haemophilia, Sep. 2022, 28(5): 713-719.

Lei et al., Induction of tolerance to factor VIII inhibitors by gene therapy with immunodominant A2 and C2 domains presented by B cells as Ig fusion proteins, Blood, 2005, 105(12): 4865-4670.

Lenting et al., Von Willebrand factor interaction with FVIII: development of long-acting FVIII therapies, Blood, 2016, 128: SCI-8.

Lenting, et al. (Aug. 20, 1999) "the light chain of factor VIII comprises a binding site for low density lipoprotein receptor-related protein", the Journal of Biological Chemistry, vol. 274, No. 34, p. 23734-23739.

Lenting, et al. (Dec. 1, 1998) "the Life Cycle of Coagulation Factor VIII in View of its Structure and Function", Blood, vol. 92, No. 11, pp. 3983-3996.

Lenting, et al. (Jul. 2007) "Clearance Mechanisms of von Willebrand Factor and Factor VIII", Journal of Thrombosis and Haemostasis, vol. 5, No. 7, pp. 1353-1360.

Lentz et al., Results from a large multinational clinical trial (guardian 1) using prophylactic treatment with turocotocog alfa in adolescent and adult patients with severe haemophilia A: safety and efficacy., Haeomophilia. 2013, 691-697.

Leong, et al. (Feb. 4, 2003) "Optimized Expression and Specific Activity of 11-12 by Directed Molecular Evolution", Proceedings of the National Academy of Sciences of the United States of America, vol. 100, No. 3, pp. 1163-1168.

Leong, et al. (Nov. 2001) "Adapting Pharmacokinetic Properties of a Humanized Anti-Interleukin-8 Antibody for therapeutic Applications Using Site- Specific Pegylation", Cytokine, vol. 16, Issue 3, pp. 106-119.

Lethagen, et al. (Nov. 1986) "Clinical Application of the Chromogenic Assay of Factor VIII in Haemophilia A, and Different Variants of von Willebrand's Disease", Scandinavian Journal of Haematology, vol. 37, No. 5, pp. 448-453.

Leung, et al. (1989) "A Method for Random Mutagenesis of a Defined DNA Segment Using a modified Polymerase Chain Reaction", Technique, vol. 1, pp. 11-15.

Leung-Hagesteijn, et al. (1992) "Unc-5, A Transmembrane Protein with Immunoglobulin and Thrombospondin Type 1 Domains, Guides Cell and Pioneer Axon Migrations in C", Cell, vol. 71, No. 2, pp. 289-299.

Levitt, et al. (1976) "A Simplified Representation of Protein Conformations for Rapid Simulation of Protein Folding", Journal of Molecular Biology, vol. 104, No. 1, pp. 59-107.

(56) References Cited

OTHER PUBLICATIONS

Levy, et al. (2007) "Isolation of Trans-Acting Genes That Enhance Soluble Expression of ScFv Antibodies in the E", Journal of Immunological Methods, vol. 321, No. 1-2, pp. 164-173.
Leyte et al., "Sulfation of Tyr$^{1680}$of Human Blood Coagulation Factor VII Is Essential for the Interaction of Factor with von Willebrand Factor*", The Journal of Biological Chemistry, Jan. 15, 1991, vol. 266, No. 2, pp. 740-746.
Leyte, et al. (1989) "The Interaction Between Human Blood-Coagulation Factor VIII and Von Willebrand Factor: Characterization of a High-Affinity Binding Site on Factor VIII", Biochemical, Journal 257, No. 3, pp. 679-683.
Li, et al. (1997) "The Physical Exchange of Factor VIII (FVIII) between von Willebrand Factor and Activated Platelets and the Effect of the FVIII B-Domain on Platelet Binding", Biochemistry, vol. 36, pp. 10760-10767.
Lillicrap, D. (2008) "Extending Half-Life in Coagulation Factors: Where Do We Stand?", Thrombosis Research, vol. 122, Supplement 4, pp. S2-S8.
Lin, et al. (2007) "Metal-Chelating Affinity Hydrogels for Sustained Protein Release", Journal of Biomedical Materials Research, Part A, vol. 83, No. 4, pp. 954-964.
Lippi, et al. (2007) "Diagnostic Approach to Inherited Bleeding Disorders", Clinical Chemistry and Laboratory Medicine, vol. 45, No. 1, pp. 2-12.
Lirazan, et al. (2000) "the Spasmodic Peptide Defines a New Conotoxin Superfamily", Biochemistry, vol. 39, No. 7, pp. 1583-1588.
Lissitchkov et al., "A Phase 1 Sequential Pharmacokinetic (PK) Evaluation of Octocog Alfa, Rurioctocog Alfa Pegol, ad Efanesoctocog Alfa in Severe Hemophilia A", Abstract, Haemophilia, 107-108, NHF 2022 Congress: Aug. 25-27, 2022.
Lissitchkov et al., "A Phase 1 Sequential Pharmacokinetic (PK) Evaluation of Octocog Alfa, Rurioctocog Alfa Pegol, ad Efanesoctocog Alfa in Severe Hemophilia A", Presentation slides, World Federation of Hemophilia, NHF 2022 Congress: Aug. 25-27, 2022.
Lissitchkov et al., "A Phase 1 Sequential Pharmacokinetic (PK) Evaluation of Octocog Alfa, Rurioctocog Alfa Pegol, and Efanesoctocog Alfa in Severe Hemophilia A", Efanesoctocog alfa Phase 1 PK Abstract—Encore, NHF 2022 Congress: Aug. 25-27, 2022.
Lissitchkov et al., "A Phase 1 Sequential Pharmacokinetic (PK) Evaluation of Octocog Alfa, Rurioctocog Alfa Pegol, and Efanesoctocog Alfa in Severe Hemophilia A", Poster, Blood 2022 Congress: Sep. 11-14, 2022, Sydney.
Lissitchkov et al., "A Phase 1 Sequential Pharmacokinetic (PK) Evaluation of Octocog Alfa, Rurioctocog Alfa Pegol, and Efanesoctocog Alfa in Severe Hemophilia A", Poster, NHF 74th Annual Bleeding Disorders Conference (BDC) 2022, Aug. 25-27, 2022.
Lissitchkov et al., "Efanesoctocog alfa for hemophilia A: results from a phase 1 repeat-dose study", Blood Advances, Feb. 11, 2022, 6(4): 1089-1094.
Lissitchkov et al., "Efanesoctocog alfa Phase 1 PK" Abstract Encore, Blood 2022 Congress: Sep. 11-14, 2022, Sydney.
Lissitchkov et al., "Phase 1 Repeat Dosing with BIVV001: The First Investigational Factor VIII Product to Break through the Von Willebrand Factor-Imposed Half-Life Ceiling", Blood, Amer Soc of Hematology US, Nov. 13, 2019, 134: 625.
Liu et al., "Evaluation of Antibody Responses to rFVIIIFc compared to Xyntha® and Advate® in Hemophilia A Mice", Haemophilia, 2012, vol. 18, Suppl. 3.
Liu, et al. (1997) "the Human Beta-Defensin-1 and Alpha-Defensins are Encoded by Adjacent Genes: Two Peptide Families with Differing Disulfide Topology Share a Common Ancestry", Genomics, vol. 43, No. 3, pp. 316-320.
Liu, et al. (2007) "Evaluation of PEG-FVIII Molecules with Prolonged Half-lives in a Murine FVIII Dependent Bleeding Model", Journal of Thrombosis and Haemostasis, vol. 9, Suppl. 2: P-M-035, Isth Meeting, Abstract: Factor VIII, Factor V, Exhibition Area, International Society on Thrombosis and Haemostasis, United States, 1 page.
Liu, et al. (2011) "Recombinant FVIII Fe Fusion Protein Is Fully Active in Treating Acute Injury and Demonstrates Prolonged Prophylactic Efficacy in Hemophilia a Mice", Journal of Thrombosis and Haemostasis vol. 9, Suppl. 2: P-WE-131, ISTH Meeting, International Society on Thrombosis and Haemostasis, United States.
Lobet et al., "Optimal Management of Hemophilic Arthropathy and Hematomas," Journal of Blood Medicine, 2014, No. 5, pp. 207-218.
Logan, et al. (Jun. 1984) "Adenovirus Tripartite Leader Sequence Enhances Translation of mRNAs Late After Infection", Proceedings of the National Academy of Sciences, vol. 81, No. 12, pp. 3655-3659.
Lollar, et al. (Jun. 1994) "Inhibition of Human Factor Villa by Anti-A2 Subunit Antibodies", the Journal of Clinical Investigation, vol. 93, No. 6, pp. 2497-2504.
Lollar, et al., "Coagulant Properties of Hybrid Human/Porcine Factor VIII Molecules", Journal of Biological Chemistry, vol. 267, pp. 23652-23657, Nov. 25, 1992.
Lollar, et al., "Structural Basis for The Deceased Procoagulant Activity of Human Factor VIII Compared to The Porcine Homolog", Journal of Biological Chemistry, vol. 266, No., pp. 12481-12486, Jul. 5, 1991.
London, et al. (Jul. 20, 2000) "Zymogen Factor IX Potentiates Factor IXa- Catalyzed Factor X Activation", Biochemistry, vol. 39, No. 32, pp. 9850-9858.
Low, et al., "Oral and Pulmonary Delivery of FSH-Fc Fusion Proteins via Neonatal Fc Receptor-Mediated Transcytosis", Human Reproduction, vol. 20, No. 7, Oxford University Press, pp. 1805-1813, Jul. 1, 2005.
Lowman, et al. (Nov. 12, 1991) "Selecting High-Affinity Binding Proteins by Monovalent Phage Display", Biochemistry, vol. 30, No. 45, p. 10832- 10838.
Loyter, et al. (Jan. 1982) "Mechanisms of DNA Uptake by Mammalian Cells: Fate of Exogenously Added DNA Monitored by the Use of Fluorescent Dyes", Proceedings of the National Academy of Sciences, vol. 79, No. 2, pp. 422-426.
Lozier, et al. (2002) "the Chapel Hill Hemophilia a Dog Colony Exhibits a Factor VIII Gene Inversion", Proceedings of the National Academy of Sciences USA, vol. 99, No. 20, pp. 12991-12996.
Lusher, Hemophilia: From plasma to recombinant factors, 2008, In: 50 Years in Hematology Research That Revolutionized Patient Care. Washington, DC: American Society of Hematology, pp. 25-27. Available from: http://www.hematology.org/Publications/50 Years in Hematology/4323.aspx.
Mackett, et al. (Dec. 1982) "Vaccinia Virus: A Selectable Eukaryotic Cloning and Expression Vector", Proceedings of the National Academy of Sciences of the United States of America, vol. 79, No. 23, pp. 7415-7419.
Mackett, et al. (Mar. 1984) "General Method for Production and Selection of Infectious Vaccinia Virus Recombinants Expressing Foreign Genes", Journal of Virology, vol. 49, No. 3, pp. 857-864.
Maggio (2006) "A Renaissance in Peptide therapeutics is Underway", Drug Delivery Reports, pp. 23-26.
Maggio, Edward (Jul. 2006) "Intravail: Highly Effective Intranasal Delivery of Peptide and Protein Drugs", Expert Opinion on Drug Delivery, vol. 3, No. 4, pp. 529-539.
Mahlangu et al., Efficacy and safety of rVIII-SingleChain: results of a phase 1/3 multicenter clinical trial in severe hemophilia A, Blood, Aug. 2016, 128(5): 630-637.
Mahlangu et al., Emicizumab Prophylaxis in Patients Who Have Hemophilia A without Inhibitors, The New England Journal of Medicine, 2018, 811-822.
Maillere (Jun. 15, 1993) "Role of Thiols in the Presentation of a Snake Toxin to Murine T Cells", Journal of Immunology, vol. 150, No. 12, pp. 5270-5280.
Maillere, et al. (Apr. 1995) "Immunogenicity of a Disulphide-Containing Neurotoxin: Presentation to T-Cells Requires a Reduction Step", Toxicon, vol. 33, No. 4, pp. 475-482.
Mair et al., Thinking about the burden of treatment, BMJ, 2014, 349.
Malardier, et al. (May 15, 1989) "Cloning of the Nitrate Reductase Gene (niaD) of Aspergillus Nidulans and its Use for Transformation of Fusarium Oxysporum", Gene, vol. 78, No. 1, pp. 147-156.

(56) References Cited

OTHER PUBLICATIONS

Malec L, et al. LBA-5 Efficacy of rFVIIIFc for first-time immune tolerance induction (ITI) therapy: Final results from the Global, Prospective VerITI-8 Study. Presented at ASH 2021.
Manco-Johnson et al., Prophylaxis usage, bleeding rates, and joint outcomes of hemophilia, 1999 to 2010: a surveillance project, Blood, 2017, 2368-2374.
Manco-Johnson et al., Prophylaxis versus episodic treatment to prevent joint disease in boys with severe hemophilia, N Engl J Med., 2007, 357(6): 535-544.
Manco-Johnson, M., "Comparing Prophylaxis with Episodic Treatment in Haemophilia A: Implications for Clinical Practice", Haemophilia., vol. 13, Supplement 2, Blackwell Publishing Ltd., England, pp. 4-9, Sep. 1, 2007.
Manco-Johson et al., Randomized, controlled, parallel-group trial of routine prophylaxis vs. on-demand treatment with sucrose-formulated recombinant factor VIII in adults with severe hemophilia A (Spinart), J Thromb Haemost., Jun. 2013, 11(6): 1119-1127.
Marshall, et al. (Aug. 25, 2004) "Enhancing the Activity of a Beta-Helical Antifreeze Protein by the Engineered Addition of Coils", Biochemistry, vol. 43, No. 37, p. 11637-11646.
Martin, et al. (Apr. 1999) "Evaluation of a Novel ELISA Screening Test for Detection of Factor VIII Inhibitory Antibodies in Haemophiliacs", Clinical & Laboratory Haematology, vol. 21, No. 2, pp. 125-128.
Martin, et al. (Jan. 2003) "Rational Design of a CD4 Mimic that Inhibits HIV-1 Entry and Exposes Cryptic Neutralization Epitopes", Nature Biotechnology, vol. 21, No. 1, pp. 71-76.
Martineau, et al. (Jul. 3, 1998) "Expression of an Antibody Fragment at High Levels in the Bacterial Cytoplasm", Journal of Molecular Biology, vol. 280, No. 1, pp. 117-127.
Matsumoto, et al. (2006) "the Measurement of Low Levels of Factor VIII or Factor IX in Hemophilia A and Hemophilia B Plasma by Clot Waveform Analysis and Thrombin Generation Assay", Journal of Thrombosis and Haemostasis, vol. 4, No. 2, pp. 377-384.
Matthews, et al. (May 21, 1993) "Substrate Phage: Selection of Protease Substrates by Monovalent Phage Display", Science, vol. 260, No. 5111, pp. 1113-1117.
Mazepa et al., Men with severe hemophilia in the United States: birth cohort analysis of a large national database, Blood, 2016, 127: 3073-3081.
McCue, et al. (Nov. 6, 2009) "Application of a Novel Affinity Adsorbent for the Capture and Purification of Recombinant Factor VIII Compounds", Journal of Chromatography A, vol. 1216, No. 45, pp. 7824-7830.
McDonald, et al. (Sep. 15, 2002) "Significance of Blood Vessel Leakiness in Cancer", Cancer Research, vol. 62, No. 18, pp. 5381-5385.
McEneny-King et al., "Development and evaluation of a generic population pharmacokinetic model for standard half-life factor VIII for use in dose individualization", Journ Pharmacokinet Pharmacodyn., Oct. 2019, 46(5): 411-426.
McKnight, et al. (Aug. 1, 1985) "Identification and Molecular Analysis of a Third Aspergillus Nidulans Alcohol Dehydrogenase Gene", the EMBO Journal, vol. 4, No. 8, pp. 2093-2099.
McNulty, et al. (Nov. 29, 2001) "High-Resolution NMR Structure of the Chemically-Synthesized Melanocortin Receptor Binding Domain AGRP (87-132) of the Agouti-Related Protein", Biochemistry, vol. 40, No. 51, p. 15520- 15527.
Meeks et al. (Apr. 2009) "Non-Classical Anti-Factor VIII C2 Domain Antibodies are Pathogenic in a Murine In vivo Bleeding Model", Journal of Thrombosis and Haemostasis, vol. 7, No. 4, pp. 658-664.
Meeks et al., Emerging benefits of Fc fusion technology in the context of recombinant factor VIII replacement therapy, Haemophilia, 2020, 26(6): 958-965.
Meeks, et al. (Dec. 15, 2007) "Antihuman Factor Viii C2 Domain Antibodies in Hemophilia a Mice Recognize a Functionally Complex Continuous Spectrum of Epitopes Dominated by Inhibitors of Factor VIII Activation", Blood, vol. 110, No. 13, pp. 4234-4242.

Mei, et al. (Oct. 2006) "Expression of Human Coagulation Factor VIII in a Human Hybrid Cell Line, HKB11", Molecular Biotechnology, vol. 34, No. 2, Humana Press Inc., pp. 165-178.
Meier, et al. (Jul. 2, 2004) "Determination of a High-Precision NMR Structure of the Minicollagen Cysteine Rich Domain from Hydra and Characterization of Its Disulfide Bond formation", FEBS Letters, vol. 569, No. 1-3, pp. 112-116.
Meloun, et al. (Oct. 15, 1975) "Complete Amino Acid Sequence of Human Serum Albumin", FEBS Letters, vol. 58, No. 1, pp. 134-137.
Mi et al., Targeting the Neonatal Fc Receptor for Antigen Delivery Using Engineered Fc Fragments, J Immunol., 2008, 181(11): 7550-7561.
Miljanich, G. P., et al. (Jan. 2004) "Ziconotide: Neuronal Calcium Channel Blocker for Treating Severe Chronic Pain", Current Medicinal Chemistry, vol. 11, No. 23, pp. 3029-3040.
Misenheimer, et al. (Dec. 16, 2005) "Biophysical Characterization of the Signature Domains of Thrombospondin-4 and Thrombospondin-2*", Journal of Biological Chemistry, vol. 280, No. 40, pp. 41229-41235.
Misenheimer, et al. (Oct. 4, 2001) "Disulfide Connectivity of Recombinant C-terminal Region of Human Thrombospondin 2", the Journal of Biological Chemistry, vol. 276, No. 49, pp. 45882-45887.
Mitraki, et al. (1989) "Protein Folding Intermediates and Inclusion Body formation", Nature Biotechnology, vol. 7, pp. 690-697.
Mize, et al. (2008) "Regulated Expression of Active Biotinylated G-Protein Coupled Receptors in Mammalian Cells", Protein Expression and Purification, vol. 57, No. 2, pp. 280-289.
Moffit et al., "Nonclinical Safety Assessment of BIVV001, A Next-Generation Recombinant Factor VIII Fc-VWF-XTEN Fusion Protein", Mar. 7, 2018.
Mogk, et al. (Sep. 2, 2002) "Mechanisms of Protein Folding: Molecular Chaperones and their Application in Biotechnology", ChemBioChem, vol. 3, Issue 9, pp. 807-814.
Moore et al., A Randomized Safety and Efficacy Study of Somavaratan (VRS-317), a Long-Acting rhGH, in Pediatric Growth Hormone Deficiency, J Clin Endocrinol Metab., 2016, 101(3): 1091-1097.
Morfini, M., "Pharmacokinetics of Factor VIII and Factor IX", Haemophilia, vol. 9, No. 1, pp. 94-99, May 1, 2003.
Morfini, Massimo (2008) "Secondary Prophylaxis with Factor IX Concentrates: Continuous Infusion", Blood Transfusion, vol. 6, Supplement 2, pp. s21-s25.
Morpurgo, et al. (Jan. 1996) "Covalent Modification of Mushroom Tyrosinase with Different Amphiphic Polymers for Pharmaceutical and Biocatalysis Applications", Applied Biochemistry and Biotechnology, vol. 56, No. 1, pp. 59-72.
Mount, et al. (Apr. 15, 2002) "Sustained Phenotypic Correction of Hemophilia B Dogs with a Factor IX Null Mutation by Liver-Directed Gene therapy", Blood, vol. 99, No. 8, pp. 2670-2676.
Mrsny, et al. (Feb. 15, 2002) "Bacterial Toxins as Tools for Mucosal Vaccination", Drug Discovery Today, vol. 7, Issue 4, pp. 247-258.
Murtuza, et al. (Mar. 23, 2004) "Transplantation of Skeletal Myoblasts Secreting An IL-1 Inhibitor Modulates Adverse Remodeling in Infarcted Murine Myocardium", Proceedings of the National Academy of Sciences of the United States of America, vol. 101, No. 12, pp. 4216-4221.
Nagao et al., PB0277 Real-world Data of Immune Tolerance Induction Using Recombinant Factor VIII Fc Fusion Protein for Hemophilia A Patients with Inhibitors in Japan: Observational Fc Adolescent and Children Treatment Study (FACTs) First Interim Reports, Res Pract Thromb Haemost., 2019, 3(S1): 290.
Narita, et al. (1998) "the Low-Density Lipoprotein Receptor-Related Protein (LRP) Mediates Clearance of Coagulation Factor Xa In Vivo", Blood, vol. 91, No. 2, pp. 555-560.
Narmoneva, et al. (Aug. 2005) "Self-Assembling Short Oligopeptides and the Promotion of Angiogenesis", Biomaterials, vol. 26, Issue 23, pp. 4837-4846.
National Heart Lung and Blood Institution, (Oct. 22, 2011), The Diagnosis, Evaluation and Management of von Willebrand Disease Scientific Overview, accessed at http://www.nhlbi.nih.gov/guidelines/vwd/2scientificoverview.htm.

(56) References Cited

OTHER PUBLICATIONS

National Hemophilia Foundation (NHF). Medical and Scientific Advisory Council (Masac). Masac Document #241: MASAC Recommendation Concerning Prophylaxis, Feb. 28, 2016.
NCBI (Jun. 11, 2015) "Serine Phosphatase RsbU, Regulator of Sigma Subunit [Amycolatopsis azurea]", Reference Sequence: WP_005158338.1, Available at URL: http://www.ncbi.nlm.nih.gov/protein/491300334?report=genbank&log$=protalign&bla st_rank=1&RID=3ERSOM7501R, 2 Pages.
NCBI "Probable Electron Transfer Flavoprotein Subunit Alpha, Mitochondrial [Galendromus Occidentalis]", NCBI Reference Sequence: XP_003746909.1 Retrieved at URL: https://www.ncbi.nlm.nih.gov/protein/391345263?report=genbank&log$=protalign&bl ast_rank=1&RID=3ERSOM7501R, 3 pages.
Needleman, et al. (Mar. 1970) "A General Method Applicable to the Search for Similarities in the Amino Acid Sequence of Two Proteins", Journal of Molecular Biology, vol. 48, No. 3, pp. 443-453.
Neumann, et al. (1982) "Gene Transfer into Mouse Lyoma Cells by Electroporation in High Electric Fields", the EMBO Journal, vol. 1, No. 7, pp. 841-845.
Newell et al., Acidic Residues C-Terminal to the A2 Domain Facilitate Thrombin-Catalyzed Activation of Factor VIII, 2008, pp. 8786-8795.
Newell et al., Residues Surrounding Arg372, Arg740, and Arg 1689 Contribute to the Rates of Thrombin-Catalyzed Cleavage of Factor VIII, 2009, p. 349.
Newman et al., "Primatization" Of Recombinant Antibodies For Immunotherapy Of Human Diseases: A Macaque/Human Chimeric Antibody Against Human CD4, 1992, pp. 1455-1460.
Ng et al., "Role of Imaging in Management of Hemophilic Patients," American Journal of Roentgenology, 2005, vol. 184, No. 5, pp. 1619-1623.
Ngo, et al. (Apr. 2008) "Crystal Structure of Human Factor VIII: Implications for the formation of the Factor IXa-Factor VIIIa Complex", Structure, vol. 16, No. 4, pp. 597-606.
Nielsen, et al. (Jul. 2003) "Di/Tri-Peptide Transporters as Drug Delivery Targets: Regulation of Transport Under Physiological and Patho-Physiological Conditions", Current Drug Targets, vol. 4, Issue 5, pp. 373-388.
Nielsen, et al. (Jul. 26, 2002) "Solution Structure of μ-Conotoxin PIIIA, a Preferential Inhibitor of Persistent Tetrodotoxin-sensitive Sodium Channels", the Journal of Biological Chemistry, vol. 277, pp. 27247-27255.
Nieman, et al. (Jul. 24, 2007) "Interaction of Thrombin with PAR1 and PAR4 at the Thrombin Cleavage Site", Biochemistry, vol. 46, No. 29, pp. 8603-8610.
Nilsson et al., Twenty-five years' experience of prophylactic treatment in severe haemophilia A and B, J Intern Med., 1992, 232(1): 25-32.
Nimmerjahn et al., Fcgamma receptors as regulators of immune responses, Nat Rev Immunol., 2008, 8(1): 34-47.
Noe, D A., et al. (November-Dec. 1996) "A Mathematical Model of Coagulation Factor VIII Kinetics", Haemostasis, vol. 26, No. 6, pp. 289-303.
Nogami, et al. (Jun. 1, 2002) "A novel mechanism of factor VIII protection by von Willebrand factor from activated protein C-Catalyzed inactivation", Blood, vol. 99, No. 11, pp. 3993-3998.
Nogami, et al. (May 2007) "Relationship Between the Binding Sites for von Willebrand Factor, Phospholipid, and Human Factor VIII C2 Inhibitor Alloantibodies within the Factor VIII C2 Domain", International Journal of Hematology, vol. 85, No. 4, pp. 317-322.
Nolan et al. Recombinant factor VIII Fc fusion protein for the treatment of severe haemophilia A: final results from the ASPIRE extension study. Haemophilia 2020:26(3):494-502.
Non-Final Office Action received for U.S. Patent Application No. 14/894, 108, mailed on May 21, 2020.
Non-Final Office Action Received for U.S. Appl. No. 13/513,424, mailed on May 5, 2014, 11 Pages.
Non-Final Office Action Received for U.S. Appl. No. 13/793,783, mailed on Mar. 11, 2015, 11 Pages.
Non-Final Office Action Received for U.S. Appl. No. 14/964,289, mailed on Apr. 10, 2018, 11 Pages.
Non-Final Office Action Received for U.S. Appl. No. 16/270,302, mailed on Feb. 18, 2021, 12 Pages.
Nord, et al. (Aug. 1997) "Binding Proteins Selected from Combinatorial Libraries of an α-Helical Bacterial Receptor Domain", Nature Biotechnology, vol. 15, Issue 8, pp. 772-777.
Notice of Allowance Received for U.S. Appl. No. 13/513,424, mailed on Feb. 3, 2015, 16 Pages.
Notice of Allowance Received for U.S. Appl. No. 13/793,783, mailed on Sep. 9, 2015, 12 Pages.
Notice of Allowance Received for U.S. Appl. No. 14/964,289, mailed on Nov. 8, 2018, 9 Pages.
NUWIQ [package insert], SE-112 75, Sweden: Octapharma, 2017.
O'Hara et al., "New challenges for an expanding generation of older persons with haemophilia", J Haem Pract 2022, 9(1), 13 pages.
O'Brien, et al. (Apr. 15, 1990) "Purification and Characterization of Factor VIII 372-Cys: A Hypofunctional Cofactor from A Patient with Moderately Severe Hemophilia A", Blood, vol. 75, No. 8, pp. 1664-1672.
O'Connell, et al. (Aug. 2, 2002) "Phage versus Phagemid Libraries for Generation of Human Monoclonal Antibodies", Journal of Molecular Biology, vol. 321, Issue 1, pp. 49-56.
Office Action mailed Apr. 16, 2013, in U.S. Appl. No. 12/806,005, Schellenberger, et al., filed on Aug. 2, 2010.
Office Action mailed Apr. 17, 2019, for U.S. Appl. No. 15/110,673, inventor Ekta Seth Chhabra, filed Jul. 8, 2016.
Office Action mailed Apr. 30, 2018, in U.S. Appl. No. 14/379,196 inventor Ekta Seth Chhabra, filed Aug. 15, 2014.
Office Action mailed Aug. 23, 2012, in U.S. Appl. No. 12/848,984, Schellenberger, et al., filed on Aug. 2, 2010.
Office Action mailed Aug. 7, 2018, for U.S. Appl. No. 14/379,192, inventor Ekta Seth Chhabra, filed Feb. 20, 2015.
Office Action mailed Dec. 12, 2017 in U.S. Appl. No. 14/371,948, inventor Ekta Seth Chhabra, filing date Jul. 11, 2014, 21 pages.
Office Action mailed Feb. 25, 2014, in U.S. Appl. No. 13/392,509, Schellenberger, et al., filed on Feb. 24, 2012.
Office Action mailed Jan. 14, 2014, in U.S. Appl. No. 12/796,650, Schellenberger, et al., filed on Jun. 8, 2010.
Office Action mailed Jan. 26, 2018, in U.S. Appl. No. 14/895,264 inventor Ekta Seth Chhabra, filed Dec. 2, 2015.
Office Action mailed Jul. 2, 2013 in U.S. Appl. No. 13/392,511, Schellenberger, V. et al., filed Jun. 27, 2012.
Office Action mailed Jul. 21, 2017, in U.S. Appl. No. 14/413,765, inventor Ekta Seth Chhabra, filed Jan. 9, 2015.
Office Action mailed Jun. 17, 2015, in U.S. Appl. No. 14/317,888, Schellenberger, et al., filed on Jun. 27, 2014.
Office Action mailed Jun. 18, 2020, for U.S. Appl. No. 16/154,310, inventor Ekta Seth Chhabra, filed Oct. 8, 2018.
Office Action mailed Jun. 21, 2013, in U.S. Appl. No. 12/806,004, Schellenberger, et al., filed on Aug. 2, 2010.
Office Action mailed Jun. 25, 2018 in U.S. Appl. No. 14/371,948 inventor Ekta Seth Chhabra, filed Jul. 11, 2014.
Office Action mailed Mar. 16, 2018, for U.S. Appl. No. 14/379,192, inventor Ekta Seth Chhabra, filed Feb. 20, 2015.
Office Action mailed Mar. 22, 2013, in U.S. Appl. No. 12/796,650, Schellenberger, et al., filed on Jun. 8, 2010.
Office Action mailed Mar. 29, 2017, in U.S. Appl. No. 14/413,765 inventor Ekta Seth Chhabra, filed Jan. 9, 2015.
Office Action mailed Mar. 9, 2016 in U.S. Appl. No. 14/218,524, filed Mar. 18, 2014.
Office Action mailed Mar. 9, 2020, for U.S. Appl. No. 14/371,948, inventor Ekta Seth Chhabra, filed Jul. 11, 2014.
Office Action mailed May 7, 2013, in U.S. Appl. No. 12/699,761, Schellenberger, et al., filed on Feb. 3, 2010.
Office Action mailed May 17, 2017, in U.S. Appl. No. 14/371,948, inventor Ekta Seth Chhabra, filed Jul. 11, 2014.
Office Action mailed May 20, 2014 in U.S. Appl. No. 13/392,511, Schellenberger, V et al., filed Jun. 27, 2012.
Office action mailed May 23, 2017, in U.S. Appl. No. 14/894,108, inventor Ekta Seth Chhabra, filed May 3, 2016.
Office Action mailed May 30, 2017, in U.S. Appl. No. 14/379,192, inventor Ekta Seth Chhabra, filed Feb. 20, 2015.

(56) References Cited

OTHER PUBLICATIONS

Office Action mailed Nov. 1, 2016, in U.S. Appl. No. 14/379,192, inventor Ekta Seth Chhabra, filed Feb. 20, 2015.
Office Action mailed Nov. 18, 2019, for U.S. Appl. No. 14/895,264, inventor Ekta Seth Chhabra, filed Dec. 2, 2015.
Office Action mailed Nov. 24, 2015 in U.S. Appl. No. 14/317,888, filed Jun. 27, 2014.
Office Action mailed Oct. 5, 2012, in U.S. Appl. No. 12/806,004, Schellenberger, et al., filed on Aug. 2, 2010.
Office Action mailed Oct. 20, 2014 in U.S. Appl. No. 13/392,511, Schellenberger, V. et al., filed Jun. 27, 2012.
Office Action mailed Sep. 11, 2013, in U.S. Appl. No. 12/848,984, Schellenberger, et al., filed on Aug. 2, 2010.
Office Action mailed Sep. 19, 2019, for U.S. Appl. No. 14/371,948, inventor Ekta Seth Chhabra, filed Jul. 11, 2014.
Office Action mailed Sep. 25, 2017, in U.S. Appl. No. 14/379,196, Kulman, filed on Feb. 15, 2013.
Office Action mailed Sep. 27, 2017, in U.S. Appl. No. 14/379,192, inventor Ekta Seth Chhabra, filed Feb. 20, 2015.
Office Action mailed Sep. 5, 2018, in U.S. Appl. No. 14,379,196, inventor Kulman, J., et al., filed Aug. 15, 2014.
Office Action mailed Sep. 7, 2018, in U.S. Appl. No. 14/895,264 inventor Ekta Seth Chhabra, filed Dec. 2, 2015.
Office Action mailed, Oct. 29, 2019 in U.S. Appl. No. 15/110,673 inventor Ekta Seth Chhabra, filed Jul. 8, 2016.
Office Action Received for European Patent Application No. 10835255.0, mailed on Aug. 6, 2015, 4 Pages.
Office Action Received for European Patent Application No. 10835255.0, mailed on Feb. 7, 2017, 4 Pages.
Office Action Received for European Patent Application No. 10835255.0, mailed on Jun. 3, 2016, 3 Pages.
Office Action Received for European Patent Application No. 17194648.6, mailed on Jul. 10, 2019, 4 Pages.
Office Action Received for European Patent Application No. 17194648.6, mailed on Mar. 18, 2020, 4 Pages.
Ofir, et al. (May 2005) "Versatile Protein Microarray Based on Carbohydrate- Binding Modules", Proteomics, vol. 5, No. 7, pp. 1806-1814.
Oganesyan, et al., "Structural Characterization of a Human Fc Fragment Engineered for Extended Serum Half-Life", Molecular Immunology, vol. 46, No. 8-9, pp. 1750-1755, May 1, 2009.
Ökten, et al. (Aug. 1, 2004) "Myosin VI Walks Hand-Over-Hand Along Actin", Nature Structural & Molecular Biology, vol. 11, pp. 884-887.
Oldenburg et al. Improved joint health in subjects with severe haemophilia A treated prophylactically with recombinant factor VIII Fc fusion protein. Haemophilia. 2018:24(1): 77-84.
Oldenburg et al., Controlled, cross-sectional MRI evaluation of joint status in severe haemophilia A patients treated with prophylaxis vs on demand, Haemophilia, 2015, 21:171-179.
Oldenburg et al., Genetic risk factors for inhibitors to factors VIII and IX, Haemophilia, 2006, 12(6): 15-22.
Oldenburg et al., Prophylaxis in adult patients with severe haemophilia A., Thrombosis Research, 2014, s33-s37.
Oldenburg, Optimal treatment strategies for hemophilia: achievements and limitations of current prophylactic regimens, Blood, 2015, 125: 2038-2044.
O'Leary, et al. (Jan. 2005) "Solution Structure and Dynamics of a Prototypical Chordin-like Cysteine-rich Repeat (von Willebrand Factor Type C Module) from Collagen IIA", Journal of Biological Chemistry, vol. 279, No. 51, pp. 53857- 53866.
Orlova, et al. (Apr.-Jun. 2013) "Blood Clotting Factor VIII: From Evolution to therapy", Acta Naturae, vol. 5, No. 2, pp. 19-39.
Ormo, et al. (1996) "Crystal Structure of the Aequorea Victoria Green Fluorescent Protein", Science, vol. 273, No. 5280, pp. 1392-1395.
Osterud, et al. (Jul. 18, 1972) "Activation of the Coagulation Factor VII by Tissue Thromboplastin and Calcium", Biochemistry, vol. 11, No. 15, pp. 2853-2857.

Padiolleau-Lefevre, et al. (Mar. 2007) "Expression and Detection Strategies for an ScFv Fragment Retaining the Same High Affinity than Fab and Whole Antibody: Implications for therapeutic Use in Prion Diseases", Molecular Immunology, vol. 44, Issue 8, pp. 1888-1896.
Pallaghy, et al. (Nov. 20, 1993) "Three-dimensional Structure in Solution of the Calcium Channel Blocker ω-Conotoxin", Journal of Molecular Biology, vol. 234, Issue 2, pp. 405-420.
Pallaghy, et al. (Oct. 1994) "A Common Structural Motif Incorporating a Cystine Knot and a Triple-Stranded β-sheet in Toxic and Inhibitory Polypeptides", Protein Science, vol. 3, Issue 10, pp. 1833-1839.
Palmiter, et al. (1983) "Metallothionein-Human GH Fusion Genes Stimulate Growth of Mice", Science, vol. 222, No. 4625, pp. 809-814.
Pan, et al. (Dec. 1993) "Structure and Expression of Fibulin-2, A Novel Extracellular Matrix Protein with Multiple EGF-Like Repeats and Consensus Motifs for Calcium Binding", Journal of Cell Biology, vol. 123, Issue 5, pp. 1269-1277.
Pan, et al., "Enhanced efficacy of recombinant FVIII in noncovalent complex with PEGylated liposome in hemophilia A mice", Blood Journal, vol. 114, No. 13, pp. 2802-2811, Sep. 24, 2009.
Panda, et al. (2003) "Bioprocessing of therapeutic Proteins from the Inclusion Bodies of *Escherichia coli*", Advances in Biochemical Engineering / Biotechnology, vol. 85, pp. 43-93.
Panicali, et al. (Aug. 1982) "Construction of Poxviruses as Cloning Vectors: Insertion of the Thymidine Kinase Gene from Herpes Simplex Virus into the DNA of Infectious Vaccinia Virus", Proceedings of the National Academy of Sciences of the United States of America, vol. 79, No. 16, pp. 4927-4931.
Park, et al. (2010) "A Diagnostic Challenge: Mild Hemophilia B with Normal Activated Partial Thromboplastin Time", Blood Coagulation & Fibrinolysis, vol. 21, No. 4, pp. 368-371.
Partial European Search Report received for European Patent Application No. 12868427.1, mailed on Sep. 18, 2015, 7 Pages.
Pasi et al. Improvement in pain-related quality of life in patients with hemophilia A treated with rFVIIIFc individualized prophylaxis: post hoc analysis from the A-LONG study. Therapeutic Advances in Hematology. 2022.
Patarroyo-White et al., "A FVIII/VWF Chimeric Protein with VWF Independent Pharmacokinetic Properties", XXV Congress of the International Society of Thrombosis and Haemostasis (ISTH), Jun. 20-25, 2015, Toronto, Canada.
Patra, et al. (Mar. 2000) "Optimization of Inclusion Body Solubilization and Renaturation of Recombinant Human Growth Hormone from *Escherichia coli*", Protein Expression and Purification, vol. 18, Issue 2, pp. 182-192.
Pelegrini (Nov. 2005) "Plant Gamma-Thionins: Novel insights on The Mechanism of Action of a Multi-Functional Class of Defense Proteins", The International Journal of Biochemistry & Cell Biology, vol. 37, No. 11, pp. 2239-2253.
Pepinsky, et al. (Jun. 2001) "Improved Pharmacokinetic Properties of a Polyethylene Glycol-Modified form of Interferon-β-1a with Preserved In vitro Bioactivity", Journal of Pharmacology and Experimental therapeutics, vol. 297, vol. 3, pp. 1059-1066.
Peters RT, et al., Prolonged activity of factor IX as a monomeric Fc fusion protein, Blood, 2010, 115(10): 2057-2064.
Petersen, et al. (Nov. 25, 2003) "the Dual Nature of Human Extracellular Superoxide Dismutase: one Sequence and Two Structures", Proceedings of the National Academy of Sciences of the United States of America, vol. 100, No. 24, pp. 13875-13880.
Pi, et al. (Feb. 2006) "Analysis of Expressed Sequence Tags from the Venom Ducts of Conus Striatus: Focusing on the Expression Profile of Conotoxins", Biochimie, vol. 88, Issue 2, pp. 131-140.
Pierce, Glenn, MD, Ph.D., "Innovation in Hemophilia: From Blood to Genes, and the Unintended Consequences Along the Way", ISPE Annual Meeting & Expo, Oct. 29-Nov. 1, 2017, https://www2.ispe.org/imis/conference- handouts/NA17CEOCT1/Pierce_NA17CEOCT1_Innovation-in-Hemophilia-From- Blood-to-Genes-and-the-Unintended-Consequences-Along-the-Way.pdf.
Pimanda, et al. (Nov. 2002) "the von Willebrand Factor-Reducing Activity of Thrombospondin-1 is Located in the Calcium-Binding/

(56) References Cited

OTHER PUBLICATIONS

C-Terminal Sequence and Requires a Free Thiol at Position 974", Blood, vol. 100, No. 8, pp. 2832-2838.
Pipe et al., "A global comparative field study to evaluate the factor VIII activity of efanesoctocog alfa by one-stage clotting and chromogenic substrate assays at clinical haemostasis laboratories", Haemophilia, Oct. 30, 2023, 1-10.
Pipe et al., "Efanesoctocog Alfa Activity Assessment with One-Stage Clotting (OSA) and Chromogenic Substrate (CSA) Factor VIII Assays", Abstract, Haemophilia, Feb. 5, 2023.
Pipe et al., "Efanesoctocog Alfa Activity Assessment with One-Stage Clotting (OSA) and Chromogenic Substrate (CSA) Factor VIII Assays", Poster, 16th Annual Congress of the European Association for Haemophilia and Allied Disorders, Feb. 7-10, 2023.
Pipe et al., "Characterization of a Genetically Engineered Inactivation-Resistant Coagulation Factor VIIIa", PNAS USA, Oct. 1997, vol. 94, pp. 11851-11856.
Pipe et al., Life in the shadow of a dominant partner: the FVIII-VWF association and its clinical implications for hemophilia A, Blood, 2016, 128(16): 2007-2016.
Pipe, S.W., "Functional roles of the factor VIII B domain", Haemophilia, vol. 15, 2009, pp. 1187-1196.
Pipe, Stewen W. (2005) "the Promise and Challenges of Bioengineered Recombinant Clotting Factors", Journal of Thrombosis and Haemostasis, vol. 3, No. 8, pp. 1692-1701.
Pittman, et al., "Biochemical, Immunological, and in Vivo Functional Characterization of B-Domain-Deleted Factor VIII", Blood, vol. 81, pp. 2925-2935, Jan. 1, 1993.
Podust et al. Extension of in vivo half-life of biologically active molecules by XTEN protein polymers. J Control Release. 2016; 240:52-66.
Pokidysheva, et al. (2004) "the Structure of the Cys-Rich Terminal Domain of Hydra Minicollagen, Which Is Involved in Disulfide Networks of the Nematocyst Wall", the Journal of Biological Chemistry, vol. 279, No. 29, pp. 30395- 30401.
Pool et al., High potency antihaemophilic factor concentrate prepared from cryoglobulin precipitate, Nature, 1964,203: 312.
Pool, et al. (Sep. 8, 1966) "Ineffectiveness of intramuscularly injected Factor 8 concentrate in two Hemophilic patients", the New England Journal of Medicine, vol. 275, No. 10, pp. 547-548.
Popkov, et al. (2004) "Isolation of Human Prostate Cancer Cell Reactive Antibodies Using Phage Display Technology", Journal of Immunological Methods, vol. 291, No. 1-2, pp. 137-151.
Powell et al., Safety and prolonged activity of recombinant factor VIII Fc fusion protein in hemophilia A patients, Blood, 2012, 119(13): 3031-3037.
Prilusky, et al. (2005) "FoldIndex@: A Simple tool to Predict Whether A Given Protein Sequence is intrinsically Unfolded", Bioinformatics, vol. 21, No. 16, pp. 3435-3438.
Prinz, et al. (1997) "the Role of the Thioredoxin and Glutaredoxin Pathways in Reducing Protein Disulfide Bonds in the *Escherichia Coli* Cytoplasm", the Journal of Biological Chemistry, vol. 272, No. 25, pp. 15661-15667.
Proft, T. (Jan. 2010) "Sortase-Mediated Protein Ligation: An Emerging Biotechnology Tool for Protein Modification and Immobilisation", Biotechnology Letters, vol. 32, No. 1, pp. 1-10.
Purvis et al., "Two Cys Residues Essential for Von Willebrand Factor Multimer Assembly in the Golgi", Proc Natl Acad Sci USA, vol. 104 (40), pp. 15647- 15652.
Puthenveetil, et al. (Nov. 2009) "Yeast Display Evolution of a Kinetically Efficient 13-Amino Acid Substrate for Lipoic Acid Ligase", Journal of the American Chemical Society, vol. 131, No. 45, pp. 16430-16438.
Qi, et al. (2005) "Structural Features and Molecular Evolution of Bowman-Birk Protease Inhibitors and their Potential Application", Acta Biochimica Et Biophysica Sinica, vol. 37, No. 5, pp. 283-292.
Rajani et al., OC 75.5 Recombinant Factor VIII Fc Fusion Protein Inhibits Inflammatory Osteoclast Formation in vitro, Research and Practice in Thrombosis and Haemostasis, 2019, 3(S1): 126.

Ramgren., A clinical and medico-social study of haemophilia in Sweden, Acta Med Scand Suppl., 1962,379: 111-190.
Rao, et al. (1985) "Activation of Human Factor VII During Clotting In Vitro", Blood, vol. 65, No. 1, pp. 218-226.
Rao, et al. (1998) "Molecular and Biotechnological aspects of Microbial Proteases", Microbiology and Molecular Biology Reviews: MMBR, vol. 62, No. 3, pp. 597-635.
Rasmussen, et al. (2002) "Tumor Cell-Targeting by Phage-Displayed Peptides", Cancer Gene therapy, vol. 9, No. 7, pp. 606-612.
Rath T, et al., Fc-fusion proteins and FcRn: structural insights for longer-lasting and more effective therapeutics, Crit Rev Biotechnol., 2015, 35(2): 235-254.
Raut, et al., "Phospholipid Binding of Factor VIII in Different Therapeutic Concentrates", British Journal of Haematology, vol. 107, No. 2, Blackwell Science Ltd, pp. 323-329, Nov. 1, 1999.
Rawlings, et al. (2004) "Evolutionary Families of Peptidase Inhibitors", the Biochemical Journal, vol. 378, Part 3, pp. 705-716.
Rawlings, et al. (2008) "MEROPS: The Peptidase Database", Nucleic Acids Research vol. 36, Supplement 1, pp. D320-D325.
Rebay, et al. (1991) "Specific EGF Repeats of Notch Mediate Interactions with Delta and Serrate Implications for Notch as a Multifunctional Receptor", Cell, vol. 67, No. 4, pp. 687-699.
Recht, et al., "Clinical Evaluation of Moroctocog Alfa(AF-CC), A New Generation of B-Domain Deleted Recombinant Factor VIII (BDDrFVIII) for Treatment of Haemophilia A: Demonstration of Safety, Efficacy, and Pharmacokinetic Equivalence to Full-Length Recombinant Factor VIII", Haemophilia, vol. 15, No. 4, pp. 869-880, Jul. 1, 2009.
Reding et al., Safety and efficacy of BAY 94-9027, a prolonged-half-life factor VIII. J Thromb Haemost., 2017, Mar. 15(3): 411-419.
Restriction Requirement received for U.S. Appl. No. 13/513,424, mailed on Dec. 16, 2013, 8 Pages.
Restriction Requirement received for U.S. Appl. No. 13/793,783, mailed on Oct. 21, 2014, 6 Pages.
Restriction Requirement received for U.S. Appl. No. 16/270,302, mailed on Aug. 20, 2020, 8 Pages.
Rizzo, et al. (2010) "Fluorescent Protein Tracking and Detection", in Live Cell Imaging: A Laboratory Manual, pp. 3-34.
Roberge, et al. (2006) "Construction and Optimization of a Cc49-Based ScFv- Beta-Lactamase Fusion", Protein Engineering, Design & Selection: PEDS, vol. 19, No. 4, pp. 141-145.
Rodriguez-Merchan, Carlos E. (2003) "Management of Musculoskeletal Complications of Hemophilia", Seminars in Thrombosis and Hemostasis., vol. 29, No. 01, pp. 87-96.
Rodriguez-Santana et al., "Differential humanistic and economic burden of mild, moderate and severe haemophilia in european adults: a regression analysis of the Chess II study", Orphanet Journal of Rare Diseases. 2022, 17(148), 10 pages.
Rodriguez-Santana et al., "Health-related quality of life, direct medical and societal costs among children with moderate or severe haemophilia in Europe: multivariable models of the Chess-PAEDs study", Orphanet Journal of Rare Diseases, 2022, 17(150), 9 pages.
Ron, et al., "Expression of Biologically Active Recombinant Keratinocyte Growth Factor—Structure/Function Analysis of Amino-Terminal Truncation Mutants", Journal of Biological Chemistry, vol. 268, No. 4, pp. 2984-2988, Jan. 1, 1993.
Roopenian et al., FcRn: the neonatal Fc receptor comes of age, Nat Rev Immunol., 2007, 7(9): 715-725.
Roosendaal et al., Blood-induced joint damage in hemophilia, Semin Thromb Haemost., 2003, 29(1): 37-42.
Roovers, et al. (Mar. 2007) "Efficient Inhibition of EGFR Signaling and of Tumour Growth by Antagonistic anti-EFGR Nanobodies", Cancer Immunology, Immunotherapy, vol. 56, No. 3, pp. 303-317.
Rosa, et al. (2000) "Influence of the Co-Encapsulation of Different Non-Ionic Surfactants on the Properties of PLGA insulin-Loaded Micro spheres", Journal of Controlled Release, vol. 69, No. 2, pp. 283-295.
Rosen (1984) "Assay of Factor VIII:C with a chromogenic substrate", Scandinavian Journal of Haematology, vol. 33, Supplement 40, pp. 139-145.

(56) References Cited

OTHER PUBLICATIONS

Rosen, et al. (1985) "Clinical Application of a Chromogenic Substrate Method", Thrombosis and Haemostasis, vol. 54, No. 4, pp. 818-823.
Rosenfeld, et al. (1998) "Biochemical, Biophysical, and Pharmacological Characterization of Bacterially Expressed Human Agouti-Related Protein", Biochemistry, vol. 37, No. 46, pp. 16041-16052.
Rostin, et al., "B-Domain Deleted Recombinant Coagulation Factor VIII Modified with Monomethoxy Polyethylene Glycol", Bioconjugate Chemistry, vol. 11, No. 3, pp. 387-396, May 15, 2000.
Roussel, et al. (2001) "Complexation of Two Proteic insect inhibitors to the Active Site of Chymotrypsin Suggests Decoupled Roles for Binding and Selectivity", The Journal of Biological Chemistry, vol. 276, No. 42, pp. 38893-38898.
Routledge, et al. (Oct. 1, 1995) "The Effect of Aglycosylation on The Immunogenicity of a Humanized Therapeutic CD3 Monoclonal Antibody", Transplantation, vol. 60, No. 8, pp. 847-853.
Ruther, et al. (Oct. 1983) "Easy Identification of cDNA Clones", The EMBO Journal, vol. 2, No. 10, pp. 1791-1794.
Rychkov, et al. (2007) "Joint Neighbors Approximation of Macromolecular Solvent Accessible Surface Area", Journal of Computational Chemistry, vol. 28, No. 12, pp. 1974-1989.
Saenko et al., A mechanism of inhibition of factor VIII binding to phospholipid by von Willebrand factor, J Biol Chem, 1995, 270(23): 13826-13833.
Saenko, et al. (1997) "the Acidic Region of the Factor VIII Light Chain and the C2 Domain Together form the High Affinity Binding Site for Von Willebrand Factor", Journal of Biological Chemistry, vol. 272, No. 29, p. 18007-18014.
Saenko, et al. (1999) "Role of The Low-Density Lipoprotein-Related Protein Receptor in Mediation of Factor VIII Catabolism", The Journal of Biological Chemistry, vol. 274, No. 53, pp. 37685-37692.
Saenko, et al. (2005) "the Future of Recombinant Coagulation Factors", Journal of Thrombosis and Haemostasis, vol. 1, pp. 922-930.
Saenko, et al. (Apr. 15, 1994) "A Role for The C2 Domain of Factor VIII in Binding to von Willebrand Factor", Journal of Biological Chemistry, vol. 269, No. 15, pp. 11601-11605.
Saenko, et al. (Jul. 2006) "Strategies Towards a Longer Acting Factor VIII", Haemophilia, vol. 12, Supplement 3, pp. 42-51.
Sahdev, et al. (Jan. 2008) "Production of Active Eukaryotic Proteins Through Bacterial Expression Systems: A Review of the Existing Biotechnology Strategies", Molecular and Cellular Biochemistry, vol. 307, No. 1-2, pp. 249-264.
Sakata, PAR-1 Thrombin Receptor Antagonist, 2012, pp. 47-50.
Salloum, et al. (Apr. 2009) "Anakinra in Experimental Acute Myocardial Infarction- Does Dosage or Duration of Treatment Matter?", Cardiovascular Drugs and therapy Sponsored by the International, Society of Cardiovascular Pharmacotherapy, vol. 23, No. 2, pp. 129-135.
Sandberg et al., "Structural and Functional Characterization of B-Domain Deleted Recombinant Factor VIII", Seminars in Hematology, Apr. 2001, vol. 38, No. 2, Suppl. 4, pp. 4-12.
Sanofi, "Capital Markets Day, Play to Win", Presentation Slides, Dec. 10, 2019.
Sanofi, "Press Release: Efanesoctocog alfa met primary and key secondary endpoints in pivotal study in hemophilia A, demonstrating superiority to prior factor prophylaxis treatment", Mar. 9, 2022, 3 pages.
Sanofi, "Press Release: FDA approves once-weekly aLTUVIIIO™, a new class of factor VIII therapy for hemophilia A that offers signiciant bleed protection. This positive event triggers impairment erversal, impacting 2022 IFRS net income; No. change on business net income (non-IFRS)", Feb. 24, 2023, 2 pages.
Sanofi, "Press Release: FDA grants priority review to efanesoctocof alfa for people with hemophilia A", Aug. 30, 2022, 3 pages.
Sanofi, "FDA grants efanesoctocog alfa Breakthrough Therapy designation for hemophilia A", Press Release, Jun. 1, 2022.
Sanofi, A Phase 1/2a, Open-Label, Dose-Escalation Study to Determine the Safety, Tolerability, and Pharmacokinetic of a Single Intravenous Injection of rFVIIIFc-VWF-XTEN (BIVV001) in Previously Treated Adults with Severe Hemophilia A, Model Patient Information Sheet and Informed Consent Form, Protocol No. 242HA101, EudraCT No. 2017-001140-34, Version 3, Jun. 13, 2017, 12 pages.
Sanofi, A Phase 3 Open-Label Multicenter Study of the Safety, Efficacy, and Pharmacokinetics of Intravenous Recombinant Coagulation Factor VIII Fc-von Willebrand Factor-XTEN Fusion Protein (rFVIIIFc-VWF-XTEN; BIVV001) in Previously Treated Patients under 12 Years of Age With Severe Hemophilia A, Core Study Information and Informed Consent Form, Protocol No. EFC16293, Nov. 6, 2019.
Sanofi, Hemophilia Investor Event Presentation slides, Jul. 13, 2022, 48 pages.
Sanofi, 'Media Update: Sanofi to present new clinical data reinforcing novel therapies across rare blood disorders at ASH 2022, Nov. 30, 2022, 4 pages.
Sanofi, R&D Investor Event: Lead with innovation, Presentation slides, Jun. 23, 2020, 82 pages.
Saqib U, et al. Phytochemicals as modulators of M1-M2 macrophages in inflammation. Oncotarget. 2018;9(25): 17937-17950.
Scandella, et al. (1989) "Localization of Epitopes for Human Factor VIII Inhibitor Antibodies by Immunoblotting and Antibody Neutralization", Blood, vol. 74, No. 5, pp. 1618-1626.
Scandella, et al. (Aug. 1, 1988) "Epitope Mapping of Human Factor VIII Inhibitor Antibodies by Deletion Analysis of Factor VIII Fragments Expressed in Escherichia Coli", Proceedings of the National Academy of Sciences, vol. 85, No. 16, pp. 6152-6156.
Schatz, P. J. (1993) "Use of Peptide Libraries to Map the Substrate Specificity of a Peptide-Modifying Enzyme: A 13 Residue Consensus Peptide Specifies Biotinylation In *Escherichia Coli*", Biotechnology, vol. 11, No. 10, pp. 1138-1143.
Schellenberger et al., A recombinant polypeptide extends the in vivo half-life of peptides and proteins in a tunable manner, Nat Biotechnol., 2009, 27(12): 1186-1190.
Schellenberger, et al. (1993) "Analysis of Enzyme Specificity by Multiple Substrate Kinetics", Biochemistry, vol. 32, No. 16, pp. 4344-4348.
Schlapschy, et al. (Jun. 1, 2007) "Fusion of a Recombinant Antibody Fragment with a Homo-Amino-Acid Polymer: Effects on Biophysical Properties and Prolonged Plasma Half-Life", Protein Engineering, Design and Selection, vol. 20, No. 6, pp. 273-284.
Scholle, et al. (2005) "Efficient Construction of a Large Collection of Phage-Displayed Combinatorial Peptide Libraries", Combinatorial Chemistry High Throughput Screening, vol. 8. No. 6, pp. 545-551.
Schulte, et al., "Prolonged In-Vivo Half-Life of FVIIa by Fusion to Albumin", Blood, 2007, vol. 110, No. 11, Abstract 3142, American Society of Hematology.
Schulte, S (2011) "Pioneering Designs for Recombinant Coagulation Factors", Thrombosis Research, vol. 128, Supplement 1, pp. S9-S12.
Schulte, Stefan (Dec. 2008) "Use of Albumin Fusion Technology to Prolong the Half-Life of Recombinant Factor", Thrombosis Research, vol. 122, Supplement 4, pp. S14-S19.
Schulte, Stefan, "Half-Life Extension Through Albumin Fusion Technologies", Thrombosis Research, vol. 124, Supplement 2, pp. S6-S8, Dec. 1, 2009.
Schultz-Cherry, et al. (1994) "The Type 1 Repeats of Thrombospondin 1 Activate Latent Transforming Growth Factor-Beta", the Journal of Biological Chemistry, vol. 269, No. 43, pp. 26783-26788.
Schultz-Cherry, et al. (1995) "Regulation of Transforming Growth Factor-Beta Activation by Discrete Sequences of Thrombospondin 1", Journal of Biological Chemistry, vol. 270, No. 13, pp. 7304-7310.
Schulz, et al. (2005) "Potential of Nir-Ft-Raman Spectroscopy in Natural Carotenoid Analysis", Biopolymers, vol. 77, No. 4, pp. 212-221.
Schwab et al., Intravenous immunoglobulin therapy: how does IgG modulate the immune system?, Nat Rev Immunol., 2013, 13(3): 176-189.

(56) References Cited

OTHER PUBLICATIONS

Scott et al., Factor VIII: Perspectives on Immunogenicity and Tolerogenic Strategies. Front Immunol. 2020, 10: 3078.

Shaikh, et al. "Examining the impact of haemophilia treatment on health-related quality of life", Haemophilia, 2022, 28(5): 796-805.

Shapiro et al., "Recombinant factor VIII Fc fusion protein: extended-interval dosing maintains low bleeding rates and correlates with von Willebrand factor levels", Journal of Thrombosis and Haemostasis, Nov. 2014, 12(11): 1788-1800.

Shapiro et al., Recombinant factor IX-Fc fusion protein (rFIXFc) demonstrates safety and prolonged activity in a phase 1/2a study in hemophilia B patients, Blood, 2012, 119(3): 666-672.

Sheffield, et al. (2004) "Effects of Genetic Fusion of Factor IX to Albumin on In Vivo Clearance in Mice and Rabbits", British Journal of Haematology, vol. 126, No. 4, pp. 565-573.

Shen, et al. (1998) "A Type I Peritrophic Matrix Protein from the Malaria Vector Anopheles Gambiae Binds to Chitin Cloning, Expression, and Characterization", Journal of Biological Chemistry, vol. 273, No. 28, pp. 17665-17670.

Shen, et al. (Feb. 1, 2008) "The Tertiary Structure and Domain organization of Coagulation Factor VIII", Blood, vol. 111, No. 3, pp. 1240-1247.

Shields, et al. (Mar. 2, 2001) "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R", Journal of Biological Chemistry, vol. 276, No. 9, pp. 6591-6604.

Shima, et al. (1993) "A Factor VIII Neutralizing Monoclonal Antibody and A Human Inhibitor Alloantibody Recognizing Epitopes in The C2 Domain inhibit Factor VIII Binding to Von Willebrand Factor and to Phosphatidylserine", Journal of Thrombosis and Haemostasis, vol. 69, No. 3, pp. 240-246.

Shimomura, et al. (1962) "Extraction, Purification and Properties of Aequorin, a Bioluminescent Protein from the Luminous Hydromedusan, Aequorea", Journal of Cellular and Comparative Physiology, vol. 59, pp. 223-239.

Shukla et al., "Interaction of Arginine with Proteins and the Mechanism by Which It Inhibits Aggression", J Phys Chem B., 2010, 114: 13426-13438.

Sidhu, et al. (2000) "Phage Display for Selection of Novel Binding Peptides", Methods in Enzymology, vol. 328, No., pp. 333-363.

Silverman, et al. (2005) "Multivalent Avimer Proteins Evolved by Exon Shuffling of a Family of Human Receptor Domains", Nature Biotechnology, vol. 23, No. 12, pp. 1556-1561.

Simonet, et al. (2002) "Structural and Functional Properties of a Novel Serine Protease Inhibiting Peptide Family in Arthropods", Comparative Biochemistry and Physiology. Part B, Biochemistry & Molecular Biology, vol. 132, No. 1, pp. 247-255.

Simonsen, et al. (May 1983) "Isolation and Expression of An Altered Mouse Dihydrofolate Reductase cDNA", Proceedings of the National Academy of Sciences of the United States of America, vol. 80, No. 9, pp. 2495-2499.

Singh, et al. (Dec. 2001) "ProPred: Prediction of HLA-DR Binding Sites", Bioinformatics, vol. 17, No. 12, pp. 1236-1237.

Skinner et al. "WFH: Closing the global gap - achieving optimal care", Haemophilia, 2012, 18(Suppl. 4): 1-12.

Skinner, et al. (1989) "Purification and Characterization of Two Classes of Neurotoxins from the Funnel Web Spider, Agelenopsis Aperta", the Journal of Biological Chemistry, vol. 264, No. 4, pp. 2150-2155.

Skotnicki et al., Efficacy, safety, and pharmacokinetic profiles of a plasma- derived VWF/FVIII concentrate (VONCENTO®) in subjects with haemophilia A (Swift-Ha study). Thrombosis Resarch, Jan. 2016, 137: 119-125.

Smith et al., "FcγRIIB in Autoimmunity and Infection: Evolutionary and Therapeutic Implications," Nature Reviews Immunology, 2010, vol. 10, No. 5, pp. 328-343.

Smith, et al. (1988) "Single-Step Purification of Polypeptides Expressed in Escherichia Colias Fusions with Glutathione S-Transferase", Gene, vol. 67, No. 1, pp. 31-40.

Smith, et al. (1997) "Phage Display", Chemical Reviews, vol. 97, vol. 2, pp. 391-410.

Smith, et al. (Dec. 1981) "Comparison of Biosequences", Advances in Applied Mathematics, vol. 2, No. 4, pp. 482-489.

Smith, et al. (May 1983) "Molecular Engineering of the Autographa Californica Nuclear Polyhedrosis Virus Genome: Deletion Mutations within the Polyhedrin Gene", Journal of Virology, vol. 46, No. 2, pp. 584-593.

So, et al. (2001) "Contribution of Conformational Stability of Hen Lysozyme to Induction of Type 2 T-Helper Immune Responses", Immunology, vol. 104, No. 3, pp. 259-268.

Soucie et al., The frequency of joint hemorrhages and procedures in nonsevere hemophilia A vs B, Blood Adv., 2018,2: 2136-2144.

Southern, et al. (1982) "Transformation of Mammalian Cells to Antibiotic Resistance with a Bacterial Gene Under Control of the Sv40 Early Region Promoter", Journal of Molecular and Applied Genetics 1, No. 4, pp. 327-341.

Spencer, et al. (2011) "Lentiviral Vector Platform for Production of Bioengineered Recombinant Coagulation Factor VIII", Molecular therapy, vol. 19, No. 2, pp. 302-309.

Spira, et al., "Evaluation of Liposomal Dose in Recombinant Factor VIII Reconstituted with Pegylated Liposomes for the Treatment of Patients with Severe Haemophilia A", Thrombosis and Haemostasis, vol. 100, No. 4, pp. 429434, Jan. 1, 2008.

Spira, et al., "Prolonged Bleeding-Free Period Following Prophylactic Infusion of Recombinant Factor VIII Reconstituted with Pegylated Liposomes", Blood, vol. 108, No. 12, pp. 3668-3673, Jan. 1, 2006.

Srivastava et al., Treatment Guidelines Working Group on behalf of the World Federation of Hemophilia, Guidelines for the management of hemophilia, Haemophilia, 2013, 19(1): e1-47.

Srivastava et al., WFH Guidelines for the Management of Hemophilia, 3rd edition, Haemophilia. 2020, 26 Suppl 6: 1-158.

Srivastava, et al. (2005) "Application of Self-Assembled Ultra-Thin Film Coatings to Stabilize Macromolecule Encapsulation in Alginate Micro spheres", Journal of Microencapsulation, vol. 22, No. 4, pp. 397-411.

Srour, et al., "Modified Expression of Coagulation Factor VIII by Addition of a Glycosylation Site at the N Terminus of the Protein", Annals of Hematology, vol. 87, Issue 2, pp. 107-112, Feb. 1, 2008.

Staber et al., " Efanesoctocog alfa half-life and clearance are independent of von Willebrand factor (VWF) in severe hemophilia A: a post hoc analysis from Phase 1/2a studies", Abstract, Blood 2022 Congress: Sep. 11-14, 2022, Sydney.

Staber et al., " Efanesoctocog alfa half-life and clearance are independent of von Willebrand factor (VWF) in severe hemophilia A: a post hoc analysis from Phase 1/2a studies", Poster, Blood 2022 Congress: Sep. 11-14, 2022, Sydney.

Staber et al., "Efanesoctocog alfa Exhibits Von Willebrand Factor-Independent Pharmacokinetics in Severe Hemophilia A: A Post Hoc Analysis From Phase 1/2a Studies", Abstract, THSNA 2022 Summit Abstract Proceedings, American Journal of Hematology, E104.

Staber et al., "Efanesoctocog alfa Exhibits Von Willebrand Factor-Independent Pharmacokinetics in Severe Hemophilia A: A Post Hoc Analysis From Phase 1/2a Studies", Presentation Slides, THSNA 2022 Summit Abstract Proceedings, 14 pages.

Staber et al., "Efanesoctocog Alfa Half-Life and Clearance Are Independent of von Willebrand Factor in Severe Hemophilia A: A Post Hoc Analysis From Phase 1/2a Studies", 44th Congress of the Japanese Society on Thrombosis and Hemostasis, Jun. 23-25, 2022.

Staber et al., "Efanesoctocog Alfa Half-Life and Clearance Are Independent of von Willebrand Factor in Severe Hemophilia A: A Post Hoc Analysis From Phase 1/2a Studies", Efanesoctocog alfa half-life and VWF independence Abstract - Encore, NHF 2022 Congress: Aug. 25-27, 2022, Houston & Virtual.

Staber et al., "Efanesoctocog Alfa Half-Life and Clearance Are Independent of von Willebrand Factor in Severe Hemophilia A: A Post Hoc Analysis From Phase 1/2a Studies", Presentation Slides, NHF 7th Annual Bleeding Disorders Conference (BDC) 2022, Aug. 25-27, 2022.

Staber et al., "Efanesoctocog Alfa Half-Life and Clearance Are Independent of von Willebrand Factor in Severe Hemophilia A: A

(56) References Cited

OTHER PUBLICATIONS

Post Hoc Analysis From Phase 1/2a Studies", Presentation Slides, The 44th Congress of the Japanese Society on Thrombosis and Hemostasis, 13 pages.
Staber et al., "The 44th Congress of the Japanese Society on Thrombosis and Hemostasis: Abstract Submission Form", 2022.
Stamos, et al. (2004) "Crystal Structure of the HGF Beta-Chain in Complex with the Sema Domain of the Met Receptor", The EMBO Journal, vol. 23, No. 12, pp. 2325-2335.
Steipe, et al. (Jul. 15, 1994) "Sequence Statistics Reliably Predict Stabilizing Mutations in a Protein Domain", Journal of Molecular Biology, vol. 240, No. 3, pp. 188-192.
Stemmer, et al. (1995) "Single-Step Assembly of a Gene and Entire Plasmid from Large Nos. of Oligodeoxyribonucleotides", Gene, vol. 164, Number 1, pp. 49-53.
Stemmer, W. P. (1994) "Rapid Evolution of a Protein in Vitro by DNA Shuffling", Nature, vol. 370, No. 6488, pp. 389-0391.
Stennicke, et al., "Generation and Biochemical Characterization of Glycopegylated Factor VIIa Derivatives", Thrombosis and Haemostasis, vol. 100, No. 5, pp. 920-928, Jan. 1, 2008.
Stickler, et al. (2003) "Human Population-Based Identification of CD4+ T-Cell Peptide Epitope Determinants", Journal of Immunological Methods, vol. 281, No. 1-2, pp. 95-108.
Stieltjes, et al., "Continuous Infusion of B-Domain Deleted Recombinant factor VIII ReFacto) in Patients with Haemophilia a Undergoing Surgery: Clinical Experience", Haemophilia, vol. 10, Issue 5, pp. 452-458, Sep. 1, 2004.
Stites, et al. (1995) "Empirical Evaluation of the Influence of Side Chains on the Conformational Entropy of the Polypeptide Backbone", Proteins: Structure, Function, and Bioinformatics, vol. 22, No. 2, pp. 132-140.
Stoll, et al. (2000) "Mechanistic Analysis of Carrier-Mediated Oral Delivery of Protein therapeutics", Journal of Controlled Release, vol. 64, No. 1-3, pp. 217-228.
Strohl, Fusion Proteins for Half-Life Extension of Biologics as a Strategy to Make Biobetters. BioDrugs. 2015;29(4): 215-239.
Sturniolo, et al. (1999) "Generation of Tissue-Specific and Promiscuous HLA Ligand Database Using DNA Microarrays and Virtual HLA Class II Matrices", Nature Biotechnology, vol. 17, No. 6, pp. 555-561.
Subramani, et al. (1981) "Expression of the Mouse Dihydrofolate Reductase Complementary Deoxyribonucleic Acid in Simian Virus 40 Vectors", Molecular and Cellular Biology, vol. 1, No. 9, pp. 854-864.
Suetake, et al. (2000) "Chitin-Binding Proteins in Invertebrates and Plants Comprise a Common Chitin-Binding Structural Motif", the Journal of Biological Chemistry, vol. 275, No. 24, p. 17929-17932.
Suetake, et al. (2002) "Production and Characterization of Recombinant Tachycitin, the Cys-Rich Chitin-Binding Protein", Protein Engineering, vol. 15, No. 9, pp. 763-769.
Summers, et al. (1978) "Baculovirus Structural Polypeptides", Virology, vol. 84, No. 2, pp. 390-402.
Supplementary European Search Report received for European Patent Application No. 12868427 mailed on Sep. 18, 2015, 8 pages.
Tagalakis et al., The epidemiology of peripheral vein infusion thrombophlebitis: A critical review, Am J Med., 2002, 113(2): 146-51.
Takahashi, et al. (2000) "Solution Structure of Hanatoxin1, a Gating Modifier of Voltage-Dependent K (+) Channels: Common Surface Features of Gating Modifier Toxins", Journal of Molecular Biology, vol. 297, No. 3, pp. 771-780.
Takenobu, et al. (2002) "Development of P53 Protein Transduction Therapy Using Membrane-Permeable Peptides and the Application to oral Cancer Cells", Molecular Cancer therapeutics, vol. 1, No. 12, pp. 1043-1049.
Tam, et al. (1998) "A Biomimetic Strategy in the Synthesis and Fragmentation of Cyclic Protein", Protein Science, vol. 7, No. 7, pp. 1583-1592.
Tavladoraki, et al. (1999) "A Single-Chain Antibody Fragment is Functionally Expressed in the Cytoplasm of Both *Escherichia Coli* and Transgenic Plants", European Journal of Biochemistry/FEBS, vol. 262, No. 2, pp. 617-624.
Tax, et al. (1994) "Sequence of C. Elegans lag-2 Reveals a Cell-Signalling Domain Shared with Delta and Serrate of Drosophila", Nature, vol. 368, No. 6467, pp. 150-154.
Terpe, K. (2003) "Overview of Tag Protein Fusions: from Molecular and Biochemical Fundamentals to Commercial Systems", Applied Microbiology and Biotechnology, vol. 60, No. 5, pp. 523-533.
Terraube et al., "Factor VIII and Von Willebrand Factor Interaction: Biological, Clinical and Therapeutic Importance", Haemophilia, 16(1): 3-13.
Thai, et al. (2004) "Antigen Stability Controls Antigen Presentation", the Journal of Biological Chemistry, vol. 279, No. 48, pp. 50257-50266.
Thermo Scientific (2012) "Instructions: Imidoester Crosslinkers: DMA, DMP, Dms, DTBP", https://tools.thermofisher.com/content/sfs/manuals/MAN0011314_ImidoesterCrsLnk DMA_DMP_DMS_DTBP_UG.pdf, 2 Pages.
Thomas, Patrica S. (1980) "Hybridization of Denatured RNA and Small DNA Fragments Transferred to Nitrocellulose", Proceedings of the National Academy of Sciences vol. 77, No. 9, pp. 5201-5205.
Thompson, Structure and Function of the Factor VIII Gene and Protein, Thromb and Hemost., 2003, 29(1), pp. 11-22.
Thornburg et al., Treatment adherence in hemophilia, Patient Preference and Adherence, 2017,11: 1677-1686.
Tiede et al., Enhancing the pharmacokinetic properties of recombinant factor VIII: first-in-human trial of glycoPEGylated recombinant factor VIII in patients with hemophilia A, J Thromb Haemost., 2013, 11(4): 670-678.
Toby et al., Recombinant Factor IX Fc Fusion Protein Maintains Full Procoagulant Properties and Exhibits Prolonged Efficacy in Hemophilia B Mice, PLOS One, 2016, 11(2): e0148255.
Tolkatchev, et al. (2000) "Design and Solution Structure of a Well-Folded Stack of Two Beta-Hairpins Based on the Amino-Terminal Fragment of Human Granulin A", Biochemistry, vol. 39, No. 11, pp. 2878-2886.
Toole, et al. (Nov. 22-28, 1984) "Molecular Cloning of a cDNA Encoding Human Antihaemophilic Factor", Nature, vol. 312, No. 5992, pp. 342-347.
Torres, et al. (1999) "Solution Structure of a Defensin-Like Peptide from Platypus Venom", the Biochemical Journal, vol. 341, Part 3, pp. 785-794.
Towfighi, et al. (2005) "Comparative Measurement of Anti-Factor VIII Antibody by Bethesda Assay and ELISA Reveals Restricted Isotype Profile and Epitope Specificity", Acta Haematologica, vol. 4, No. 2, pp. 84-90.
Tuddenham, et al. (1982) "Response to Infusions of Polyelectrolyte Fractionated Human Factor VIII Concentrate in Human Haemophilia A and Von Willebrand's Disease", British Journal of Haematology, vol. 52, No. 2, pp. 259-267.
Tur, et al. (2003) "Novel Approach for Immunization, Screening and Characterization of Selected ScFv Libraries Using Membrane Fractions of Tumor Cells", International Journal of Molecular Medicine, vol. 11, No. 4, pp. 523-527.
Turacek et al., Structure and Function of a Recombinant von Willebrand Factor Drug Candidate, Seminars in Thrombosis and Hemostasis, 2010, 36(5): 510-521.
U.S. Appl. No. 14/466,567 to Schellenberger et al., filed Aug. 22, 2014 (Not Published).
U.S. Appl. No. 14/517,680 to Schellenberger et al., filed Oct. 17, 2014 (Not Published).
UNIPROTKB (Dec. 16, 2014) "ELNE_HUMAN", UniProtKB, Accession No. P08246; Retrieved from http://www.uniprot.org/uniprot/P08246, 19 Pages.
UNIPROTKB (Dec. 16, 2014) "FA10_HUMAN", UniProtKB, Accession No. P00742, Retrieved from https://www.uniprot.org/uniprot/P00742, 25 p.
UNIPROTKB (Dec. 16, 2014) "FA11_HUMAN", UniProtKB, Accession No. P03951, Retrieved from https://www.uniprot.org/uniprot/P03951, 22 Pages.
UNIPROTKB (Dec. 16, 2014) "FA12_HUMAN", UniProtKB, Accession No. P00748; Retrieved from https://www.uniprot.org/uniprot/P03951, 14 Pages.

(56) References Cited

OTHER PUBLICATIONS

UNIPROTKB (Dec. 16, 2014) "FA7_HUMAN", UniProtKB, Accession No. P08709, Retrieved from https://www.uniprot.org/uniprot/P08709, 27 Pages.
UNIPROTKB (Dec. 16, 2014) "FA9_HUMAN", UniProtKB, Accession No. P00740, 26 Pages.
UNIPROTKB (Dec. 16, 2014) "KLKB1_HUMAN", UniProtKB, Accession No. P03952; Retrieved from https://www.uniprot.org/uniprot/P03952, 11 Pages.
UNIPROTKB (Dec. 16, 2014) "MMP12_HUMAN", UniProtKB, Accession No. P39900, Retrieved from https://www.uniprot.org/uniprot/P39900, 12 Pages.
UNIPROTKB (Dec. 16, 2014) "MMP17_HUMAN", UniProtKB, Accession No. Q9ULZ9, Retrieved from https://www.uniprot.org/uniprot/Q9ULZ9, 11 Pages.
UNIPROTKB (Dec. 16, 2014) "MMP20 Human", UniProtKB, Accession No. O60882, Retrieved from https://www.uniprot.org/uniprot/O60882, 10 pages.
UNIPROTKB (Dec. 16, 2014) "THRB_HUMAN", accession No. P00734, accessed at http://www.uniprot.org/uniprot/P00734, 42 Pages.
UNIPROTKB (Dec. 16, 2014,) "MMP13_HUMAN", UniProtKB, Accession No. P45452; Retrieved from https://www.uniprot.org/uniprot/P45452, 15 Pages.
United Kingdom Haemophilia Centre Doctors' Organisation (UKHCDO), Ukhcdo Bleeding Disorder Statistics for 2010-2011, a report from the National Haemophila Database, 2011, Available at: http://www.ukhcdo.org/docs/AnnualReports/2011/LTKHCDO%20Bleeding%20Disord er%20Statistics%20for%202010-2011.pdf.
Urlaub, et al. (Jul. 1980) "Isolation of Chinese Hamster Cell Mutants Deficient in Dihydrofolate Reductase Activity", Proceedings of the National Academy of Sciences of the United States of America, vol. 77, No. 7, pp. 4216-4220.
Uttamapinant, et al. (Jun. 2010) "Fluorophore Ligase for Site-Specific Protein Labeling Inside Living Cells", Proceedings of the National Academy of Sciences, vol. 107, No. 24, pp. 10914-10919.
Uversky, et al. (2000) "Why Are "Natively Unfolded" Proteins Unstructured Under Physiologic Conditions?", Proteins: Structure, Function and Genetics, vol. 41, No. 3, pp. 415-427.
Vaccaro, et al., "Engineering the Fc Region of Immunoglobulin G to Modulate In Vivo Antibody Levels", Nature Biotechnology, vol. 23, No. 10, pp. 1283-1288, Oct. 1, 2005.
Valente, et al. (2006) "Optimization of the Primary Recovery of Human Interferon Alpha2B from *Escherichia Coli*Inclusion Bodies", Protein Expression and Purification, vol. 45, No. 1, pp. 226-234.
Valentino et al., A randomized comparison of two prophylaxis regimens and a paired comparison of on-demand and prophylaxis treatments in hemophilia A management, J Thromb Haemost., 2012,10(3):359-367.
Valjakka, et al. (1998) "Unreliability of the Chou-Fasman Parameters in Predicting Protein Secondary Structure", Protein Engineering, vol. 11, No. 5, pp. 345-348.
Van Den Hooven, et al. (2001) "Disulfide Bond Structure of the AVR9 Elicitor of the Fungal Tomato Pathogen Cladosporium Fulvum: Evidence for a Cystine Knot", Biochemistry, vol. 40, No. 12, pp. 3458-3466.
Van Genderen et al., Measuring patients' perceptions on their functional abilities: validation of the Haemophilia Activities List, Haemophilia Jan. 2006, 12(1):36-46.
Van Vlijmen, et al. (2004) "A Novel Database of Disulfide Patterns and Its Application to the Discovery of Distantly Related Homologs", Journal of Molecular Biology, vol. 335, No. 4, pp. 1083-1092.
Vanhercke, et al. (2005) "Reducing Mutational Bias in Random Protein Libraries", Analytical Biochemistry, vol. 339, No. 1, pp. 9-14.
Vardar, et al. (2003) "Nuclear Magnetic Resonance Structure of a Prototype Lin12-Notch Repeat Module from Human Notch1", Analytical Biochemistry, vol. 339, No. 1, pp. 7061-7067.
Vehar, et al. (Nov. 1984) "Structure of Human Factor VIII", Nature, vol. 312, No. 5992, pp. 337-342.

Venkatachalam, et al. (1969) "Conformation of Polypeptide Chains", Annual Review of Biochemistry, vol. 38, pp. 45-82.
Venkateswarlu, Divi (Feb. 25, 2010) "Structural Investigation of Zymogenic and Activated forms of Human Blood Coagulation Factor Viii: A Computational Molecular Dynamics Study", BMC Structural Biology vol. 10, Article No. 7, 20 Pages.
Venkateswarlu, Structural Insights Into The Interaction Of Blood Coagulation Co-Factor Villa with factor IXa: A Computational Protein-Protein Docking And Molecular Dynamics, 2014, Sep. 26, pp. 408-414.
Ventura, S. (2005) "Sequence Determinants of Protein Aggregation: Tools to Increase Protein Solubility", Microbial Cell Factories, vol. 4, No. 1, 11 Pages.
Verbruggen, et al. (1995) "the Nijmegen modification of the Bethesda assay for factor VIII:C inhibitors: improved specificity and reliability", Journal of Thrombosis and Haemostasis, vol. 73, No. 2, pp. 247-251.
Verbruggen, et al. (Nov. 2009) "Improvements in Factor VIII Inhibitor Detection: From Bethesda to Nijmegen", Seminars in Thrombosis and Hemostasis, vol. 35, No. 8, pp. 752-759.
Vestergaard-Bogind, et al. (1985) "Single-File Diffusion Through the Ca2+- Activated K+ Channel of Human Red Cells", the Journal of Membrane Biology, vol. 88, No. 1, pp. 67-75.
Viel KR, Ameri A, Abshire TC, Iyer RV, Watts RG, Lutcher C, et al. Inhibitors of factor VIII in black patients with hemophilia. N Engl J Med. 2009;360(16): 1618-27.
Voisey, et al. (2002) "Agouti: from Mouse to Man, from Skin to Fat", Pigment Cell Research Sponsored by the European Society for Pigment Cell Research and the International Pigment Cell Society, vol. 15, No. 1, pp. 10-18.
Von Drygalski et al., "Change in Hemophilia Joint Health Score (HJHS) During the Phase 3 XTEND-1 Study of Efanesoctocog Alfa in Patients with Severe Hemophilia A", Eahad Oral Presentation Script, 16th Annual Congress of the European Association for Haemophilia and Allied Disorders, Feb. 7-10, 2023.
Von Drygalski et al., "Change in Hemophilia Joint Health Score (HJHS) During the Phase 3 XTEND-1 Study of Efanesoctocog Alfa in Patients with Severe Hemophilia A", Presentation Slides, 16th Annual Congress of the European Association for Haemophilia and Allied Disorders, Feb. 7-10, 2023.
Von Drygalski et al., "Consensus on Outcomes of Physical Functional and Activites for Persons with Haemophilia: Results from the IPOP Study", Haemophilia, 2023, 14-15.
Von Drygalski et al., "Efanesoctocog Alfa Prophylaxis for Patients with Severe Hemophilia A", The New England Journal of Medicine, Jan. 26, 2023, 388(4): 310-318.
Von Drygalski et al., "Efficacy, Safety, and Pharmacokinetics of Once-Weekly Efanesoctocog Alfa (BIVV001) Prophylaxis in Previously Treated Patients With Severe Hemophilia A: Results From the Phase 3 XTEND-1 Study", Abstract, ISTH 2022 Congress Meeting, 3 pages.
Von Drygalski et al., "Efficacy, Safety, and Pharmacokinetics of Once-Weekly Efanesoctocog Alfa (BIVV001) Prophylaxis in Previously Treated Patients With Severe Hemophilia A: Results From the Phase 3 XTEND-1 Study", Presentation Slides, ISTH 2022 Congress Meeting, London, England, 16 pages.
Von Mackensen S, Gringeri A & the Haem-A-QoL study Group. Health-related Quality of Life in Adult Patients with Haemophilia - Assessment with a New Disease- specific Questionnaire (Haem-A-QoL). Journal Of Thrombosis and Haemostasis. 2005;3(Sup1):P0813.
Vorobjev, et al. (November-Dec. 1999) "Oligonucleotide Conjugated to Linear and Branched High Molecular Weight Polyethylene Glycol as Substrates for RNase H", Nucleosides and Nucleotides, vol. 18, No. 11-12, pp. 2745-2750.
Vranken, et al. (1999) "A 30-Residue Fragment of the Carp Granulin-1 Protein Folds into a Stack of Two Beta-Hairpins Similar to That Found in the Native Protein", the Journal of Peptide Research: official Journal of the American Peptide Society, vol. 53, No. 5, pp. 590-597.
Wagenvoord, et al. (1989) "Development of a Simple Chromogenic Factor VIII Assay for Clinical Use", Haemostasis, vol. 19, No. 4, pp. 196-204.

(56) References Cited

OTHER PUBLICATIONS

Walker, et al. (2003) "Using Protein-Based Motifs to Stabilize Peptides", the Journal of Peptide Research, vol. 62, No. 5, pp. 214-226.

Wang, et al. (1988) "Parenteral formulations of Proteins and Peptides: Stability and Stabilizers", Journal of Parenteral Science and Technology, vol. 42, pp. S2-S24.

Wang, et al. (1999) "Structure-Function Studies of Omega-Atracotoxin, a Potent Antagonist of Insect Voltage-Gated Calcium Channels", European Journal of Biochemistry/ FEBS, vol. 264, No. 2, pp. 488-494.

Ward, et al. (Apr. 1995) "the Effector Functions of Immunoglobulins: Implications for therapy", therapeutic immunology, vol. 2, No. 2, pp. 77-94.

Ward, et al. (Oct. 12, 1989) "Binding Activities of a Repertoire of Single Immunoglobulin Variable Domains Secreted from Escherichia coli", Nature, vol. 341, No. 6242, pp. 544-546.

Wasley, et al. (Apr. 25, 1993) "PACE/Furin can Process the Vitamin K-Dependent Pro-Factor IX Precursor within the Secretory Pathway", the Journal of Biological Chemistry, vol. 268, No. 12, pp. 8458-8465.

Watters, et al. (1997) "An Optimized Method for Cell-Based Phage Display Panning", Immunotechnology, vol. 3, No. 1, pp. 21-29.

Weimer, et al. (Apr. 2008) "Prolonged In-Vivo Half-Life of Factor Vlla by Fusion to Albumin", Thrombosis and Haemostasis, vol. 99, No. 04, pp. 659-667.

Weiss, et al. (1977) "Stabilization of Factor VIII in Plasma by the Von Willebrand Factor: Studies on Posttransfusion and Dissociated Factor Viii and In Patients with Von Willebrand's Disease", the Journal of Clinical Investigation, vol. 60, No. 2, pp. 390-404.

Weiss, et al. (1995) "A Cooperative Model for Receptor Recognition and Cell Adhesion: Evidence from the Molecular Packing In the 1.6-A Crystal Structure of the Pheromone Er-1 from the Ciliated Protozoan Euplotes Raikovi", Proceedings of the National Academy of Sciences of the United States of America, vol. 92, No. 22, p. 10172-10176.

Wentzel, et al. (1999) "Sequence Requirements of the GPNG Beta-Turn of the Ecballium Elaterium Trypsin Inhibitor Ii Explored by Combinatorial Library Screening", the Journal of Biological Chemistry, vol. 274, No. 30, pp. 21037-21043.

Werle, et al. (2006) "the Potential of Cystine-Knot Microproteins As Novel Pharmacophoric Scaffolds in Oral Peptide Drug Delivery", Journal of Drug Targeting, vol. 14, No. 3, pp. 137-146.

Werther, et al. (1996) "Humanization of An Anti-Lymphocyte Function-associated Antigen (LFA)-1 Monoclonal Antibody and Reengineering of the Humanized Antibody for Binding to Rhesus Lfa-1", Journal of Immunology, vol. 157, No. 1, pp. 4986-4995.

Weyand et al., "Treatment of Bleeding Episodes with Efanesoctocog Alfa in Patients with Severe Haemophilia A in the Phase 3 XTEND-1 Study", Abstract, Haemophilia, 136-137.

Weyand et al., "Treatment of Bleeding Episodes with Efanesoctocog Alfa in Patients with Severe Haemophilia A in the Phase 3 XTEND-1 Study", Poster, 16th Annual Congress of the European Association for Haemophilia and Allied Disorders, Feb. 7-10, 2023.

White et al., A multicenter study of recombinant factor VIII (Recombinate) in previously treated patients with hemophilia A, The Recombinate Previously Treated Patient Study Group, Thromb Haemost., 1997, 77(4): 660-667.

White, et al. (1989) "Factor VIII Gene and Hemophilia A", Blood, vol. 73, No. 1, pp. 1-12.

Whitlow, et al. (1994) "Multivalent Fvs: Characterization of Single-Chain Fv Oligomers and Preparation of a Bispecific Fv", Protein Engineering, vol. 7, No. 8, pp. 1017-1026.

Wigler, et al. (Jul. 1978) "Biochemical Transfer of Single-Copy Eucaryotic Genes Using Total Cellular DNA As Donor", Cell, vol. 14, No. 3, pp. 725-731.

Williams, What Are Platelets and Why Are They Important? Johns Hopkins Medicine, Obtained from url: https:// www.hopkinsmedicine. org/health/conditions- and-diseases/what-are-platelets-and-why-are-they-important. (Year: 2010).

Wilson et al., "Impact of Efanesoctocog Alfa Prophylaxis on Pain in Previously Treated Patients with Hemophilia A: Results from the XTEND-1 Phase 3 Study", Abstract, HTRS Mar. 10-12, 2023, Orlando, Florida.

Wilson et al., "Impact of Efanesoctocog Alfa Prophylaxis on Pain in Previously Treated Patients with Hemophilia A: Results from the XTEND-1 Phase 3 Study", Poster, HTRS Mar. 10-12, 2023, Orlando, Florida.

Wilson et al., "Efficacy of Efanesoctocog Alfa on Physical Functioning: Results From the XTEND-1 Phase 3 Clinical Trial in Previously Treated Patients With Hemophilia A", Abstract, HTRS Mar. 10-12, 2023, Orlando, Florida, 5 pages.

Wilson et al., "Efficacy of Efanesoctocog Alfa on Physical Functioning: Results From the XTEND-1 Phase 3 Clinical Trial in Previously Treated Patients With Hemophilia A", Presentation Slides, HTRS Mar. 10-12, 2023, Orlando, Florida, 14 Pages.

Winter, et al. (Jun. 1, 1993) "Humanized Antibodies", Immunology Today, vol. 14, No. 6, pp. 243-246.

Witmer et al., Associations between intracranial haemorrhage and prescribed prophylaxis in a large cohort of haemophilia patients in the United States, Br J Haematol., 2011, 152(2): 211-216.

Witmer et al., Factor VIII inhibitors in hemophilia A: rationale and latest evidence. TherAdv Hematol., 2013;4(1): 59-72.

Wittrup, K. D. (2001) "Protein Engineering by Cell-Surface Display", Current Opinion in Biotechnology, vol. 12, No. 4, pp. 395-399.

Wood, et al. (Nov. 22-28, 1984) "Expression of Active Human Factor VIII from Recombinant DNA Clones", Nature, vol. 312, No. 5992, pp. 330-337.

Woof, et al. (Feb. 2004) "Human Antibody-Fc Receptor Interactions Illuminated by Crystal Structures", Nature Reviews Immunology, vol. 4, pp. 89-99.

World Federation of Haemophilia (WFH), World Federation of Hemophilia Report on the Annual Global Survey 2010, Montreal, Quebec: World Federation of Hemophilia, Dec. 2011.

World Federation of Hemophilia, World Federation of Hemophilia Report on the Annual Global Survey 2017. Montreal, Quebeck: World Federation of Hemophilia, Oct. 2018. Available at: http://www1.wfh/org/publications/files/pdf-1714.pdf.

World Health Organization (Who), Who Handbook for Reporting Results of Cancer Treatment, Geneva, 1979, Available at: http://apps.who.int/iris/bitstream/10665/37200/1/WHO_OFFSET_48.pdf.

Worn, et al. (2000) "Correlation Between In Vitro Stability and In Vivo Performance of Anti-Gcn4 Intrabodies As Cytoplasmic Inhibitors", the Journal of Biological Chemistry, vol. 275, No. 4, pp. 2795-2803.

Worn, et al. (2001) "Stability Engineering of Antibody Single-Chain Fv Fragments", Journal of Molecular Biology, vol. 305, No. 5, pp. 989-1010.

Wrammert, et al. (May 2008) "Rapid Cloning of High-Affinity Human Monoclonal Antibodies Against Influenza Virus", Nature, vol. 453, No. 7195, pp. 667-671.

Wright, et al. (1999) "Intrinsically Unstructured Proteins: Re-Assessing the Protein Structure- Function Paradigm", Journal of Molecular Biology, vol. 293, No. 2, pp. 321-331.

Wu et al., Pharmacokinetics of Peptide-Fc fusion proteins, J Pharm Sci., 2014, 103(1): 53-64.

Xia et al., "A Physiologically Based Pharmacokinetic (PBPK) Model to Characterize BIVV001 Activity, A New Class of Factor VIII (FVIII) With High Sustained Factor Activity", Poster, 14th Annual Congress of the European Association for Haemophilia and Allied Disorders, Feb. 3-5, 2021, 4 pages.

Xiong, et al. (2004) "A Novel Adaptation of the Integrin Psi Domain Revealed from Its Crystal Structure", the Journal of Biological Chemistry, vol. 279, No. 39, pp. 40252-40254.

Xu, et al. (2000) "Solution Structure of Bmp02, A New Potassium Channel Blocker from the Venom of the Chinese Scorpion Buthus Martensi Karsch", Biochemistry, vol. 39, No. 45, p. 13669-13675.

Xyntha [package insert], Philadelphia, PA: Wyeth Pharmaceuticals Inc, 2015.

(56) References Cited

OTHER PUBLICATIONS

Yamazaki, et al. (2003) "A Possible Physiological Function and the Tertiary Structure of a 4-Kda Peptide in Legumes", European Journal of Biochemistry / FEBS, vol. 270, No. 6, pp. 1269-1276.
Yang, et al. (1995) "CDR Walking Mutagenesis for the Affinity Maturation of a Potent Human Anti-Hiv-1 Antibody into the Picomolar Range", Journal of Molecular Biology, vol. 254, No. 3, pp. 392-403.
Yang, et al. (1999) "Intestinal Peptide Transport Systems and oral Drug Availability", Pharmaceutical Research, vol. 16, No. 9, pp. 1331-1343.
Yang, et al. (2003) "Tailoring Structure-Function and Pharmacokinetic Properties of Single-Chain Fv Proteins by Site-Specific PEGylation", Protein Engineering, vol. 16, No. 10, pp. 761-770.
Yang, et al. (2005) "RONN: The Bio-Basis Function Neural Network Technique Applied to the Detection of Natively Disordered Regions in Proteins", Bioinformatics, vol. 21, No. 16, pp. 3369-3376.
Yankai, et al. (2006) "Ten Tandem Repeats of ß-hCG 109-118 Enhance Immunogenicity and Anti-Tumor Effects of B-hCG C-Terminal Peptide Carried by Mycobacterial Heat-Shock Protein HSP65", Biochemical and Biophysical Research Communications, vol. 345, No. 4, pp. 1365-1371.
Yee et al., A von Willebrand factor fragment containing the D'D3 domains is sufficient to stabilize coagulation factor VIII in mice, Blood, 2014, 124(3): 445-452.
Yoon, et al., NF-KB and STAT3 Cooperatively Induce IL6 in Starved Cancer Cells, Oncogene, vol. 31, No. 29, pp. 3467-3481, 2011.
Yuan, et al. (1997) "Solution Structure of the Transforming Growth Factor Beta- Binding Protein-Like Module, a Domain Associated with Matrix Fibrils", the EMBO, Journal 16, No. 22, pp. 6659-6666.
Yuen et al., A long-acting human growth hormone with delayed clearance (VRS- 317): results of a double-blind, placebo-controlled, single-ascending dose study in growth hormone-deficient adults, J Clin Endocrinol Metab., 2013, 98(6): 2595-2603.
Zambidis et al., Epitope-specific tolerance induction with an engineered immunoglobulin, Proc Natl Acad Sci USA. 1996; 93(10): 5019-5024.
Zapotocka, et al. "First experience of a hemophilia monitoring platform: florio HAEMO", Thromb Haemost. 2022, 6(e12685).
Zaveckas, et al. (Jun. 1, 2007) "Effect of Surface Histidine Mutations and their No. on the Partitioning and Refolding of Recombinant Human Granulocyte- Colony Stimulating Factor (Cys17ser) in Aqueous Two-Phase Systems Containing Chelated Metal Ions", Journal of Chromatography B, vol. 852, Issues 1-2, pp. 409-419.
Zhang, Design Of FRET-Based GFP Probes For Detection Of Protease Inhibitors, 2004, Oct. 15, pp. 674-678.
Zhang, et al. (Oct. 2009) "Factor VIII Inhibitors: Risk Factors and Methods for Prevention and Immune Modulation", Clinical Reviews in Allergy & Immunology, vol. 37, Issue 2, pp. 114-124.
Zhou JY, et al. Joint Bleeding Tendencies in Adult Patients With Hemophilia: It's Not All Pharmacokinetics. Clin Appl Thromb Hemost., 2019;25:1076029619862052.
Zhou, et al. (Jul. 12, 2012) "Sequence and Structure Relationships within Von Willebrand Factor", Blood, vol. 120, No. 2, pp. 449-458.
Zhou, et al. (Jun. 2005) "Procoagulant Stimulus Processing by the Intrinsic Pathway of Blood Plasma Coagulation", Biomaterials, vol. 26, Issue 16, pp. 2965-2973.
Zhu, et al. (Sep. 1999) "Molecular Cloning and Sequencing of Two 'Short Chain' and Two 'Long Chain' K (+) Channel-Blocking Peptides from the Chinese Scorpion Buthus Martensii Karsch", FEBS Letters, vol. 457, No. 3, pp. 509-514.
Zmachinsky, "Modern approaches to treatment of hemophilia", Meditsinskie novosti (Medical news), 2013, 3: 28-30. https://cyberleninka.ru/article/n/covremennye-podhody-k-lecheniyu-gemofilii/viewer.
Zucker et al., The In Vitro Association of Antihemophilic Factor and von Willebrand Factor, Thromb Haemostas, 1983, 49(1): 37-41.

U.S. Appl. No. 13/365,166, 2013/0017997, filed Aug. 19, 2011, Jan. 17, 2013, Volker Schellen-Berger, Factor VIII Compositions and Methods of Making and Using Same.
U.S. Appl. No. 13/423,031, 2012/0178691, filed Aug. 19, 2011, Jul. 12, 2012, Volker Schellen-Berger, Factor VIII Compsitions and Methods of making and Using Same.
U.S. Appl. No. 17/097,978, filed Nov. 13, 2020, Volker Schellen-Berger. Factor VIII C
U.S. Appl. No. 17/826,932, 2023/0011438, filed May 27, 2022, Ekta Seth Chhabra, Chimeric Factor VIII Polypeptides and Uses Thereof.
U.S. Appl. No. 14/379,192, 2016/0158929, U.S. Pat. No. 10,421,798, filed Feb. 20, 2015, Jun. 11, 2015, Sep. 24, 2019, Volker Schellen-Berger, Factor VIII Compositions and Methods of Making and Using Same.
U.S. Appl. No. 14/894,108, 2016/0251408, filed May 3, 2016, Sep. 1, 2016, Ekta Seth Chhabra, Thrombin Cleavable Linker with XTEND and Its Uses Thereof.
U.S. Appl. No. 18/358,601, 2024/0083875, filed Jul. 25, 2023, Mar. 14, 2024, Ekta Seth Chhabra, Thrombin Cleavable Linker with XTEND and Its Uses Thereof.
U.S. Appl. No. 14/430,848, 2015/0252345, filed Sep. 25, 2013, Sep. 10, 2015, Glenn Pierce, Methods Of Using Fix Plypeptides.
U.S. Appl. No. 15/619,196, 2018/0002684, filed Jun. 9, 2017, Jan. 4, 2018, Jan. 18, 2022, Glenn Pierce, Methods Of Using Fix Polypeptides.
U.S. Appl. No. 13/513,424, 2013/0108629, U.S. Pat. No. 9,050,318, filed Dec. 28, 2012, May 2, 2013, Jun. 9, 2015, Jennifer A. Dumont, Factor VIII-FC Chimeric And Hybrid Polypeptides, And Methods Of Use Thereof.
U.S. Appl. No. 13/793,783, 2013/0274194, U.S. Pat. No. 9,241,978, filed Mar. 11, 2013, Oct. 17, 2013, Jan. 26, 2016, Jennifer A. Dumont, Factor VIII-FC Chimeric And Hybrid Polypeptides, And Methods Of Use Thereof.
U.S. Appl. No. 16/270,302, 2019/0262429, U.S. Pat. No. 11,266,720 filed Feb. 7, 2019, Aug. 29, 2019, Mar. 8, 2022, Jennifer A. Dumont, Factor VIII-FC Chimeric And Hybrid Polypeptides, And Methods Of Use Thereof.
U.S. Appl. No. 17/587,941, 2022/0265780, filed Jan. 28, 2022, Aug. 25, 2022, Jennifer A. Dumont, Factor VIII-FC Chimeric And Hybrid Polypeptides, And Methods of Use Thereof.
U.S. Appl. No. 13/809,276, 2013/0202595, U.S. Pat. No. 9,670,475, filed Jul. 11, 2011, Aug. 8, 2013, Jun. 6, 2017, Glenn Pierce, Factor IX Polypeptides and Methods of Use Thereof.
U.S. Appl. No. 13/793,796, 2013/0171175, U.S. Pat. No. 9,233,145, filed Mar. 11, 2013, Jul. 4, 2013, Jan. 12, 2016, Glenn Pierce, Factor IX Polypeptides and Methods of Use Thereof.
U.S. Appl. No. 14/982,934, 2016/0257943, U.S. Pat. No. 9,867,973, filed Dec. 29, 2015, Sep. 8, 2016, Jan. 16, 2018, Glenn Pierce, Factor IX Polypeptides and Methods of Use Thereof.
U.S. Appl. No. 15/043,457, 2016/0243206, U.S. Pat. No. 9,629,903 filed Feb. 12, 2016. Aug. 25, 2016, Apr. 25, 2017, Glenn Pierce, Factor IX Polypeptides and Methods of Use Thereof.
U.S. Appl. No. 15/043,445, 2016/0346365, U.S. Pat. No. 9,675,676 filed Feb. 12, 2016, Dec. 1, 2016, Jun. 13, 2017, Glenn Pierce, Factor IX Polypeptides and Methods of Use Thereof.
U.S. Appl. No. 15/043,455, 2016/0166657, U.S. Pat. No. 9,623,091, filed Feb. 12, 2016, Jun. 16, 2016, Apr. 18, 2017, Glenn Pierce, Factor IX Polypeptides and Methods of Use Thereof.
U.S. Appl. No. 15/820,080, 2018/0207244 Abandoned, filed Nov. 21, 2017, Jul. 26, 2018, Glenn Pierce, Factor IX Polypeptides and Methods of Use Thereof.
U.S. Appl. No. 15/890,284, 2018/0228878, U.S. Pat. No. 10,561,714, filed Feb. 6, 2018, Aug. 16, 2018, Feb. 18, 2020, Glenn Pierce, Factor IX Polypeptides and Methods of Use Thereof.
U.S. Appl. No. 15/790,290, 2018/0132205 Abandoned, filed Feb. 6, 2018, May 10, 2018, Glenn Pierce, Factor IX Polypeptides and Methods of Use Thereof.
U.S. Appl. No. 16/271,686, 2019/0192640, U.S. Pat. No. 10,658,943, filed Feb. 8, 2019, Jun. 27, 2019, Feb. 25, 2020, Glenn Pierce, Factor IX Polypeptides and Methods of Use Thereof.
U.S. Appl. No. 16/271,689, 2019/0192641, U.S. Pat. No. 10,548,954, filed Feb. 8, 2019, Jun. 27, 2019, Feb. 4, 2020, Glenn Pierce, Factor IX Polypeptides and Methods of Use Thereof.

(56) References Cited

OTHER PUBLICATIONS

U.S. Appl. No. 16/907,985, 2021/0008178, filed Jun. 22, 2020, Jan. 14, 2021, Glenn Pierce, Factor IX Polypeptides and Methods of Use Thereof.
U.S. Appl. No. 17/032,354, 2021/0023185, U.S. Pat. No. 10,898,554, filed Sep. 25, 2020, Jan. 28, 2021, Jan. 26, 2021, Glenn Pierce, Factor IX Polypeptides and Methods of Use Thereof.
U.S. Appl. No. 13/365,166, 2013/0017997, filed Aug. 19, 2011, Jan. 17, 2013, Volks Schellen-Berger, Factor VIII Compositions And Methods Of Making and Using Same.
U.S. Appl. No. 13/423,031, 2012/0178691, filed Aug. 19, 2011, Jul. 12, 2012, Volker Schellen-Berger, Factor VIII Compositions And Methods Of Making And Using Same.
U.S. Appl. No. 14/317,888, 2015/0038421, filed Aug. 19, 2011, Feb. 5, 2015, Volker Schellen-Berger, Factor VIII Compositions And Methods Of Making And Using Same.
U.S. Appl. No. 15/163,561, 2016/0376344, filed Aug. 19, 2011, Dec, 29, 2016, Volker Schellen-Berger, Factor VIII Compositions And Methods Of Making And Using Same.
U.S. Appl. No. 16/369,820, 2019/0315835, filed Mar. 29, 2019, Oct. 17, 2019, Volker Schellen-Berger, Factor VIII Compositions And Methods Of Making And Using Same.
U.S. Appl. No. 17/097,978, filed Nov. 13, 2020, Volker Schellen-Berger, Factor VIII Compositions And Methods Of Making And Using Same.
U.S. Appl. No. 17/240,351, 2023/0019286, filed Apr. 26, 2021, Jan. 19, 2023, Volker Schellen-Berger, Factor VIII Compositions And Methods Of Making And Using Same.
U.S. Appl. No. 14/371,948, 2015/0023959, filed Jul. 11, 2014, Jan. 22, 2015, Ekta Seth Chhabra, Chimeric Factor VIII Polypeptides And Uses Thereof.
U.S. Appl. No. 16/357,189, filed Mar. 18, 2019, Ekta Seth Chhabra, Chimeric Factor VIII Polypeptides And Uses Thereof.
U.S. Appl. No. 17/826,932, 2023/0011438, Ekta Seth Chhabra, Chimeric Factor VIII Polypeptides And Uses Thereof.
U.S. Appl. No. 14/379,192, 2015/0158929, U.S. Pat. No. 10,421,798, filed Feb. 20, 2015, Jun. 11, 2015, Sep. 24, 2019, Volker Schellen-Berger, Factor VIII Compositions And Methods Of Making And Using Same.
U.S. Appl. No. 16/521,789, 2020/0087379, filed Jul. 25, 2019, Mar. 19, 2020, Volker Schellen-Berger, Factor VIII Compositions And Methods Of Making And Using Same.
U.S. Appl. No. 18/064,571, 2023/0322900, filed Dec. 12, 2022, Oct. 12, 2023, Volker Schellen-Berger, Factor VIII Compositions And Methods of Making and Using Same.
U.S. Appl. No. 14/413,765, 2015/0266943, U.S. Pat. No. 10,138,291, filed Jan. 9, 2015, Sep. 24, 2015, Nov. 27, 2018, Ekta Seth Chhabra, Factor VIII Complex With XTEN and Von Willebrand Factor Protein, And Uses Thereof.
U.S. Appl. No. 16/154,310, 2019/0169267, U.S. Pat. No. 11,091,534, filed Oct. 8, 2018, Jun. 6, 2019, Aug. 17, 2021, Ekta Seth Chhabra, Factor VIII Complex With XTEN And Von Willebrand Factor Protein, And Uses Thereof.
U.S. Appl. No. 17/358,142, 2022/0056108, filed Jun. 25, 2021, Feb. 24, 2022, Ekta Seth Chhabra, Factor VIII Complex With XTEN And Von Willebrand Factor Protein, And Uses Thereof.
U.S. Appl. No. 14/430,848, 2015/0252345, filed Sep. 25, 2013, Sep. 10, 2015, Glenn Pierce, Methods Of Using Fix Polypeptides.
U.S. Appl. No. 15/619,196, 2018/0002684, U.S. Pat. No. 11,225,650, filed Jun. 9, 2017, Jan. 4, 2018, Jan. 18, 2022, Glenn Pierce, Methods Of Using Fix Polypeptides.
U.S. Appl. No. 17/378,200, 2022/0064622, filed Jul. 16, 2021, Mar. 3, 2022, Glenn Pierce, Methods Of Using Fix Polypeptides.
U.S. Appl. No. 14/895,264, 2016/0229903, filed Dec. 2, 2015, Aug. 11, 2016, Ekta Seth Chhabra, Thrombin Cleavable Linker.
U.S. Appl. No. 14/894,108, 2016/02541408, filed May 3, 2016, Sep. 1, 2016, Ekta Seth Chhabra, Thrombin Cleavable Linker With XTEN And Its Uses Thereof.
U.S. Appl. No. 17/479,705, 2022/0106383, filed Sep. 20, 2021, Apr. 7, 2022, Ekta Seth Chhabra, Thrombin Cleavable Linker With XTEN and Its Uses Thereof.
U.S. Appl. No. 18/358,601, 2024/0083875, filed Jul. 25, 2023, Mar. 14, 2024, Ekta Seth Chhabra, Thrombin Cleavable Linker With XTEN and Its Uses Thereof.
U.S. Appl. No. 15/110,673, 2017/0073393, U.S. Pat. No. 11,192,936, filed Jul. 8, 2016, Mar. 16, 2017, Dec. 7, 2021, Ekta Seth Chhabra, Factor VIII Chimeric Proteins And Uses Thereof.
U.S. Appl. No. 17/519,719, 2022/0275057, filed Nov. 5, 2021, Sep. 1, 2022, Ekta Seth Chhabra, Factor VIII Chimeric Proteins And Uses Thereof.
*U.S. Appl. No. 17/217,752, 2022/0010347, filed Mar. 30, 2021, Jan. 13, 2022, Bettina Strack-Logue, Methods Of Treating Hemophilic Arthropathy Using CHimeric Clotting Factors.
U.S. Appl. No. 16/415,893, 2019/0375822, filed May 17, 2019, Dec. 12, 2019, Ekta Seth Chhabra, Methods Of Treating Hemophilia A.
U.S. Appl. No. 18/322,159, filed May 23, 2023, Ekta Seth Chhabra. Methods Of Treating Hemophilia A.
U.S. Appl. No. 18/656,168, filed May 6, 2024, Ekta Seth Chhabra, Methods of Treating Hemophilia A.
U.S. Appl. No. 18/572,006, filed Jun. 23, 2022, Tyler Carlage, Formulations Of Factor VIII Chimeric Proteins And Uses Thereof.
Ducore et al., "Alprolix (recombinant Factor IX Fc fusion protein): extended half-life product for the prophylaxis and treatment of hemophilia B", Expert Rev Hemat., Oct. 2014, 7(5): 559-571.
Van Hlyckama Vlieg et al., "High levels of factor IX increase the risk of venous thrombosis", Blood, Jun. 15, 2000, 95(12): 3678-3682.
Wyseure et al., "Advances and challenges in hemophilic arthropathy", Seminars in Hematology, Jan. 2016, 53(1): 10-19.

* cited by examiner

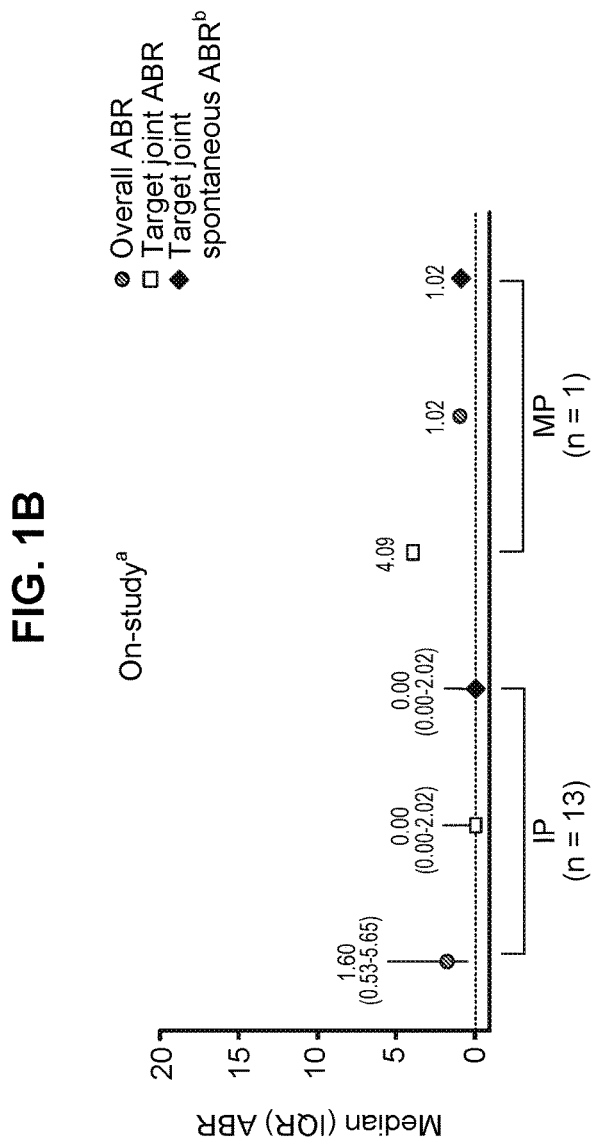
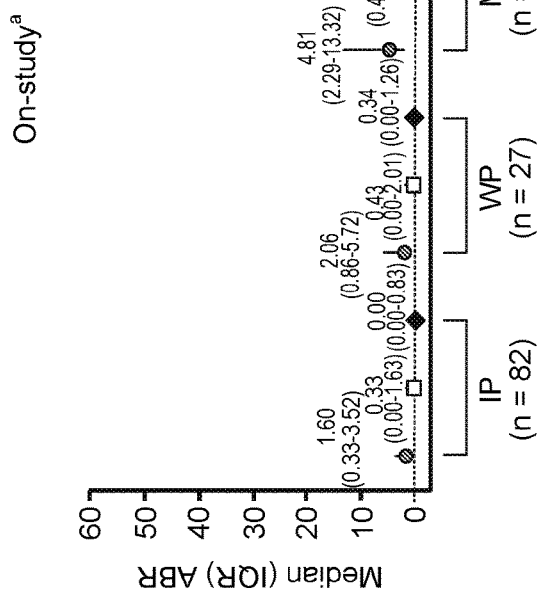
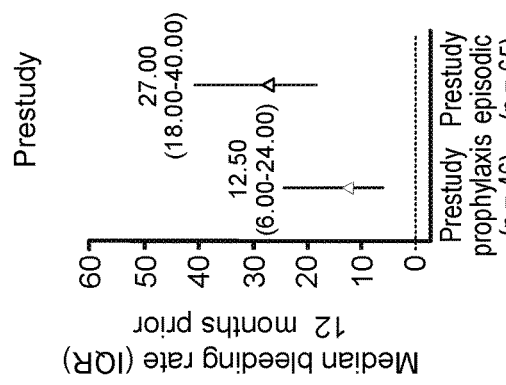
FIG. 1A  FIG. 1B  FIG. 1C  FIG. 1D

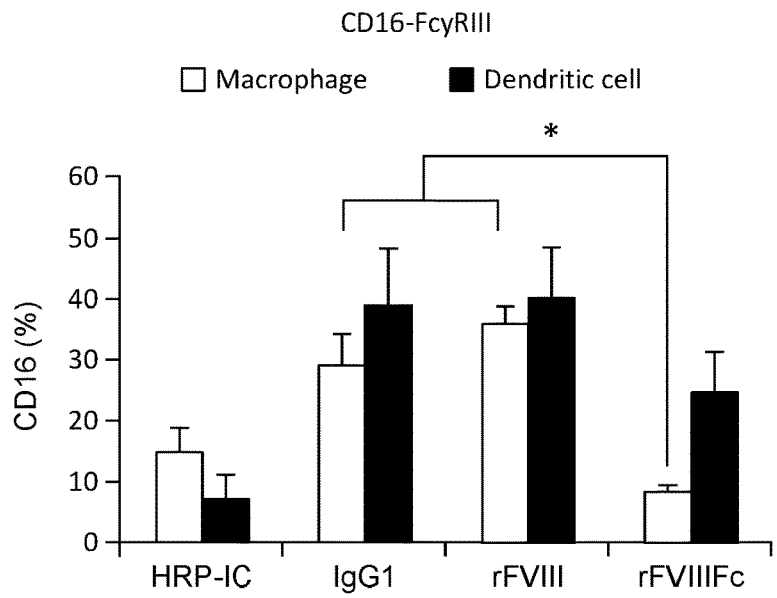
FIG. 17A
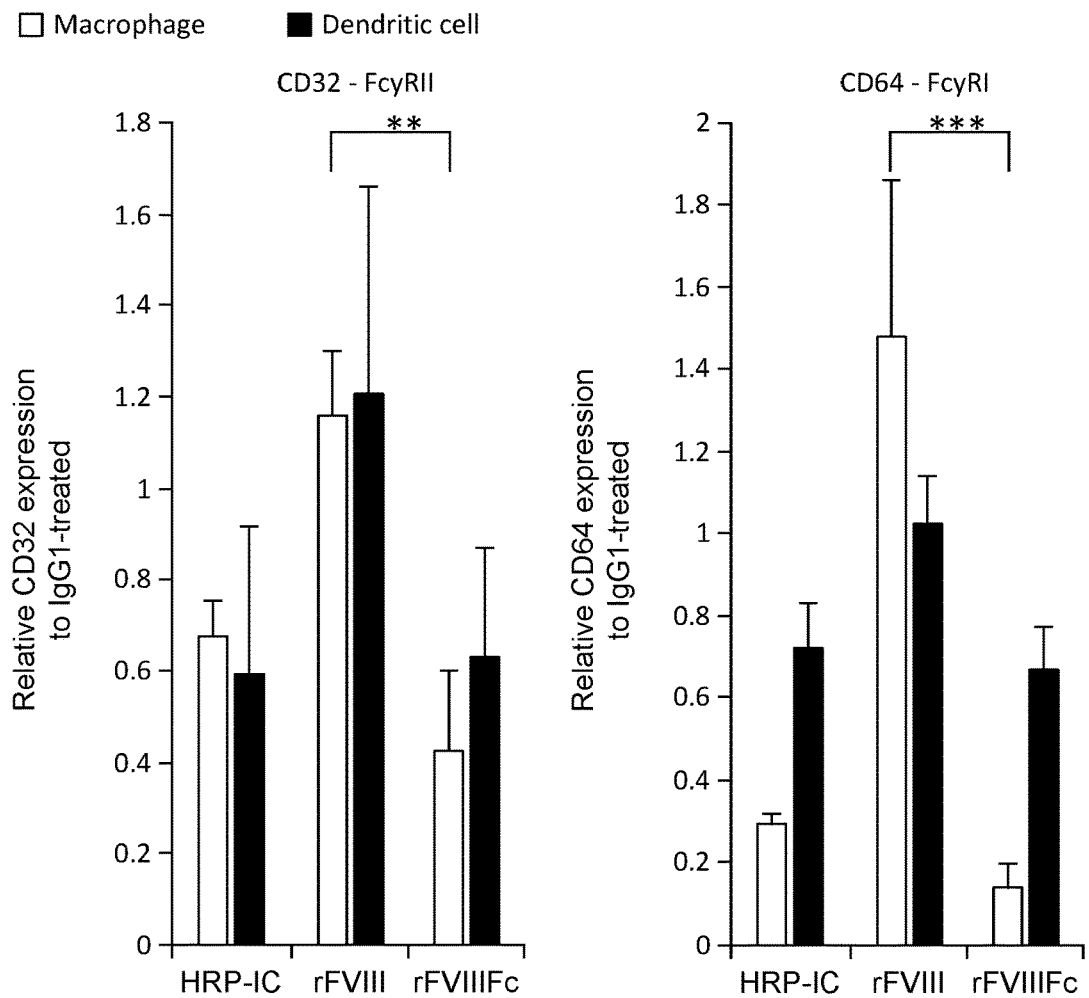
FIG. 17B
FIG. 17C

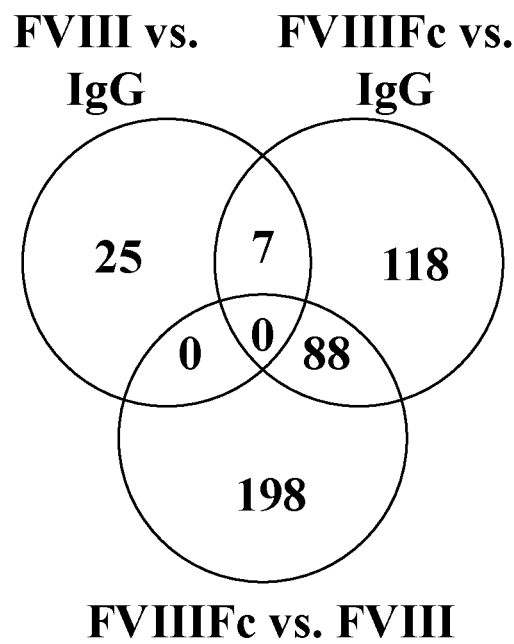
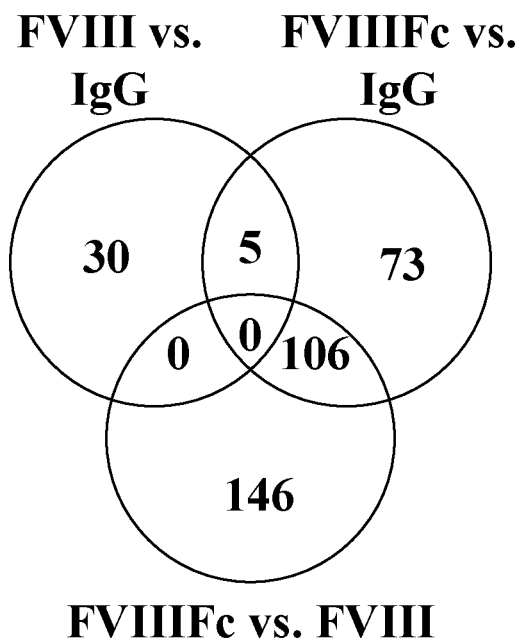
FIG. 20A
FIG. 20B

METHODS OF TREATING HEMOPHILIC ARTHROPATHY USING CHIMERIC CLOTTING FACTORS

CROSS-REFERENCE TO RELATED APPLICATIONS

This application is a 35 U.S.C. § 371 filing of International Patent Application No. PCT/US2017/064302, filed Dec. 1, 2017, which claims the benefit of U.S. Provisional Patent Application Serial Nos. 62/429,509, filed Dec. 2, 2016, 62/529,896, filed Jul. 7, 2017, 62/550,488, filed Aug. 25, 2017, and 62/558,793, filed Sep. 14, 2017, each of which are incorporated herein by reference in their entirety.

FIELD OF THE DISCLOSURE

The present disclosure relates generally to the field of therapeutics for hemostatic disorders.

BACKGROUND

Hemophilia an X-linked bleeding disorder caused by mutations and/or deletions in genes encoding coagulation proteins, in particular the Factor VIII (FVIII) gene, resulting in a deficiency of FVIII activity (hemophilia A), or the Factor IX gene, resulting in a deficiency of FIX activity (hemophilia B) (see, e.g., Peyvandi, F. et al. *Haemophilia* 12:82-89 (2006)). The disease is characterized by spontaneous hemorrhage and excessive bleeding after trauma. Treatment of hemophilia is by replacement therapy targeting restoration of FVIII and/or FIX activity to prevent spontaneous bleeding (see, e.g., Mannucci, P. M., et al., *N. Engl. J. Med.* 344:1773-1779 (2001).

Over time, the repeated bleeding into muscles and joints, which often begins in early childhood, results in hemophilic arthropathy and joint damage. Hemophilic arthropathy is a common and severe complication associated with hemophilia, which often results in pain, deformity, and disability. The most common patients to suffer from hemophilic arthropathy are young males, between the ages of 3 and 15 years old. While the knees are the most likely joints to be affected, hemophilic arthropathy can also present in the elbow, ankles, shoulders, and the spine. Hemophilic arthropathy is known to be irreversible. Currently available treatment for hemophilic arthropathy is thus limited.

Accordingly, there is a need to develop new ways of treating hemophilic arthropathy.

BRIEF SUMMARY

One aspect of the preset disclosure provides a method of treating reversible hemophilic arthropathy of a joint in a human having hemophilia comprising administering to the human an effective amount of a chimeric protein comprising a clotting factor and an Fc region or a composition comprising the chimeric protein. In some embodiments, the reversible hemophilic arthropathy comprises synovitis. In certain embodiments, the reversible hemophilic arthropathy comprises a microbleed or a sub-clinical bleed.

Another aspect of the present disclosure provides a method of treating synovitis in a human having hemophilia comprising administering to the human an effective amount of a chimeric protein comprising a clotting factor and an Fc region or a composition comprising a clotting factor and an Fc region. In some embodiments, the synovitis is associated with hemophilic arthropathy.

Another aspect of the present disclosure provides a method of reducing the occurrence of vascular remodeling in a joint of a human having hemophilia comprising administering to the human an effective amount of a chimeric protein comprising a clotting factor and an Fc region. Another aspect of the present disclosure provides a prophylactic treatment of vascular remodeling in a joint of a human having hemophilia comprising administering to the human an effective amount of a chimeric protein comprising a clotting factor and an Fc region or a composition comprising a clotting factor and an Fc region.

Another aspect of the present disclosure provides a method of improving the surrounding soft tissue of a joint of a human having hemophilia comprising administering to the human an effective amount of a chimeric protein comprising a clotting factor and an Fc region or a composition comprising a clotting factor and a Fc region.

In some embodiments, the administration improves a joint health score (HJHS) in the human. In some embodiments, the administration reduces joint pain in the human.

In certain embodiments, the Fc region specifically binds to a low affinity immunoglobulin gamma Fc region receptor II-b (FcγRIIB) In some embodiments, the Fc region specifically binds to dendritic cell-specific intercellular adhesion molecule-3-grabbing non-integrin (DC-SIGN).

In some aspects, the method further comprises identifying the human in need of the treatment. In some embodiments, the identifying comprises using an imaging system. In certain embodiments, the imaging system comprises a radiography, a magnetic resonance imaging, an ultrasonography, power Doppler sonography, or any combination thereof. In some embodiments, the human expresses one or more biomarkers associated with joint inflammation.

In some aspects, the clotting factor is selected from the group consisting of factor VII (FVII), factor VIIa (FVIIa), factor VIII (FVIII), factor IX (FIX), factor X (FX), von Willebrand factor (VWF), an antigen-binding portion thereof that specifically binds to FIX and FX, or any combination thereof. In some embodiments, the chimeric protein comprises FVIII-Fc. In other embodiments, the chimeric protein comprises FIX-Fc. In one embodiment, the chimeric protein comprises a factor VIII portion and a VWF portion, wherein the FVIII portion comprises a FVIII polypeptide or a fragment thereof, wherein the VWF portion comprises a VWF polypeptide or a fragment thereof, wherein the FVIII portion is linked to a first Fc region, wherein the VWF portion is linked to a second Fc region, and wherein the first Fc region and the second Fc region are associated with each other.

In some embodiments, the chimeric protein further comprises a half-life extending moiety. In certain embodiments, the half-life extending moiety comprises albumin or a fragment thereof, an albumin binding moiety, a PAS sequence, a HAP sequence, transferrin or a fragment thereof, polyethylene glycol (PEG), polysialic acid, hydroxyethyl starch (HES), a derivative thereof, or any combination thereof.

In some aspects, the effective amount of the composition, e.g., the chimeric protein, comprising FVIII and an Fc region is from about 20 IU/kg to about 300 IU/kg. In some embodiments, the chimeric protein comprising FVIII-Fc is administered at a dosing interval of about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, or about 24 days.

In other aspects, the effective amount of the chimeric protein comprising FIX-Fc is from about 20 IU/kg to about 100 IU/kg. In some embodiments, the chimeric protein comprising FIX-Fc is administered at a dosing interval of about three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days.

In one particular embodiment, the chimeric protein comprises a FVIII portion, a VWF portion, a first Fc region, and a second Fc region; wherein the FVIII portion comprises a FVIII polypeptide or a fragment thereof; wherein the VWF portion comprises a VWF polypeptide or a fragment thereof; wherein the FVIII portion is linked to the first Fc region; wherein the VWF portion is linked to the second Fc region; and wherein the first Fc region and the second Fc region are associated with each other.

EMBODIMENTS

E1. A method of treating reversible hemophilic arthropathy of a joint in a human having hemophilia comprising administering to the human an effective amount of a chimeric protein comprising a clotting factor and an Fc region.

E2. The method of E1, wherein the reversible hemophilic arthropathy comprises synovitis.

E3. The method of E1 or E2, wherein the reversible hemophilic arthropathy comprises a microbleed.

E4. A method of treating synovitis in a human having hemophilia comprising administering to the human an effective amount of a chimeric protein comprising a clotting factor and an Fc region.

E5. The method of E4, wherein the synovitis is associated with hemophilic arthropathy.

E6. A method of preventing or reducing the occurrence of vascular remodeling in a joint of a human having hemophilia comprising administering to the human an effective amount of a chimeric protein comprising a clotting factor and an Fc region.

E7. A method of improving the surrounding soft tissue of a joint of a human having hemophilia comprising administering to the human an effective amount of a chimeric protein comprising a clotting factor and an Fc region.

E8. The method of any one of E1 to E7, wherein the administration improves a joint health score (HJHS) in the human.

E9. The method of E8, wherein the joint health score is a sum of joint totals and Global Gait score.

E10. The method of E9, wherein the joint totals are measured based on swelling, duration of swelling, muscle atrophy, crepitus on motion, flexion loss, extension loss, joint pain, and strength.

E11. The method of E9, wherein the Global Gait score is measured based on walking, stair, running, or hopping on one leg.

E12. The method of any one of E1 to E11, wherein the administration reduces joint pain in the human.

E13. The method of any one of E1 to E12, wherein the joint is selected from the group consisting of one or both elbows, one or both knees, one or both ankles, one or both shoulders, one or both hips, one or both wrists, one or more joints of the hand, one or more joints of the foot, and any combination thereof.

E14. The method of any one of E1 to E13, wherein the joint is an elbow.

E15. The method of any one of E1 to E13, wherein the joint is a knee.

E16. The method of any one of E1 to E13, wherein the joint is an ankle.

E17. The method of any one of E1 to E16, wherein the Fc region specifically binds to a low affinity immunoglobulin gamma Fc region receptor II-b (FcγRIIB).

E18. The method of any one of E1 to E17, wherein the Fc region specifically binds to dendritic cell-specific intercellular adhesion molecule-3-grabbing non-integrin (DC-SIGN).

E19. The method of any one of E1 to E18, further comprising identifying the human in need of the treatment.

E20. The method of E19, wherein the identifying comprises using an imaging system.

E21. The method of E20, wherein the imaging system comprises a radiography, a magnetic resonance imaging, an ultrasonography, power Doppler sonography, or any combination thereof.

E22. The method of E21, wherein the human expresses one or more biomarkers associated with joint inflammation.

E23. The method of any one of E1 to E22, wherein the clotting factor is selected from the group consisting of factor VII (FVII), factor VIIa (FVIIa), factor VIII (FVIII), factor IX (FIX), factor X (FX), von willebrand factor (VWF), an antigen-binding portion thereof that specifically binds to FIX and FX, or any combination thereof.

E24. The method of any one of E1 to E23, wherein the chimeric protein comprises FVIII-Fc.

E25. The method of any one of E1 to E23, wherein the chimeric protein comprises FIX-Fc.

E26. The method of any one of E1 to E24, wherein the chimeric protein comprises a factor VIII portion and a VWF portion, wherein the FVIII portion comprises a FVIII polypeptide or a fragment thereof, wherein the VWF portion comprises a VWF polypeptide or a fragment thereof, wherein the FVIII portion is linked to a first Fc region, wherein the VWF portion is linked to a second Fc region, and wherein the first Fc region and the second Fc region are associated with each other.

E27. The method of any one of E23, E24, and E26, wherein the FVIII polypeptide comprises full length mature FVIII.

E28. The method of any one of E23, E24, and E26, wherein the FVIII polypeptide comprises a B domain deleted FVIII.

E29. The method of E28, wherein the B domain deleted FVIII comprises a deletion of all or part of the B domain of FVIII.

E30. The method of E28 or E29, wherein the B domain deleted FVIII comprises a deletion of amino acid residues 746 to 1648 of mature FVIII.

E31. The method of any one of E23, E24, and E25 to E30, wherein the VWF polypeptide comprises a VWF fragment comprising a D' domain and a D3 domain of VWF.

E32. The method of any one of E1 to E31, wherein the chimeric protein further comprises a half-life extending moiety.

E33. The method of E32, wherein the half-life extending moiety comprises albumin or a fragment thereof, an albumin binding moiety, a PAS sequence, a HAP sequence, transferrin or a fragment thereof, polyethylene glycol (PEG), polysialic acid, hydroxyethyl starch (HES), a derivative thereof, or any combination thereof.

E34. The method of E32 or E33, wherein the half-life extending moiety is inserted within the clotting factor.

E35. The method of E32 or E33, wherein the half-life extending moiety is inserted between the clotting factor and the Fc region.

E36. The method of any one of E24 and E26 to E35, wherein the effective amount of the chimeric protein comprising FVIII and an Fc region is from about 20 IU/kg to about 300 IU/kg.

E37. The method of E36, wherein the effective amount of the chimeric protein comprising FVIII-Fc is from about 20 IU/kg to about 275 IU/kg, about 20 IU/kg to about 250 IU/kg, about 20 IU/kg to about 200 IU/kg, about 20 IU/kg to about 175 IU/kg, about 20 IU/kg to about 150 IU/kg, from about 20 IU/kg to about 125 IU/kg, from about 20 IU/kg to about 100 IU/kg, from about 20 IU/kg to about 90 IU/kg, from about 20 IU/kg to about 80 IU/kg, from about 20 IU/kg to about 70 IU/kg, from about 20 IU/kg to about 60 IU/kg, from about 20 IU/kg to about 50 IU/kg, from about 20 IU/kg to about 40 IU/kg, from about 20 IU/kg to about 30 IU/kg, from about 30 IU/kg to about 100 IU/kg, from about 40 IU/kg to about 100 IU/kg, from about 50 IU/kg to about 100 IU/kg, from about 60 IU/kg to about 100 IU/kg, from about 70 IU/kg to about 100 IU/kg, from about 80 IU/kg to about 100 IU/kg, from about 90 IU/kg to about 100 IU/kg, from about 100 IU/kg to about 200 IU/kg, from about 150 IU/kg to about 200 IU/kg, from about 200 IU/kg to about 300 IU/kg, from about 225 IU/kg to about 300 IU/kg, from about 250 IU/kg to about 300 IU/kg, from about 275 IU/kg to about 300 IU/kg, or from about 25 IU/kg to about 75 IU/kg.

E38. The method of E36 or E37, wherein the effective amount of the chimeric protein comprising FVIII-Fc is about 25 IU/kg to about 65 IU/kg.

E39. The method of any one of E24 and E26 to E38, wherein the chimeric protein comprising FVIII-Fc is administered at a dosing interval of about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, or about 24 days.

E40. The method of any one of E24 and E26 to E38, wherein the chimeric protein comprising FVIII-Fc is administered at a dosing interval of about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 14 days, about 3 to about 14 days, about 4 to about 14 days, about 5 to about 14 days, about 6 to about 14 days, about 7 to about 14 days, about 8 to about 14 days, about 9 to about 14 days, about 10 to about 14 days, about 11 to about 14 days, about 12 to about 14 days, about 13 to about 14 days, or about 5 to about 10 days.

E41. The method of any one of E24 and E26 to E40, wherein the chimeric protein comprising FVIII-Fc is administered at a dosing interval about 3 days to about 5 days.

E42. The method of E25, wherein the effective amount of the chimeric protein comprising FIX-Fc is from about 20 IU/kg to about 100 IU/kg.

E43. The method of E25 or E42, wherein the effective amount of the chimeric protein comprising FIX-Fc is from about 20 IU/kg to about 100 IU/kg, from about 30 IU/kg to about 100 IU/kg, from about 40 IU/kg to about 100 IU/kg, from about 50 IU/kg to about 100 IU/kg, from about 60 IU/kg to about 100 IU/kg, from about 70 IU/kg to about 100 IU/kg, from about 80 IU/kg to about 100 IU/kg, from about 90 IU/kg to about 100 IU/kg, from about 20 IU/kg to about 90 IU/kg, from about 20 IU/kg to about 80 IU/kg, from about 20 IU/kg to about 70 IU/kg, from about 20 IU/kg to about 60 IU/kg, from about 20 IU/kg to about 50 IU/kg, from about 20 IU/kg to about 40 IU/kg, or from about 20 IU/kg to about 30 IU/kg.

E44. The method of any one of E25 and E42 to E44, wherein the effective amount of the chimeric protein comprising FIX-Fc is about 50 IU/kg to E100 IU/kg.

E45. The method of any one of E25 and E42 to E44, wherein the chimeric protein comprising FIX-Fc is administered at a dosing interval of about three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, or E28 days.

E46. The method of any one of E25 and E42 to E45, wherein the chimeric protein comprising FIX-Fc is administered at a dosing interval of about 1 to about 21 days, about 1 to about 20 days, about 1 to about 19 days, about 1 to about 18 days, about 1 to about 17 days, about 1 to about 16 days, about 1 to about 15 days, about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 21 days, about 3 to about 21 days, about 4 to about 21 days, about 5 to about 21 days, about 6 to about 21 days, about 7 to about 21 days, about 8 to about 21 days, about 9 to about 21 days, about 10 to about 21 days, about 11 to about 21 days, about 12 to about 21 days, about 13 to about 21 days, about 14 to about 21 days, about 15 to about 21 days, about 16 to about 21 days, about 17 to about 21 days, about 18 to about 21 days, about 19 to about 21 days, about 20 to about 21 days, about 5 to about 10 days, about 10 to about 15 days, about 15 to about 20 days.

E47. The method of any one of E25 and E42 to E46, wherein the chimeric protein comprising FIX-Fc is administered at a dosing interval of about 7 days, about 8 days, about 9 days, about 10 days, about 11 days, about 12 days, about 13 days, or about 14 days.

E48. The method of any one of E1 to E32, wherein the chimeric protein comprises a FVIII portion, a VWF portion, a first Fc region, and a second Fc region; wherein the FVIII portion comprises a FVIII polypeptide or a fragment thereof; wherein the VWF portion comprises a VWF polypeptide or a fragment thereof; wherein the FVIII portion is linked to the first Fc region; wherein the VWF portion is linked to the second Fc region; and wherein the first Fc region and the second Fc region are associated with each other.

E49. The method of any one of E1 to E47, wherein the Fc region of the chimeric protein facilitates localization of the chimeric protein to the joint.

E50. The method of any one of E1 to E49, wherein the human is less than 6 years old.

E51. The method of any one of E1 to E49, wherein the human is 6 years old to less than 12 years old.

E52. The method of any one of E1 to E49, wherein the human is 12 years old or older.

E53. The method of any one of E1 to E52, wherein the clotting factor distributes to tissues outside of the plasma compartment as well as in the plasma compartment.

BRIEF DESCRIPTION OF THE FIGURES

FIGS. 1A-1F show prestudy (FIGS. 1A, 1C, and 1E) and on-study median (FIGS. 1B, 1D, and 1F) (IQR) annualized bleeding rates (ABRs) for subjects from FVIII-Fc study (FIGS. 1A and 1B) and FVIII-Fc study for kids (FIGS. 1C-1F) with target joints at baseline. FIGS. 1C-1D show combined data from the FVIII-Fc study for kids, whereas FIGS. 1E-1F show the same data stratified based on the age of the subject (less than 6 years of age and between 6 and less than 12 years of age).

FIG. 2B distinguishes between the presence (yes; triangles) and absence (no; circles) of target joints at baseline.

FIG. 10B further shows overall on-study ABR (dark circles), overall target joint ABR (grey diamonds), and target joint spontaneous ABR (grey triangles). WP=weekly prophylaxis; IP=individualized interval prophylaxis; and MP=modified prophylaxis (FIGS. 10A-10B).

FIG. 15A; and extension: FIG. 15B), knee (flexion: FIG. 15C; and extension: FIG. 15D), and ankle (plantar flexion: FIG. 15E; and dorsi flexion: FIG. 15F) joints, with the modified hemophilia joint health scores (HJHS) and degrees of flexion/extension overlaid.

FIGS. 17A-17C are graphical representations of the relative macrophage and dendritic cell surface expression levels of the Fcγ receptors CD16 (FIG. 17A), CD32 (FIG. 17B), and CD64 (FIG. 17C) following treatment with horseradish peroxidase immune complexes (HRP-IC; positive control), IgG1, recombinant FVIII (rFVIII), or a rFVIII Fc fusion protein (rFVIIIFc). Asterisks (*) indicate degree of significance (n=3; *=P≤0.05, =P≤0.01, *=P≤0.005, significance for HRP-IC as compared with the other treatments is not shown).

FIG. 18A shows signaling, as measured by Syk phosphorylation, in THP-1 monocytic cell line ("THP-1"), monocytes, peripheral blood monocyte-derived macrophages ("macrophage"), and peripheral blood monocyte-derived dendritic cells treated with HRP-IC, IgG1, rFVIII or rFVIIIFc for 15 minutes. FIG. 18B shows relative Syk phosphorylation in macrophages treated with rFVIIIFc ("WT"), mutant rFVIIIFc that is unable to bind to neonatal Fc receptor ("FcRn mutant"), or with mutant rFVIIIFc that is unable to bind to FcγR ("FcgR mutant"). FIG. 18C shows the relative production of the proinflammatory cytokines interleukin 1b (IL-1b), IL-6, IL-8, IL-10, and tumor necrosis factor alpha (TNFa) in macrophages twenty-four hours following treatment with HRP-IC, IgG1, rFVIII or rFVIIIFc.

FIGS. 20A-20M are graphical representations of gene expression patterns of tolerogenic macrophages following treatment with rFVIII or rFVIIIFc. FIGS. 20A-20B are Venn diagrams, illustrating the distribution of genes that were significantly downregulated (FIG. 20A) and the distribution of genes that were significantly upregulated (FIG. 20B) in monocyte-derived macrophages treated with IgG1, rFVIII, or rFVIIIFc for six hours (n=3). FIGS. 20C-20G are graphs showing the relative expressions of various NRF2 and lipid metabolism pathway genes, such as heme oxygenase 1 (Hmox1; FIG. 20C), peroxisome proliferator-activated receptor gamma (PPARγ; FIG. 20D), lipoprotein lipase (LPL; FIG. 20E), early growth response 2 (EGR2; FIG. 20F), and solute carrier organic anion transporter family member 4A1 (SLCO4A1; FIG. 20G); CD206 at 6 hours (FIG. 20I) and 12 hours (FIG. 20J) post treatment; and arginase 1 (ARG1; FIG. 20L) as measured by quantitative PCR, following treatment with rFVIII or rFVIIIFc. Asterisks (*) indicate degree of significance (n=8; *P≤0.05, P≤0.01, *P≤0.005; FIGS. 20C-20G). FIGS. 20K and 20M are graphs showing the number of cells collected by flow cytometry expressing CD206. In addition, rFVIIIFc-educated macrophages were found to exhibit a characteristic M2-like phenotype (FIGS. 20I-20M). In particular, macrophages treated with rFVIIIFc had higher relative CD206 (also known as mannose receptor C-type 1; MRC1) expression than cells treated with rFVIII after 6 hours (FIG. 20I) and after 24 hours (FIG. 20J), and macrophages treated with rFVIIIFc had higher relative ARG1 expression than cells treated with rFVIII after 24 hours (FIG. 20M).

DETAILED DESCRIPTION

Figure 1E:
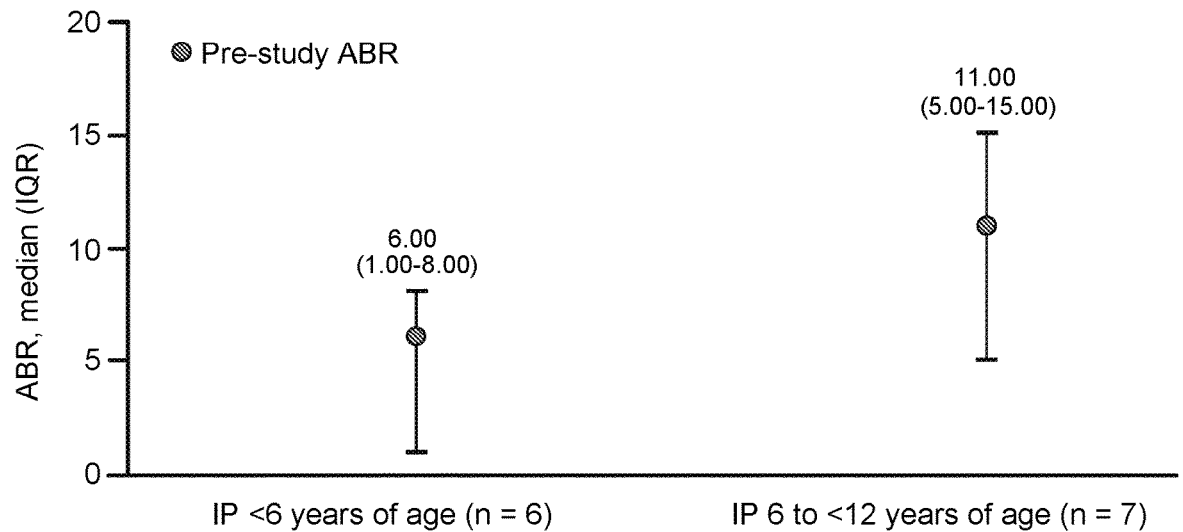

The present disclosure provides methods of treating reversible hemophilic arthropathy of a joint in a human having hemophilia comprising administering to the human an effective amount of a chimeric protein comprising a clotting factor and an Fc region or a composition comprising a clotting factor and an Fc region. The chimeric protein disclosed herein can also be used to treat synovitis, a microbleed, inflammation of one or more joints, vascular remodeling, or any combination thereof in a joint of a human having hemophilia. In certain embodiments, the methods of the present invention improve the surrounding soft tissue of a joint of a human having hemophilia.

I. Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

"Administering," as used herein, means to give a pharmaceutically acceptable composition, e.g., a chimeric protein, disclosed herein to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. Chimeric protein and hybrid proteins can be administered as part of a pharmaceutical composition comprising at least one excipient. In some embodiments, the composition, e.g., the chimeric protein is administered to a human through a gene therapy, e.g., wherein one or more polynucleotides encoding the clotting factor and/or the Fc region are administered to the human, and the clotting factor and/or the Fc region are expressed in the human.

"Treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition, but does not include prophylaxis or prevention of hemophilic arthropathy or its symptoms thereof. In one embodiment, the term "treating" or "treatment" means improving a Hemophilia Joint Health Score (HJHS) or a modified HJHS (mHJHS) for a subject. In some embodiments, the overall HJHS or mHJHS is improved. In some embodiments, the individual score for one or more target joints is improved. In some embodiments, the term "treating" or "treatment" means improving a quality of life (QoL) score for a subject. In certain embodiments, a QoL score analyzes the subject's disposition related to sports and leisure, physical health, dealing with hemophilia, family planning, feeling (toward hemophilia) future, partnership and sexuality, treatment, view (of yourself), work and school, or any combination thereof. In other embodiments, the term "treating" or "treatment" means reducing the effects and/or severity of one or more microbleed. In another embodiment, the term "treating" or "treatment" means reducing swelling and/or inflammation and/or pain in one or more target joint. In another embodiment, the term "treating" or "treatment" means reducing vascular remodeling in one or more target joint.

"Prevent" or "preventing," as used herein, refers to decreasing or reducing the occurrence or severity of a particular outcome. In some embodiments, preventing an outcome is achieved through prophylactic treatment.

The term "comparable" as used herein means a compared rate or level resulted from using, e.g., the chimeric polypeptide is equal to, substantially equal to, or similar to the reference rate or level. The term "similar" as used herein means a compared rate or level has a difference of no more than 10% or no more than 15% from the reference rate or level (e.g., FXa generation rate by a chimeric polypeptide consisting essentially of or consisting of two Fc portions and processed FVIII, wherein said processed FVIII is fused to one Fc of the two Fc portions). The term "substantially equal" means a compared rate or level has a difference of no more than 0.01%, 0.5% or 1% from the reference rate or level.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (Factor VIII deficiency), hemophilia B (Factor IX deficiency or "Christmas disease") and hemophilia C (Factor XI deficiency, mild bleeding tendency). Other hemostatic disorders include, e.g., Von Willebrand disease, Factor XI deficiency (PTA deficiency), Factor XII deficiency, deficiencies or structural abnormalities in fibrinogen, prothrombin, Factor V, Factor VII, Factor X or Factor XIII, Bernard-Soulier syndrome, which is a defect or deficiency in GPIb. GPIb, the receptor for VWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

"Area under the plasma concentration versus time curve (AUC)," as used herein, is the same as the term of art in pharmacology, and is based upon the rate and extent of absorption of FVIII following administration. AUC is determined over a specified time period, such as 12, 18, 24, 36, 48, or 72 hours, or for infinity using extrapolation based on the slope of the curve. Unless otherwise specified herein, AUC is determined for infinity. The determination of AUC can be carried out in a single subject, or in a population of subjects for which the average is calculated.

The term "procoagulant activity" is meant the ability of the coagulation factor, e.g., a FVIII or a FIX protein, of the invention to participate in the clotting cascade in blood, substituting for the native coagulation factor, e.g., native FVIII or FIX. For example, a recombinant FIX protein of the invention has procoagulant activity when it can convert Factor X (FX) to activated Factor X (FXa) in the presence of Factor VIII (FVIII), as tested, e.g., in a chromogenic assay. In another embodiment, the FIX activity is an ability to generate a tenase complex. In other embodiments, the FIX activity is an ability to generate thrombin (or a clot).

References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al., *J. Exp. Med.* 180: 2377 (1994), incorporated herein by reference in its entirety.) An Fc can comprise the CH2 and CH3 domains of an immunoglobulin with or without the hinge region of the immunoglobulin. Exemplary Fc variants are provided in WO 2004/101740 and WO 2006/074199, incorporated herein by reference in its entirety.

"Hybrid" polypeptides and proteins, as used herein, means a combination of a chimeric polypeptide with a second polypeptide. The chimeric polypeptide and the second polypeptide in a hybrid can be associated with each other via protein-protein interactions, such as charge-charge or hydrophobic interactions. The chimeric polypeptide and the second polypeptide in a hybrid can be associated with each other via disulfide or other covalent bond(s). Hybrids are described in WO 2004/101740 and WO 2006/074199, each of which is incorporated herein by reference in its entirety. See also U.S. Pat. Nos. 7,404,956 and 7,348,004, each of which is incorporated herein by reference in its entirety. The second polypeptide can be a second copy of the same chimeric polypeptide or it can be a non-identical chimeric polypeptide.

As used herein, an "amino acid corresponding to," "site corresponding to," or "equivalent amino acid" in a protein sequence is identified by alignment to maximize the identity or similarity between a first protein sequence, e.g., a FVIII or a FIX sequence, and a second protein sequence, e.g., a second FVIII or a second FIX sequence. The number used to identify an equivalent amino acid in a second protein sequence is based on the number used to identify the corresponding amino acid in the first protein sequence.

As used herein, the term "insertion site" refers to an amino acid residue number in a polypeptide (typically a mature polypeptide; e.g., a mature FVIII or a mature FIX polypeptide), or fragment, variant, or derivative thereof, which is immediately upstream of the position at which a heterologous moiety can be inserted. An "insertion site" is specified as a number, the number being the number of the amino acid specified protein sequence to which the insertion site corresponds, which is immediately N-terminal to the position of the insertion. For example, the phrase "the EGF2 domain comprises a heterologous moiety at an insertion site which corresponds to amino acid 105" of a given sequence indicates that the heterologous moiety is located between two amino acids corresponding to amino acid 105 and amino acid 106 of the sequence. However, one of skill in the art would readily be able to identify a corresponding position in any variant of the indicated protein, and the present disclosure is not limited to insertions made solely in the variants specifically disclosed herein. Rather, the insertions disclosed herein can be made in any related variants or fragments thereof having activity at a position corresponding to a position of the variants disclosed herein.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which a heterologous moiety (e.g., a half-life extending moiety) is inserted between two adjacent amino acids.

The terms "inserted," "is inserted," "inserted into" or grammatically related terms, as used herein refers to the position of a heterologous moiety (e.g., a half-life extending moiety) in a fusion polypeptide relative to the analogous position in specified protein (e.g., a FVIII or a FIX protein). Those of skill in the field will understand how to identify corresponding insertion positions with respect to other polypeptide sequences, e.g., other FVIII and FIX variants. As used herein the terms refer to the characteristics of the recombinant polypeptide disclosed herein, and do not indicate, imply or infer any methods or process by which the fusion polypeptide was made. For example, in reference to a fusion polypeptide provided herein, the phrase "a heterologous moiety is inserted into the EGF2 domain immediately downstream of residue 105 of the FIX polypeptide" means that the fusion polypeptide comprises a heterologous moiety immediately downstream of an amino acid which corresponds to amino acid 105 in a particular FIX variant, e.g., bounded by amino acids corresponding to amino acids 105 and 106 of the FIX variant.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a FVIII domain or a FIX domain of the invention with an Ig Fc domain. A fusion protein is created, for example, by chemical synthesis, or by creating and translating a polynucleotide in which the peptide regions are encoded in the desired relationship. A fusion protein can further comprise a second amino acid sequence associated with the first amino acid sequence by a covalent, non-peptide bond or a non-covalent bond.

The terms "heterologous" and "heterologous moiety" mean that a polynucleotide, polypeptide, or other moiety is derived from a distinct entity from that of the entity to which it is being compared. For instance, a heterologous polypeptide can be synthetic, or derived from a different species, different cell type of an individual, or the same or different type of cell of distinct individuals. In one aspect, a heterologous moiety is a polypeptide fused to another polypeptide to produce a fusion polypeptide or protein. In another aspect, a heterologous moiety is a non-polypeptide such as PEG conjugated to a polypeptide or protein.

The terms "linked" and "fused" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence is linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme that is activated during the clotting cascade, such that cleavage of such sites occurs at the site of clot formation. Exemplary such sites include, e.g., those recognized by thrombin, Factor XIa or Factor Xa. Other enzymatic cleavage sites are known in the art.

As used herein, the term "processing site" or "intracellular processing site" refers to a type of enzymatic cleavage site in a polypeptide which is a target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxyterminal side of the sequence motif Arg-[any residue]-(Lys or Arg)-Arg. As used herein the "furin" family of enzymes includes, e.g., PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

In constructs that include more than one processing or cleavage site, it will be understood that such sites may be the same or different.

A "processable linker" as used herein refers to a linker comprising at least one intracellular processing site, which is described elsewhere herein.

"Baseline," as used herein, is the lowest measured plasma level of a given analyte, e.g., a clotting factor (e.g., FVIII or FIX), in a subject prior to administering a dose. The plasma levels can be measured at two time points prior to dosing: at a screening visit and immediately prior to dosing. Alternatively, (a) the baseline in subjects whose pretreatment clotting factor activity is <1%, who have no detectable clotting factor antigen, and have nonsense genotypes can be defined as 0%, (b) the baseline for subjects with pretreatment clotting factor activity <1% and who have detectable clotting factor antigen can be set at 0.5%, (c) the baseline for subjects whose pretreatment clotting factor activity is between 1-2% is $C_{min}$ (the lowest activity throughout the PK study), and (d) the baseline for subjects whose pretreatment clotting factor activity is ≥2% can be set at 2%.

"Equivalent dose," as used herein, means the same dose of clotting factor activity, e.g., FVIII activity or FIX activity, as expressed in International Units, which is independent of molecular weight of the polypeptide in question. For example, one International Unit (IU) of FVIII activity corresponds approximately to the quantity of FVIII in one milliliter of normal human plasma. Several assays are available for measuring clotting factor activity, including the European Pharmacopoeia chromogenic substrate assay and a one stage clotting assay.

"Dosing interval," as used herein, means the dose of time that elapses between multiple doses being administered to a subject. The comparison of dosing interval can be carried out in a single subject or in a population of subjects and then the average obtained in the population can be calculated.

"Subject," as used herein means a human individual. Subject can be a patient who is currently suffering from a bleeding disorder or is expected to be in need of such a treatment. In some embodiments, the subject has never been previously treated with the clotting factor (i.e., the subject is a previously untreated subject or previously untreated patient). In some embodiments, the subject is a fetus and the methods comprise administering the composition, e.g., the chimeric polypeptide, to the mother of the fetus and the administration to the subject occurs from the mother across the placenta. In some embodiments, the subject is a child or an adult. In some embodiments, the subject is a child less than one-year-old, less than two-year-old, less than three-year-old, less than four-year-old, less than five-year-old, less than six-year-old, less than seven-year-old, less than eight-year-old, less than nine-year-old, less than ten-year-old, less than eleven-year-old, or less than twelve-year-old. In some embodiments, the child is less than one-year old. In certain embodiments, the subject is less than 6 years old. In other embodiments, the subject is between 6 and less than 12 years old. In other embodiments, the subject is 12 years old or older. In some embodiments, the child or adult subject develops a bleeding disorder, wherein the onset of the symptoms of the bleeding disorder is after the one-year-old age. In some embodiments, the administration of the composition, e.g., the chimeric polypeptide, to the subject is sufficient to prevent, inhibit, or reduce development of an immune response selected from a humoral immune response, a cell-mediated immune response, or both a humoral immune response and a cell-mediated immune response against the clotting factor.

A "therapeutic dose," "dose," "effective dose," or "dosing amount" as used (interchangeably) herein, means a dose that achieves a therapeutic goal, as described herein. In some embodiments, a "therapeutic dose" means a dose that improves an HJHS, mHJHS, or a QoL score, as compared to the HJHS, mHJHS, or a QoL score prior to the treatment. In some embodiments, a "therapeutic dose" means a dose that reduces swelling, inflammation, and/or pain in one or more joints in a subject as compared to the level of swelling, inflammation, and/or pain in the joint prior to the treatment. In some embodiments, a "therapeutic dose" means a dose that reduces the effects and/or severity of one or more microbleed, as compared to the effects and/or severity of the microbleed prior to the treatment. In another embodiment, a "therapeutic dose" means a dose that reduces vascular remodeling in one or more target joint, as compared to the vascular remodeling prior to the treatment.

Also included in the present invention are fragments or variants of polypeptides, and any combination thereof. The term "fragment" or "variant" when referring to polypeptides used in the methods of the present disclosure include any polypeptides which retain at least some of the properties (e.g., Fc variant or coagulation activity for a FVIII or a FIX variant) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules used in the methods of the present disclosure include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions. One particular FIX variant disclosed herein is the R338L FIX (Padua) variant. See, e.g., Simioni, P., et al., "X-Linked Thrombophilia with a Mutant Factor IX (Factor IX Padua)," *NEJM* 361:1671-75 (October 2009), which is incorporated by reference herein in its entirety.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity may be curated either automatically or manually.

The polynucleotide variants can contain alterations in the coding regions, non-coding regions, or both. In one embodiment, the polynucleotide variants contain alterations which produce silent substitutions, additions, or deletions, but do not alter the properties or activities of the encoded polypeptide. In another embodiment, nucleotide variants are produced by silent substitutions due to the degeneracy of the genetic code. In other embodiments, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-la. They used random mutagenesis to generate over 3,500 individual IL-la mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, FVIII is modified, e.g., pegylated, at any convenient location. In some embodiments, FVIII is pegylated at a surface exposed amino acid of FVIII, e.g., a surface exposed cysteine, which can be an engineered cysteine. Id. In some embodiments, modified FVIII, e.g., pegylated FVIII, is a chimeric or fusion FVIII.

The term "downstream" refers to a nucleotide sequence that is located 3' to a reference nucleotide sequence. "Downstream" can also refer to a peptide sequence that is located C-terminal to a reference peptide sequence.

The term "upstream" refers to a nucleotide sequence that is located 5' to a reference nucleotide sequence. "Upstream" can also refer to a peptide sequence that is located N-terminal to a reference peptide sequence.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide, which encodes a gene product, e.g., a polypeptide, can include a promoter and/or other transcription or translation control elements operably associated with one or more coding regions. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions, which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, and poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, micro-injection, transduction, cell fusion, DEAE dextran, calcium phosphate precipitation, lipofection (lysosome fusion), use of a gene gun, or a DNA vector transporter.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

As used herein, the term "host cell" refers to a cell or a population of cells harboring or capable of harboring a recombinant nucleic acid. Host cells can be a prokaryotic cells (e.g., E. coli), or alternatively, the host cells can be eukaryotic, for example, fungal cells (e.g., yeast cells such as Saccharomyces cerevisiae, Pichia pastoris, or Schizosaccharomyces pombe), and various animal cells, such as insect cells (e.g., Sf-9) or mammalian cells (e.g., HEK293F, CHO, COS-7, NIH-3 T3).

"Volume of distribution at steady state (Vss)," as used herein, has the same meaning as the term used in pharmacology, which is the apparent space (volume) into which a drug distributes. Vss=the amount of drug in the body divided by the plasma concentration at steady state.

II. Methods of the Invention

The present disclosure is based on the discovery that a clotting factor fused to an Fc region can be used to reverse hemophilic arthropathy. Hemophilic arthropathy was previously known to be irreversible once it is developed, as soft tissue changes could only be visualized by Mill. The currently known options for an individual suffering from hemophilic arthropathy include a surgery or a sclerosing agent to remove hypertrophied synovium. A sclerosing agent, either radioactive or chemical material, can impede further cartilaginous and bony deterioration; however, it is not capable of reversing hemophilic arthropathy. Arthroplasty of the knee and hip have been successful in reducing pain and loss of motion when other efforts to control synovial hypertrophy fail. Hilgartner M., Current Opinion in Pediatrics: February 2002, V14, Issue 1, pp. 46-49.

The present disclosure therefore provides methods of treating hemophilic arthropathy of a joint in a human having hemophilia comprising administering to the human an effective amount of a composition, e.g., a chimeric protein, comprising a clotting factor and an Fc region or a polynucleotide encoding the chimeric protein. The treatment of hemophilic arthropathy can reverse, partially or completely, the hemophilic arthropathy (e.g., one or more symptoms of hemophilic arthropathy). Therefore, in one embodiment, the present disclosure provides a method of treating a human having hemophilia who has already developed hemophilic arthropathy, e.g., synovitis.

In general, hemophilic arthropathy refers to joint disease that occurs in a human subject suffering from hemophilia as a long-term consequence or repeated bleeding into the subject's joints. Spontaneous bleeding into one or more joints is common in hemophilia patients. Joints with several consecutive bleeds within a 6 month period are often referred to as "target joints," and these joints often progress to hemophilic arthropathy.

Hemophilic arthropathy can present with various symptoms, including, but not limited to, synovial hyperlacia, chronic inflammation (including synovitis), fibrosis, haemosiderosis, subarticular cyst formation, pain, reduced range of motion, muscle atrophy, ankylosis, osteoporosis, cartilage degeneration with collapse of the joint space, and any combination thereof. Hemophilic arthropathy includes various stages: (i) Stage I including soft-tissue swelling, but no skeletal abnormalities; (ii) Stage II including overgrowth and osteoporosis of the epiphysis, joint integrity is maintained. There are no bone cysts and no narrowing of the articular cartilage space. The radiologic Stage II parallels the clinical stage of subacute hemophilic arthropathy; (iii) Stage III including minimal to moderate joint space narrowing with subchondral cysts. Widening of the intercondylar notch of the knee and the trochlear notch of the ulna. In the knee there may be squaring of the patella. Articular cartilage is still preserved and hemophilic arthropathy is still reversible; (iv) Stage IV including destruction of articular cartilage with severe narrowing of the joint space. The other osseous changes found in stage III are more pronounced; and (v) Stage V including total loss of joint space with fibrous ankylosis of the joint. There is marked incongruity of the articular structures with severe irregular hypertrophy of the epiphysis.

The present disclosure provides that treatment with a composition, e.g., a chimeric protein, comprising a clotting factor and an Fc region is capable of reducing and/or ameliorating the symptoms of reversible hemophilic arthropathy. In some embodiments, the composition, e.g., the chimeric protein, can treat one more stages of hemophilic arthropathy, e.g., Stages I, II, and/or III. As used herein, a "reversible" hemophilic arthropathy is a manifestation of hemophilic arthropathy that can partially or completely revert to its original, healthy state following treatment. In contrast, an "irreversibly" hemophilic arthropathy is a manifestation of hemophilic arthropathy that is permanent and that will not improve following treatment. Therefore, the present methods can improve, reduce, or ameliorate (or reverse either partially or completely) one or more symptoms of hemophilic arthropathy, e.g., synovial hyperlacia, chronic inflammation (including synovitis), haemosiderosis, subarticular cyst formation, pain, reduced range of motion, swelling, vascular remodeling, or any combination thereof.

The hemophilic arthropathy (reversible) treated using the methods of the present disclosure can affect any joint in the body. In some embodiments, the joint is a load bearing joint, e.g., a joint selected from the group consisting of one or both knees, one or both ankles, one or both hips, one or more joints of the foot, and any combination thereof. In another embodiment, the joint is a non-load bearing joint, e.g., a joint selected from the group consisting of one or both elbows, one or both shoulders, one or both wrists, one or more joints of the hand, or any combination thereof. In another embodiment, the joint is a knee.

In some embodiments, the reversible hemophilic arthropathy comprises synovitis. Synovitis refers to inflammation of the synovial membrane, which surrounds the joint. In some embodiments, the synovitis is of any joint in the body. In some embodiments, the synovitis presents as swelling of the joint, and the methods of the present disclosure reduce the swelling of the joint. In some embodiments, the synovitis presents as pain in the joint, and the methods of the present disclosure reduce the pain in the joint. In other embodiments, the synovitis presents as decreased range of motion of the joint, and the methods of the present invention increase the range of motion of the joint.

In other embodiments, the reversible hemophilic arthropathy comprises a microbleed in a joint. In some embodiments, the reversible hemophilic arthropathy is the result of a microbleed. A microbleed refers to a very small bleed in one or more joints, which can lead to hemophilic arthropathy following repeated occurrences. In some embodiments, the reversible hemophilic arthropathy comprises an acute joint bleed. In some embodiments, the reversible hemophilic arthropathy is the result of an acute joint bleed. An acute joint bleed refers to a more substantial bleeding episode in one or more joints.

In certain embodiments, the reversible hemophilic arthropathy comprises inflammation of one or more joints. In some embodiments, the inflammation is in any joint in the body. In some embodiments, the inflammation presents as swelling of the joint, and the methods of the present disclosure reduce the swelling of the joint. In some embodiments, the inflammation presents as pain in the joint, and the methods of the present disclosure reduce the pain in the joint. In other embodiments, the inflammation presents as decreased range of motion of the joint, and the methods of the present invention increase the range of motion of the joint. In certain embodiments, the method further provides measuring inflammation in one or more joints prior to administration of the effective amount of a composition or a chimeric protein comprising a clotting factor and an Fc region. In some embodiments, the method further provides measuring inflammation in one or more joints after administration of the effective amount of a composition or a chimeric protein comprising a clotting factor and an Fc region.

In other embodiments, the hemophilic arthropathy is evidenced by the expression of one or more biomarkers associated with joint inflammation and/or joint damage. In some embodiments, one or more biomarkers are upregulated in the human indicating increased joint inflammation and/or joint damage. In some embodiments, one or more biomarkers are downregulated in the human indicating increased joint inflammation and/or joint damage. In some embodiments, a human in need of treatment is identified based on the expression of one or more biomarkers associated with increased responsiveness to treatment using the methods of the present disclosure.

In some embodiments, the present methods increase localization of the clotting factor to one or more target joints. In certain embodiments, the composition or a chimeric protein comprising a clotting factor and an Fc region localizes to a target joint following administration more so than the clotting factor alone. In certain embodiments, the composition or a chimeric protein comprising a clotting factor and an Fc region remains localized to the one or more target joints for a longer period of time than the clotting factor alone following administration.

In yet other embodiments, the present methods further comprise identifying a subject who exhibits one or more markers for reversible hemophilic arthropathy and then administering a composition or a chimeric protein comprising a clotting factor and an Fc region.

In some embodiments, the methods of the present invention prevent or reduce the occurrence of vascular remodeling in a joint of a human having hemophilia. A common element associated with hemophilic arthropathy is remodeling of the vasculature surrounding a joint, in particular a target joint. Vascular remodeling can be characterized by increased angiogenesis and increased occurrence of microbleeds into the joint. In some embodiments, the present disclosure provides a method of prophylactic treatment or reduction of the occurrence of vascular remodeling in a joint of a human having hemophilia comprising administering to the human an effective amount of a composition or a chimeric protein comprising a clotting factor and an Fc region. In other embodiments, the present disclosure provides a method of reversing existing vascular remodeling associated with hemophilic arthropathy in a joint of a human having hemophilia comprising administering to the human an effective amount of a composition or a chimeric protein comprising a clotting factor and an Fc region. In some embodiments, the vascular remodeling is in any joint in the body. In certain embodiments, the vascular remodeling is in a target joint. In other embodiments, the vascular remodeling is in a joint other than a target joint. In certain embodiments, the vascular remodeling is in a load bearing joint, e.g., a joint selected from the group consisting of one or both knees, one or both ankles, one or both hips, one or more joints of the foot, and any combination thereof. In another embodiment, the vascular remodeling is in a non-load bearing joint, e.g., a joint selected from the group consisting of one or both elbows, one or both shoulders, one or both wrists, one or more joints of the hand, or any combination thereof. In another embodiment, the vascular remodeling is in a knee. In some embodiments, the vascular remodeling is in a muscle. In some embodiments, the vascular remodeling is in the spleen and/or the liver.

In certain embodiments, the methods of the present invention improve the surrounding soft tissue of a joint of a human having hemophilia. Another common pathology of hemophilic arthropathy is hyperproliferation of the soft tissue of the joint. In some embodiments, the soft tissue improved by the methods of the present disclosure is in any joint in the body. In certain embodiments, the soft tissue improved by the methods of the present disclosure is in a target joint. In other embodiments, the soft tissue improved by the methods of the present disclosure is in a joint other than a target joint.

In some embodiments, the methods of the present invention reduce the severity of one or more symptom associated with hyperproliferation of the soft tissue of a joint. In some embodiments, the hyperproliferation of the soft tissue of a joint presents as swelling of the joint, and the methods of the present disclosure reduce the swelling of the joint. In some embodiments, the hyperproliferation of the soft tissue of a joint presents as pain in the joint, and the methods of the present disclosure reduce the pain in the joint. In other embodiments, the hyperproliferation of the soft tissue of a joint presents as decreased range of motion of the joint, and the methods of the present invention increase the range of motion of the joint.

The methods disclosed herein can be practiced on a subject who has been treated and has shown decreased hemophilic arthropathy to prevent further developments of hemophilic arthropathy of one or more joints. In some embodiments, the methods of the present disclosure are applied to a subject to treat an existing hemophilic arthropathy of one or more joints and to prevent the development of further hemophilic arthropathy one the same or a different joint.

In some embodiments, the method of the present disclosure allows the clotting factor to distribute to tissues outside of the plasma compartment as well as in the plasma compartment.

The methods of the present disclosure improve the joint health of one or more joint in a human having hemophilia. Joint health can be measured using any metrics known in the art. In some embodiments, joint health is measured using the hemophilia joint health score (HJHS) system (see Feldman et al., "Hemophilia Joint Health Score (HJHS) 2.1," available at http://www.wfh.org/en/page.aspx?pid=885 (last accessed Nov. 18, 2016), which is incorporated by reference herein in its entirety). The HJHS measures joint health, in the domain of body structure and function (i.e. impairment), of the joints most commonly affected by bleeding in hemophilia: the knees, ankles, and elbows. Though it was primarily designed for children with hemophilia aged 4-18 years with mild joint impairment (e.g., treated with prophylaxis), in can be applied to any population. In some embodiments, the HJHS measures swelling, duration (of swelling), muscle atrophy, crepitus on motion, flexion loss, extension loss, joint pain, and strength for each of the left and right elbows, left and right knees, and left and right ankles of a human having hemophilia. In some embodiments, each parameter is assigned a numerical score. In one particular embodiment, standard HJHS, version 2.1 is used to measure joint health. In some embodiments, swelling is scored from 0 to 3, with 0 being no swelling, and 3 being severe swelling. In some embodiments, duration of swelling is scored from 0 to 1, with 0 being no swelling or swelling for less than 6 months, and 1 being swelling for greater than or equal to 6 months. In some embodiments, muscle atrophy is scored from 0 to 2, 0 being no atrophy, and 2 being severe atrophy. In some embodiments, crepitus in motion is scored from 0 to 2, 0 being no crepitus in motion, and 2 being severe crepitus in motion. In some embodiments, flexion loss is scored from 0 to 3, 0 being less than 5° flexion loss, and 3 being greater than 20° flexion loss. In some embodiments, extension loss is scored from 0 to 3, 0 being less than 5° extension loss, and 3 being greater than 20° extension loss. In some embodiments, joint pain is scored from 0 to 2, with 0 being no pain through active range of motion, and 2 being pain through active range of motion. In some embodiments, global gait is scored, with 0 reflecting that all skills are within normal limits; 1, 2, and 3 reflecting that 1, 2, and 3 skills, respectively, are not within normal limits; and 4 reflecting that no skills are within normal limits. In certain embodiments, the global gait score is measured based on walking, climbing stairs, running, and/or hopping on one leg. In some embodiments, the scores are combined to generate a total score. In other embodiments, individual scores for one or more joints are evaluated as an indication of the health of the one or more joints.

In other embodiments, a modified HJHS system is used to measure joint health. In some embodiments, the mHJHS differs from the standard HJHS, version 2.1, in that the response options for joint pain and gait were condensed into fewer categories, an assessment for instability was added, and the total score is lower (range, 0-116; 0 indicates normal joint function, 116 indicates severe disease) compared with the standard HJHS (range, 0-124). Scores preceded by a bleed within 2 weeks were excluded. Scores for joints that underwent surgical interventional were imputed using last observation carry forward. To evaluate year-by-year change, rFVIIIFc extension study subjects who had mHJHS data at 4 time points (rFVIIIFc pivotal phase 3 trial baseline, rFVIIIFc extension study baseline, rFVIIIFc extension study Year 1, and rFVIIIFc extension study Year 2) were included in this post hoc analysis. Change in mHJHS score from rFVIIIFc pivotal phase 3 trial baseline to rFVIIIFc extension study Year 2 (negative value indicates improvement) was summarized using descriptive statistics. Change in mHJHS score from rFVIIIFc pivotal phase 3 trial baseline to follow-up visits was summarized for: (1) total score (range, 0-116; by pre-study regimen (prophylactic versus episodic); by severity of functional impairment based on initial mHJHS; and by presence of target joints at baseline; (2) target joints (range, 0-19: sum of all questions for a single target joint); (3) Weight bearing (e.g., ankle and knee) and non-weight bearing (e.g., elbow) joints (range, 0-38: sum of right and left joints of a single location); and (4) individual components (range of motion (range, 0-36: combination of questions "Extension loss [dorsiflexion of ankles]" and "Flexion loss [plantarflexion of ankles]" of all joints); swelling (range, 0-24: combination of questions "Swelling" and "Duration of swelling" of all joints); and strength (range, 0-6: sum of all joints)).

In some embodiments, joint scoring is done separately for the 6 joints (left ankle—LA, right ankle—RA, left elbow—LE, right elbow—RE, left knee—LK, right knee—RK). In some embodiments, swelling is scored according to the following: 0=none; 1=mild; 2=moderate; 3=severe. In some embodiments, duration of swelling is scored according to the following: 0=no swelling or ≤6 months; 1=>6 months. In some embodiments, muscle atrophy is scored according to the following: 0=none; 1=mild; 2=severe. In some embodiments, crepitus on motion is scored according to the following: 0=absent; 1=present. In some embodiments, flexion loss, including loss of plantarflexion of ankles, is scored according to the following: 0=none; 1=mild; 2=moderate; 3=severe. In some embodiments, extension loss, including loss of dorsiflexion of ankles, is scored according to the following: 0=none; 1=mild; 2=moderate; 3=severe. In some embodiments, instability is scored according to the following: 0=none; 1=significant pathologic joint laxity. In some embodiments, joint pain is scored according to the following: 0=no pain, either through range or at end range of motion; 1=present. In some embodiments, strength is scored according to the following: 0=normal (holds position against gravity and maximum resistance); 1=minimal decrease (holds position against gravity and moderate resistance, but not maximum resistance); 2=mild decrease (holds position against gravity or minimal resistance); 3=moderate decrease (able to move joint if gravity eliminated); 4=severe decrease (trace or no muscle contraction). In certain embodiments, for scoring flexion loss and extension loss at knees and elbows, the following applies: none=approximately 0-5 degrees; mild=approximately 5-10 degrees; moderate=approximately 11-20 degrees; and severe=approximately >20 degrees.

In some embodiments, gait is scored once (range is 0-2), wherein 0=no difficulty with walking or climbing up/down stairs; 1=no difficulty with walking, but difficulty with stairs; and 2=difficulty with walking and with stairs.

In certain embodiments, joint scoring is done separately for the 6 joints (left ankle—LA, right ankle—RA, left elbow—LE, right elbow—RE, left knee—LK, right knee—RK) according to the following categories and scales (range is 0-19 for each joint and 0-114 for all six joints): swelling (0=none; 1=mild; 2=moderate; 3=severe); duration of swelling (0=no swelling or ≤6 months; 1=>6 months); muscle atrophy (0=none; 1=mild; 2=severe); crepitus on motion (0=absent; 1=present); flexion loss, including loss of plantarflexion of ankles (0=none; 1=mild; 2=moderate; 3=severe); extension loss, including loss of dorsiflexion of ankles (0=none; 1=mild; 2=moderate; 3=severe); instability (0=none; 1=significant pathologic joint laxity); joint pain (0=no pain, either through range or at end range of motion; 1=present); strength (0=normal (holds position against gravity and maximum resistance); 1=minimal decrease (holds position against gravity and moderate resistance, but not maximum resistance); 2=mild decrease (holds position against gravity or minimal resistance); 3=moderate decrease (able to move joint if gravity eliminated); 4=severe decrease (trace or no muscle contraction); wherein, for scoring flexion loss and extension loss at knees and elbows, the following applies: none=approximately 0-5 degrees;

mild=approximately 5-10 degrees; moderate=approximately 11-20 degrees; and severe=approximately >20 degrees.

In some embodiments, the present disclosure provides a method of treating reversible hemophilic arthropathy of a joint in a human having hemophilia comprising administering to the human an effective amount of a composition or a chimeric protein comprising a clotting factor and an Fc region, wherein the administration improves a HJHS score of the human relative to the HJHS score prior to the administration. In some embodiments, the HJHS score is a total HJHS score, which includes the sum of all joint scores measured plus a global gate score. In some embodiments, the HJHS score is a total HJHS score, which includes the sum of all joint scores measured and not a global gate score. In other embodiments, the HJHS score is for one or both elbows, one or both knees, one or both ankles, or any combination thereof. In one particular embodiment, the HJHS score is for an elbow. In another embodiment, the HJHS score is for a knee. In another embodiment, the HJHS score is for an ankle. In another embodiment, the HJHS score reflects global gait.

In some embodiments, the present disclosure provides a method of treating reversible hemophilic arthropathy of a joint in a human having hemophilia comprising administering to the human an effective amount of a composition or a chimeric protein comprising a clotting factor and an Fc region, wherein the administration reduces joint pain in the human. In some embodiments, the joint pain is reduced relative to the joint pain prior to the administration. In certain embodiments, the method further provides measuring joint pain in one or more joints prior to administration of the effective amount of a composition or a chimeric protein comprising a clotting factor and an Fc region. In some embodiments, the method further provides measuring joint pain in one or more joints after administration of the effective amount of a composition or a chimeric protein comprising a clotting factor and an Fc region.

In certain embodiments, the effects of the present methods are observed in one or more joints of the human. In some embodiments, the effects of the present methods are observed in at least one joint. In some embodiments, the effects of the present methods are observed in at least two, at least three, at least four, at least five, at least six, at least seven, at least eight, at least nine, or at least ten joints.

In some embodiments, the methods of the present disclosure further comprise identifying a human in need of treatment, e.g., identifying a subject having hemophilic arthropathy. Hemophilic arthropathy can be detected and/or monitored using any methods known in the art. In some embodiments, an imaging system is used to detect and/or monitor a hemophilic arthropathy in a subject. In some embodiments, the imaging system comprises any imaging system known in the art that is used to characterize joints. For example, in certain embodiments, the imaging system comprises a radiography, a magnetic resonance imaging, an ultrasonography, power Doppler sonography, or any combination thereof.

In some embodiments, the subject has been previously treated with a clotting factor protein not fused to an Fc portion. This clotting factor can be a full length or mature clotting factor. In some embodiments, such clotting factor can be ADVATE®, RECOMBINATE®, KOGENATE FS®, HELIXATE FS®, XYNTHA®/REFACTO AB®, HEMOFIL-M®, MONARC-M®, MONOCLATE-P®, HUMATE-P®, ALPHANATE®, KOATE-DVI®, AFSTYLA®, AND HYATE:C®, IDELVION®.

II.A. Chimeric Proteins

The methods of treating reversible hemophilic arthropathy disclosed herein are generally applicable chimeric proteins or compositions comprising a clotting factor and an Fc region, wherein the clotting factor can be any known clotting factor, fragment thereof, or variant thereof, and wherein the Fc region can be any known Fc region, fragment thereof, or variant thereof. In some embodiments, the composition comprises a chimeric protein comprising the clotting factor and the Fc region. In some embodiments, the clotting factor is selected from the group consisting of factor VII (FVII), factor VIIa (FVIIa), factor VIII (FVIII), factor IX (FIX), factor X (FX), von willebrand factor (VWF), or any combination thereof. Accordingly, the present disclosures regarding FVIIIFc and FIXFc chimeric polypeptides, and their uses, are equally applicable to other chimeric polypeptides comprising a clotting factor portion and an Fc portion. Any clotting factor or any fragment thereof or any variant thereof can be used in the methods of the present disclosure.

Not being bound by any theory, it is believed that an Fc region fused to a clotting factor is useful in treating reversible hemophilic arthropathy. Inflammation in hemophilia occurs during bleeding into joints. It has been shown that TNF-α, an inflammatory cytokine involved in hemophilic arthropathy, induces NF-κB signaling and thereby upregulates FcRn expression in human monocytes (Liu et al., *J Immunol*, 2007. 179(5): p. 2999-3011). FcRn can thus be upregulated at sites of inflammation, allowing Fc-containing proteins to localize to sites of inflammation through binding to the receptor Fc receptors as part of the regulation of the inflammatory processes. The Fc region fused to a clotting factor can also interact with inhibitory Fc receptors that can cause immune modulation and down regulation of inflammatory pathways. For example, rFVIIIFc could block the Fc neonatal receptor (FcRn) and activate Fcγ receptors (FcγR), leading to altered levels of pro- and anti-inflammatory molecules. Thus, in some embodiments, the Fc region of the chimeric protein facilitates localization of the chimeric protein to the joint, e.g., the site of inflammation and/or injury and/or damage.

In other embodiments, the clotting factor can be a clotting factor mimic. Clotting factor mimics can manifest one or more clotting factor activities. For example, an antibody or antibody binding portion thereof can act like FVIII by binding to both Factor IX and Factor X. Such antibodies or antigen binding portions thereof can be used for the present methods if the antibodies or antigen biding portions thereof contains an Fc region. In another embodiment, the clotting factor is a peptide that has a FVIII activity.

In this respect, the present disclosure provides in general a method of treating reversible hemophilic arthropathy in a subject in need thereof comprising administering to the subject a chimeric polypeptide comprises a clotting factor portion and an Fc portion.

II.A.1. Factor VIII

"Factor VIII," abbreviated throughout the instant application as "FVIII," as used herein, means functional FVIII polypeptide in its normal role in coagulation, unless otherwise specified. Thus, the term FVIII includes variant polypeptides that are functional. "A FVIII protein" is used interchangeably with FVIII polypeptide (or protein) or FVIII. Examples of the FVIII functions include, but are not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632). The full length polypeptide and polynucleotide sequences are known, as are many functional fragments, mutants and modified versions. Various FVIII amino acid and nucleotide sequences are disclosed in, e.g., US Publication Nos. 2015/0158929 A1, 2014/0308280 A1, and 2014/0370035 A1 and International Publication No. WO 2015/106052 A1, each of which is incorporated by reference in its entirety. FVIII polypeptides include, e.g., full-length FVIII, full-length FVIII minus Met at the N-terminus, mature FVIII (minus the signal sequence), mature FVIII with an additional Met at the N-terminus, and/or FVIII with a full or partial deletion of the B domain. FVIII variants include B domain deletions, whether partial or full deletions.

In some embodiments, the FVIII of the chimeric protein or composition of the present disclosure comprises a B domain deleted FVIII. A "B domain" of FVIII, as used herein, is the same as the B domain known in the art that is defined by internal amino acid sequence identity and sites of proteolytic cleavage by thrombin, e.g., residues Ser741-Arg1648 of mature human FVIII. The other human FVIII domains are defined by the following amino acid residues, relative to mature human FVIII: A1, residues Ala1-Arg372; A2, residues Ser373-Arg740; A3, residues Ser1690-Ile2032; C1, residues Arg2033-Asn2172; C2, residues Ser2173-Tyr2332 of mature FVIII. The sequence residue numbers used herein without referring to any SEQ ID Numbers correspond to the FVIII sequence without the signal peptide sequence (19 amino acids) unless otherwise indicated. The A3-C1-C2 sequence, also known as the FVIII heavy chain, includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art. In one embodiment, the B domain of FVIII is deleted ("B-domain-deleted FVIII" or "BDD FVIII"). An example of a BDD FVIII is REFACTO® (recombinant BDD FVIII). In one particular embodiment the B domain deleted FVIII variant comprises a deletion of amino acid residues 746 to 1648 of mature FVIII.

A "B-domain-deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563 and Int'l Publ. No. WO 2015106052 A1 (PCT/US2015/010738). In some embodiments, a B-domain-deleted FVIII sequence used in the methods of the present disclosure comprises any one of the deletions disclosed at col. 4, line 4 to col. 5, line 28 and Examples 1-5 of U.S. Pat. No. 6,316,226 (also in U.S. Pat. No. 6,346,513). In another embodiment, a B-domain deleted Factor VIII is the 5743/Q1638 B-domain deleted Factor VIII (SQ BDD FVIII) (e.g., Factor VIII having a deletion from amino acid 744 to amino acid 1637, e.g., Factor VIII having amino acids 1-743 and amino acids 1638-2332 of mature FVIII). In some embodiments, a B-domain-deleted FVIII used in the methods of the present disclosure has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted FVIII has a deletion of most of the B domain, but still contains amino-terminal sequences of the B domain that are essential for in vivo proteolytic processing of the primary translation product into two polypeptide chain, as disclosed in WO 91/09122. In some embodiments, a B-domain-deleted FVIII is constructed with a deletion of amino acids 747-1638, i.e., virtually a complete deletion of the B domain. Hoeben R. C., et al. *J. Biol. Chem.* 265 (13): 7318-7323 (1990). A B-domain-deleted Factor VIII may also contain a deletion of amino acids 771-1666 or amino acids 868-1562 of FVIII. Meulien P., et al. *Protein Eng.* 2(4): 301-6 (1988). Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., *DNA* (1987) 6:553-564)), 741 through 1648 (Pasek (PCT application No. 88/00831)), or 816 through 1598 or 741 through 1648 (Lagner (Behring Inst. Mitt. (1988) No 82:16-25, EP 295597)). In one particular embodiment, the B-domain-deleted FVIII comprises a deletion of amino acid residues 746 to 1648 of mature FVIII. In another embodiment, the B-domain-deleted FVIII comprises a deletion of amino acid residues 745 to 1648 of mature FVIII.

In other embodiments, BDD FVIII includes a FVIII polypeptide containing fragments of the B-domain that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103(a): 3412-3419 (2004), Kasuda, A, et al., *J. Thromb. Haemost.* 6: 1352-1359 (2008), and Pipe, S. W., et al., *J. Thromb. Haemost.* 9: 2235-2242 (2011) (i.e., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., *Blood* 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9: 2235-2242 (2011). In some embodiments, the BDD FVIII comprises a single chain FVIII that contains a deletion in amino acids 765 to 1652 corresponding to the mature full length FVIII (also known as rVIII-SingleChain and AFSTYLA®). See U.S. Pat. No. 7,041,635. Each of the foregoing deletions may be made in any FVIII sequence.

A great many functional FVIII variants are known, as is discussed above and below. In addition, hundreds of non-functional mutations in FVIII have been identified in hemophilia patients, and it has been determined that the effect of these mutations on FVIII function is due more to where they lie within the 3-dimensional structure of FVIII than on the nature of the substitution (Cutler et al., *Hum. Mutat.* 19:274-8 (2002)), incorporated herein by reference in its entirety. In addition, comparisons between FVIII from humans and other species have identified conserved residues that are likely to be required for function (Cameron et al., *Thromb. Haemost.* 79:317-22 (1998); U.S. Pat. No. 6,251, 632), incorporated herein by reference in its entirety.

In some embodiments, an effective amount of the composition or a chimeric protein comprising a FVIII and an Fc region is equivalent to an effective amount of the FVIII without the Fc region. In certain embodiments, the effective amount is from about 10 IU/Kg to about 300 IU/kg. In some embodiments, the effective amount is from about 20 IU/Kg to about 300 IU/kg. In some embodiments, the effective amount is about 20 IU/kg to about 250 IU/kg, about 20 IU/kg to about 200 IU/kg, about 20 IU/kg to about 190 IU/kg, about 20 IU/kg to about 180 IU/kg, about 20 IU/kg to about 170 IU/kg, about 20 IU/kg to about 160 IU/kg, about 20 IU/kg to about 150 IU/kg, about 20 IU/kg to about 140 IU/kg, about 20 IU/kg to about 130 IU/kg, from about 20 IU/kg to about 120 IU/kg, from about 20 IU/kg to about 110 IU/kg, from about 20 IU/kg to about 100 IU/kg, from about 20 IU/kg to about 90 IU/kg, from about 20 IU/kg to about 80 IU/kg, from about 20 IU/kg to about 70 IU/kg, from about 20 IU/kg to about 60 IU/kg, from about 25 IU/kg to about 100 IU/kg, from about 25 IU/kg to about 90 IU/kg, from about 25 IU/kg to about 80 IU/kg, from about 25 IU/kg to about 70 IU/kg, from about 25 IU/kg to about 65 IU/kg. In one particular embodiment, the effective amount is from about 20 IU/kg to about 100 IU/kg. In another embodiment, the effective amount is from about 25 IU/kg to about 65 IU/kg. In other embodiments, the effective amount is from about 20 IU/kg to about 100 IU/kg, from about 30 IU/kg to about 100 IU/kg, from about 40 IU/kg to about 100 IU/kg, from about 50 IU/kg to about 100 IU/kg, from about 60 IU/kg to about 100 IU/kg, from about 70 IU/kg to about 100 IU/kg, from about 80 IU/kg to about 100 IU/kg, from about 90 IU/kg to about 100 IU/kg, from about 20 IU/kg to about 90 IU/kg, from about 20 IU/kg to about 80 IU/kg, from about 20 IU/kg to about 70 IU/kg, from about 20 IU/kg to about 60 IU/kg, from about 20 IU/kg to about 50 IU/kg, from about 20 IU/kg to about 40 IU/kg, or from about 20 IU/kg to about 30 IU/kg.

In some embodiments, the effective amount is about 10 IU/kg, about 15 IU/kg, about 20 IU/kg, about 25 IU/kg, about 30 IU/kg, about 35 IU/kg, about 40 IU/kg, about 45 IU/kg, about 50 IU/kg, about 55 IU/kg, about 60 IU/kg, about 65 IU/kg, about 70 IU/kg, about 75 IU/kg, about 80 IU/kg, about 85 IU/kg, about 90 IU/kg, about 95 IU/kg, about 100 IU/kg, about 105 IU/kg, about 110 IU/kg, about 115 IU/kg, about 120 IU/kg, about 125 IU/kg, about 130 IU/kg, about 135 IU/kg, about 140 IU/kg, about 145 IU/kg, about 150 IU/kg, about 155 IU/kg, about 160 IU/kg, about 165 IU/kg, about 170 IU/kg, about 175 IU/kg, about 180 IU/kg, about 185 IU/kg, about 190 IU/kg, about 195 IU/kg, about 200 IU/kg, about 225 IU/kg, about 250 IU/kg, about 275 IU/kg, or about 300 IU/kg. In one particular embodiment, the effective amount is about 50 IU/kg. In another embodiment, the effective amount is about 100 IU/kg. In another embodiment, the effective amount is about 200 IU/kg.

The dosing interval when administering the composition or the chimeric protein comprising FVIII and an Fc region or a fragment thereof can be at least about one and one-half times longer than the dosing interval required for an equivalent dose of said clotting factor without the Fc domain. The dosing interval can be at least about one and one-half to six times longer, one and one-half to five times longer, one and one-half to four times longer, one and one-half to three times longer, or one and one-half to two times longer, than the dosing interval required for an equivalent dose of said FVIII without the Fc domain.

In some embodiments, the effective dose of the composition or the chimeric protein comprising a FVIII and an Fc region is administered to the human at a dosing interval of about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, or about 24 days. In some embodiments, the effective dose of the composition or chimeric protein comprising a FVIII and an Fc region is administered to the human at a dosing interval of about 25 days, about 26 days, about 27 days, about 28 days, about 29 days, about 30 days, about 45 days, or about 60 days.

In some embodiments, the composition or chimeric protein comprising a FVIII and an Fc region is administered at a dosing interval of about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 14 days, about 3 to about 14 days, about 4 to about 14 days, about 5 to about 14 days, about 6 to about 14 days, about 7 to about 14 days, about 8 to about 14 days, about 9 to about 14 days, about 10 to about 14 days, about 11 to about 14 days, about 12 to about 14 days, about 13 to about 14 days, or about 5 to about 10 days. In other embodiments, the composition or chimeric protein comprising a FVIII and an Fc region is administered at a dosing interval of about 1 to about 21 days, about 1 to about 20 days, about 1 to about 19 days, about 1 to about 18 days, about 1 to about 17 days, about 1 to about 16 days, about 1 to about 15 days, about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 21 days, about 3 to about 21 days, about 4 to about 21 days, about 5 to about 21 days, about 6 to about 21 days, about 7 to about 21 days, about 8 to about 21 days, about 9 to about 21 days, about 10 to about 21 days, about 11 to about 21 days, about 12 to about 21 days, about 13 to about 21 days, about 14 to about 21 days, about 15 to about 21 days, about 16 to about 21 days, about 17 to about 21 days, about 18 to about 21 days, about 19 to about 21 days, about 20 to about 21 days, about 5 to about 10 days, about 10 to about 15 days, about 15 to about 20 days. In certain embodiments, the composition or chimeric protein comprising a FVIII and an Fc region is administered at a dosing interval of about 2 to about 6 days. In another embodiments, the chimeric protein comprising a FVIII and an Fc region is administered at a dosing interval of about 3 to about 5 days.

In one embodiment, the effective dose is 25-65 IU/kg (25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 62, 64, or 65 IU/kg) and the dosing interval is once every 3-5, 3-6, 3-7, 3, 4, 5, 6, 7, or 8 or more days, or three times per week, or no more than three times per week. In another embodiment, the effective dose is 65

IU/kg and the dosing interval is once weekly, or once every 6-7 days. The doses can be administered repeatedly as long as they are necessary (e.g., at least 10, 20, 28, 30, 40, 50, 52, or 57 weeks, at least 1, 2, 3, 4, 5, 6, 7, 8, 9, or 10 years). In one particular embodiment, the effective dose is about 25-65 IU/kg and the dosing interval is once every 3-5 days.

The composition or chimeric protein comprising a FVIII and an Fc region can be formulated for any appropriate manner of administration, including, for example, topical (e.g., transdermal or ocular), oral, buccal, nasal, vaginal, rectal or parenteral administration.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. The composition can be also for example a suspension, emulsion, sustained release formulation, cream, gel or powder. The composition can be formulated as a suppository, with traditional binders and carriers such as triglycerides.

In one example, the pharmaceutical formulation is a liquid formulation, e.g., a buffered, isotonic, aqueous solution. In another example, the pharmaceutical composition has a pH that is physiologic, or close to physiologic. In other examples, the aqueous formulation has a physiologic or close to physiologic osmolarity and salinity. It can contain sodium chloride and/or sodium acetate.

In some embodiments, the chimeric protein comprising a FVIII and an Fc region used in the methods of the present invention is formulated in a pharmaceutical composition comprising: (a) the chimeric polypeptide; (b) one or more stabilizing agents selected from sucrose, trehalose, raffinose, arginine, or mixture thereof; (c) sodium chloride (NaCl); (d) L-histidine; (e) calcium chloride; and (f) polysorbate 20 or polysorbate 80. In certain embodiments, the pharmaceutical composition comprises: (a) 50 IU/ml to 2500 IU/ml of the chimeric polypeptide; (b) 10 mg/ml to 25 mg/ml of sucrose; (c) 8.8 mg/ml to 14.6 mg/ml sodium chloride (NaCl); (d) 0.75 mg/ml to 2.25 mg/ml L-histidine; (e) 0.75 mg/ml to 1.5 mg/ml calcium chloride dihydrate; and (f) 0.08 mg/ml to 0.25 mg/ml polysorbate 20 or polysorbate 80. In some examples, the pharmaceutical composition used in the methods of the present disclosure is lyophilized.

In some embodiments, the pharmaceutical composition does not comprise an immune cell. In some embodiments, the pharmaceutical composition does not comprise a cell.

II.A.2. Factor IX

Human Factor IX (FIX) is a serine protease that is an important component of the intrinsic pathway of the blood coagulation cascade. "Factor IX" or "FIX," as used herein, refers to a coagulation factor protein and species and sequence variants thereof, and includes, but is not limited to, the 461 single-chain amino acid sequence of human FIX precursor polypeptide ("prepro"), the 415 single-chain amino acid sequence of mature human FIX (, and the R338L FIX (Padua) variant. FIX includes any form of FIX molecule with the typical characteristics of blood coagulation FIX. As used herein "Factor IX" and "FIX" are intended to encompass polypeptides that comprise the domains Gla (region containing γ-carboxyglutamic acid residues), EGF1 and EGF2 (regions containing sequences homologous to human epidermal growth factor), activation peptide ("AP," formed by residues R136-R180 of the mature FIX), and the C-terminal protease domain ("Pro"), or synonyms of these domains known in the art, or can be a truncated fragment or a sequence variant that retains at least a portion of the biological activity of the native protein.

FIX or sequence variants have been cloned, as described in U.S. Pat. Nos. 4,770,999 and 7,700,734, and cDNA coding for human Factor IX has been isolated, characterized, and cloned into expression vectors (see, e.g., Choo et al., Nature 299:178-180 (1982); Fair et al., Blood 64:194-204 (1984); and Kurachi et al., Proc. Natl. Acad. Sci., U.S.A. 79:6461-6464 (1982)). One particular variant of FIX, the R338L FIX (Padua) variant, characterized by Simioni et al, 2009, comprises a gain-of-function mutation, which correlates with a nearly 8-fold increase in the activity of the Padua variant relative to native FIX. FIX variants can also include any FIX polypeptide having one or more conservative amino acid substitutions, which do not affect the FIX activity of the FIX polypeptide.

In some embodiments, the FIX comprises coagulation factor IX (recombinant), albumin fusion protein (also known as rIX-FP and IDELVION®).

The FIX polypeptide is 55 kDa, synthesized as a prepropolypeptide chain composed of three regions: a signal peptide of 28 amino acids (amino acids 1 to 28), a propeptide of 18 amino acids (amino acids 29 to 46), which is required for gamma-carboxylation of glutamic acid residues, and a mature Factor IX of 415 amino acids. The propeptide is an 18-amino acid residue sequence N-terminal to the gamma-carboxyglutamate domain. The propeptide binds vitamin K-dependent gamma carboxylase and then is cleaved from the precursor polypeptide of FIX by an endogenous protease, most likely PACE (paired basic amino acid cleaving enzyme), also known as furin or PCSK3. Without the gamma carboxylation, the Gla domain is unable to bind calcium to assume the correct conformation necessary to anchor the protein to negatively charged phospholipid surfaces, thereby rendering Factor IX nonfunctional. Even if it is carboxylated, the Gla domain also depends on cleavage of the propeptide for proper function, since retained propeptide interferes with conformational changes of the Gla domain necessary for optimal binding to calcium and phospholipid. In humans, the resulting mature Factor IX is secreted by liver cells into the blood stream as an inactive zymogen, a single chain protein of 415 amino acid residues that contains approximately 17% carbohydrate by weight (Schmidt, A. E., et al. (2003) Trends Cardiovasc Med, 13: 39).

The mature FIX is composed of several domains that in an N- to C-terminus configuration are: a GLA domain, an EGF1 domain, an EGF2 domain, an activation peptide (AP) domain, and a protease (or catalytic) domain. A short linker connects the EGF2 domain with the AP domain. FIX contains two activation peptides formed by R145-A146 and R180-V181, respectively. Following activation, the single-chain FIX becomes a 2-chain molecule, in which the two chains are linked by a disulfide bond. Clotting factors can be engineered by replacing their activation peptides resulting in altered activation specificity. In mammals, mature FIX must be activated by activated Factor XI to yield Factor IXa. The protease domain provides, upon activation of FIX to FIXa, the catalytic activity of FIX. Activated Factor VIII (FVIIIa) is the specific cofactor for the full expression of FIXa activity.

In other embodiments, a FIX polypeptide comprises an Thr148 allelic form of plasma derived Factor IX and has structural and functional characteristics similar to endogenous Factor IX.

A great many functional FIX variants are known. International publication number WO 02/040544 A3 discloses mutants that exhibit increased resistance to inhibition by heparin at page 4, lines 9-30 and page 15, lines 6-31. International publication number WO 03/020764 A2 discloses FIX mutants with reduced T cell immunogenicity in Tables 2 and 3 (on pages 14-24), and at page 12, lines 1-27. International publication number WO 2007/149406 A2 discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2 discloses FIX mutants that exhibit increased clotting activity at page 5, line 14 to page 6, line 5. International publication number WO 09/051717 A2 discloses FIX mutants having an increased number of N-linked and/or O-linked glycosylation sites, which results in an increased half-life and/or recovery at page 9, line 11 to page 20, line 2. International publication number WO 09/137254 A2 also discloses Factor IX mutants with increased numbers of glycosylation sites at page 2, paragraph [006] to page 5, paragraph [011] and page 16, paragraph [044] to page 24, paragraph [057]. International publication number WO 09/130198 A2 discloses functional mutant FIX molecules that have an increased number of glycosylation sites, which result in an increased half-life, at page 4, line 26 to page 12, line 6. International publication number WO 09/140015 A2 discloses functional FIX mutants that an increased number of Cys residues, which can be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety.

In addition, hundreds of non-functional mutations in FIX have been identified in hemophilia subjects, many of which are disclosed in Table 5, at pages 11-14 of International publication number WO 09/137254 A2. Such non-functional mutations are not included in the invention, but provide additional guidance for which mutations are more or less likely to result in a functional FIX polypeptide.

Factor IX coagulant activity is expressed as International Unit(s) (IU). One IU of FIX activity corresponds approximately to the quantity of FIX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®). The invention contemplates sequences that have homology to FIX sequences, sequence fragments that are natural, such as from humans, non-human primates, mammals (including domestic animals), and non-natural sequence variants which retain at least a portion of the biologic activity or biological function of FIX and/or that are useful for preventing, treating, mediating, or ameliorating a coagulation factor-related disease, deficiency, disorder or condition (e.g., bleeding episodes related to trauma, surgery, of deficiency of a coagulation factor). Sequences with homology to human FIX can be found by standard homology searching techniques, such as NCBI BLAST.

In some embodiments, an effective amount of the composition or chimeric protein comprising a FIX and an Fc region is equivalent to an effective amount of the FIX without the Fc region. In certain embodiments, the effective amount is from about 0.1 IU/kg to about 500 IU/kg. In some embodiments, the effective amount is from about 10 IU/Kg to about 400 IU/kg. In some embodiments, the effective amount is from about 20 IU/Kg to about 300 IU/kg. In some embodiments, the effective amount is about 20 IU/kg to about 275 IU/kg, about 20 IU/kg to about 250 IU/kg, about 20 IU/kg to about 225 IU/kg, about 20 IU/kg to about 200 IU/kg, about 20 IU/kg to about 175 IU/kg, about 20 IU/kg to about 150 IU/kg, about 20 IU/kg to about 100 IU/kg, from about 20 IU/kg to about 90 IU/kg, from about 20 IU/kg to about 80 IU/kg, from about 20 IU/kg to about 70 IU/kg, from about 20 IU/kg to about 60 IU/kg, from about 20 IU/kg to about 50 IU/kg, from about 20 IU/kg to about 40 IU/kg, from about 20 IU/kg to about 30 IU/kg, from about 30 IU/kg to about 100 IU/kg, from about 40 IU/kg to about 100 IU/kg, from about 50 IU/kg to about 100 IU/kg, from about 60 IU/kg to about 100 IU/kg, from about 70 IU/kg to about 100 IU/kg, from about 80 IU/kg to about 100 IU/kg, from about 90 IU/kg to about 100 IU/kg, from about 100 IU/kg to about 200 IU/kg, from about 150 IU/kg to about 200 IU/kg, or from about 25 IU/kg to about 75 IU/kg. In one particular embodiment, the effective amount is from about 20 IU/kg to about 100 IU/kg.

In some embodiments, the effective amount is about 10 IU/kg, about 15 IU/kg, about 20 IU/kg, about 25 IU/kg, about 30 IU/kg, about 35 IU/kg, about 40 IU/kg, about 45 IU/kg, about 50 IU/kg, about 55 IU/kg, about 60 IU/kg, about 65 IU/kg, about 70 IU/kg, about 75 IU/kg, about 80 IU/kg, about 85 IU/kg, about 90 IU/kg, about 95 IU/kg, about 100 IU/kg, about 105 IU/kg, about 110 IU/kg, about 115 IU/kg, about 120 IU/kg, about 125 IU/kg, about 130 IU/kg, about 135 IU/kg, about 140 IU/kg, about 145 IU/kg, about 150 IU/kg, about 155 IU/kg, about 160 IU/kg, about 165 IU/kg, about 170 IU/kg, about 175 IU/kg, about 180 IU/kg, about 185 IU/kg, about 190 IU/kg, about 195 IU/kg, or about 200 IU/kg. In one particular embodiment, the effective amount is about 50 IU/kg. In another embodiment, the effective amount is about 100 IU/kg.

The dosing interval when administering the composition or chimeric protein comprising FIX and an Fc region or a fragment thereof can be at least about one and one-half times longer than the dosing interval required for an equivalent dose of said FIX without the Fc domain. The dosing interval can be at least about one and one-half to six times longer, one and one-half to five times longer, one and one-half to four times longer, one and one-half to three times longer, or one and one-half to two times longer, than the dosing interval required for an equivalent dose of said FIX without the Fc domain. In some embodiments, the dosing interval is at least about one and one-half, two, two and one-half, three, three and one-half, four, four and one-half, five, five and one-half or six times longer than the dosing interval required for an equivalent dose of said FIX without the Fc domain. The dosing interval can be about every three, four, five, six, seven, eight, nine, ten, eleven, twelve, thirteen, or fourteen days or longer. The dosing interval can be at least about one and one-half to 5, one and one-half, 2, 3, 4, or 5 days or longer. For on-demand treatment, the dosing interval of said chimeric polypeptide or hybrid is about once every 24-36, 24-48, 24-72, 24-96, 24-120, 24-144, 24-168, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours or longer.

In some embodiments, the effective dose of the composition or chimeric protein comprising a FIX and an Fc region is administered to the human at a dosing interval of about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, or about 24 days. In some embodiments, the effective dose of the composition or chimeric protein comprising a FVIII and an Fc region is administered to the human at a dosing interval of about 25 days, about 26 days, about 27 days, about 28 days, about 29 days, about 30 days, about 45 days, or about 60 days. In certain embodiments, the effective dose of the composition or chimeric protein comprising a FVIII and an Fc region is administered to the human at a dosing interval of about 7 days, about 8 days, about 9 days, about 10 days, about 11 days, about 12 days, about 13 days, or about 14 days. In one particular embodiment, the effective dose of the composition or chimeric protein comprising a FVIII and an Fc region is administered to the human at a dosing interval of about 2 days (e.g., about 48 hours). In another embodiment, the effective dose of the composition or chimeric protein comprising a FVIII and an Fc region is administered to the human at a dosing interval of about 7 days. In another embodiment, the effective dose of the composition or chimeric protein comprising a FVIII and an Fc region is administered to the human at a dosing interval of about 10 days. In some embodiments, an effective dose of the composition or chimeric protein comprising a FVIII and an Fc region is administered to the human at a dosing interval of every 6-10 hours. In certain embodiments, the effective dose of the composition or chimeric protein comprising a FVIII and an Fc region is administered to the human at a dosing interval of every day.

In some embodiments, the composition or chimeric protein comprising a FVIII and an Fc region is administered at a dosing interval of about 1 to about 21 days, about 1 to about 20 days, about 1 to about 19 days, about 1 to about 18 days, about 1 to about 17 days, about 1 to about 16 days, about 1 to about 15 days, about 1 to about 14 days, about 1 to about 13 days, about 1 to about 12 days, about 1 to about 11 days, about 1 to about 10 days, about 1 to about 9 days, about 1 to about 8 days, about 1 to about 7 days, about 1 to about 6 days, about 1 to about 5 days, about 1 to about 4 days, about 1 to about 3 days, about 1 to about 2 days, about 2 to about 21 days, about 3 to about 21 days, about 4 to about 21 days, about 5 to about 21 days, about 6 to about 21 days, about 7 to about 21 days, about 8 to about 21 days, about 9 to about 21 days, about 10 to about 21 days, about 11 to about 21 days, about 12 to about 21 days, about 13 to about 21 days, about 14 to about 21 days, about 15 to about 21 days, about 16 to about 21 days, about 17 to about 21 days, about 18 to about 21 days, about 19 to about 21 days, about 20 to about 21 days, about 5 to about 10 days, about 10 to about 15 days, about 15 to about 20 days.

In one embodiment, the effective dose is a dose that can maintain 1-50 IU/dL of circulating FIX (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 IU/dL). In another embodiment, the effective dose is 50 IU/kg and the dosing interval is once weekly. In another embodiment, the dosing interval is 100 IU/kg, and the dosing interval is once every 10 days. The doses can be administered repeatedly as long as they are necessary (e.g., at least 10, 20, 28, 30, 40, 50, 52, or 57 weeks, at least 1, 2, 3, 4, 5, 6, 7, 8, 9, or 10 years).

The composition or chimeric protein comprising a FIX and an Fc region can be formulated for any appropriate manner of administration, including, for example, topical (e.g., transdermal or ocular), oral, buccal, nasal, vaginal, rectal or parenteral administration.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. The composition can be also for example a suspension, emulsion, sustained release formulation, cream, gel or powder. The composition can be formulated as a suppository, with traditional binders and carriers such as triglycerides.

In one example, the pharmaceutical formulation is a liquid formulation, e.g., a buffered, isotonic, aqueous solution. In another example, the pharmaceutical composition has a pH that is physiologic, or close to physiologic. In other examples, the aqueous formulation has a physiologic or close to physiologic osmolarity and salinity. It can contain sodium chloride and/or sodium acetate.

In some embodiments, the chimeric protein comprising a FIX and an Fc region used in the methods of the present invention is formulated in a pharmaceutical composition comprising: (a) the chimeric polypeptide; (b) a carbohydrate mixture comprising sucrose and mannitol; (c) sodium chloride (NaCl); (d) L-histidine; and (e) polysorbate 20 or polysorbate 80. In certain embodiments, the pharmaceutical composition comprises: (a) between about 25 IU/ml and about 700 IU/ml of the Factor IX polypeptide; (b) between about 10 mg/ml and about 20 mg/ml of sucrose; (c) between about 20 mg/ml and about 40 mg/ml of mannitol; (d) between about 3 mg/ml and about 4 mg/ml NaCl; (e) between about 3 mg/ml and about 6 mg/ml L-histidine; (f) between about 0.08 mg/ml and about 0.2 mg/ml of polysorbate 20 or polysorbate 80; or (g) any combination thereof. In some examples, the pharmaceutical composition used in the methods of the present disclosure is lyophilized.

In some embodiments, the pharmaceutical composition does not comprise an immune cell. In some embodiments, the pharmaceutical composition does not comprise a cell.

II.A.3 Fc

The compositions or chimeric proteins of the disclosure include an Fc domain or a portion thereof that binds to FcRn, FcγRIIB and/or DC-SIGN. In some embodiments, the Fc domain is fused to the clotting factor, e.g., as part of a chimeric protein comprising a clotting factor and an Fc region. In other embodiments, the Fc domain is fused to a polypeptide other than the clotting factor, wherein the composition comprises a (1) clotting factor and (2) a chimeric protein comprising an Fc domain and an additional polypeptide. In some embodiments, the Fc domain is co-administered with the clotting factor. The Fc domain or a portion thereof can improve pharmacokinetic or pharmacodynamic properties of the chimeric protein. In certain embodiments, the Fc domain or a portion thereof extends a half-life of a molecule fused to the Fc domain or a portion thereof. In some embodiments, the Fc region of the chimeric protein facilitates localization of the chimeric protein to the joint.

As used herein, the term "Fc domain" or "Fc region" as used herein, means the functional portion of a polypeptide which corresponds to the Fc domain of native Ig, i.e., as formed by the dimeric association of the respective Fc domains of its two heavy chains. A native Fc domain forms a homodimer with another Fc domain. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, Nature 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

In some embodiments, the Fc region specifically binds to FcRn. The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other Ig classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

Fc regions useful in the present invention encompass molecules that can specifically bind FcRn, FcγRIIB, and/or DC-SIGN, including whole IgG, the Fc fragment of IgG, and other fragments that include the complete binding region of the FcRn receptor. The region of the Fc portion of IgG that binds to FcRn, FcγRIIB, and/or DC-SIGN has been described.

In one particular embodiment, the Fc region specifically binds to a low affinity immunoglobulin gamma Fc region receptor II-b (FcγRIIB) FcγRIIB is an inhibitory Fc receptor, which controls aspects of inflammatory response. In particular, activation of FcγRIIB inhibits activating signals that lead to inflammation. Thus, in effect, activation of FcγRIIB inhibits inflammation.

In another embodiment, the Fc region specifically binds to dendritic cell-specific intercellular adhesion molecule-3-grabbing non-integrin (DC-SIGN). DC-SIGN, also known as CD209) is a C-type lectin receptor expressed by most myeloid derived cells, including certain monocytes, dendritic cells, and macrophages. Studies in mice have revealed that activation of DC-SIGN may inhibit inflammation. See Nimerjahn, Chapter 5, Molecular and Cellular Pathways Involved in the Anti-inflammatory Activity of IgG, Molecular Mechanisms of Antibody Activity, New York, NY 2013: 113-138.

Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6 M^{-1}$, or higher than $10^8 M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In certain embodiments, a chimeric protein of the invention comprises one or more truncated Fc regions that are nonetheless sufficient to confer FcRn, FcγRIIB, and/or DC-SIGN binding properties to the Fc region. For example, the portion of an Fc region that binds to FcRn, FcγRIIB, and/or DC-SIGN (i.e., the FcRn, FcγRIIB, and/or DC-SIGN binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn, FcγRIIB, and/or DC-SIGN binding portion. FcRn, FcγRIIB, and/or DC-SIGN binding portions may be derived from heavy chains of any isotype, including IgG1, IgG2, IgG3 and IgG4. In one embodiment, an FcRn, FcγRIIB, and/or DC-SIGN binding portion from an antibody of the human isotype IgG1 is used. In another embodiment, an FcRn, FcγRIIB, and/or DC-SIGN binding portion from an antibody of the human isotype IgG4 is used.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc regions denoted as F, F1, or F2 herein may be obtained from a number of different sources. In one embodiment, an Fc region of the polypeptide is derived from a human Ig. It is understood, however, that an Fc region may be derived from an Ig of another mammalian species, including for example, a rodent (e.g. a mouse, rat, rabbit, or guinea pig) or non-human primate (e.g. chimpanzee, macaque) species. Moreover, the polypeptide of the Fc domains or portions thereof may be derived from any Ig class, including IgM, IgG, IgD, IgA and IgE, and any Ig isotype, including IgG1, IgG2, IgG3 and IgG4. In another embodiment, the human isotype IgG1 is used.

In certain embodiments, the Fc variant confers a change in at least one effector function imparted by an Fc region comprising the wild-type Fc domain (e.g., an improvement or reduction in the ability of the Fc region to bind to Fc receptors (e.g., reduction in binding to FcγRI or FcγRIII or improvement in binding to FcRn or FcγRII), complement proteins (e.g. C1q), or other Fc binding partners (e.g., improvement in binding to DC-SIGN), or to trigger antibody-dependent cytotoxicity (ADCC), phagocytosis, or complement-dependent cytotoxicity (CDCC)). In other embodiments, the Fc variant provides an engineered cysteine residue.

The Fc regions of the invention may employ art-recognized Fc variants which are known to impart a change (e.g., an enhancement or reduction) in effector function and/or FcR binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286879, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

The Fc region can be modified according to well recognized procedures such as site directed mutagenesis and the like to yield modified Fc fragments or portions thereof that will be bound by FcRn, FcγRIIB, and/or DC-SIGN. Such modifications include modifications remote from the FcRn, FcγRIIB, and/or DC-SIGN contact sites as well as modifications within the contact sites that preserve or even enhance binding to the FcRn, FcγRIIB, and/or DC-SIGN. For example, the following single amino acid residues in human IgG1 Fc (Fc γ1) can be substituted without significant loss of Fc binding affinity for FcRn, FcγRIIB, and/or DC-SIGN: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238.

As an example, a specific embodiment incorporates the N297A mutation, removing a highly conserved N-glycosylation site. In addition to alanine other amino acids may be substituted for the wild type amino acids at the positions specified above. Mutations may be introduced singly into Fc giving rise to more than one hundred Fc regions distinct from the native Fc. Additionally, combinations of two, three, or more of these individual mutations may be introduced together, giving rise to hundreds more Fc regions. Moreover, one of the Fc region of a construct of the invention may be mutated and the other Fc region of the construct not mutated at all, or they both may be mutated but with different mutations.

In one embodiment, the Fc domain or a portion thereof is a polypeptide including SEQ ID NO: 3 of U.S. Pat. No. 5,739,277 and optionally further including a sequence selected from SEQ ID NOs: 11, 1, 2, and 31 of U.S. Pat. No. 5,739,277.

In certain embodiments, the Fc domain or a portion thereof is hemi-glycosylated. For example, the chimeric protein comprising two Fc regions may contain a first, glycosylated, Fc region (e.g., a glycosylated CH2 region) and a second, aglycosylated, Fc region (e.g., an aglycosylated CH2 region). In one embodiment, a linker may be interposed between the glycosylated and aglycosylated Fc regions. In another embodiment, the Fc region is fully glycosylated, i.e., all of the Fc regions are glycosylated. In other embodiments, the Fc region may be aglycosylated, i.e., none of the Fc moieties are glycosylated.

In certain embodiments, a chimeric protein of the invention comprises an amino acid substitution to an Fc domain or a portion thereof (e.g., Fc variants), which alters the antigen-independent effector functions of Fc domain, in particular the circulating half-life of the protein.

An Fc region used in the invention may also comprise an art recognized amino acid substitution which alters the glycosylation of the chimeric protein. For example, the Fc region of the chimeric protein linked to a FVIII protein or a FIX protein may comprise an Fc region having a mutation leading to reduced glycosylation (e.g., N- or O-linked glycosylation) or may comprise an altered glycoform of the wild-type Fc moiety (e.g., a low fucose or fucose-free glycan).

In one embodiment, an unprocessed chimeric protein of the invention may comprise a genetically fused Fc region (i.e., scFc region) having two or more of its constituent Ig constant region or a portion thereof independently selected from the Ig constant region or a portion thereof described herein. In one embodiment, the Fc regions of a dimeric Fc region are the same. In another embodiment, at least two of the Fc regions are different. For example, the Fc regions of the proteins of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc regions of the protein of the invention may differ in sequence at one or more amino acid positions. For example, at least two of the Fc regions may differ at about 5 amino acid positions (e.g., 1, 2, 3, 4, or 5 amino acid positions), about 10 positions, about 15 positions, about 20 positions, about 30 positions, about 40 positions, or about 50 positions).

In some embodiments, a chimeric protein used in the methods of the present disclosure comprises more than one polypeptide chain. In some embodiments, the chimeric protein comprises two polypeptide chains. In certain embodiments, the first polypeptide chain comprises a clotting factor and a first Fc region, and the second polypeptide chain comprises a second Fc region. In certain embodiments, the first Fc region and the second Fc region are associated by a covalent bond. In one embodiment, the first Fc region and the second Fc region are associated by a peptide bond. In another embodiment, the first Fc region and the second Fc region are associated by a disulfide bond.

In one particular embodiment, the chimeric protein comprises a factor VIII portion and a von Willebrand factor (VWF) portion, wherein the FVIII portion comprises a FVIII polypeptide or a fragment thereof, wherein the VWF portion comprises a VWF polypeptide or a fragment thereof, wherein the FVIII portion is linked to a first Fc region, wherein the VWF portion is linked to a second Fc region, and wherein the first Fc region and the second Fc region are associated with each other. In certain embodiments, the VWF portion comprises the D' and D3 domains of VWF. In one embodiment, the first polypeptide, the second polypeptide, or both the first polypeptide and the second polypeptide further comprise one or more half-life extending moieties.

An Fc region or a portion thereof for producing a chimeric protein used in the methods of the present disclosure may be obtained from a number of different sources. In some embodiments, an Fc region or a portion thereof is derived from a human Ig. It is understood, however, that the Fc region or a portion thereof may be derived from an Ig of another mammalian species, including for example, a rodent (e.g. a mouse, rat, rabbit, guinea pig) or non-human primate (e.g. chimpanzee, macaque) species. Moreover, the Fc region or a portion thereof may be derived from any Ig class, including IgM, IgG, IgD, IgA, and IgE, and any Ig isotype, including IgG1, IgG2, IgG3, and IgG4. In one embodiment, the human isotype IgG1 is used.

A variety of the Fc region gene sequences (e.g., human Fc gene sequences) are available in the form of publicly accessible deposits. Fc sequences can be selected having a particular effector function (or lacking a particular effector function) or with a particular modification to reduce immunogenicity. Many sequences of antibodies and antibody-encoding genes have been published and suitable Fc region sequences can be derived from these sequences using art recognized techniques. The genetic material obtained using any of the foregoing methods may then be altered or synthesized to obtain chimeric proteins used in the methods of the present disclosure. It will further be appreciated that the scope of this invention encompasses alleles, variants and mutations of constant region DNA sequences.

The sequences of the Fc or a portion thereof can be cloned, e.g., using the polymerase chain reaction and primers which are selected to amplify the domain of interest. To clone a sequence of the Fc region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, CA (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

II.B. Half-Life Extending Moieties

In some embodiments, a chimeric protein used in the methods of the present disclosure further comprises one or more half-life extending moieties. Half-life of a clotting factor can be determined by any method known to those of skill in the art, e.g., FVIII activity assays (chromogenic assay or one stage clotting aPTT assay) to detect plasma FVIII activity levels or FVIII/FIX ELISA to detect plasma FVIII/FIX antigen level. In a particular embodiment, half-life of the clotting activity of a clotting factor is determined by one stage clotting assay. In a more particular embodiment, half-life of the clotting activity of a clotting factor is determined in mice, either HemA mice or FVIII and von Willebrand Factor double knockout (DKO) mice.

In certain aspects, a heterologous moiety which increases half-life of the clotting factor of the invention comprises, without limitation, a heterologous polypeptide such as albumin, an immunoglobulin Fc region, an XTEN sequence, the C-terminal peptide (CTP) of the β subunit of human chorionic gonadotropin, a PAS sequence, a HAP sequence, a transferrin, albumin-binding moieties, or any fragments, derivatives, variants, or combinations of these polypeptides. In other related aspects a half-life extending moiety can include an attachment site for a non-polypeptide moiety such as polyethylene glycol (PEG), hydroxyethyl starch (HES), polysialic acid, or any derivatives, variants, or combinations of these moieties. In certain embodiments, the half-life extending moiety comprises albumin or a fragment thereof, an albumin binding moiety, a PAS sequence, a HAP sequence, transferrin or a fragment thereof, polyethylene glycol (PEG), polysialic acid, hydroxyethyl starch (HES), a derivative thereof, or any combination thereof. In some embodiments, the half-life extending moiety does not comprise an XTEN. In other embodiments, the half-life extending moiety comprises an XTEN.

In other embodiments, a chimeric protein of the invention is conjugated to one or more polymers. The polymer can be water-soluble or non-water-soluble. The polymer can be covalently or non-covalently attached to the clotting factor, the Fc, or to other moieties conjugated to either the clotting factor or the Fc. Non-limiting examples of the polymer can be poly(alkylene oxide), poly(vinyl pyrrolidone), poly(vinyl alcohol), polyoxazoline, or poly(acryloylmorpholine). Additional types of, e.g., polymer-conjugated FVIII are disclosed in U.S. Pat. No. 7,199,223, which is disclosed by reference in its entirety.

In certain aspects, a chimeric protein of the invention can comprise one, two, three or more half-life extending moieties, which can each be the same or different molecules.

In some embodiments, the half-life extending moiety is fused to the N-terminus or the C-terminus of the chimeric polypeptide. In some embodiments, the half-life extending moiety is fused to the N-terminus or the C-terminus of the clotting factor. In some embodiments, the half-life extending moiety is fused to the N-terminus or the C-terminus of the Fc. In certain embodiments, the half-life extending moiety is inserted within the clotting factor of the chimeric protein.

In some embodiments, the chimeric protein comprises FVIII or a portion thereof, and the half-life extending moiety is inserted within the FVIII at one or more positions disclosed in U.S. Patent Publ. No. 2015-0158929 A1 and/or Int'l Publication No. WO 2015106052 A1, which are incorporated by reference herein in their entirety. In one particular embodiment, the half-life extending moiety is inserted within the B domain (or a fragment thereof) of the FVIII. In one particular embodiment, the half-life extending moiety is inserted within the FVIII immediately downstream of amino acid residue 745 of mature FVIII.

In other embodiments, the chimeric protein comprises FIX or a portion thereof, and the half-life extending moiety is inserted within the FIX at one or more positions disclosed in Int'l Appl. No. PCT/US16/045401. In one particular embodiment, the half-life extending moiety is inserted within the FIX at an insertion site immediately downstream of an amino acid residue selected from the group consisting of amino acid 103, amino acid 105, amino acid 142, amino acid 149, amino acid 162, amino acid 166, amino acid 174, amino acid 224, amino acid 226, amino acid 228, amino acid 413 of mature Padua FIX. In one embodiment, the chimeric protein comprises a FIX and an Fc region, wherein the FIX comprises a half-life extending moiety inserted within the activation peptide (AP) domain of the FIX. In one particular embodiment, the chimeric protein comprises a FIX and an Fc region, wherein the FIX comprises a half-life extending moiety inserted within the FIX immediately downstream of amino acid residue 166 of mature Padua FIX.

II.B.1. Albumins

In certain aspects, a chimeric protein used in the methods of the present disclosure comprises at least one albumin polypeptide or fragment, variant, or derivative thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

The albumin-binding polypeptides (ABPs) can compromise, without limitation, bacterial albumin-binding domains, albumin-binding peptides, or albumin-binding antibody fragments that can bind to albumin. Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides are disclosed in Dennis et al., J. Biol. Chem. 2002, 277: 35035-35043 (2002). Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties.

In certain aspects, a chimeric protein used in the methods of the present disclosure comprises at least one attachment site for a non-polypeptide small molecule, variant, or derivative that can bind to albumin thereof. For example, the chimeric protein can include one or more organic albumin-binding moieties. An example of such albumin-binding moieties is 2-(3-maleimidopropanamido)-6-(4-(4-iodophenyl)butanamido)hexanoate ("Albu" tag) as disclosed by Trussel et al., Bioconjugate Chem. 20:2286-2292 (2009).

II.B.2. XTENs

In certain aspects, a chimeric protein used in the methods of the present disclosure comprises at least one XTEN polypeptide or fragment, variant, or derivative thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a chimeric protein partner, XTENs can serve as a carrier, conferring certain desirable pharmacokinetic, physicochemical and pharmaceutical properties, e.g., when fused with or inserted into the clotting factor of the chimeric protein. Such desirable properties include but are not limited to enhanced pharmacokinetic parameters and solubility characteristics.

An XTEN sequence fused with or inserted into the clotting factor of the chimeric protein used in the methods of the present disclosure can confer to the chimeric protein one or more of the following advantageous properties: conformational flexibility, enhanced aqueous solubility, high degree of protease resistance, low immunogenicity, low binding to mammalian receptors, or increased hydrodynamic (or Stokes) radii. In certain aspects, an XTEN sequence can increase pharmacokinetic properties such as longer half-life (e.g., in vivo half-life) or increased area under the curve (AUC), so that the chimeric protein stays in vivo and has procoagulant activity for an increased period of time compared to the chimeric protein without the XTEN.

Examples of XTEN sequences that can be inserted into recombinant FVIII proteins of the invention are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, WO 2011028344 A2, or WO 2015106052 A1, each of which is incorporated by reference herein in its entirety.

II.B.3. VWF or a Fragment Thereof

In certain aspects, a chimeric protein used in the methods of the present disclosure comprises at least one VWF polypeptide or fragment, variant, or derivative thereof. VWF (also known as F8VWF) is a large, multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D'/D3 domain (which binds to Factor VIII), the A1 domain (which binds to platelet GPIb-receptor, heparin, and/or possibly collagen), the A3 domain (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (βHCG)).

In one embodiment, the VWF polypeptide is a VWF fragment. The term "a VWF fragment" as used herein includes, but is not limited to, functional VWF fragments comprising a D' domain and a D3 domain, which are capable of inhibiting binding of endogenous VWF to FVIII. In one embodiment, the chimeric protein used in the methods of the present disclosure comprises a clotting factor, an Fc region, and a VWF fragment, wherein the clotting factor comprises FVIII, and wherein the VWF fragment binds to the FVIII protein. In another embodiment, the VWF fragment blocks the VWF binding site on the FVIII protein, thereby inhibiting interaction of the FVIII protein with endogenous VWF. The VWF fragments include derivatives, variants, mutants, or analogues that retain these activities of VWF. In certain embodiments, the VWF fragment comprises the D' domain and D3 domain of VWF.

The 2813 monomer amino acid sequence for human VWF is reported as Accession Number_NP_000543.2_in Genbank. The nucleotide sequence encoding the human VWF is reported as Accession Number_NM_000552.3 in Genbank.

In certain embodiments, the VWF protein useful herein can be further modified to improve its interaction with FVIII, e.g., to improve binding affinity to FVIII. In other embodiments, The VWF proteins useful for the invention can have other modifications, e.g., the protein can be pegylated, glycosylated, hesylated, or polysialylated. Example VWF sequences useful in the methods of the present disclosure are provided, e.g., in U.S. Publication Nos. US 2015/0023959 A1, US 2015/0266943 A1, and US 2015/0158929. In certain embodiments, the VWF protein or a fragment thereof is fused to or co-administered with an FcRn binding partner. In some embodiments, the VWF protein or a fragment thereof is fused to an Fc or co-administered with an Fc or a polypeptide comprising an Fc. In some embodiments, the VWF protein or a fragment thereof is fused to an albumin or co-administered with an albumin or a polypeptide comprising an albumin.

II.B.4. CTP

In certain aspects, a chimeric protein used in the methods of the present disclosure comprises at least one C-terminal peptide (CTP) of the β subunit of human chorionic gonadotropin or fragment, variant, or derivative thereof. CTP peptides are known to increase the half-life of that protein. See, e.g., U.S. Pat. No. 5,712,122, incorporated by reference herein in its entirety. Non-limiting exemplary CTP peptides are disclosed in U.S. Patent Application Publication No. US 2009/0087411 A1, incorporated by reference.

II.B.5. PAS

In certain aspects, a chimeric protein used in the methods of the present disclosure comprises at least one PAS peptide or fragment, variant, or derivative thereof. A PAS peptide or PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. An amino acid polymer also can form random coil conformation when residues other than alanine, serine, and proline are added as a minor constituent in the PAS sequence. By "minor constituent" is meant that that amino acids other than alanine, serine, and proline can be added in the PAS sequence to a certain degree, e.g., up to about 12%, i.e., about 12 of 100 amino acids of the PAS sequence, up to about 10%, up to about 9%, up to about 8%, about 6%, about 5%, about 4%, about 3%, i.e. about 2%, or about 1%, of the amino acids. The amino acids different from alanine, serine and proline cab be selected from the group consisting of Arg, Asn, Asp, Cys, Gln, Glu, Gly, His, Ile, Leu, Lys, Met, Phe, Thr, Trp, Tyr, and Val. Under physiological conditions, a PAS peptide forms a random coil conformation and thereby can mediate an increased in vivo and/or in vitro stability to a recombinant protein of the invention, and has procoagulant activity.

Non-limiting examples of the PAS peptides are disclosed in, e.g., US Pat. Publ. No. 2010/0292130 A1; PCT Appl. Publ. No. WO 2008/155134 A1; and European issued patent EP2173890.

II.B.6. HAP

In certain aspects, a chimeric protein used in the methods of the present disclosure comprises at least one homo-amino acid polymer (HAP) peptide or fragment, variant, or derivative thereof. A HAP peptide can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. A HAP sequence is capable of extending half-life of a moiety fused to or linked to the HAP sequence. Non-limiting examples of the HAP sequence includes, but are not limited to $(Gly)_n$, $(Gly_4Ser)_n$ or $S(Gly_4Ser)_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200. See, e.g., Schlapschy M et al., Protein Eng. Design Selection, 20: 273-284 (2007).

II.B.7. Transferrin

In certain aspects, a chimeric protein used in the methods of the present disclosure comprises at least one transferrin peptide or fragment, variant, or derivative thereof. Any transferrin can fused with the chimeric protein used in the methods of the present disclosure. As an example, wild-type human Tf (Tf) is a 679 amino acid protein, of approximately 75 kDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov), all of which are herein incorporated by reference in their entirety.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., Trends Pharmacol. Sci. 23:206-209 (2002)). Transferrin fusion proteins have been studied for half-life extension, targeted deliver for cancer therapies, oral delivery and sustained activation of proinsulin (Brandsma et al., Biotechnol. Adv., 29: 230-238 (2011); Bai et al., Proc. Natl. Acad. Sci. USA 102:7292-7296 (2005); Kim et al., J. Pharmacol. Exp. Ther., 334:682-692 (2010); Wang et al., J. Controlled Release 155:386-392 (2011)).

II.B.8. PEG

In certain aspects, a chimeric protein used in the methods of the present disclosure comprises at least one attachment site for a non-polypeptide heterologous moiety or fragment, variant, or derivative thereof. For example, a chimeric protein used in the methods of the present disclosure can include one or more polyethylene glycol (PEG) moieties attached to one or more amino acid residues in the clotting factor and/or the Fc region.

PEGylation of a protein can refer to a conjugate formed between the protein and at least one polyethylene glycol (PEG) molecule. PEG is commercially available in a large variety of molecular weights and average molecular weight ranges. Typical examples of PEG average molecular weight ranges include, but are not limited to, about 200, about 300, about 400, about 600, about 1000, about 1300-1600, about 1450, about 2000, about 3000, about 3000-3750, about 3350, about 3000-7000, about 3500-4500, about 5000-7000, about 7000-9000, about 8000, about 10000, about 8500-11500, about 16000-24000, about 35000, about 40000, about 60000, and about 80000 Daltons. These average molecular weights are provided merely as examples and are not meant to be limiting in any way.

A chimeric protein used in the methods of the present disclosure can be PEGylated to include mono- or poly-(e.g., 2-4) PEG moieties. PEGylation can be carried out by any of the PEGylation reactions known in the art. Methods for preparing a PEGylated protein product will generally include (i) reacting a polypeptide with polyethylene glycol (such as a reactive ester or aldehyde derivative of PEG) under conditions whereby the peptide of the invention becomes attached to one or more PEG groups; and (ii) obtaining the reaction product(s). In general, the optimal reaction conditions for the reactions will be determined case by case based on known parameters and the desired result.

There are a number of PEG attachment methods available to those skilled in the art, for example Malik F et al., *Exp. Hematol.* 20:1028-35 (1992); Francis, *Focus on Growth Factors* 3(2):4-10 (1992); European Pat. Pub. Nos. EP0401384, EP0154316, and EP0401384; and International Pat. Appl. Pub. Nos. WO92/16221 and WO95/34326. As a non-limiting example, FVIII variants can contain cysteine substitutions, and the cysteines can be further conjugated to PEG polymer. See Mei et al., *Blood* 116:270-279 (2010) and U.S. Pat. No. 7,632,921, which are incorporated herein by reference in their entireties.

II.B.9. HES

In certain aspects, a chimeric protein used in the methods of the present disclosure comprises at least one hydroxyethyl starch (HES) polymer. HES is a derivative of naturally occurring amylopectin and is degraded by alpha-amylase in the body. HES exhibits advantageous biological properties and is used as a blood volume replacement agent and in hemodilution therapy in the clinics. See, e.g., Sommermeyer et al., *Krankenhauspharmazie* 8:271-278 (1987); and Weidler et al., *Arzneim.-Forschung/Drug Res.* 41: 494-498 (1991).

HES is mainly characterized by the molecular weight distribution and the degree of substitution. HES has a mean molecular weight (weight mean) of from 1 to 300 kD, from 2 to 200 kD, from 3 to 100 kD, or from 4 to 70 kD. Hydroxyethyl starch can further exhibit a molar degree of substitution of from 0.1 to 3, from 0.1 to 2, from 0.1 to 0.9, or from 0.1 to 0.8, and a ratio between C2:C6 substitution in the range of from 2 to 20 with respect to the hydroxyethyl groups. HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. There are a number of HES attachment methods available to those skilled in the art, e.g., the same PEG attachment methods described above.

II.B.10. PSA

In certain aspects, a chimeric protein used in the methods of the present disclosure comprises at least one polysialic acid (PSA) polymer. PSAs are naturally occurring unbranched polymers of sialic acid produced by certain bacterial strains and in mammals in certain cells. See, e.g., Roth J. et al. (1993) in *Polysialic Acid: From Microbes to Man*, eds. Roth J., Rutishauser U., Troy F. A. (BirkhauserVerlag, Basel, Switzerland), pp. 335-348. PSAs can be produced in various degrees of polymerization from n=about 80 or more sialic acid residues down to n=2 by limited acid hydrolysis or by digestion with neuraminidases, or by fractionation of the natural, bacterially derived forms of the polymer. There are a number of PSA attachment methods available to those skilled in the art, e.g., the same PEG attachment methods described above. In certain aspects, an activated PSA can also be attached to a cysteine amino acid residue within the clotting factor, e.g., on FVIII or FIX, or within the Fc region. See, e.g., U.S. Pat. No. 5,846,951.

II.B.11. Clearance Receptors

In certain aspects, the half-life of a chimeric protein used in the methods of the present disclosure can be extended where the clotting factor of the chimeric protein comprises FVIII and at least one fragment of a FVIII clearance receptor or FVIII-binding fragment, variant, or derivative thereof. Insertion of soluble forms of clearance receptors, such as the low density lipoprotein-related protein receptor LRP1, or fragments thereof, can block binding of FVIII to clearance receptors and thereby extend its half-life, e.g., in vivo half-life. LRP1 is a 600 kDa integral membrane protein that is implicated in the receptor-mediate clearance of a variety of proteins, including FVIII. See, e.g., Lenting et al., Haemophilia 16:6-16 (2010). Other suitable FVIII clearance receptors are, e.g., LDLR (low-density lipoprotein receptor), VLDLR (very low-density lipoprotein receptor), and megalin (LRP-2), or fragments thereof. See, e.g., Bovenschen et al., Blood 106:906-912 (2005); Bovenschen, Blood 116: 5439-5440 (2010); Martinelli et al., Blood 116:5688-5697 (2010).

III. Polynucleotides, Vectors, and Host Cells

In some aspects, the present disclosure provides a method of treating reversible hemophilic arthropathy of a joint in a human having hemophilia comprising administering to the human an effective amount of a polynucleotide or a set of polynucleotides encoding a clotting factor and/or a Fc region, e.g., encoding a chimeric protein comprising a clotting factor and an Fc region. In some embodiments, the polynucleotide or the set of polynucleotides is within an expression vector or a set of expression vectors. In certain embodiments, the expression vector or the set of expression vectors is within one or more host cells.

The polynucleotide encoding a clotting factor and/or a Fc region, e.g., encoding a chimeric protein comprising a clotting factor and an Fc region, used in the methods of the present disclosure can be a single nucleotide sequence, two nucleotide sequences, three nucleotide sequences, or more. In one embodiment, a single nucleotide sequence encodes a chimeric protein comprising a clotting factor (e.g., a FVIII or a FIX polypeptide) and an Fc region. In another embodiment, the polynucleotide comprises two nucleotide sequences, the first nucleotide sequence encoding a clotting factor (e.g., a FVIII) and the second nucleotide sequence encoding an Fc region. In another embodiment, the polynucleotide comprises two nucleotide sequences, the first nucleotide sequence encoding a clotting factor (e.g., a FVIII or a FIX) and an Fc region and the second nucleotide sequence encoding a second Fc region. In certain embodiments, the encoded Fc domains form a covalent bond after expression.

In some embodiments, the polynucleotide is codon-optimized.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

For the purposes of this invention, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An example of a vector useful for optimized expression of the chimeric proteins used in the methods of the present disclosure is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the instant invention are expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is also incorporated herein.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art, as discussed above. The transformed cells are grown under conditions appropriate for the production of the chimeric protein, and assayed for chimeric protein synthesis. Exemplary assay techniques include enzyme-linked immunosorbent assay (ELISA), radioimmunoassay (MA), or flourescence-activated cell sorter analysis (FACS), immunohistochemistry, and the like.

Having now described the present invention in detail, the same will be more clearly understood by reference to the following examples, which are included herewith for purposes of illustration only and are not intended to be limiting of the invention.

Example 1

Long-Term Efficacy of rFVIIIFc Prophylaxis in Pediatric, Adolescent, and Adult Subjects with Target Joints and Severe Hemophilia a For people with hemophilia, frequent bleeding into the same joint (a target joint) may contribute to hemophilic arthropathy (chronic joint disease). rFVIIIFc was developed to extend the half-life of factor VIII (FVIII) as compared to conventional FVIII products (Peters et al., *J. Thromb. Haemost.* 11(1):132-41 (2013)). The completed a rFVIIIFc pivotal phase 3 trial (ClinicalTrials.gov Identifier: NCT01181128; Mahlangu, et al., *Blood* 123(3):317-25 (2014)) and Kids rFVIIIFc pivotal phase 3 trial (NCT01458106; Young et al., *J. Thromb. Haemost.* 13(6): 967-77 (2015)) studies established the safety and efficacy of rFVIIIFc among adults/adolescents (patients 12-years-old or older) and children (patients less than 12 years old) with severe hemophilia A, respectively. Long-term safety and efficacy of rFVIIIFc are being evaluated in the ongoing rFVIIIFc extension study extension study (NCT01454739; Nolan et al., *Haemophilia* 22(1):72-80(2016)).

The objective of this study is to report cumulative data on the durable efficacy of rFVIIIFc and QOL in subjects with target joints at entry into rFVIIIFc pivotal phase 3 trial and Kids rFVIIIFc pivotal phase 3 trial, as of the second rFVIIIFc extension study interim data cut (Dec. 8, 2014).

Methods

Subjects with ≥1 target joint (major joint with ≥3 bleeding episodes in a 6-month period (see World Federation of Hemophilia, Guidelines for the Management of Hemophilia 2nd ed., Blackwell Publishing: Montreal, Canada (2012))) at entry into the parent study (i.e., rFVIIIFc pivotal phase 3 trial or Kids rFVIIIFc pivotal phase 3 trial) who had available prestudy (i.e., pre-parent study) and on-study data (target joint-specific and overall) were evaluated. There are 4 treatment groups in rFVIIIFc extension study (Table 1).

TABLE 1 rFVIIIFc Extension Study Treatment Regimens

| Treatment Regimen | Dosing Guidance per Protocol |
| --- | --- |
| Individualized Prophylaxis | rFVIIIFc 25-65 IU/kg every 3-5 days OR twice-weekly rFVIIIFc (20-65 IU/kg on Day 1, 40-65 IU/kg on Day 4); pediatric subjects are allowed adjustments to dose and frequency (every 2-5 days) |
| Weekly Prophylaxis | rFVIIIFc 65 IU/kg every 7 days |
| Modified Prophylaxis | Investigators could personalize dosing for subjects in whom optimal prophylaxis could not be achieved with individualized or weekly prophylaxis |
| Episodic Treatment | rFVIIIFc dosing based on type and severity of bleeding episode |

Subjects ≥12 years of age could participate in any treatment regimen in the rFVIIIFc extension study, while subjects <12 years of age could participate only in the individualized prophylaxis and modified prophylaxis treatment regimens.

Outcomes for subjects with target joints were analyzed post hoc over the cumulative duration of the parent study through the second rFVIIIFc extension study interim data cut. Outcomes included ABRs, number and resolution of target joint bleeding episodes, and prophylactic dose and dosing frequency. Analysis of target joint resolution was performed for subjects who had ≥12 months of consecutive follow-up time and who had not undergone major surgery (i.e., replacement or removal) at the target joint since the start of the follow-up period. A target joint was considered clinically resolved if there were ≤2 spontaneous bleeding episodes in the target joint during a consecutive 12-month period (Blanchette et al., *J Thromb Haemost.* 12(11):1935-39 (2014)).

QOL measures were assessed by the Haem-A-QOL index in prophylaxis subjects who were ≥17 years of age, had ≥1 resolved target joint during the study, and had Haem-A-QOL scores at both rFVIIIFc pivotal phase 3 trial baseline and rFVIIIFc extension study Year 2. Among subjects from Kids rFVIIIFc pivotal phase 3 trial, QOL was measured by the Canadian Hemophilia Outcomes-Kids Life Assessment Tool (CHO-KLAT).

Results

Study Population

Of 113 subjects from rFVIIIFc pivotal phase 3 trial who had target joints at baseline, 111 subjects with prestudy prophylactic or episodic regimens and on-study data had 287 target joints at baseline (median age, 31.0 years; interquartile range (IQR), 24.0-44.0 years; Table 2). Thirteen subjects from Kids rFVIIIFc pivotal phase 3 trial had 15 target joints at baseline and had prestudy and on-study data (median age, 6.0 years; IQR, 5.0-8.0 years; Table 2).

TABLE 2

Demographic and baseline characteristics[a]

| Characteristic | Parent Study | |
| --- | --- | --- |
| | rFVIIIFc pivotal phase 3 trial n = 111 | Kids rFVIIIFc pivotal phase 3 trial n = 13 |
| Median (IQR) age, years | 31.0 (24.0-44.0) | 6.0 (5.0-8.0) |
| Prestudy regimen | | |
| Episodic | 65 (58.6) | 3 (23.1) |
| Prophylaxis | 46 (41.4) | 10 (76.9) |
| Total number of target joints, n | 287 | 15 |
| Number of target joints, n (%)[b] | | |
| 1 | 42 (37.8) | 11 (84.6) |
| 2 | 27 (24.3) | 2 (15.4) |
| 3 | 7 (6.3) | 0 |
| >3 | 35 (31.5)[c] | 0 |
| Target joint location, n (%) | | |
| Elbow | 69 (62.2) | 4 (30.8) |
| Ankle | 65 (58.6) | 9 (69.2) |
| Knee | 48 (43.2) | 1 (7.7) |
| Shoulder | 14 (12.6) | 0 |
| Wrist | 6 (5.4) | 0 |
| Hip | 5 (4.5) | 0 |

IQR—interquartile range.
[a]Includes subjects with ≥1 target joint at entry into the parent study and with an efficiency period. A target joint is defined as a major joint (e.g., elbow, ankle, knee, shoulder, wrist, and hip) into which repeated bleeding occurred (frequency ≥3 bleeding episodes into the same joint in a consecutive 6-month period).
[b]Percentages may not total 100.0% due to rounding.
[c]Mean age of subjects was 39.9 years.

Bleeding Rates

Figure 1F:
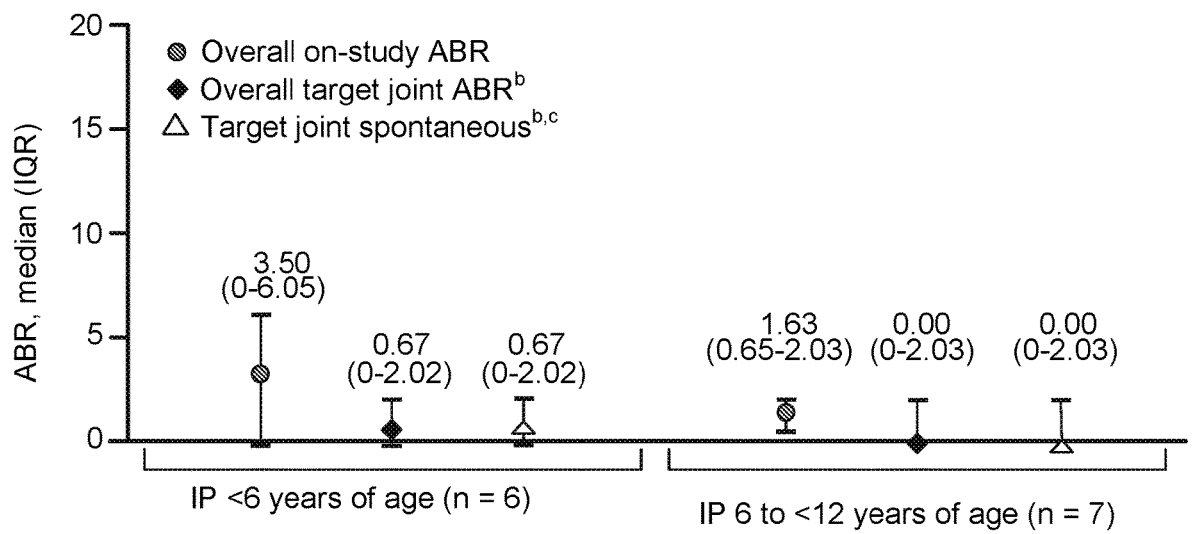

Median (IQR) on-study overall ABRs with rFVIIIFc prophylaxis were lower than bleeding rates with prestudy prophylaxis for adults/adolescents and children, 12 years old or younger (FIGS. 1A-1D). Kids rFVIIIFc pivotal phase 3 trial data was further stratified by patient age, and median prestudy and on-study ABRs are shown in FIGS. 1E and 1F. Prestudy, patients less than 6 years old had a lower median (IQR) ABR than patients aged 6 to <12 years old (FIG. 1E). On study, Patients less than 6 years old had higher overall on-study ABR, overall target joint ABR, and target joint spontaneous ABR than patients aged 6 to <12 years old (FIG. 1F).

In rFVIIIFc pivotal phase 3 trial, 46.3% of individualized prophylaxis, 40.7% of weekly prophylaxis, and 21.4% of modified prophylaxis subjects had no target joint bleeding episodes, whereas 53.8% of individualized prophylaxis subjects in Kids rFVIIIFc pivotal phase 3 trial had no target joint bleeding episodes.

Clinical Target Joint Resolution

Among subjects on prophylaxis who had target joints at baseline and 12 months of follow-up, 100% (93/93) of rFVIIIFc pivotal phase 3 trial and 100% (7/7) of Kids rFVIIIFc pivotal phase 3 trial subjects had ≥1 target joint resolved (i.e., ≤2 spontaneous bleeding episodes during 12 consecutive months); and 98.3% (231/235) and 100% (9/9) of target joints (based on all bleeds) in rFVIIIFc pivotal phase 3 trial and Kids rFVIIIFc pivotal phase 3 trial subjects were resolved, respectively.

Prophylactic Factor Consumption

The median (IQR) weekly prophylactic factor consumption among rFVIIIFc pivotal phase 3 trial (n=105) and Kids rFVIIIFc pivotal phase 3 trial (n=13) prophylaxis subjects with target joints at baseline was 76.0 (68.0-90.9) IU/kg and 83.5 (79.9-111.6) IU/kg, respectively.

Consumption was similar to subjects in the parent studies who were on prophylaxis prior to both rFVIIIFc pivotal phase 3 trial/Kids rFVIIIFc pivotal phase 3 trial and during rFVIIIFc pivotal phase 3 trial/Kids rFVIIIFc pivotal phase 3 trial and the rFVIIIFc extension study and had available prestudy and on-study dosing data (rFVIIIFc pivotal phase 3 trial, n=79, 75.0 [70.0-113.8] IU/kg; Kids rFVIIIFc pivotal phase 3 trial, n=54, 95.0 [75.0-113.0] IU/kg).

For both patient populations, median (IQR) dosing intervals were also similar between prophylaxis subjects with target joints at baseline (rFVIIIFc pivotal phase 3 trial, n=105, 3.8 [3.5-5.6] days; Kids rFVIIIFc pivotal phase 3 trial, n=13, 3.5 [3.5-3.5] days) and prophylaxis subjects in the parent study who had available prestudy and on-study dosing data (rFVIIIFc pivotal phase 3 trial, n=79, 3.5 [3.0-5.0] days; Kids rFVIIIFc pivotal phase 3 trial, n=54, 3.5 [3.5-3.5] days).

Kids rFVIIIFc pivotal phase 3 trial data was further stratified by patient age. Average weekly consumption in patients under the age of 6 was 89.6 (75.3-97.5; n=6) IU/kg at a dosing interval of 3.5 (3.5-3.5) days. For patients aged 6 to less than 12 years old, average weekly consumption was 82.2 (79.4-113.2) IU/kg at a dosing interval of 3.5 (3.0-3.6) days.

Quality of Life

QOL improved by 18% at rFVIIIFc extension study Year 2 among adults/adolescents (n=48) compared with rFVIIIFc pivotal phase 3 trial baseline (Table 3). Among Kids rFVIIIFc pivotal phase 3 trial subjects who had self-reported CHO-KLAT scores at Kids rFVIIIFc pivotal phase 3 trial baseline and rFVIIIFc extension study Year 1 (n=6), the mean (standard deviation [SD]) baseline score was 85.5 (12.1); at rFVIIIFc extension study Year 1, CHO-KLAT scores improved by 28% (mean [SD] improvement of 24.1 [15.3]).

TABLE 3

Haem-A-QOL analysis in subjects with target joints at baseline

| | Mean (SD) Score[a] at rFVIIIFc Pivotal Phase 3 Trial Baseline N = 30-48[c] | Mean (SD) Score[a] at rFVIIIFc Extension Study Month 24 N = 30-48[c] | Mean (SD) Change | P value[b] |
|---|---|---|---|---|
| Total | 30.3 (15.7) | 24.9 (15.7) | −5.4 (10.8) | 0.001 |
| Sports & Leisure | 51.5 (26.9) | 40.8 (27.6) | −10.7 (21.7) | 0.008 |
| Physical health | 42.7 (21.7) | 32.1 (27.8) | −10.6 (19.8) | 0.0005 |
| Dealing with hemophilia | 17.0 (13.6) | 15.3 (15.9) | −1.7 (17.5) | NS |
| Family planning | 15.5 (19.8) | 11.5 (18.3) | −4.0 (16.3) | NS |
| Feeling (toward hemophilia) | 23.0 (21.8) | 15.4 (19.2) | −7.7 (16.0) | 0.002 |
| Future | 38.9 (20.9) | 33.8 (23.1) | −5.1 (15.4) | 0.03 |
| Partnership & sexuality | 12.6 (20.2) | 12.2 (21.4) | −0.4 (20.6) | NS |
| Treatment | 28.3 (16.6) | 23.3 (14.1) | −5.0 (15.7) | 0.03 |
| View (of yourself) | 34.2 (22.7) | 32.1 (21.1) | −2.1 (16.8) | NS |
| Work & school | 19.6 (20.0) | 13.7 (19.1) | −6.0 (12.1) | 0.002 |

NS, not significant
[a]Haem-A-QOL scores range from 0 to 100, with higher scores representing a higher impairment in QOL for each subscore and the total score.
[b]Based on 2-tailed paired t test.
[c]48 patients were evaluable for all outcomes other than sports & leisure (n = 33), family planning (n = 30), partnership & sexuality (n = 45), and work & school (n = 44).

Conclusions

Efficacy data from the Phase 3 rFVIIIFc pivotal phase 3 trial and Kids rFVIIIFc pivotal phase 3 trial studies and the ongoing rFVIIIFc extension study show sustained low target joint annualized bleeding rates (ABRs) and effective target joint resolution in pediatric, adolescent, and adult subjects with severe hemophilia A on long-term rFVIIIFc prophylaxis. Weekly prophylactic factor consumption in this analysis of subjects with target joints at baseline was consistent with that in the overall populations of the previously published rFVIIIFc pivotal phase 3 trial and Kids rFVIIIFc pivotal phase 3 trial studies. Improvement in quality of life (QOL) was seen in subjects with target joint resolution with rFVIIIFc prophylaxis without changes in prophylactic factor consumption or dosing interval.

Example 2

Longitudinal Modified Hemophilia Joint Health Scores (mHJHS) Outcomes with Recombinant Factor VIII Fc Fusion Protein (rFVIIIFc) Prophylaxis in Subjects with Severe Hemophilia A Hemophilic arthropathy remains a challenge in the management of haemophilia (Knobe et al., *J Comorbidity*. 2011; 1(1):51-59; Simpson et al., *Expert Rev Hematol*. 2012; 5(4):459-68). Hemophilia Joint Health Score (HJHS) is a first-line tool that can be used to detect the development of hemophilic arthropathy (Oymak et al. *J Pediatr Hematol Oncol*. 2015; 37(2):e80-5). Improvement in musculoskeletal outcomes is an important measure of the effectiveness of prophylaxis treatment for hemophilia A (Blanchette et al. *Haemophilia*. 2004; 10 (Suppl. S4):97-104). The long-term safety and efficacy of rFVIIIFc among adults/adolescents and children who have completed the rFVIIIFc pivotal phase 3 trial (Mahlangu et al. *Blood*. 2014; 123(3):317-325) and Kids rFVIIIFc pivotal phase 3 trial studies (Young et al. *J Thromb Haemost*. 2015; 13(6):967-977), respectively, have been established using interim data from the ongoing rFVIIIFc extension study (Nolan et al. *Haemophilia*. 2016; 22(1):72-80). Determining the long-term impact of rFVIIIFc on musculoskeletal outcomes will require further study.

The objective of this study is to report longitudinal joint health data from rFVIIIFc pivotal phase 3 trial and rFVIIIFc extension study using the modified Hemophilia Joint Health Scores (mHJHS).

Study Participants and Design

The analysis population included adults/adolescents (≥12 years) who completed rFVIIIFc pivotal phase 3 trial and enrolled in the rFVIIIFc extension study for 2 years. Patients may have been on pre-study prophylaxis or episodic treatment. Joint health was assessed using the mHJHS at the rFVIIIFc pivotal phase 3 trial screening (after protocol amendment) and at baseline, and then annually thereafter for the rFVIIIFc extension study.

The mHJHS differs from the standard HJHS, version 2.1, in that the response options for joint pain and gait were condensed into fewer categories, an assessment for instability was added, and the total score is lower (range, 0-116; 0 indicates normal joint function, 116 indicates severe disease) compared with the standard HJHS (range, 0-124) (see Table 4). Scores preceded by a bleed within 2 weeks were excluded. Scores for joints that underwent surgical interventional were imputed using last observation carry forward. To evaluate year-by-year change, rFVIIIFc extension study subjects who had mHJHS data at 4 time points (rFVIIIFc pivotal phase 3 trial baseline, rFVIIIFc extension study baseline, rFVIIIFc extension study Year 1, and rFVIIIFc extension study Year 2) were included in this post hoc analysis. Change in mHJHS score from rFVIIIFc pivotal phase 3 trial baseline to rFVIIIFc extension study Year 2 (negative value indicates improvement) was summarized using descriptive statistics. Change in mHJHS score from rFVIIIFc pivotal phase 3 trial baseline to follow-up visits was summarized for: (1) total score (range, 0-116; by pre-study regimen (prophylactic versus episodic); by severity of functional impairment based on initial mHJHS; and by presence of target joints at baseline; (2) target joints (range, 0-19: sum of all questions for a single target joint); (3) Weight bearing (e.g., ankle and knee) and non-weight bearing (e.g., elbow) joints (range, 0-38: sum of right and left joints of a single location); and (4) individual components (range of motion (range, 0-36: combination of questions "Extension loss [dorsiflexion of ankles]" and "Flexion loss [plantarflexion of ankles]" of all joints); swelling (range, 0-24: combination of questions "Swelling" and "Duration of swelling" of all joints); and strength (range, 0-6: sum of all joints)).

TABLE 4

Differences between HJHS and mHJHS

| HJHS | mHJHS |
|---|---|
| Crepitus of motion (Scored 0-2) | Crepitus of motion (Scored 0 or 1) |
| Joint pain (Scored 0-2) | Joint pain (Scored 0 or 1) |
| Global gait (Scored 0-4) | Global Gait (Scored descriptively) |
| — | Instability (Scored 0 or 1) |
| Total score (0-124) | Total score (0-116[a]) |

[a]0 = normal joint function; 116 = severe disease

Differences between rFVIIIFc pivotal phase 3 trial baseline and rFVIIIFc extension study Year 2 were analyzed using a paired t-test. P values were not used to infer statistical significance because this analysis was ad hoc. For subgroup analyses, only descriptive statistics are provided.

Results

Baseline Characteristics

Baseline characteristics were similar between the population of completers included in this analysis (n=47) and the patient population for whom mHJHS was collected at rFVIIIFc pivotal phase 3 trial baseline and who enrolled in the rFVIIIFc extension study (n=74) (Table 5).

TABLE 5

Baseline characteristics

| | rFVIIIFc Pivotal Phase 3 Trial Baseline and Enrolled in the rFVIIIFc Extension Study n = 74[a] | rFVIIIFc PIVOTAL PHASE 3 TRIAL and rFVIIIFc Extension Study 2-year Completer n = 47[b] |
|---|---|---|
| Mean (SD) age, y | 31.6 (11.9) | 32.3 (12.8) |
| Mean (SD) weight at parent study entry, kg | 72.7 (15.1) | 73.5 (15.7) |
| Mean (SD) BMI, kg/m² | 23.8 (4.3) | 24.0 (4.1) |
| Mean (SD) baseline mHJHS score | 22.1 (18.0) | 23.4 (18.3) |
| Target joints, % | 55.4 | 51.1 |
| Pre-study treatment, % Prophylaxis | 68.9 | 63.8 |
| On-demand | 31.1 | 36.2 |
| Mean (SD) pre-study ABR | 15.8 (20.0) | 16.5 (18.4) |

[a]74 subjects on rFVIIIFc prophylaxis enrolled in rFVIIIFc pivotal phase 3 trial, have mHJHS scores, and subsequently entered the rFVIIIFc extension study.
[b]47 patients on prophylaxis reached year 2 in the rFVIIIFc extension study with data available at rFVIIIFc pivotal phase 3 trial baseline, rFVIIIFc extension study baseline, and Years 1 and 2.

Longitudinal Joint Health

Figure 2A:
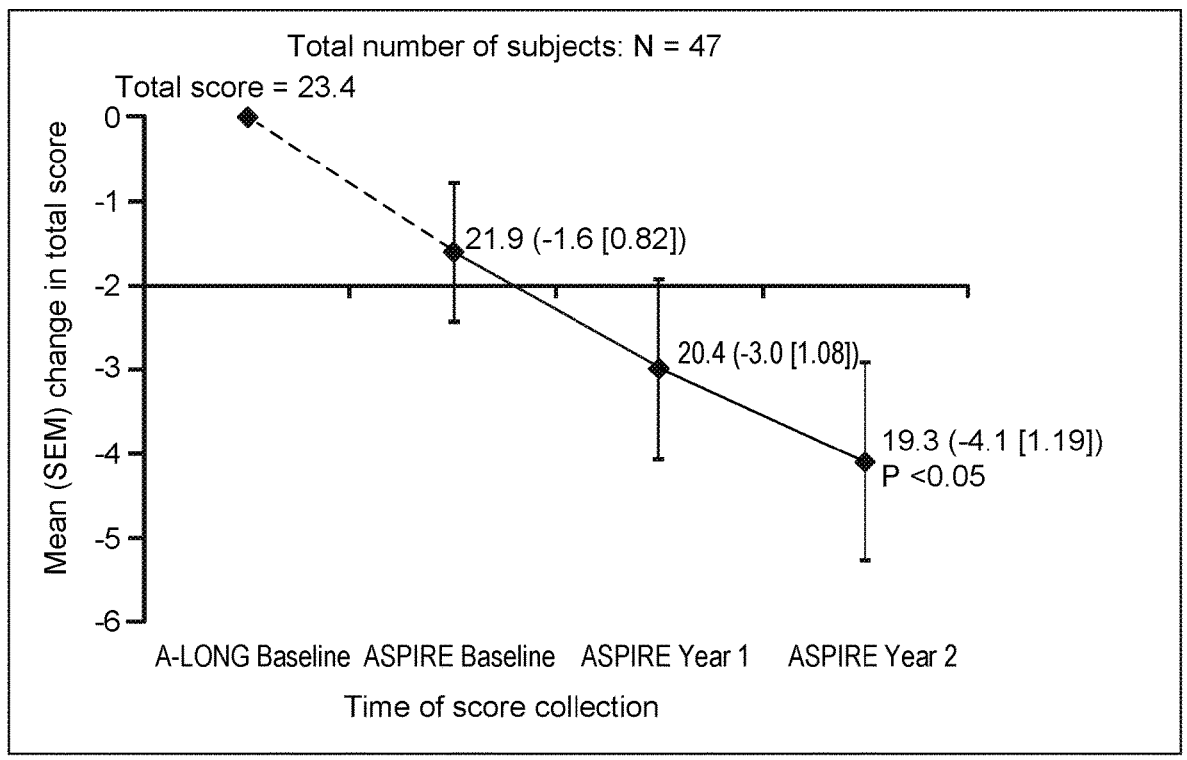
FIGS. 2A-2B show the mean change in total modified Hemophilia Joint Health Score (mHJHS; y-axis) from FVIII-Fc study base line through extension study year 2 (FIG. 2A; x-axis) and through extension study year 3 (FIG. 2B; x-axis).
Figure 2B:
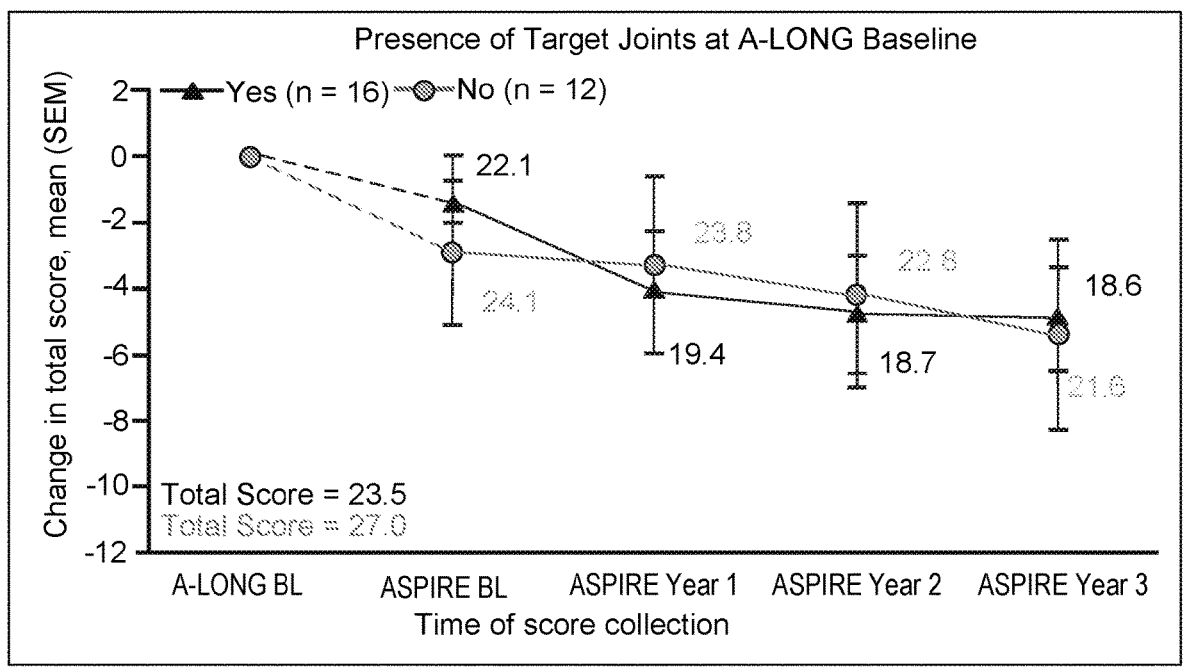
Figure 3A:
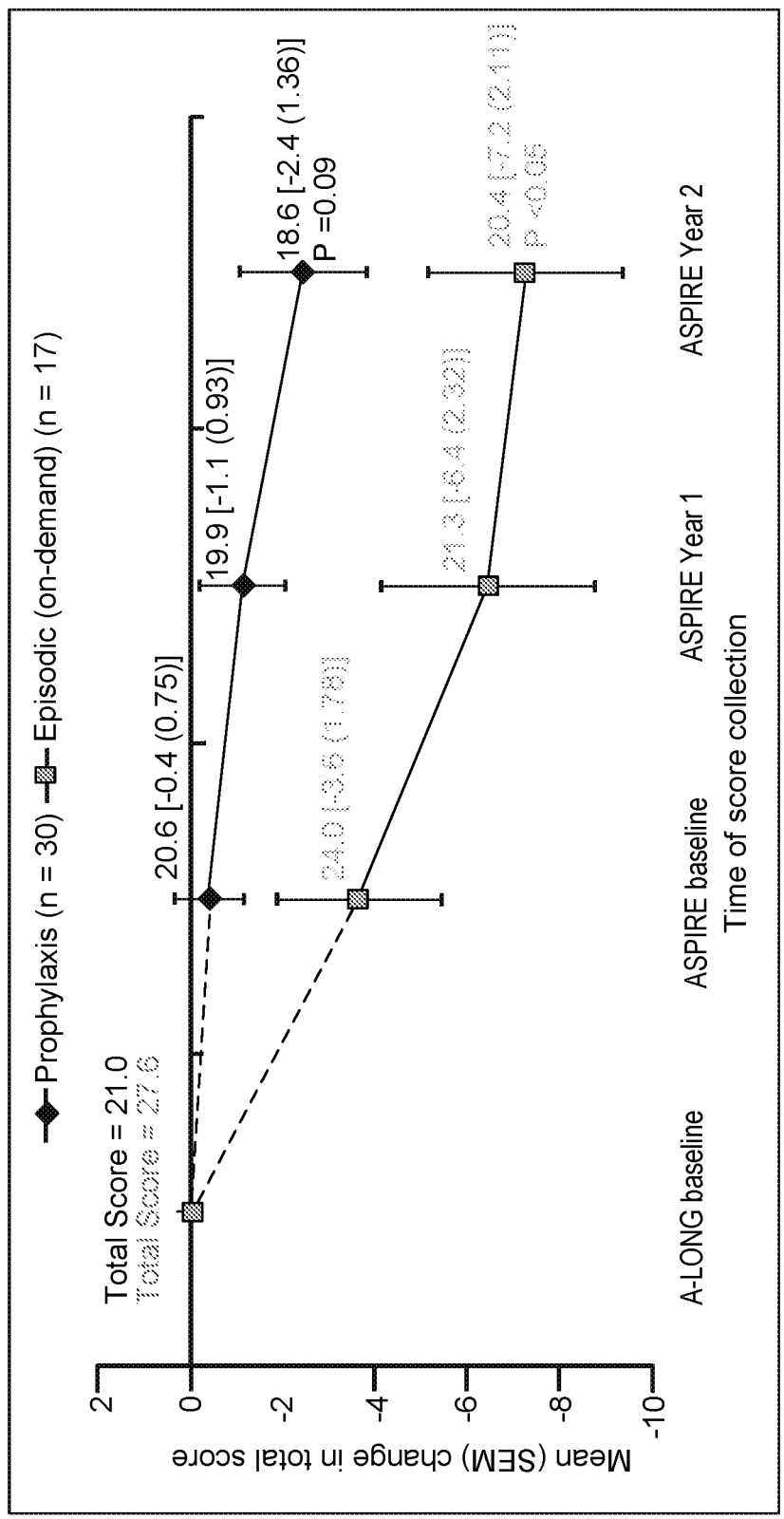
FIGS. 3A-3C show the mean change in total mHJHS (y-axis) from FVIII-Fc study base line through extension study year 2 (FIG. 3A; x-axis) and extension study year 3 (FIG. 3B) and from the FVIII-Fc study for kids through extension year 2 (FIG. 3C; x-axis) for subjects receiving prestudy prophylactic treatment and subjects receiving prestudy episodic (on-demand) treatment.
Figure 3B:
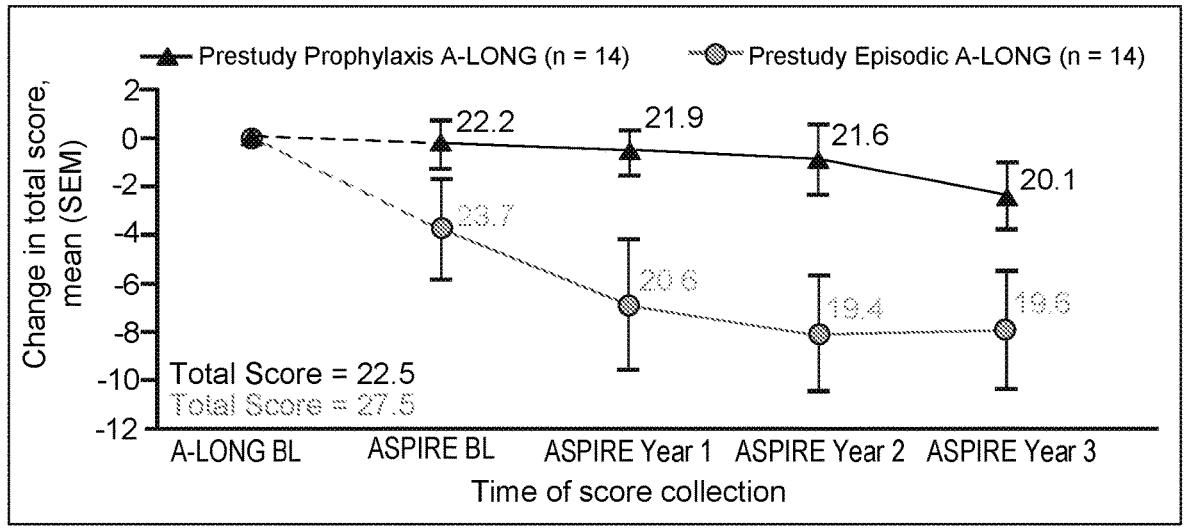
Figure 3C:
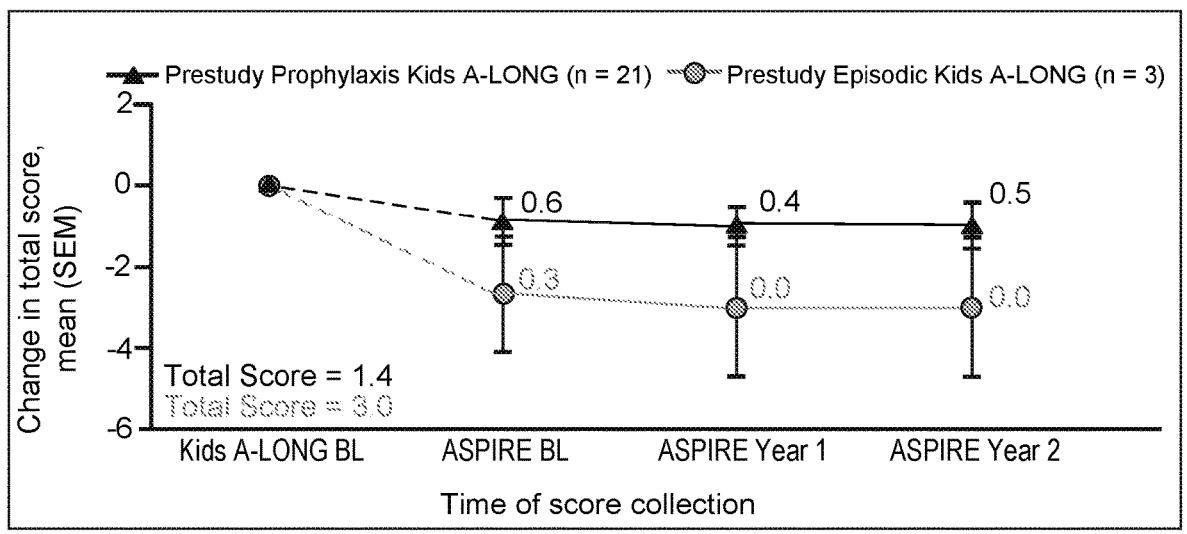
Figure 4:
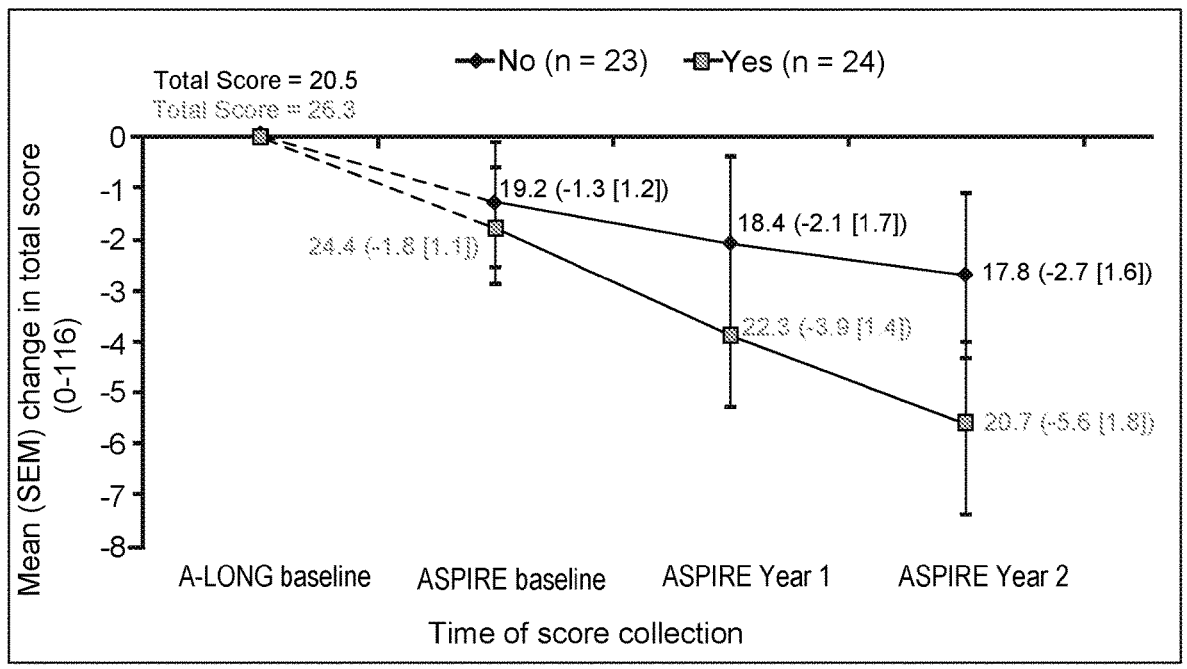
FIG. 4 shows the mean change in total mHJHS (y-axis) from FVIII-Fc study base line through year 2 (x-axis) for subjects having target joints at FVIII-Fc study baseline (squares) and subjects not having target joints at FVIII-Fc study baseline (diamonds).
Figure 5:
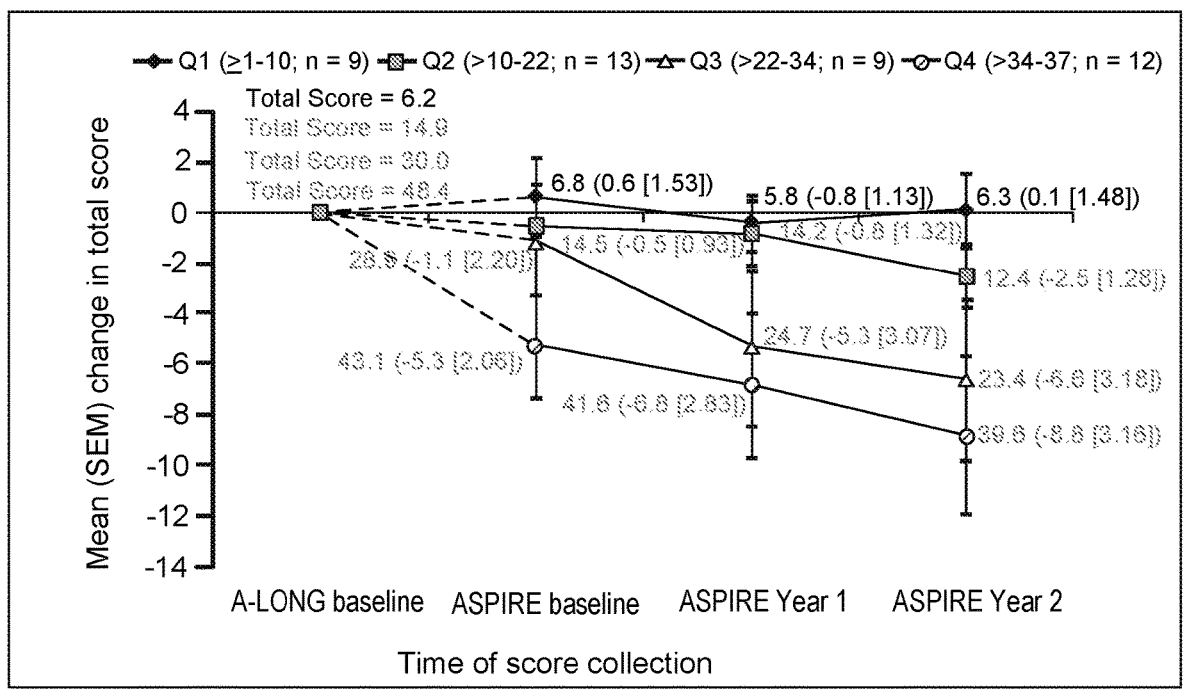
FIG. 5 shows the mean change in total mHJHS (y-axis) from FVIII-Fc study base line through year 2 (x-axis) for subjects in the lowest quartile of impairment (Q1; ≥1-10) in mHJHS scores at FVIII-Fc study baseline (diamonds), the second lowest quartile of impairment (Q2; ≥10-22) in mHJHS scores at FVIII-Fc study baseline (squares); the second highest quartile of impairment (Q3; ≥22-34) in mHJHS scores at FVIII-Fc study baseline (triangles), and the highest quartile of impairment (Q4; ≥34-37) in mHJHS scores at FVIII-Fc study baseline (diamonds).
Figure 6:
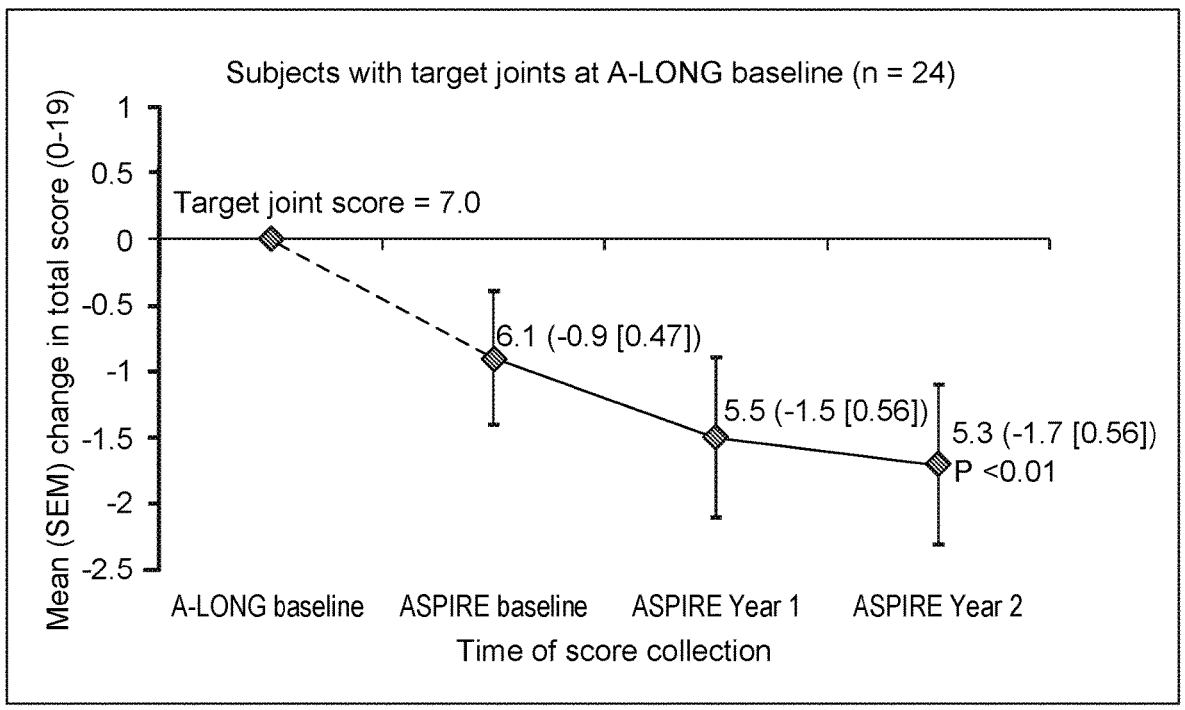
FIG. 6 shows the mean change in total mHJHS (y-axis) from FVIII-Fc study base line through year 2 (x-axis) for subjects having target joints at FVIII-Fc study baseline.
Figure 7:
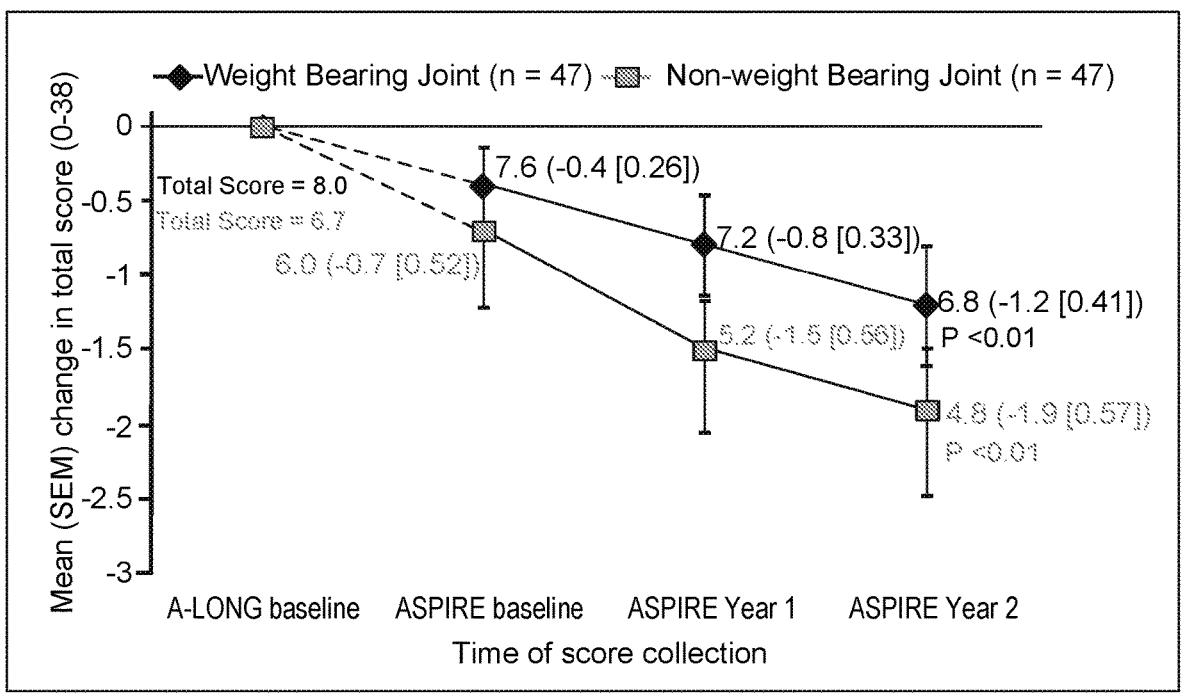
FIG. 7 shows the mean change in total mHJHS (y-axis) from FVIII-Fc study base line through year 2 (x-axis) for weight bearing joints (diamonds) and non-weight bearing target joints (squares).
Figure 8:
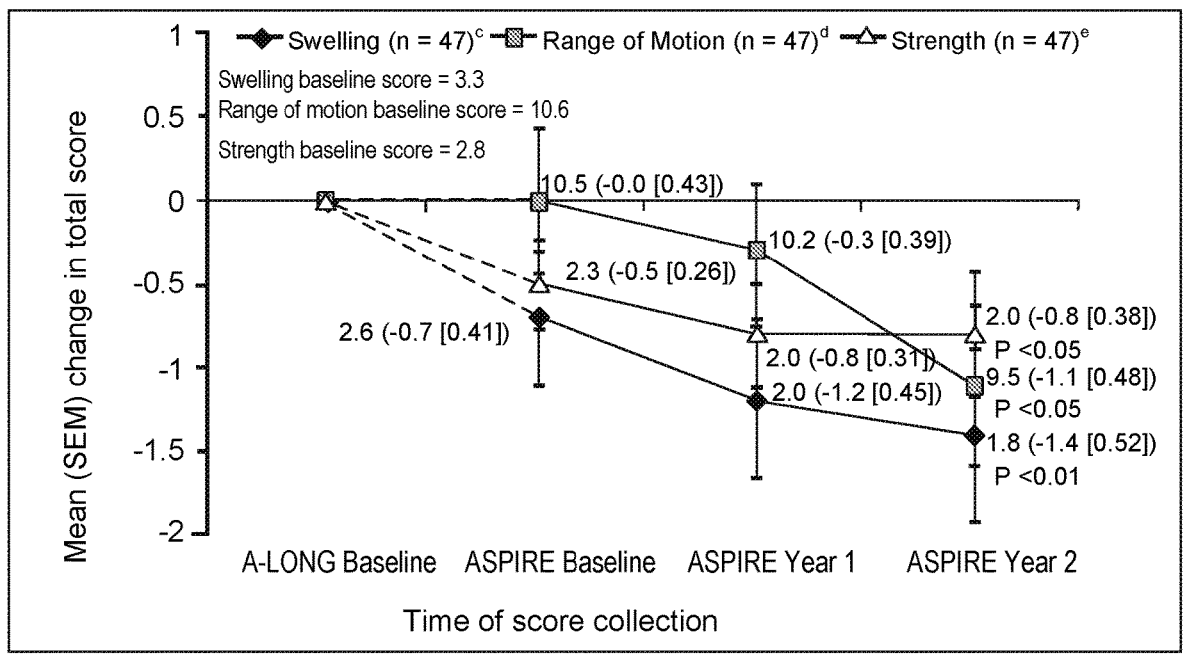
FIG. 8 shows the mean change in mHJHS (y-axis) from FVIII-Fc study base line through year 2 (x-axis) for swelling (diamonds), range of motion (squares), and strength (triangles).

Continuous improvement was observed in mHJHS score from rFVIIIFc pivotal phase 3 trial base line through rFVIIIFc extension study year 2, with an average decrease in total score from 23.4 to 19.3 (FIG. 2A). Of the seventy-four subject, twenty-four were evaluated at extension study year 3, and these improvements in mHJHS scores were seen at extension study year 3 regardless of the presence of target joints at baseline for the rFVIIIFc pivotal phase 3 trial (FIG. 2B). The average follow-up duration was 2.8 (2.5-3.3) years. Continuous improvement was observed regardless of the prestudy treatment of the patient (FIG. 3) or the presence of target joints at rFVIIIFc pivotal phase 3 trial baseline (FIG. 4). In those patients evaluated at extension study year 3, mean mHJHS total score for adults/adolescents with data at all time points was 25.0 (standard error of the mean [SEM], 2.9) at baseline. Mean (SEM) change from baseline was −2.0 (1.2) at extension study baseline, −3.8 (1.5) at extension study year 1, −4.5 (1.6) at extension study year 2, and −5.1 (1.5) at extension study year 3 (FIG. 3B). The change from baseline to extension study year 3 was statistically significant (P<0.002). The Kids rFVIIIFc pivotal phase 3 trial analysis population (n=24) also showed statistically significant mean (SEM) improvement from baseline to extension study year 2 (−1.2 [0.56]; P<0.05) (FIG. 3C). Subjects with the highest quartile of impairment in mHJHS scores at rFVIIIFc pivotal phase 3 trial baseline showed the greatest improvement in mHJHS total score from baseline to rFVIIIFc extension study year 2 (FIG. 5). Continuous improvement in mHJHS target joint scores was observed from rFVIIIFc pivotal phase 3 trial baseline to rFVIIIFc extension study year 2, with an improvement from an average of 7.0 at baseline to an average of 5.3 at rFVIIIFc extension study year 2 (FIG. 6). mHJHS joint scores for weight bearing joints decreased from an average of 8.0 to an average of 6.8 and for non-weight bearing joints from an average of 6.7 to an average of 4.8 from rFVIIIFc pivotal phase 3 trial baseline to rFVIIIFc extension study year 2 (FIG. 7). For calculation of weight bearing (ankle & knee) and non-weight bearing joint (elbow) score, a score was first derived as the sum of per-joint scores for a pair of right and left joints (ankle, knee, or elbow). Then weight bearing joint score was calculated as the average of the scores for ankle and knee, and non-weight bearing joint score was the same as the score for elbow. In addition, specific improvements in swelling, range of motion, and strength were also observed from rFVIIIFc pivotal phase 3 trial baseline to rFVIIIFc extension study year 2, which represented the most significant contributing factors to change in mHJHS total score (FIG. 8).

Figure 9:
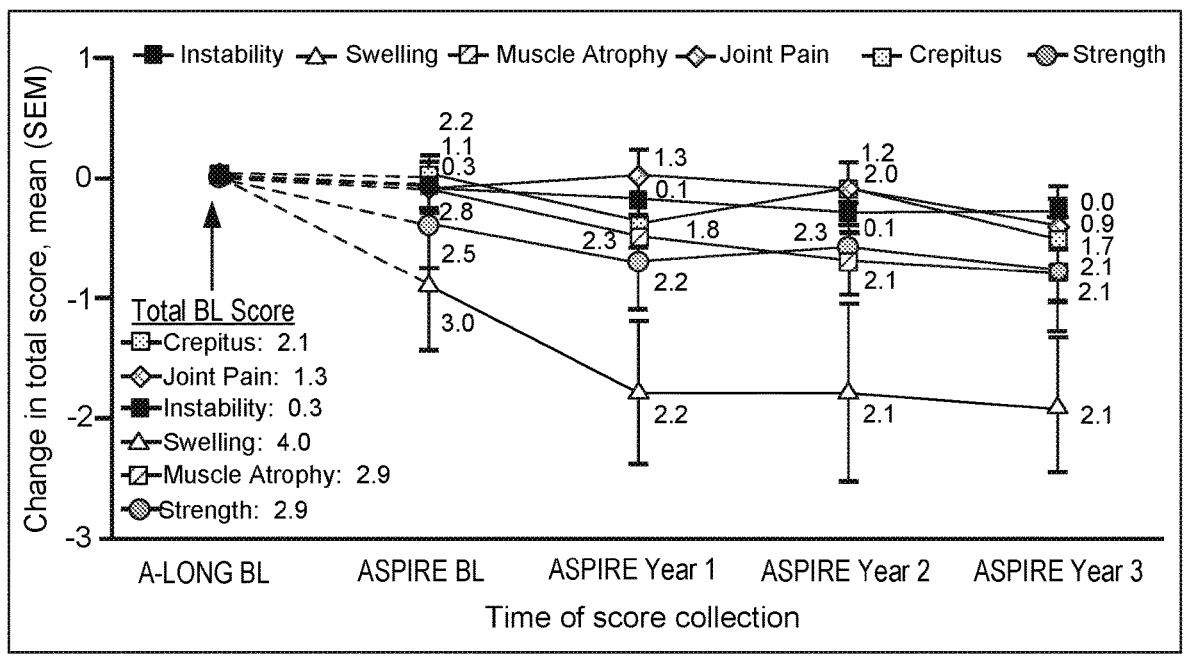
FIG. 9 shows the mean (SEM) change in mHJHS (y-axis) in FVIII-Fc study patients for joint instability (dark grey squares), swelling (black triangles), muscle atrophy (light grey squares), joint pain (light grey diamonds), crepitus (black squares), and strength (light grey circles). Total Baseline (BL) Scores for each mHJHS measurement are shown.

Statistically significant mean improvements from the rFVIIIFc pivotal phase 3 trial baseline were observed for both weight-bearing and non-weight-bearing joints (−1.1 [SEM, 0.5; P=0.036] and −3.0 [SEM, 0.8; P=0.001], respectively) at year 3. Individual components of the mHJHS that showed ≥20% reduction from baseline to year 3 were swelling (−47%), muscle atrophy (−26%), crepitus (−20%) (P<0.05 for all 3 components) and joint instability (−89%), joint pain (−31%), and strength (−26%) (FIG. 9).

Example 3

Target Joint Outcomes with Prophylaxis with rFIXFc in Adults and Adolescents with Hemophilia B In patients with severe hemophilia B, repeated bleeding into joints without sufficient treatment may lead to crippling chronic joint disease, pain, and reduced quality of life (Djambas Khayat, *J Blood Med.* 7:275-82 (2016)). Prophylactic treatment with recombinant factor IX Fc fusion protein (rFIXFc) resulted in lower annualized bleeding rates (ABRs) and fewer spontaneous/traumatic bleeding events in adolescents and adults with severe hemophilia B (Kavakli et al., *Haemophilia* 22(3):381-88 (2016); Powell et al. *N Engl J Med.* 369(24):2313-23 (2013); Powell et al., *Br J Haematol.* 168(1):124-34 (2015); Powell et al., *Br J Haematol.* 168(1):113-23 2015)). In addition to prevention of joint damage and reduction in bleeding events, prophylactic treatment with both conventional and long-acting rFIX may result in less time out of work or school, fewer hospital admissions, less frequent monitoring, and improved quality of life (Kavakli et al., *Haemophilia* 22(3):381-88 (2016); Wyrwich et al., *Haemophilia* 22(6):866-72 (2016)). Prophylactic treatment initiated early in life reduces bleeding and prevents joint damage. When initiated later in life once joint damage has transpired, prophylactic treatment still can significantly reduce the number of bleeds, including bleeds into joints (Fischer et al., *Haemophilia* 20(Suppl 4):106-13 (2014)). Adults/adolescents with severe hemophilia B who completed the rFIXFc pivotal phase 3 trial (NCT01027364) could enroll in the long-term extension study (NCT01425723; Pasi et al., *Thromb Haemost.* 117(3):508-18 (2017)) that evaluated the safety and efficacy of rFIXFc. Longitudinal outcomes from subjects with target joints at entry into rFIXFc pivotal phase 3 trial throughout the long-term extension study are reported here.

The objective of this study is to present rFIXFc pivotal phase 3 trial longitudinal data outcomes from subjects with target joints at entry through the second interim data cut of the extension study (Sep. 11, 2015).

Methods
Study Design and Population

Subjects with severe hemophilia B (≤2 IU/dL endogenous FIX) completing the rFIXFc pivotal phase 3 trial enrolled in 1 of 4 treatment groups in the extension study: (1) weekly prophylaxis (WP; 20-100 IU/kg every 7 days); (2) individualized interval prophylaxis (IP; 100 IU/kg every 8-16 days); (3) modified prophylaxis (MP; investigators could personalize dosing for subjects not achieving optimal dosing with IP or WP); and (4) episodic treatment (ET; on-demand dosing based on type and severity of bleeding episodes). Subjects could switch their treatment group at enrollment into the extension study and at any time during the study. Subjects who switched treatment groups were included in the analyses of each treatment group for the period spent on that treatment regimen, so individual subjects could be counted in more than 1 treatment group in the analysis. Subjects with ≥1 target joint (major joint with ≥3 bleeding episodes in a 3-month period) at pivotal phase 3 trial entry were evaluated.

Outcome Measures and Statistical Analyses

Outcomes were analyzed over the cumulative duration of the rFIXFc pivotal phase 3 trial through the second B-YOND interim data cut (Sep. 11, 2015). An analysis of target joint resolution was performed. Target joint resolution was defined as ≤2 spontaneous bleeds in the target joint over a consecutive 12-month period (Blanchette et al., *J Thromb Haemost.* 12(11):1935-39 (2014)).

Results

Baseline characteristics for subjects with target joints are shown in Table 6. Of 117 rFIXFc pivotal phase 3 trial subjects with on-study data, sixty had a total of 166 target joints at baseline. These subjects received rFIXFc for a cumulative median (interquartile range [IQR]) duration of 3.4 (1.4-4.2) years.

TABLE 6

| Baseline characteristics. | |
|---|---|
| Characteristic | N = 60 |
| Prestudy regimen | |
| Episodic | 44 (73.3) |
| Prophylaxis | 16 (26.7) |
| Number of target joint(s) | |
| 1 | 20 (33.3) |
| 2 | 13 (21.7) |
| 3 | 7 (11.7) |
| >3 | 20 (33.3) |
| Target joint location | |
| Knee | 42 (70.0) |
| Ankle | 33 (55.0) |
| Elbow | 28 (46.7) |
| Hip | 6 (10.0) |
| Shoulder | 3 (5.0) |
| Wrist | 3 (5.0) |

All data are n (%). rFIXFc, recombinant factor IX Fc fusion protein. Includes subjects with ≥1 target joint at entry into B-LONG and with an efficacy period (defined as the sum of all intervals of time during which subjects were treated with rFIXFc according to treatment regimens of the study, excluding surgical rehabilitation periods); bA target joint is defined as a major joint (eg, knee, ankle, elbow, hip, shoulder, and wrist) into which repeated bleeding occurred (frequency of ≥3 bleeding episodes into the same joint in a consecutive 3-month period).

Prophylactic Dosing

Average weekly dosing and dosing interval summarized in Table 7.

TABLE 7

Summary of average rFIXFc prophylactic dosing and dosing interval

| | Treatment Group | | |
|---|---|---|---|
| | WP (n = 40) | IP (n = 12) | MP (n = 12) |
| Average weekly dose, IU/kg | 45.2 (37.3-55.8) | 64.7 (46.7-82.3) | 59.7 (40.0-109.8) |

TABLE 7-continued

Summary of average rFIXFc prophylactic dosing and dosing interval

| | Treatment Group | | |
|---|---|---|---|
| | WP (n = 40) | IP (n = 12) | MP (n = 12) |
| Dosing interval, d | 6.98 (6.9-7.0) | 10.25 (8.9-13.2) | 6.57 (4.9-6.9) |

All data are median (IQR). IP, Individualized interval prophylaxis; MP, modified prophylaxis; rFIXFc, recombinant factor IX Fc fusion protein; WP, weekly prophylaxis. Only subjects with available on-study dose and dosing interval data were included in this analysis. Subjects are included in each treatment regimen they participated in for the duration of time on that regimen and, as such, may appear in more than one treatment regimen.

Bleeding Rates

Figure 10A:
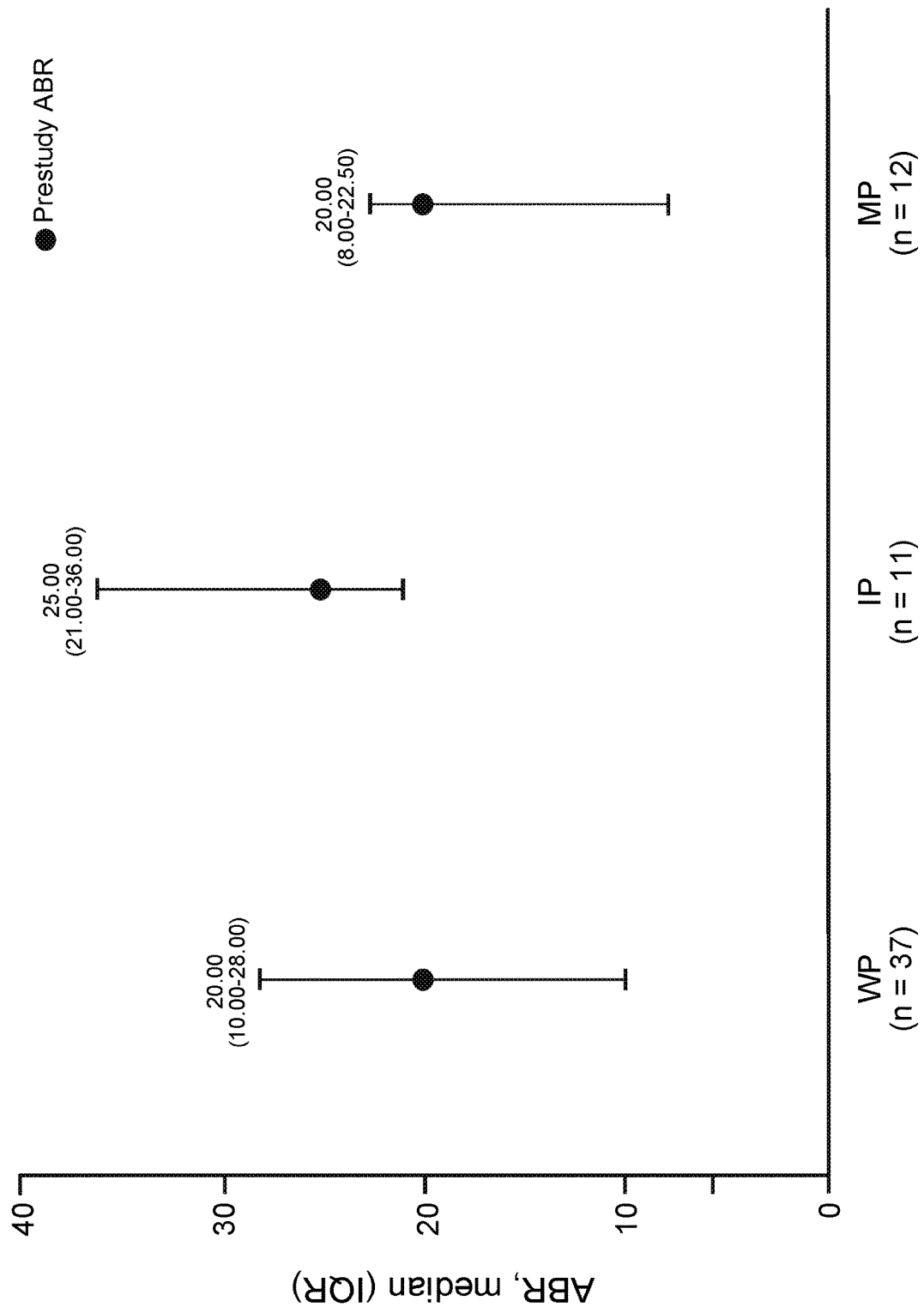
FIGS. 10A-10B show prestudy (FIG. 10A) and on-study median (FIG. 10B) (IQR) annualized bleeding rates (ABRs) for subjects from a rFIXFc study.
Figure 10B:
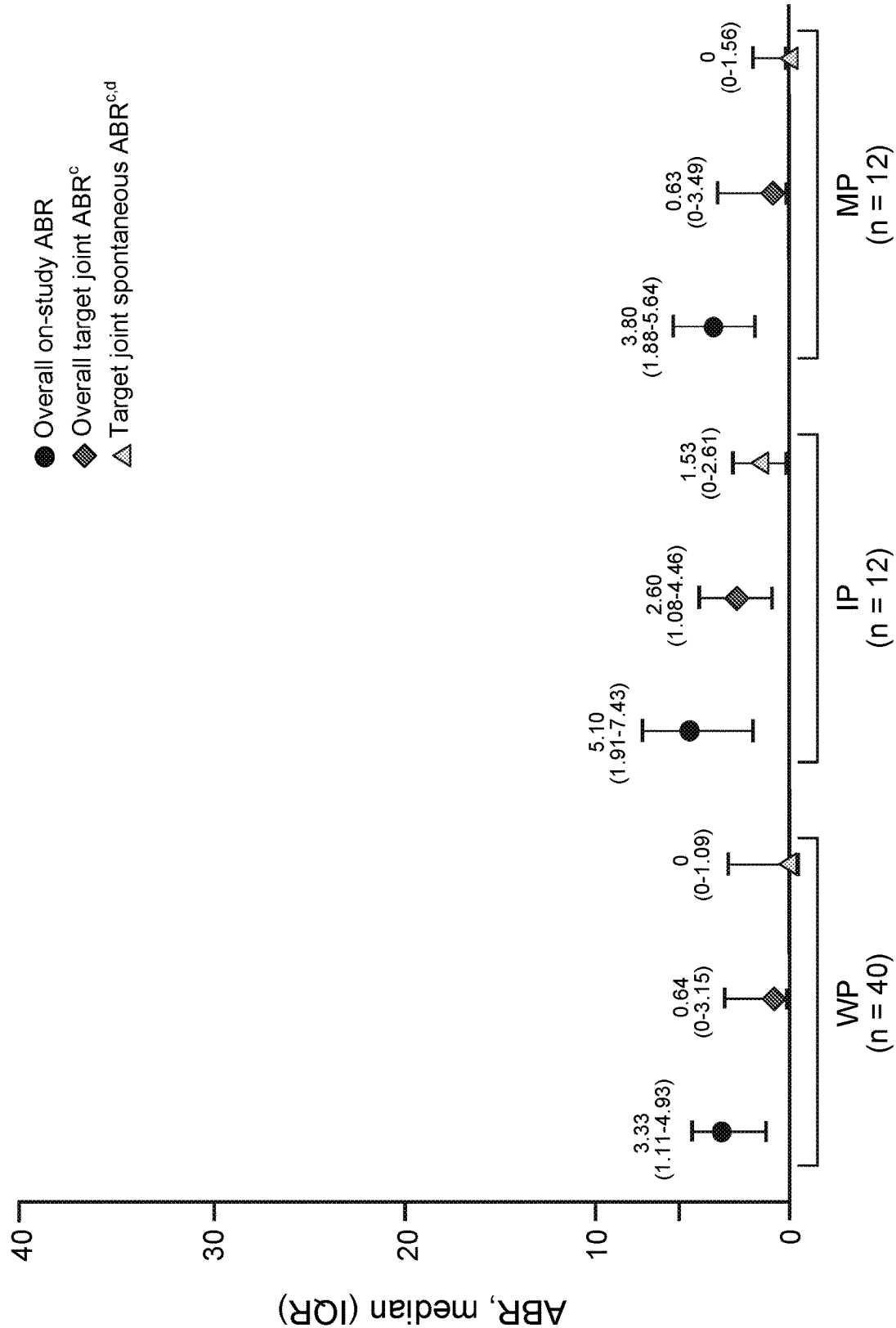

Prestudy and on-study bleeding data are shown in FIGS. 10A and 10B, respectively. Subjects receiving rFIXFc prophylaxis who did not have a target joint rebleed on-study were as follows: WP: 15 of 40 (37.5%); IP: 1 of 12 (8.3%); MP: 4 of 12 (33.3%); ET: 0 of 14 (0%). In subjects with target joints at baseline, on-study overall and target joint ABRs with rFIXFc prophylaxis were lower than bleeding rates with prestudy treatment (FIGS. 10A and 10B).

| Annualized bleeding rates for twenty-two subjects treated with a dosing interval ≥14 days, as well as sixteen subjects who ended treatment on a dosing interval ≥14 days are shown in Table 8. | | |
|---|---|---|
| Overall ABR | 1.7 (0.6-4.2) | 1.4 (0.6-2.0) |
| Spontaneous ABR | 0.7 (0.3-1.3) | 0.7 (0.3-1.0) |
| Joint ABR | 1.1 (0.3-2.7) | 0.6 (0.2-1.5) |
| Spontaneous Joint ABR | 0.3 (0.0-1.3) | 0.3 (0.0-0.8) |

Target Joint Resolution

Figure 11:
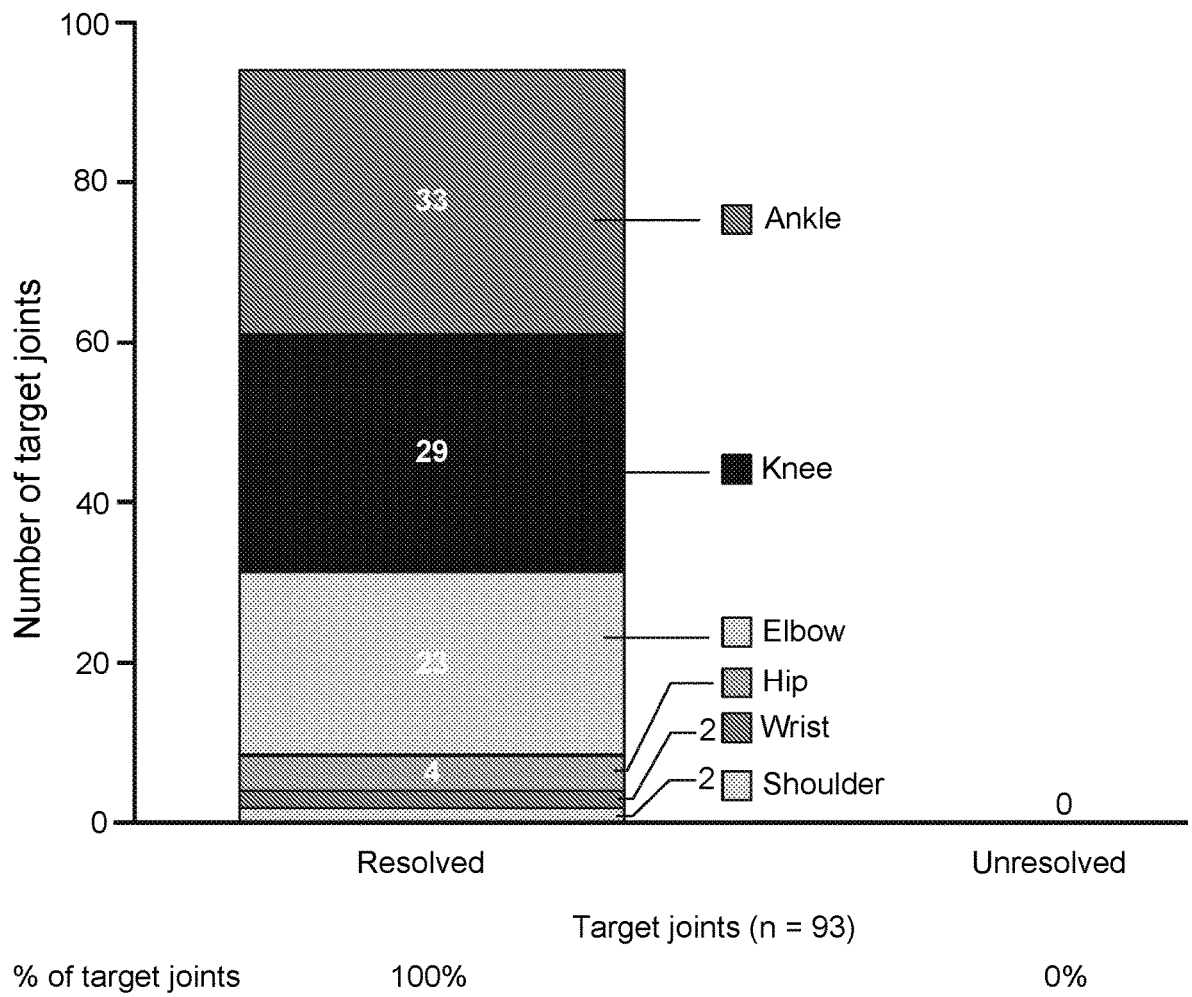
FIG. 11 is a graphical representation showing the number of evaluable target joints (ankle, knee, elbow, hip, wrist, and shoulder) resolved and unresolved in those subjects (n=37) with at least twelve months of consecutive follow-up time who had not undergone joint surgery within twelve months since the start of follow-up. The number (n) of each target joint is superimposed over the relevant data, with a total of 93 target joints evaluated. The percent of target joints resolved (100%) and unresolved (0%) is shown below the x-axis.

Overall, 100% (93/93) of target joints (in 37 subjects) resolved, as indicated two or less spontaneous bleeds in a twelve-month period (FIG. 11)

Conclusions

In adults/adolescents with severe hemophilia B, long-term rFIXFc prophylaxis resulted in target joint resolution in 100% of subjects with evaluable target joints at baseline and in low target joint ABRs across all treatment groups. Clinicians should consider the beneficial and significantly improved long-term outcomes for patients with target joints achieved with rFIXFc when designing treatment prophylaxis plans.

Example 4

Biodistribution of $^{125}$I-Labeled FIXFc, FIX, and GlycoPEGylated FIX in HemB Mice by In Vivo Single Photon Emission Tomography (SPECT)

An in vivo mouse study was conducted to evaluate biodistribution of FIX proteins at multiple times post-dosing by in vivo Single Photon Emission Tomography (SPECT). FIX proteins were labeled at lysine residues using a $^{125}$I-labeled SIB linker. Labeled FIX proteins were administered to 7-12 week old HemB mice by a single therapeutically relevant dose. $^{125}$I-SIB-FIX was administered as a single dose of 1 mg/kg (n=3); $^{125}$I-SIB-FIXFc was administered as a single dose of 2 mg/kg (n=3), and $^{125}$I-SIB-FIX-PEG was administered as a single dose of 1 mg/kg (n=3).

Localization of the labeled FIX proteins was imaged at 0.5 hrs, 2.5 hrs, 20 hrs, 48 hrs, 92 hrs, 120 hrs, 168 hrs, and/or 216 hrs (FIGS. 10A-10C). Specific localization to joint areas (e.g., right/left knee and right/left shoulder), the heart (left ventricle), and the liver was analyzed using region of interest (ROI) placement. Left Ventricle and Liver ROI were fixed volume objects, placed within the correct organ. Knee-joint ROI was defined by placing a cylinder around the bone from approximately half way down the femur to half way down the tibia/fibula. Shoulder ROI was defined by placing a uniform sphere at the center of the shoulder, then thresholding for bone within that sphere, followed by a dilation of the ROI.

Figure 12A:
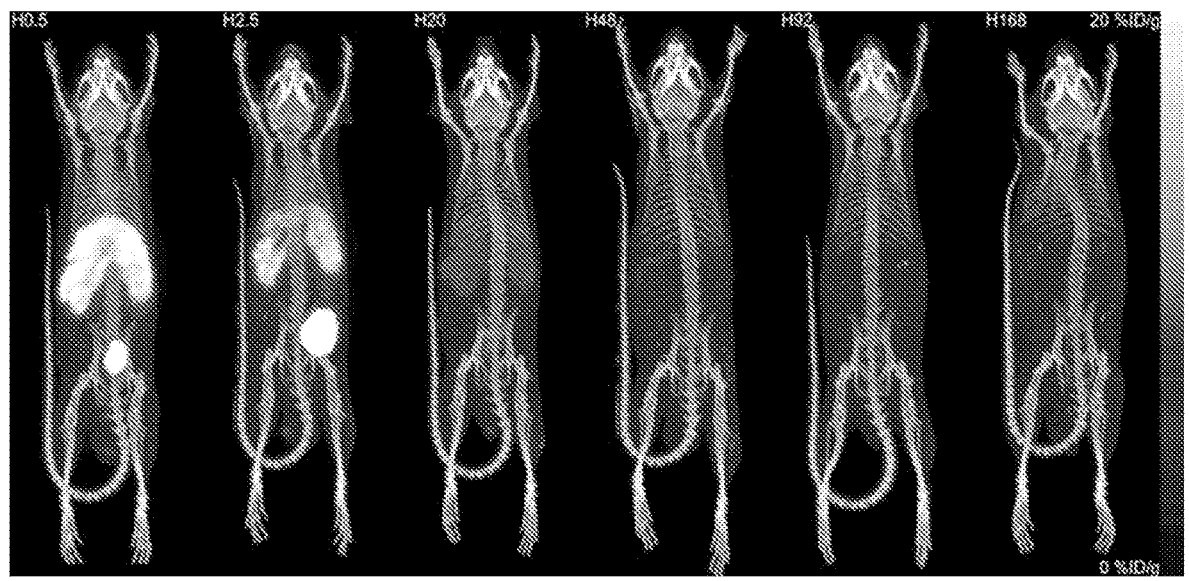
FIGS. 12A-12C are Single Photon Emission Tomography (SPECT) images of mice administered $^{125}$I-SIB-labeled FIX (FIG. 12A), $^{125}$I-SIB-labeled FIXFc (FIG. 12B), or $^{125}$I-SIB-labeled GlycoPEGylated-FIX (FIG. 12C).
Figure 12B:
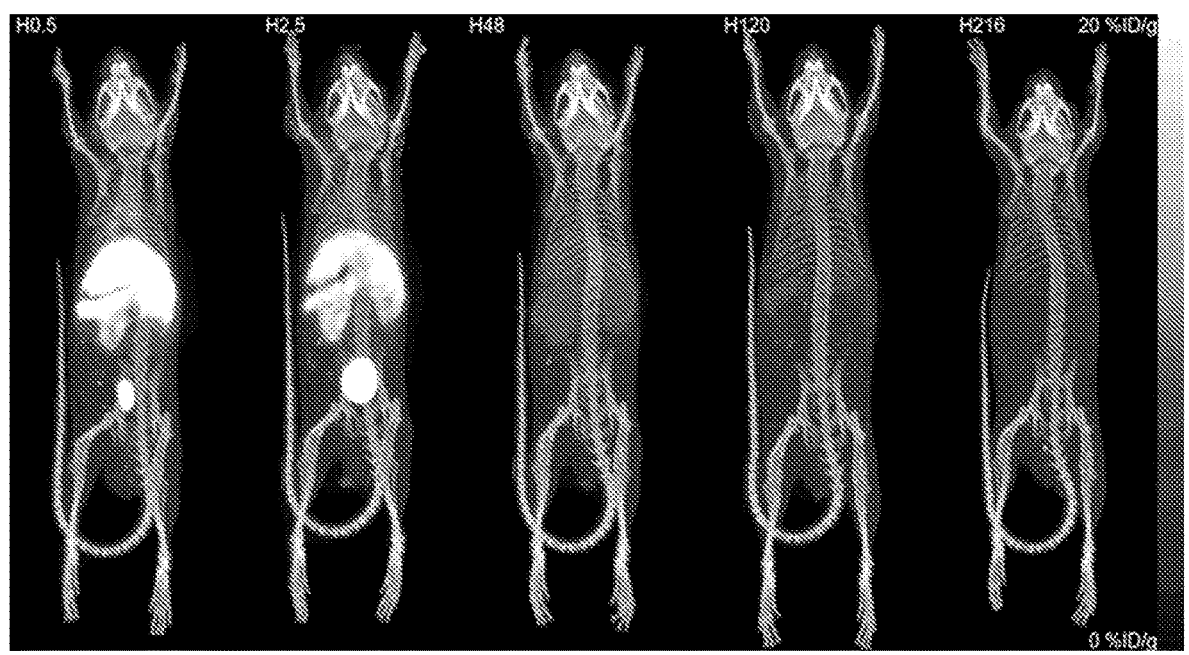
Figure 12C:
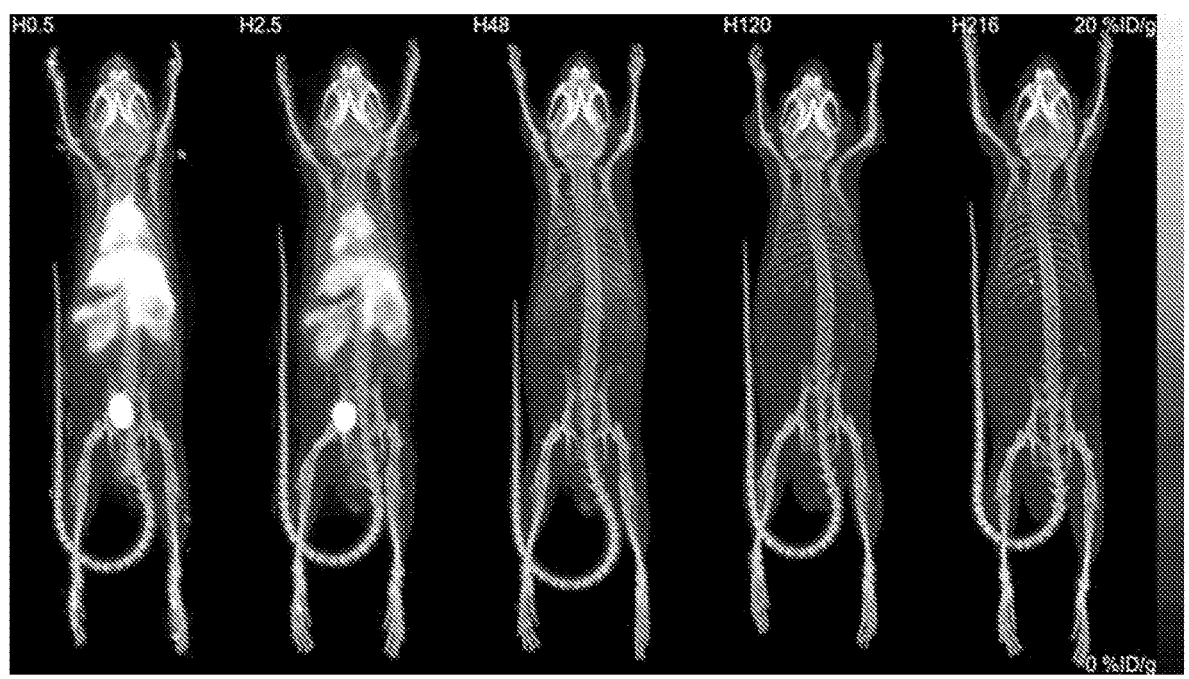
Figure 12D:
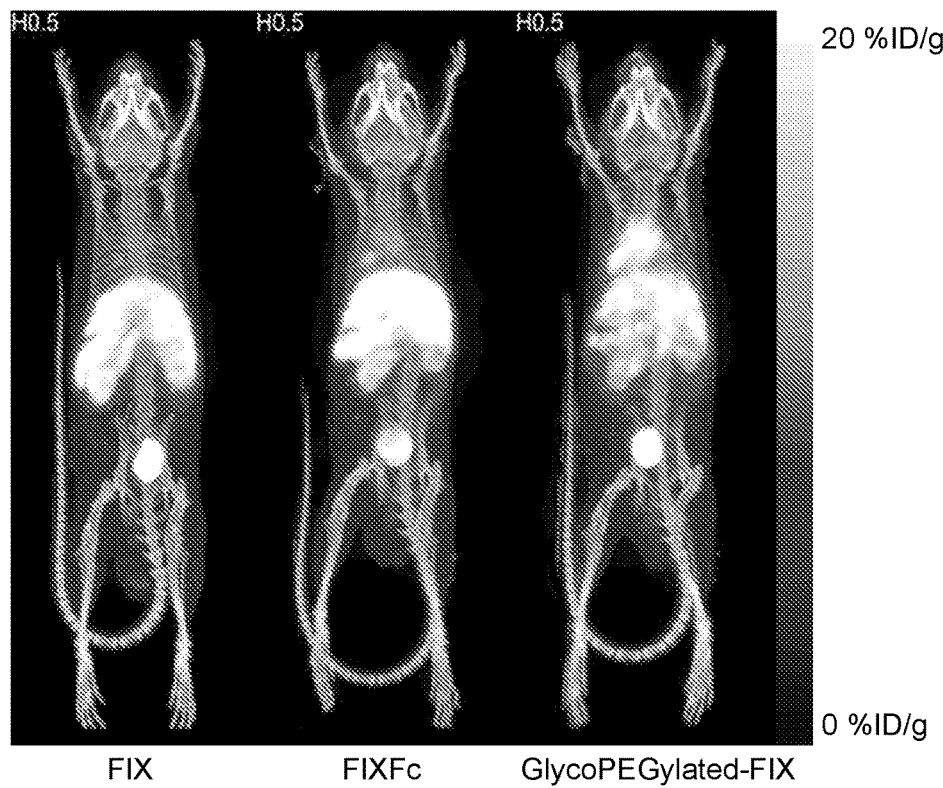
FIGS. 12D-12G show direct comparisons of mice administered $^{125}$I-SIB-labeled FIX, $^{125}$I-SIB-labeled FIXFc, or $^{125}$I-SIB-labeled GlycoPEGylated-FIX at various time points. Heat maps indicate the relative concentration (% ID/g) of $^{125}$I-SIB label in each mouse (FIGS. 12A-12G).
Figure 12E:
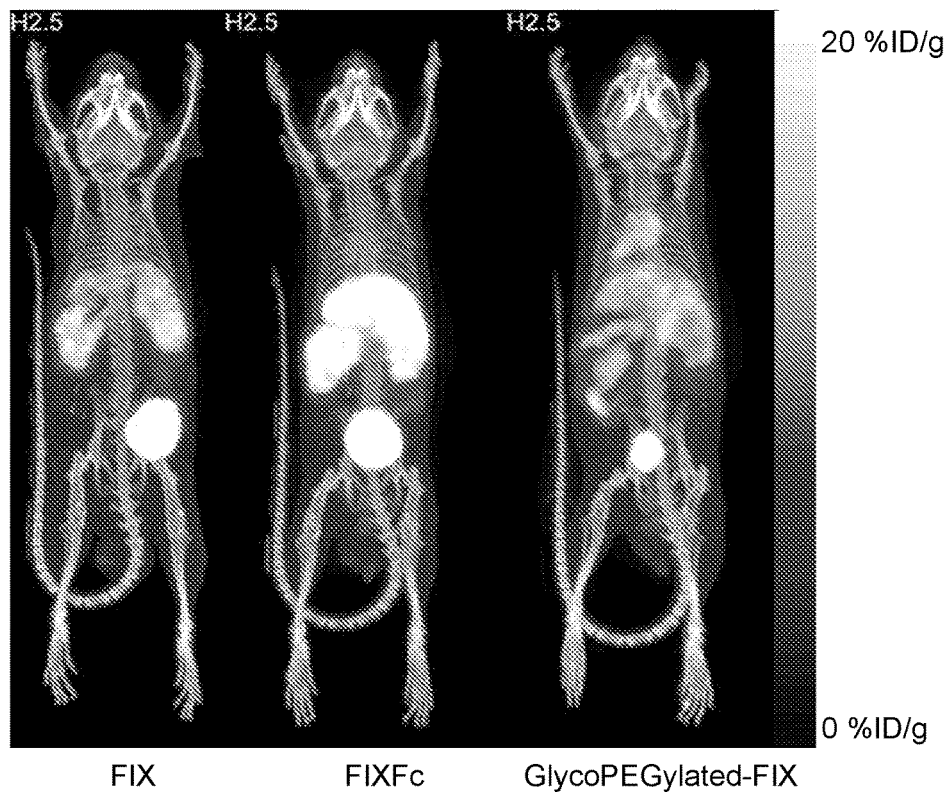
Figure 12F:
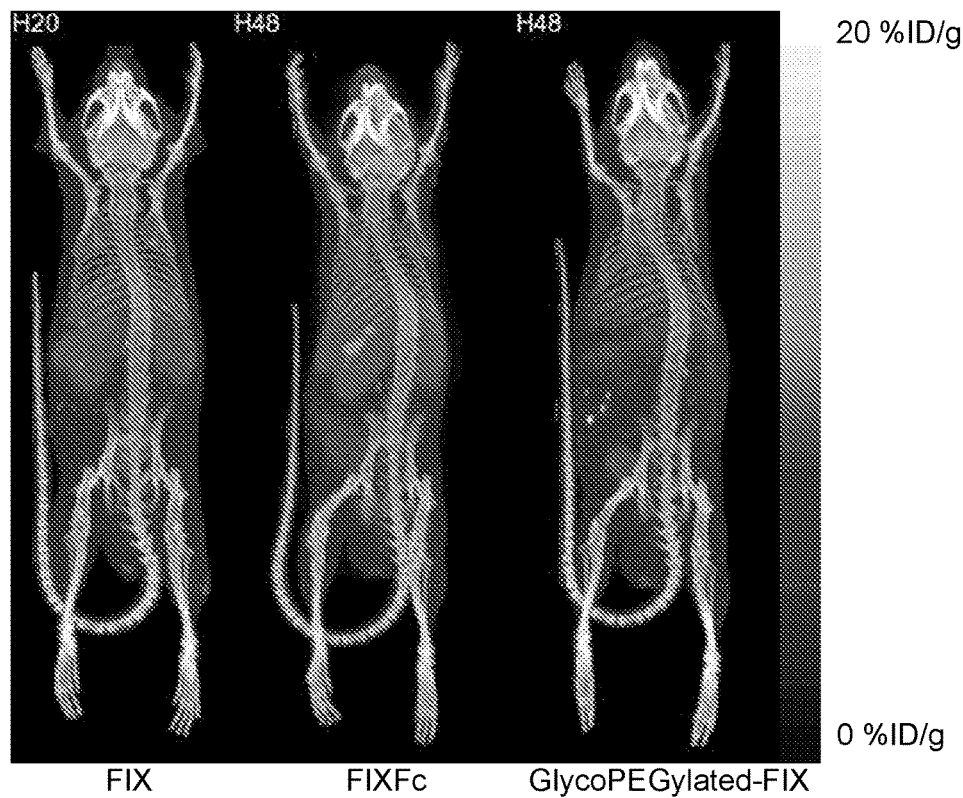
Figure 12G:
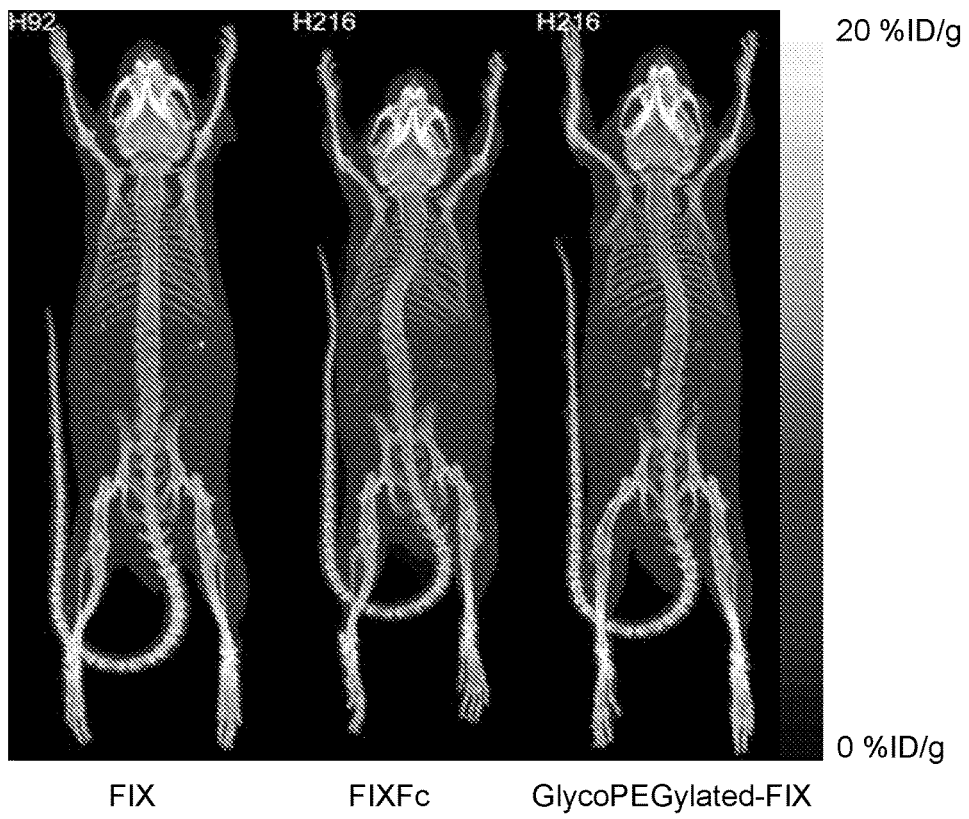
Figure 13A:
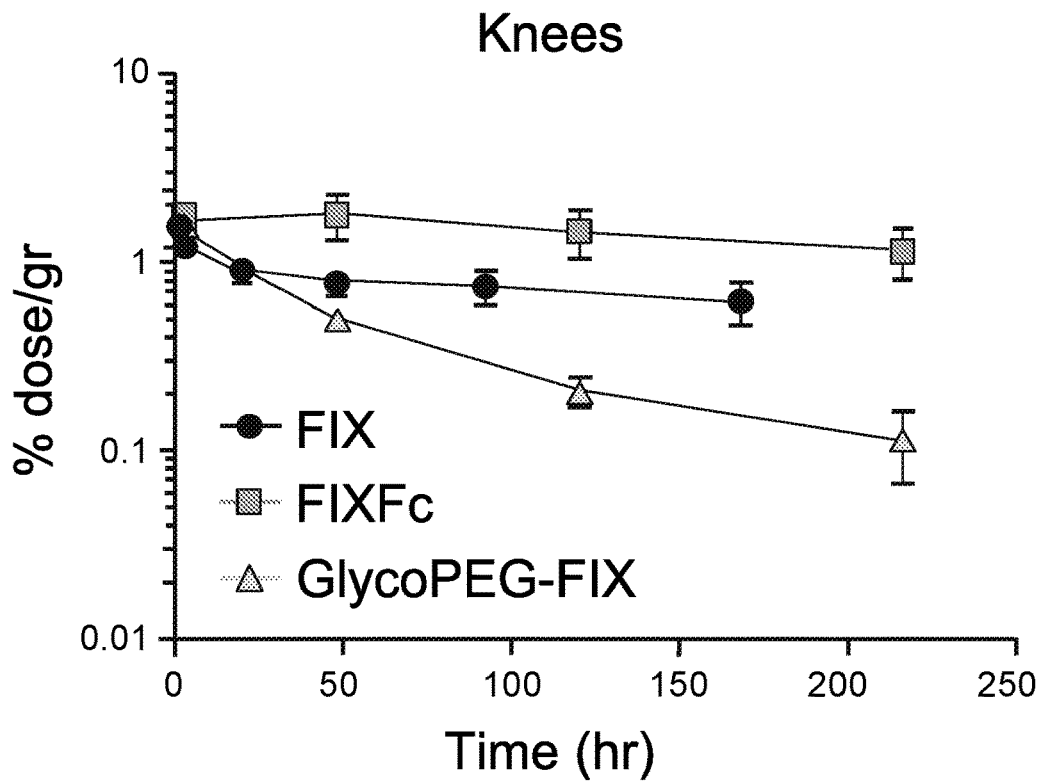
FIGS. 13A-13B are graphs illustrating the intensity of $^{125}$I-SIB label localization in the mice shown in FIGS. 12A-12G, following administration of $^{125}$I-SIB-labeled FIX, $^{125}$I-SIB-labeled FIXFc, or $^{125}$I-SIB-labeled GlycoPEGylated-FIX over time in the knees (FIG. 13A) and shoulders (FIG. 13B). Data was collected for both the right and left knees and the right and left shoulders, which were combined to generate the data shown (FIGS. 13A and 13B, respectively).
Figure 13B:
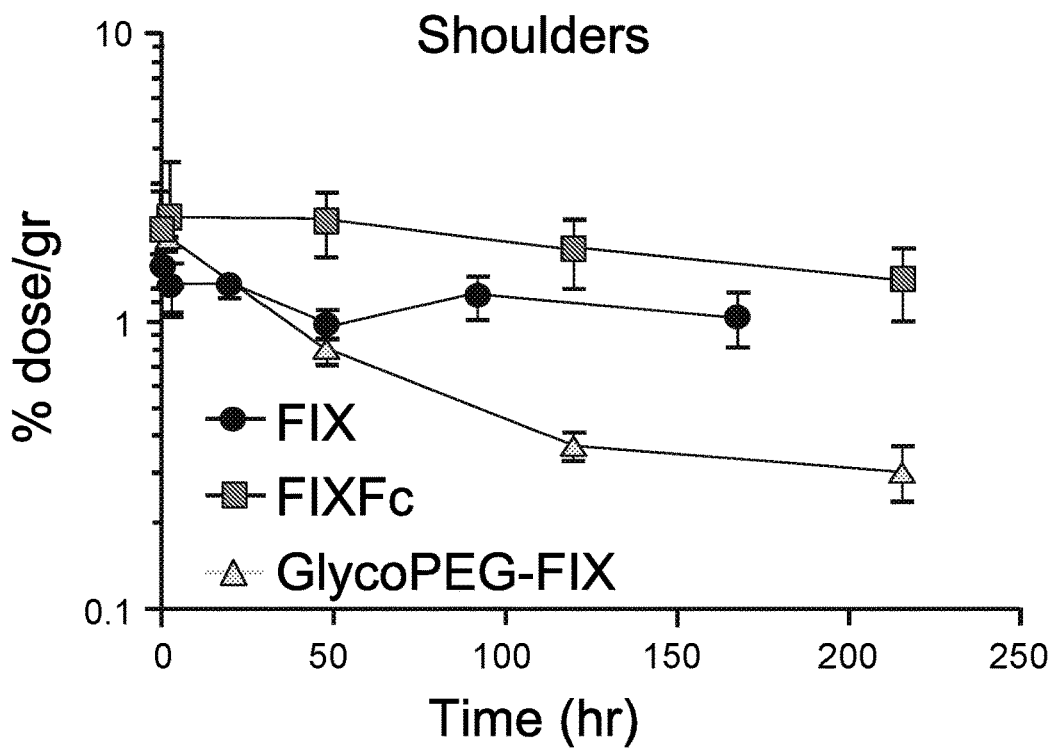

Labeled FIXFc was found to distribute to areas around the joints at 30 minutes (FIG. 12D) and 2.5 hrs (FIG. 12E) post-dosing, which persisted for 48-216 hrs post-dosing (FIGS. 12F-12G), representing the half-life and five-times the half-life, respectively. FIXFc localization to the knees (FIG. 13A) and the shoulders (FIG. 13B) was more pronounced than localization of FIX and GlycoPEG-FIX to the same joint areas.

Figure 14A:
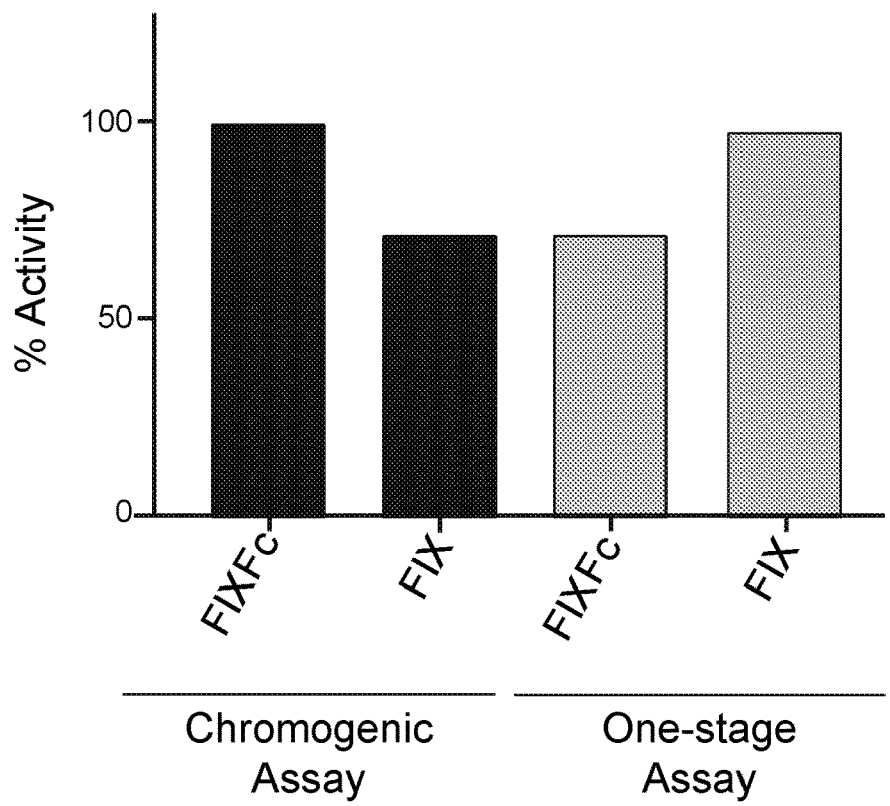
FIG. 14A is a graph illustrating the relative activity of labeled FIX and labeled FIXFc, as compared to unlabeled FIX and FIXFc, and as measured by chromogenic assay or one-stage assay.
Figure 14B:
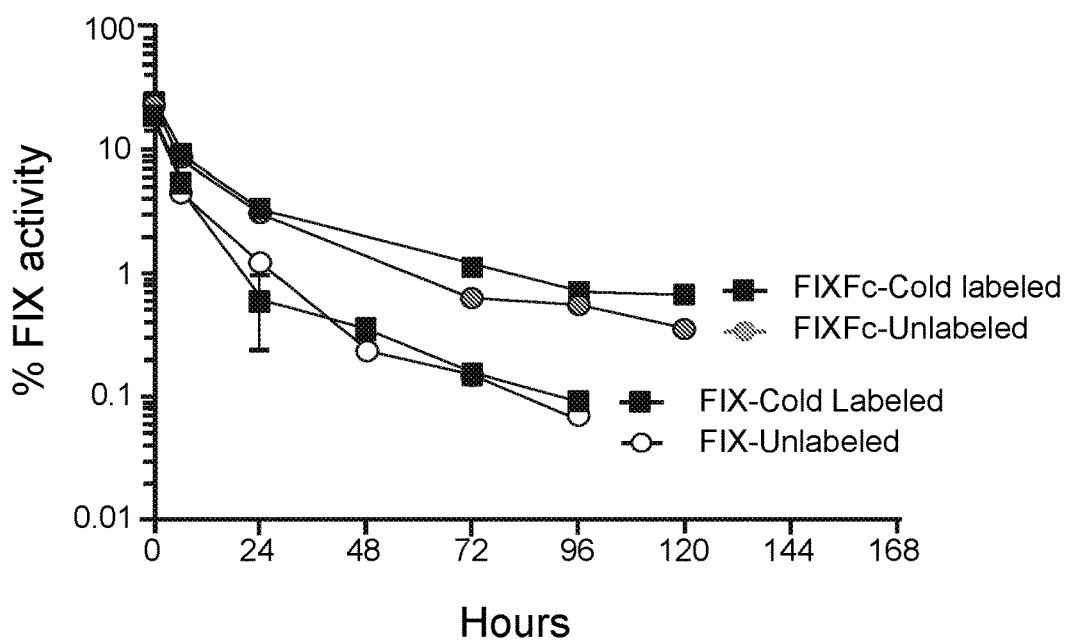
FIG. 14B is a graph illustrating the pharmacokinetics of labeled and unlabeled FIX molecules in HemB mice.
Figure 15A:
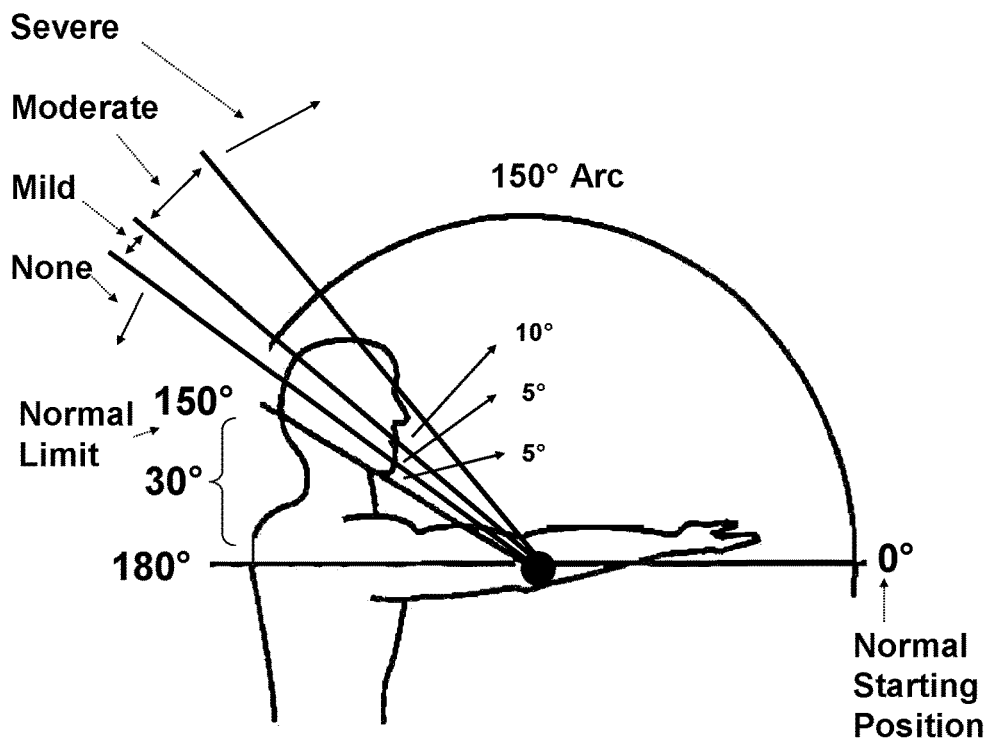
FIGS. 15A-15F are drawings illustrating the range of motions for the elbow (flexion.
Figure 15B:
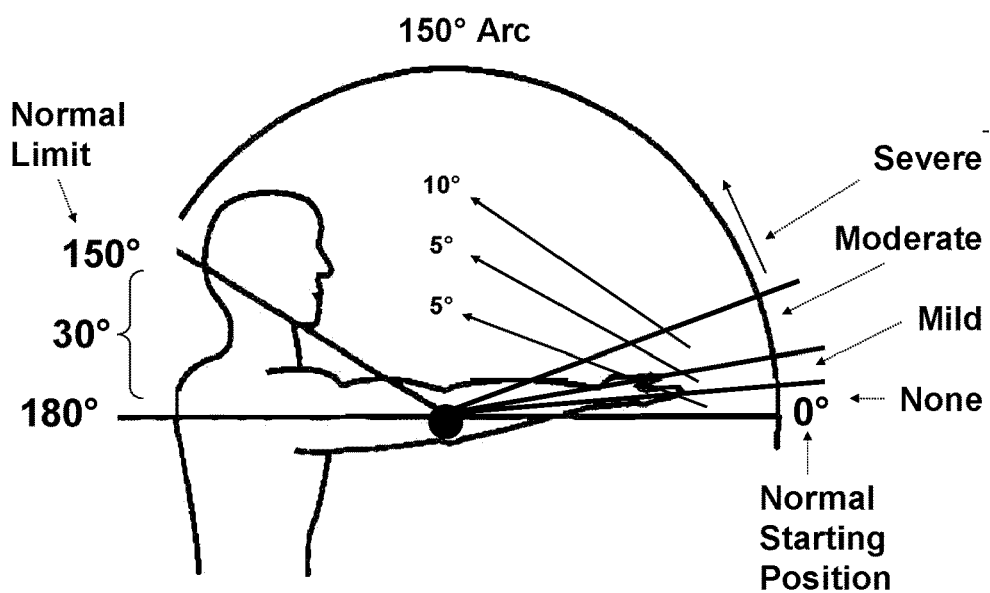
Figure 15C:
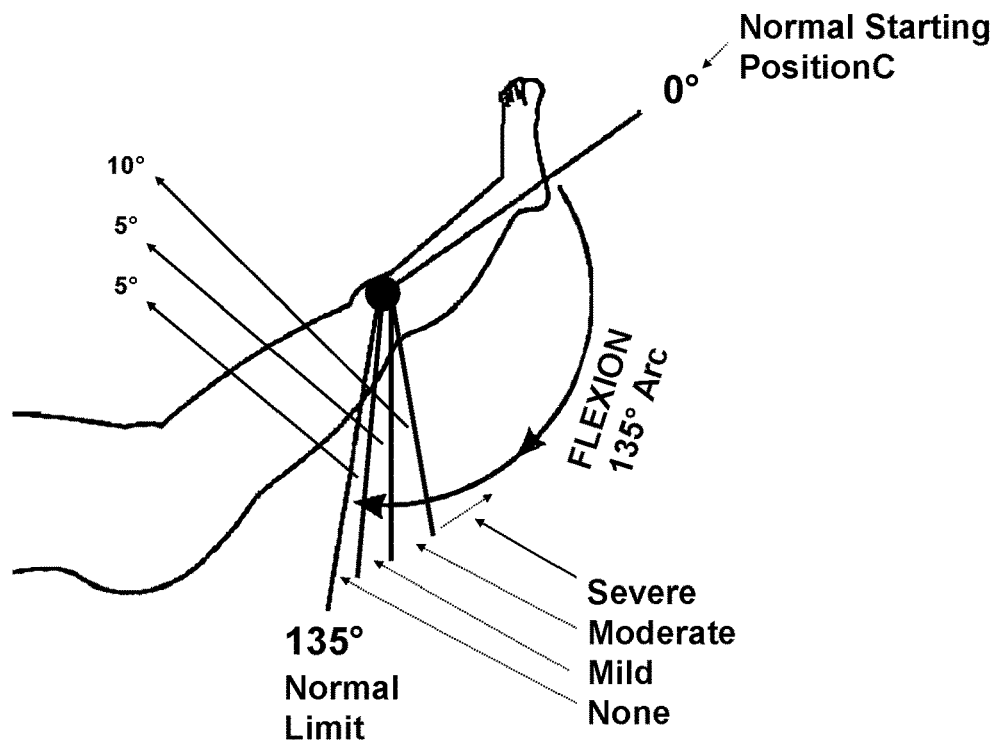
Figure 15D:
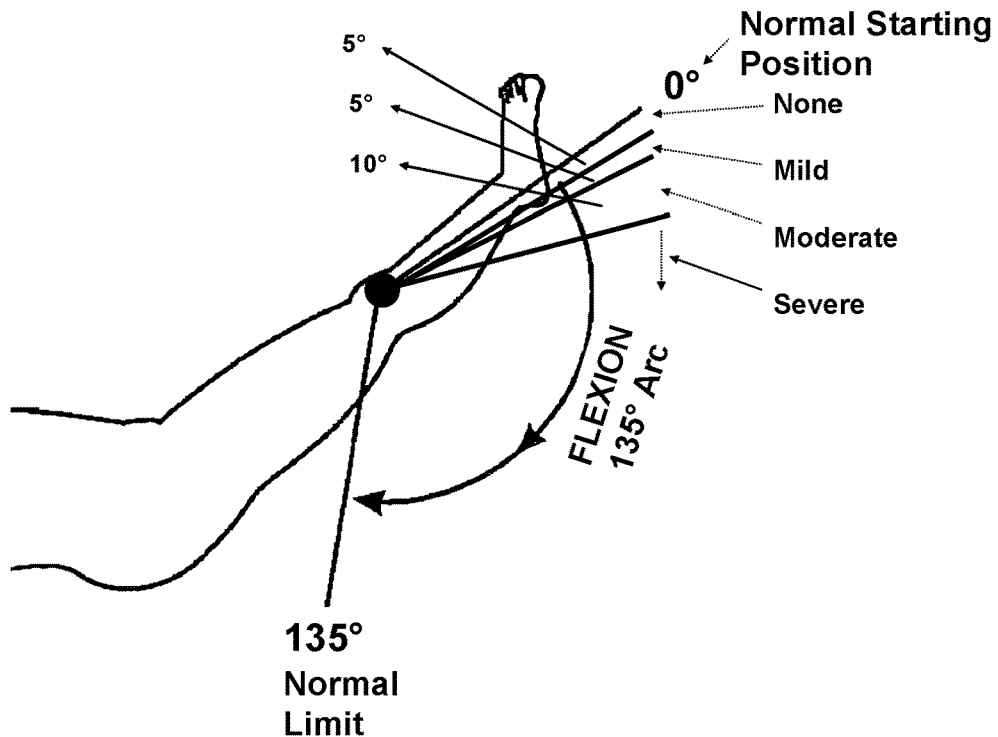
Figure 15E:
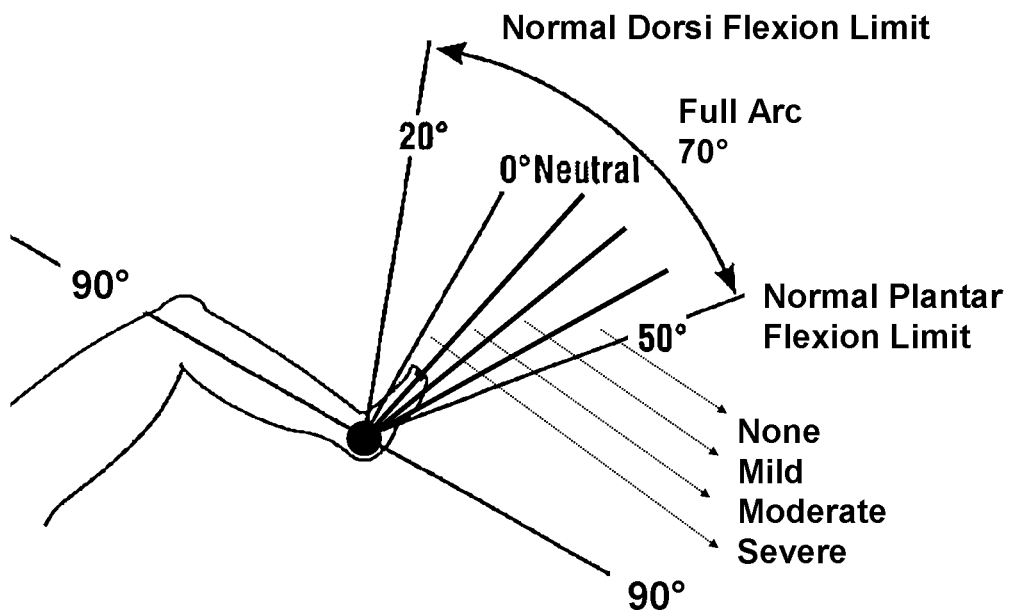
Figure 15F:
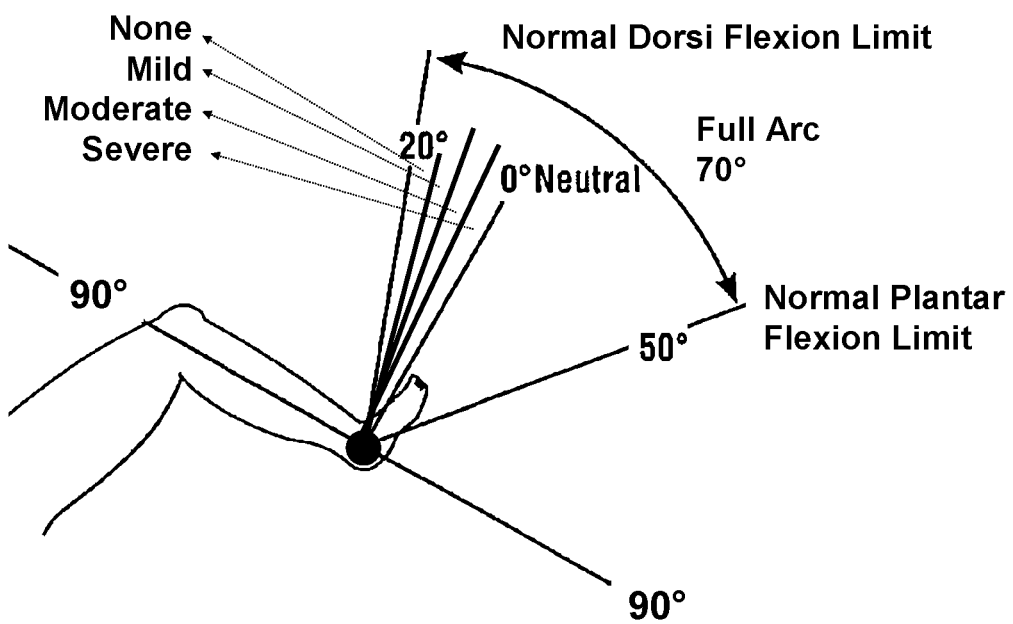

$^{125}$I-SIB labeling did not affect FIX activity of the labeled FIX proteins (FIG. 14A), nor did labeling affect the pharmacokinetic properties of the FIX proteins, as compared to unlabeled FIX proteins, following administration to HemB mice (FIG. 14B).

Example 5

Baseline Joint Assessment

Baseline Joint Assessment

Six joints (left ankle—LA, right ankle—RA, left elbow—LE, right elbow—RE, left knee—LK, right knee—RK) will be scored on a scale from 0 to 19 according to the following criteria: swelling, duration, muscle atrophy, crepitus, flexion loss, extension loss, instability, joint pain, and strength. Gait will be scored on a scale from 0 to 2 based on walking and climbing stairs. The total score will be the sum of scores from all 6 joints plus the gait score (range of 0-116 with 0 being normal and 116 being the most severe disease).

Screening Visit

The elbow, knee and ankle on each side of the body will be evaluated for joint disease at screening. Joint function should be evaluated in the absence of an active bleeding episode. A joint score of zero reflects a normal status.

Scoring Details

1. Joint scoring will be done separately for the 6 joints (LA, RA, LE, RE, LK, RK) according to these categories and scales (range is 0-19 for each joint and 0-114 for all six joints): swelling (0=none; 1=mild; 2=moderate; 3=severe); duration of swelling (0=no swelling or ≤6 months; 1=>6 months); muscle atrophy (0=none; 1=mild; 2=severe); crepitus on motion (0=absent; 1=present); flexion loss, including loss of plantarflexion of ankles (0=none; 1=mild; 2=moderate; 3=severe); extension loss, including loss of dorsiflexion of ankles (0=none; 1=mild; 2=moderate; 3=severe); instability (0=none; 1=significant pathologic joint laxity); joint pain (0=no pain, either through range or at end range of motion; 1=present); strength (0=normal (holds position against gravity and maximum resistance); 1=minimal decrease (holds position against gravity and moderate resistance, but not maximum resistance); 2=mild decrease (holds position against gravity or minimal resistance); 3=moderate decrease (able to move joint if gravity eliminated); 4=severe decrease (trace or no muscle contraction). For scoring flexion loss and extension loss at knees and elbows, the following applies: none=approximately 0-5 degrees;

mild=approximately 5-10 degrees; moderate=approximately 11-20 degrees; and severe=approximately >20 degrees.

2. Gait will be scored once (range is 0-2), wherein 0=no difficulty with walking or climbing up/down stairs; 1=no difficulty with walking, but difficulty with stairs; and 2=difficulty with walking and with stairs.

This modified hemophilia joint health score (HJHS) is based on the scoring system used in a joint scoring reliability study in boys with hemophilia (Hilliard, Funk et al., *Haemophilia* 12(5):518-525 (2006), which is incorporated by reference herein in its entirety). It has been used as a tool to evaluate musculoskeletal outcomes in a cohort of 20 boys ages 4-17 years (Saulyte Trakymiene, Ingerslev et al., *Haemophilia* 16(3):479-486 (2010), which is incorporated by reference herein in its entirety). The modifications were done to adapt the scoring system to an adult hemophilia population and according to comments in a recent validation study by the international hemophilia prophylaxis study group (Feldman, Funk et al., Arthritis Care Res (Hoboken), 2010, which is incorporated by reference herein in its entirety).

Example 6

The main complication of replacement therapy with factor in hemophilia A is the formation of inhibitors (neutralizing anti-factor VIII antibodies) in ~30% of patients with severe hemophilia A. Inhibitor development impacts treatment efficacy as well as the quality of life of affected individuals. Further understanding of how the immune system responds to recombinant factor III (rFVIII) is an ongoing effort in hemophilia research to effectively eradicate inhibitors. The extended half-life rFVIII Fc fusion protein (rFVIIIFc) is an efficacious and well-tolerated therapy to prevent and control bleeding episodes. The Fc region of this molecule is not only responsible for increasing rFVIII half-life but may promote antigen-specific tolerance, as shown in a preclinical animal model (Krishnamoorthy S, et al., *Cell Immunol.* 301:30-39 (2016)) and as suggested by immune tolerance induction case reports (Groomes C L, et al., *Pediatr Blood Cancer* 63(5):922-24 (2016); Malec L M, et al., *Haemophilia* 22(6): e552-e554 (2016); Ragni M V, et al., *Haemophilia* 22(5): e462-e464 (2016)).

Methods

Figure 16:
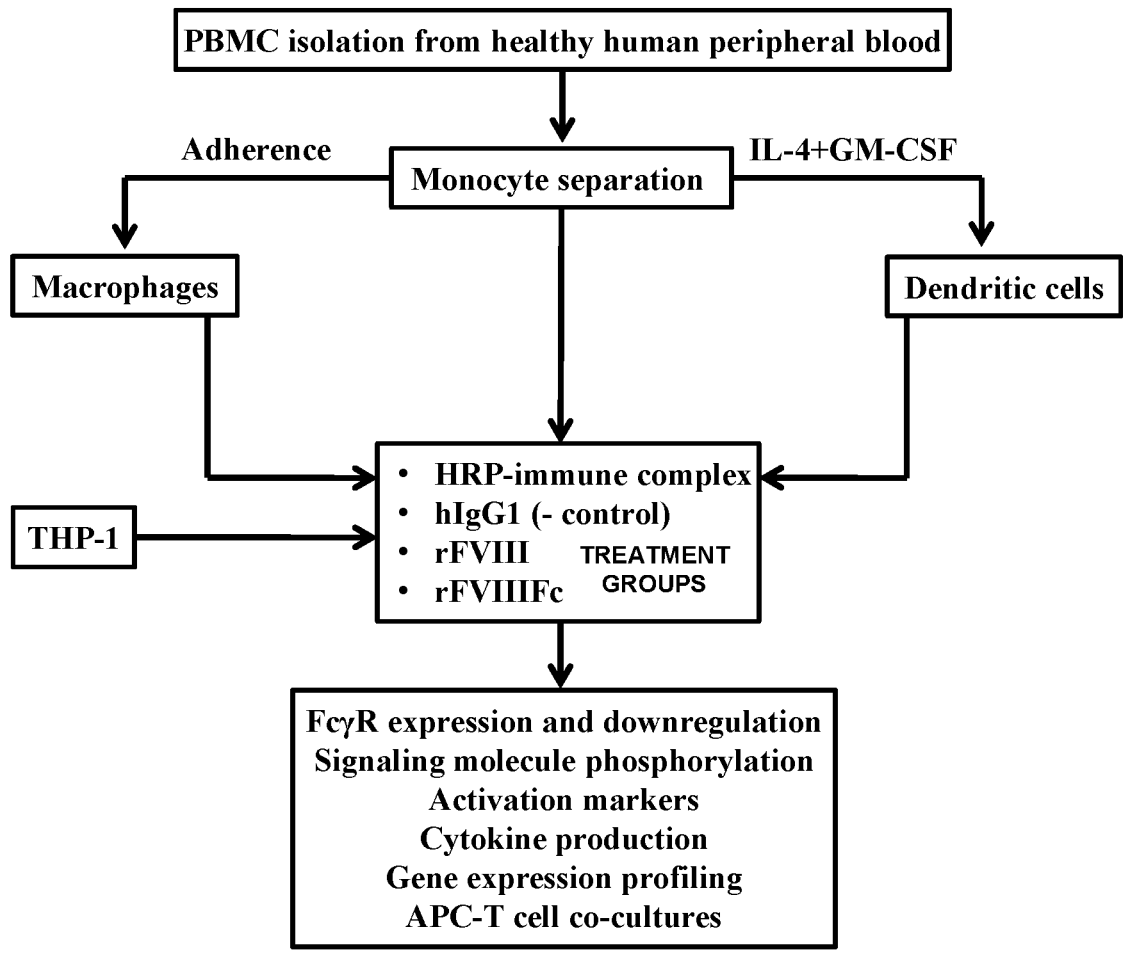
FIG. 16 is a flow diagram, outlining the methods used to investigate the effects of rFVIIIFc on FcγR binding, internalization, signaling and cytokine production, and gene expression changes, as well as subsequent interactions and effects on T cells in vitro.

Peripheral blood-derived human APCs or THP-1 monocytic cells were used to investigate the effects of rFVIIIFc on FcγR binding, internalization, signaling and cytokine production, and gene expression changes, as well as subsequent interactions and effects on T cells in vitro (FIG. 16).

Results

Figure 18A:
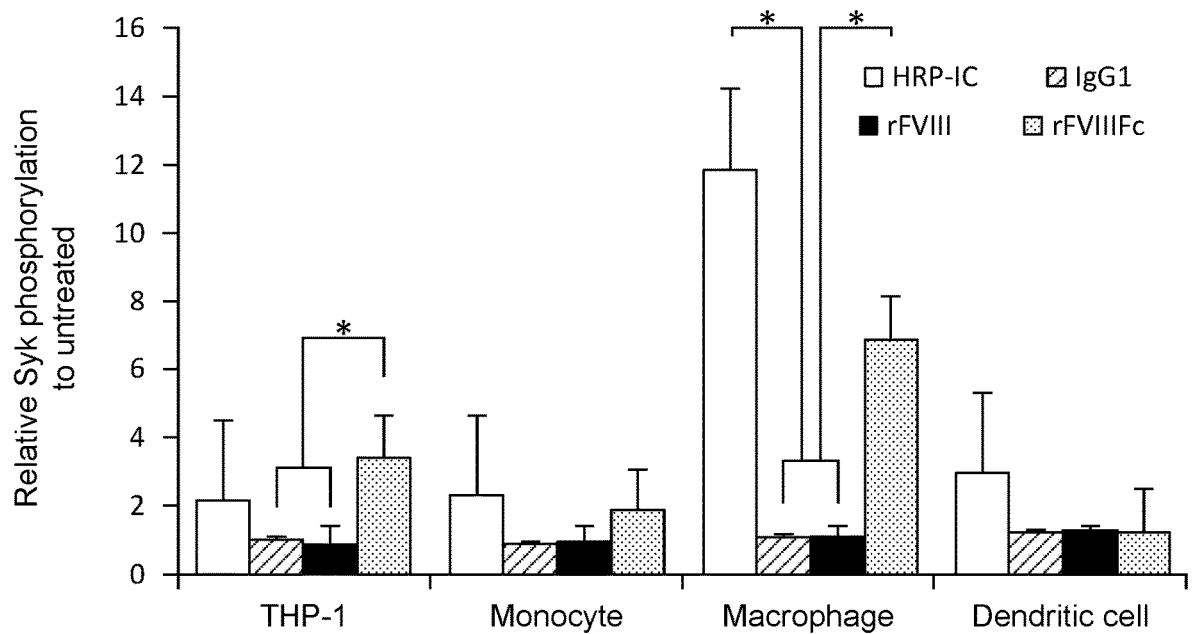
FIGS. 18A-18C are graphical representations illustrating relative signaling following treatment with rFVIII or rFVIIIFc.
Figure 18B:
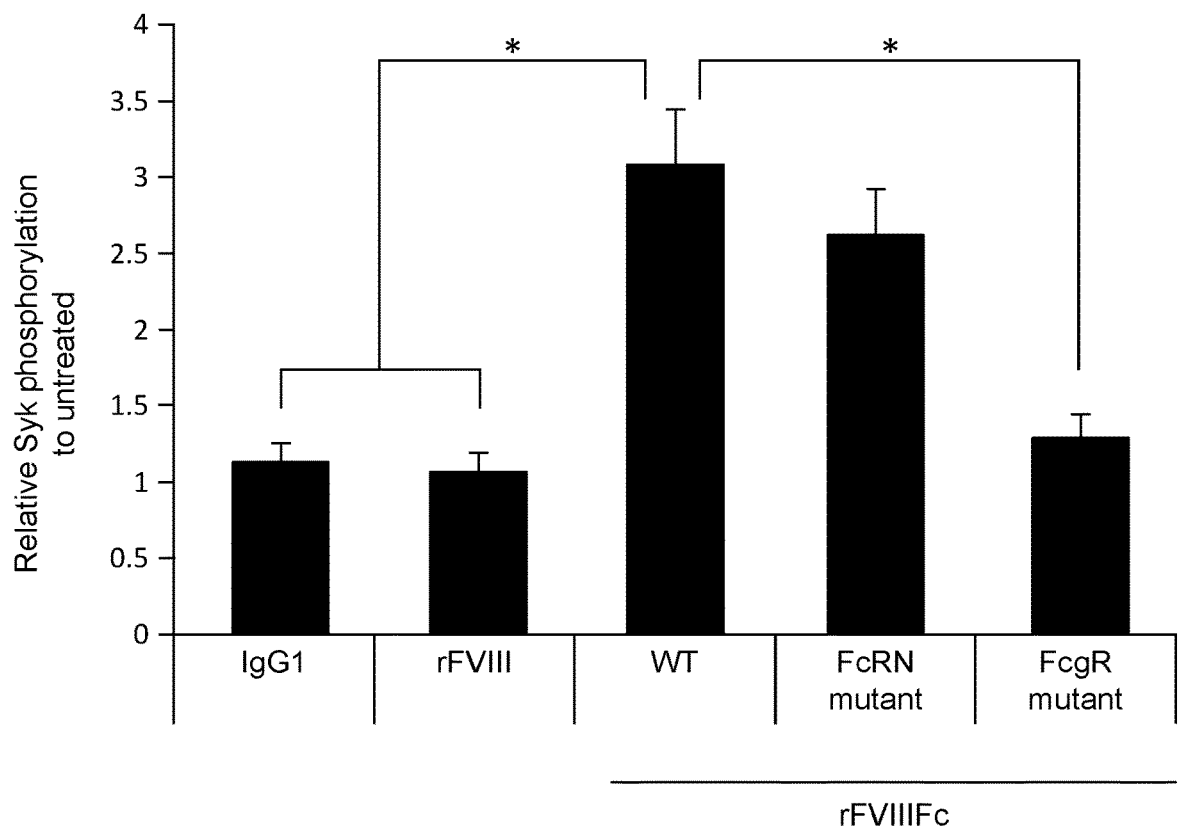
Figure 18C:
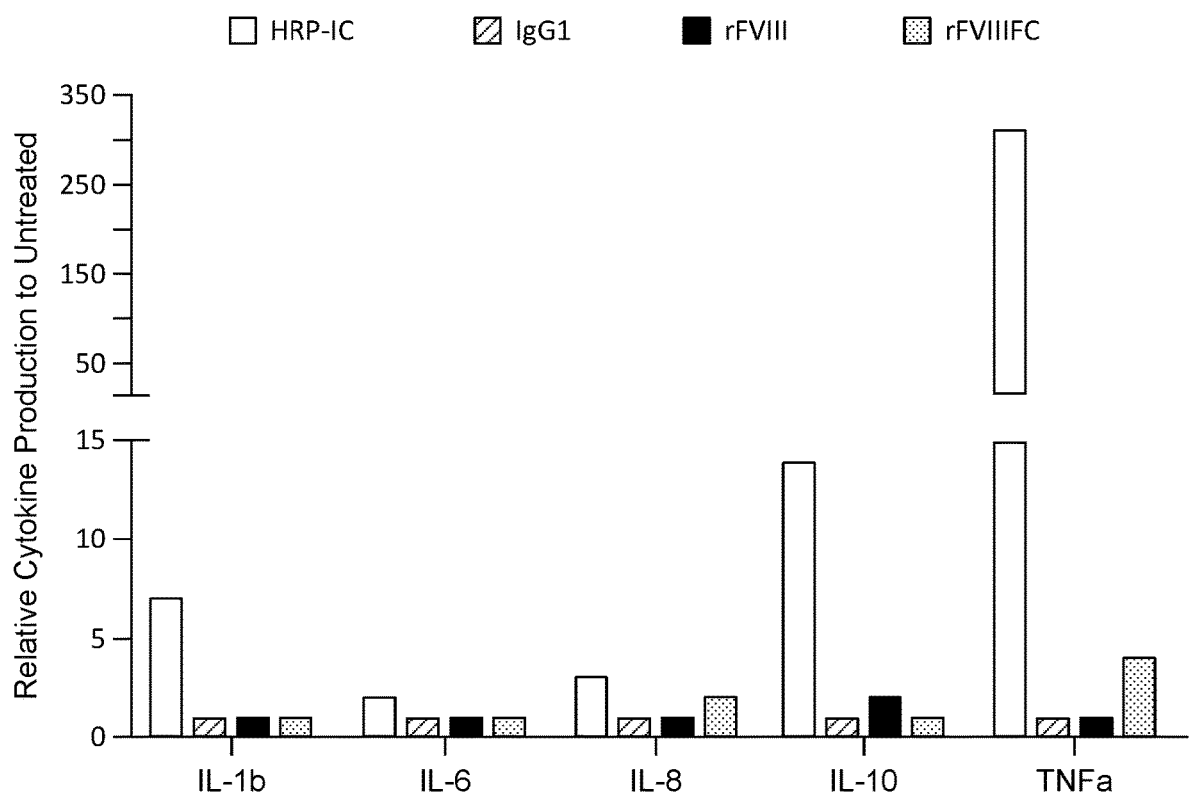
Figure 19:
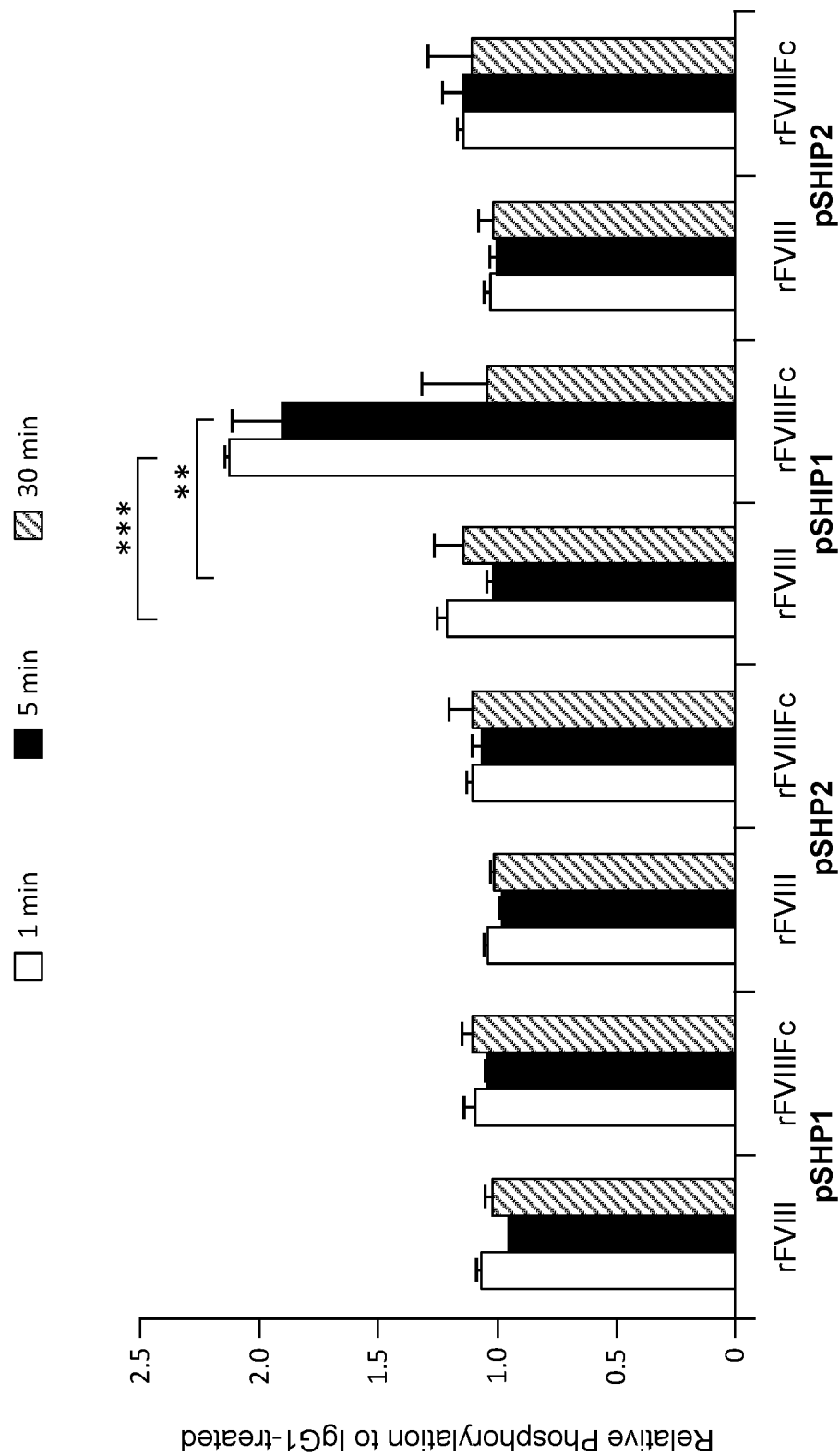
FIG. 19 shows the relative phosphorylation status of Src homology region 2 domain-containing phosphatase-1 (SHP1), pSHP2, phosphatidylinositol-3,4,5-trisphosphate 5-phosphatase 1 (SHIP1), and pSHIP2 one minute, five minutes, and thirty minutes after treatment with rFVIII or rFVIIIFc. Asterisks (*) indicate degree of significance (n=3; P≤0.01, *P≤0.005).

Decreased cell surface expression of FcγR indicates internalization upon rFVIIIFc treatment (FIGS. 17A-17C). Monocyte-derived macrophages and dendritic cells were treated with horseradish peroxidase immune complexes (HRP-IC) as positive control, human immunoglobulin G1 (IgG1) as negative control, and with recombinant factor VIII (rFVIII) or rFVIII Fc fusion protein (rFVIIIFc) at equimolar concentrations (200 nM) for 24 hours. The cell surface expression of the Fcγ receptors (FcγR) CD16 (FIG. 17A), CD32 (FIG. 17B), and CD64 (FIG. 17C) was measured by flow cytometry (n=3; $P \leq 0.01$, *$P \leq 0.005$, significance for HRP-IC to other treatments not shown). Treatment with rFVIIIFc correlated with decreased cell surface expression of CD16 (FIG. 17A), CD32 (FIG. 17B), and CD64 (FIG. 17C), as compared to surface expression following treatment with rFVIII.

rFVIIIFc engages FcγR and induces signaling in monocytes and macrophages, without subsequent proinflammatory cytokine production (FIGS. 18A-18C). THP-1 monocytic cell line, monocytes, peripheral blood monocyte-derived macrophages, and peripheral blood monocyte-derived dendritic cells were treated with HRP-IC, IgG1, rFVIII or rFVIIIFc for 15 minutes (FIG. 18A). Syk phosphorylation was measured in cell lysates using the MSD platform (n=3-7, *$P \leq 0.05$). Syk phosphorylation was measured after treating macrophages with rFVIIIFc (WT), with mutant rFVIIIFc that is unable to bind to neonatal Fc receptor (FcRn mutant), or with mutant rFVIIIFc that is unable to bind to FcγR (FcγR mutant) (n=4, *$P \leq 0.05$) (FIG. 18B). Proinflammatory cytokine production of the twenty-four-hour treated macrophages were measured by MSD ELISA (n=4, significance not shown) (FIG. 18C).

rFVIIIFc phosphorylates molecules taking part in immunoregulation, rather than molecules playing role in activation and proinflammatory cytokine production (Table 9 and FIG. 19). Phosphorylated proteins in lysates from monocyte-derived macrophages treated with rFVIIIFc for fifteen minutes were queried using the Proteome Profiler phospho-kinase and phospho-immunoreceptor arrays. A list of phosphorylated molecules in rFVIIIFc-treated macrophages identified by the Proteome Profiler assays is shown in Table 9. Phosphorylation of phosphatases responsible for inhibitory signaling were measured using the MSD platform (n=3; $P \leq 0.01$, *$P \leq 0.005$) (FIG. 19).

TABLE 9

Phosphorylated molecules in rFVIIIFc-treated macrophages identified by a Proteome Profiler assays.

Phosphorylated Proteins

Figure 20C:
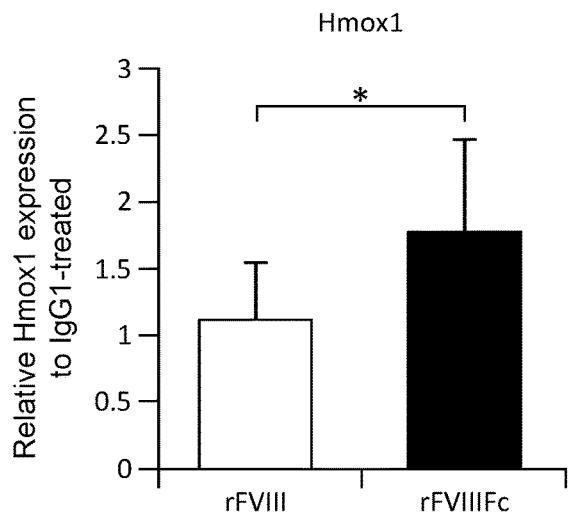
Figure 20D:
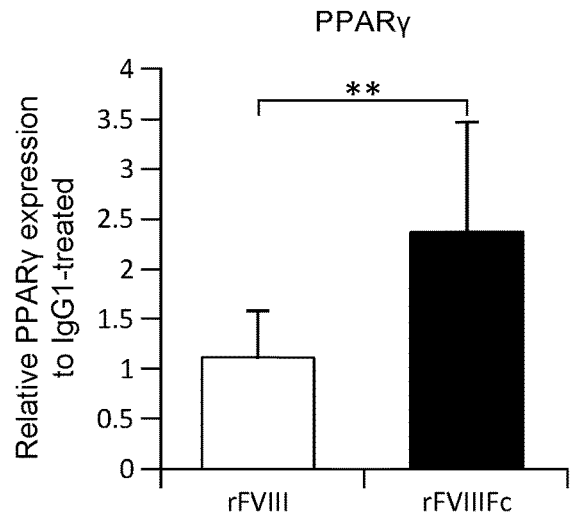
Figure 20E:
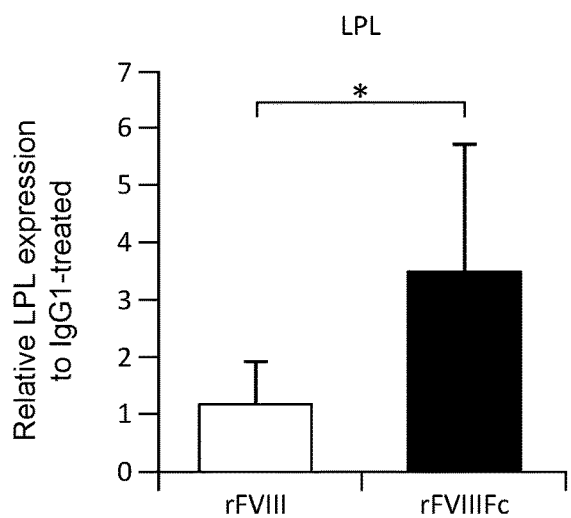
Figure 20F:
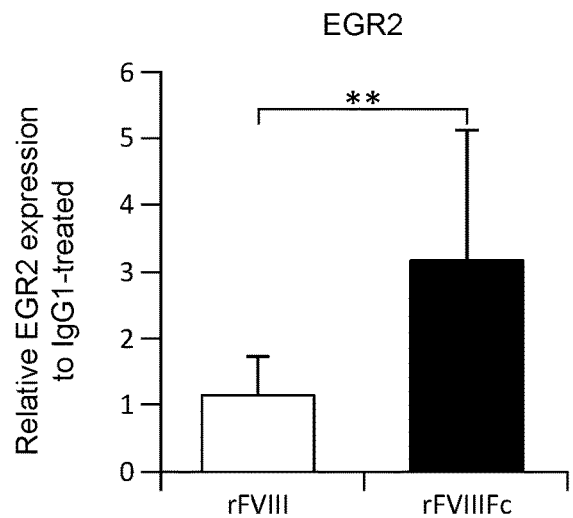
Figure 20G:
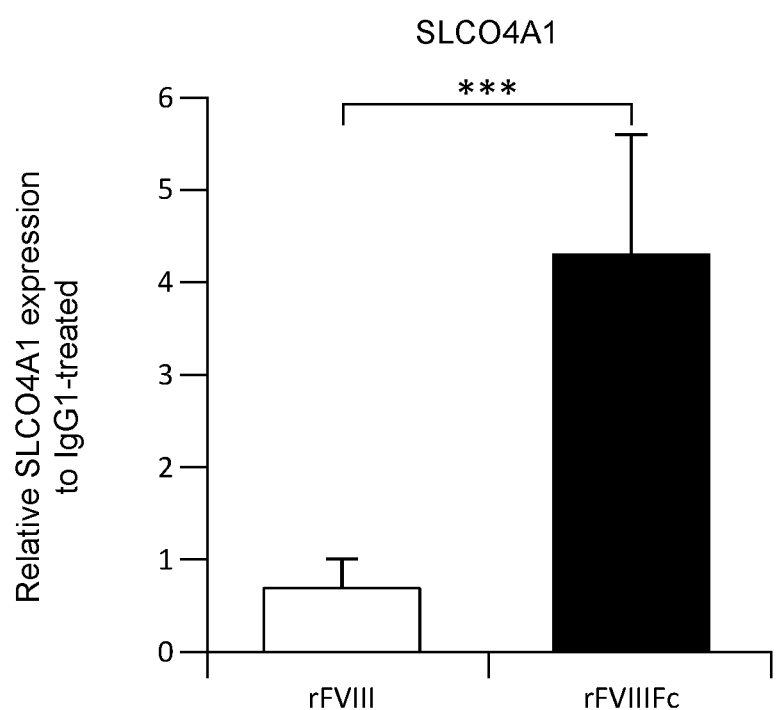
Figure 20H:
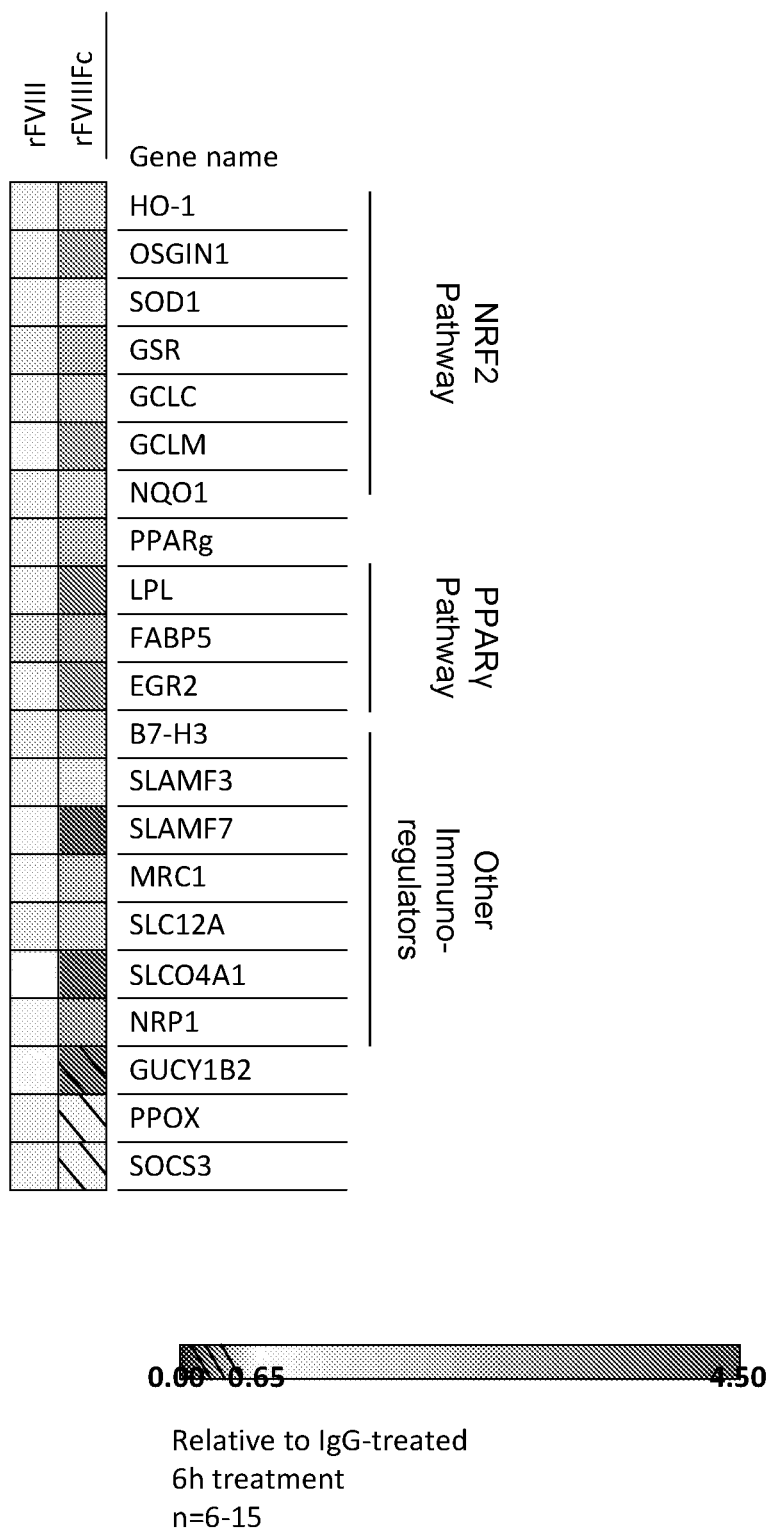
Figure 20I:
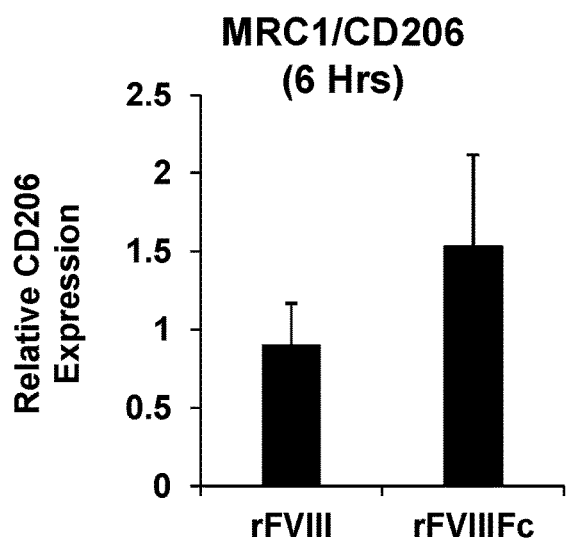
Figure 20J:
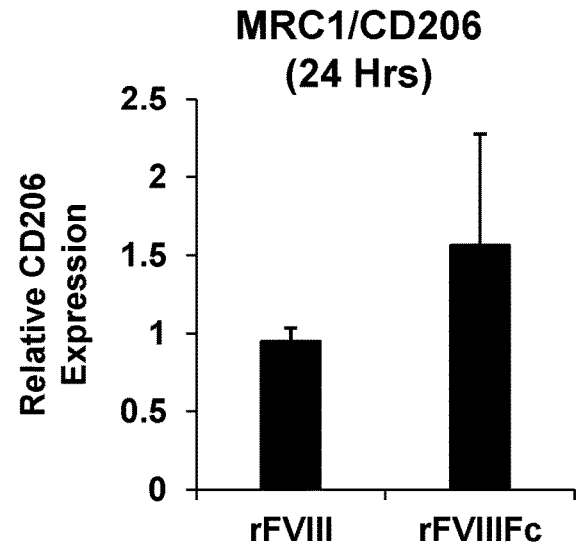
Figure 20K:
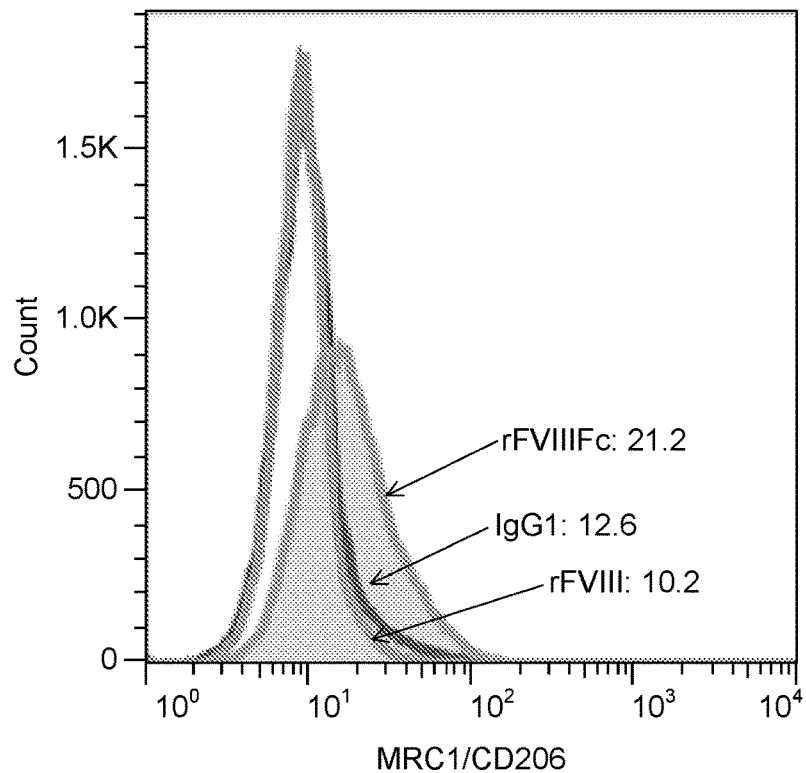
Figure 20L:
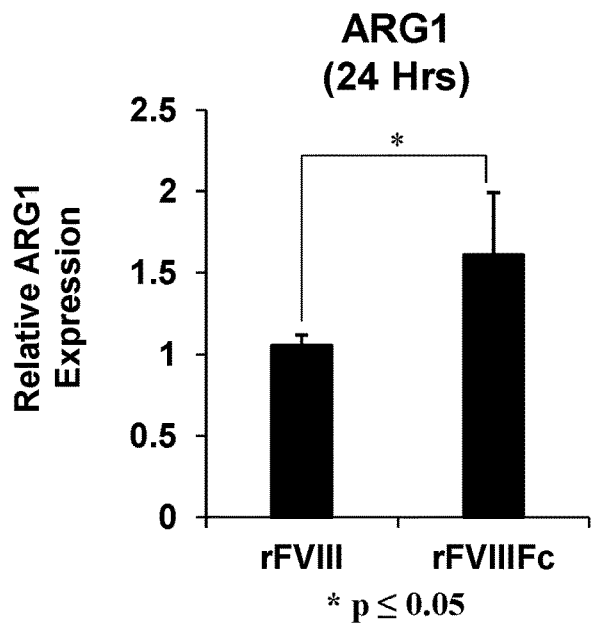
Figure 20M:
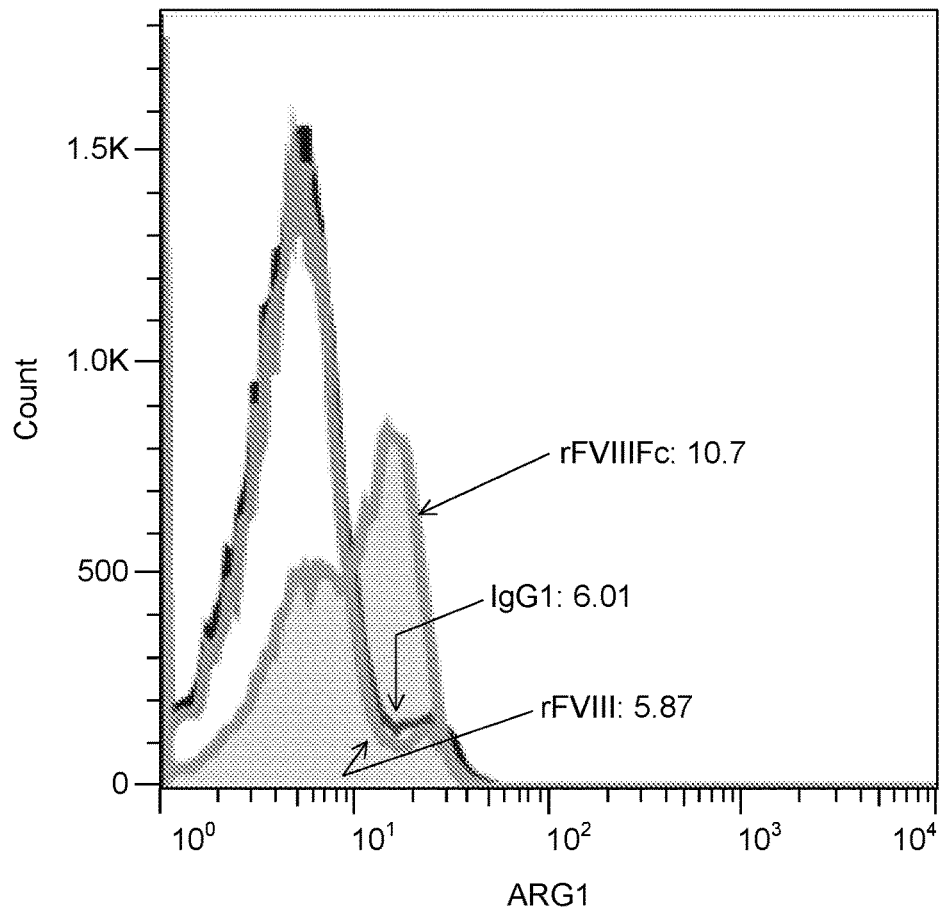

| Immunoreceptors | ILT6/CD85e | NKp46/NCR1 | FcH5/IRTA2 | Kinases | SRC | STAT5 |
|---|---|---|---|---|---|---|
| | KIR2DL4 | Siglec9 | Siglec2/CD22 | | CREB | cJun |
| | SLAMF8 | SLAMF4 | CDCIR/CLEC4α | | pRAS40 | p53 |
| | FcγRIIIA/B | FcγRIIA | DECTIN-1/CLEC7α | | ERK1/2 | WNK1 |
| | PECAM/CD31 | FcRH4/IRTA1 | KNKp44/NCR2 | | HSP27 | p70S6 |
| | CLEC-2 | SHP2 | Siglec7 | | JNK1/2/3 | FAK |
| | TREM2 | ILT2/CD85j | SLAMF5 | | AMPKα2 | GSK-3α/β |
| | SHP1 | ILT3/CD85k | Siglec3/CD33 | | STAT2 | RSK1/2/3 |
| | TREML1/TLT-1 | ILT4/CD85d | Siglec5 | | STAT6 | p53 | rFVIIIFc induces gene expression pattern characteristic of tolerogenic macrophages (FIGS. 20A-20G). Exploratory RNA sequencing was performed on monocyte-derived macrophages treated with IgG1, rFVIII, or rFVIIIFc for six hours (n=3) for genes that were significantly downregulated (FIG. 20A) and for genes that were significantly upregulated (FIG. 20B), and a pathway analysis was run on the rFVIIIFc-upregulated genes to investigate the molecular pathways represented selectively in these cells, compared to rFVIII-treated cells (Table 9). Various genes of the NRF2 and PPAR-gamma pathways were found to be upregulated, as well as various other immunoregulators (FIG. 20H). Selected genes of the NRF2 and lipid metabolism pathways were validated by Q-PCR (n=8; *P≤0.05, P≤0.01, *P≤0.005) (FIGS. 20C-20G). In addition, rFVIIIFc-educated macrophages were found to exhibit a characteristic M2-like phenotype (FIGS. 20I-20M). In particular, macrophages treated with rFVIIIFc had higher relative CD206 expression than cells treated with rFVIII after 6 hours (FIG. 20I) and after 24 hours (FIG. 20J), and macrophages treated with rFVIIIFc had higher relative ARG1 expression than cells treated with rFVIII after 24 hours (FIG. 20M).

TABLE 9

Run pathway analysis on the rFVIIIFc-upregulated genes to investigate the molecular pathways represented selectively in these cells, compared to rFVIII-treated cells.

Figure 21A:
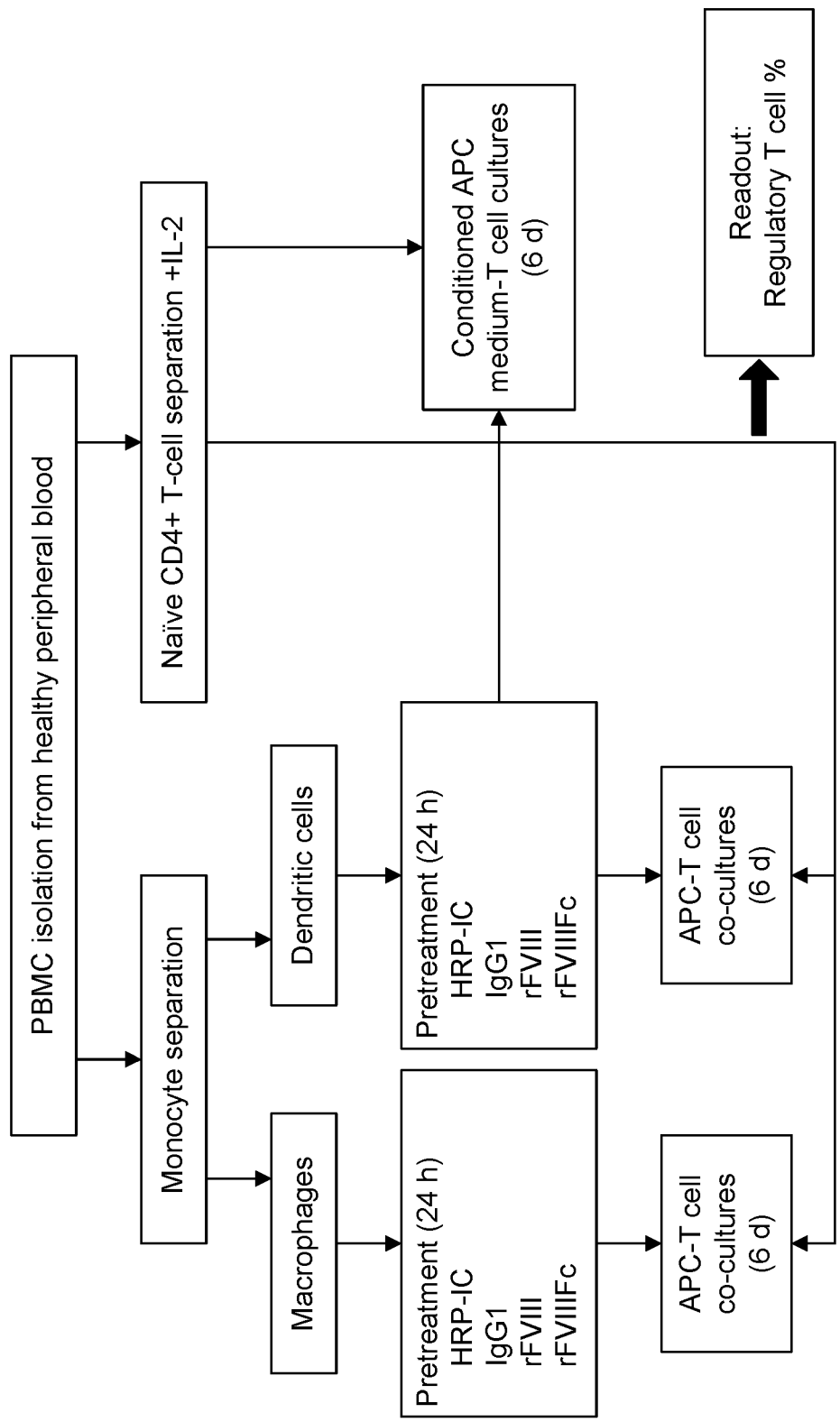
FIG. 21A is a flow chart diagraming the methods used to determine the effects of rFVIIIFc treatment on T-cell differentiation.
Figure 21B:
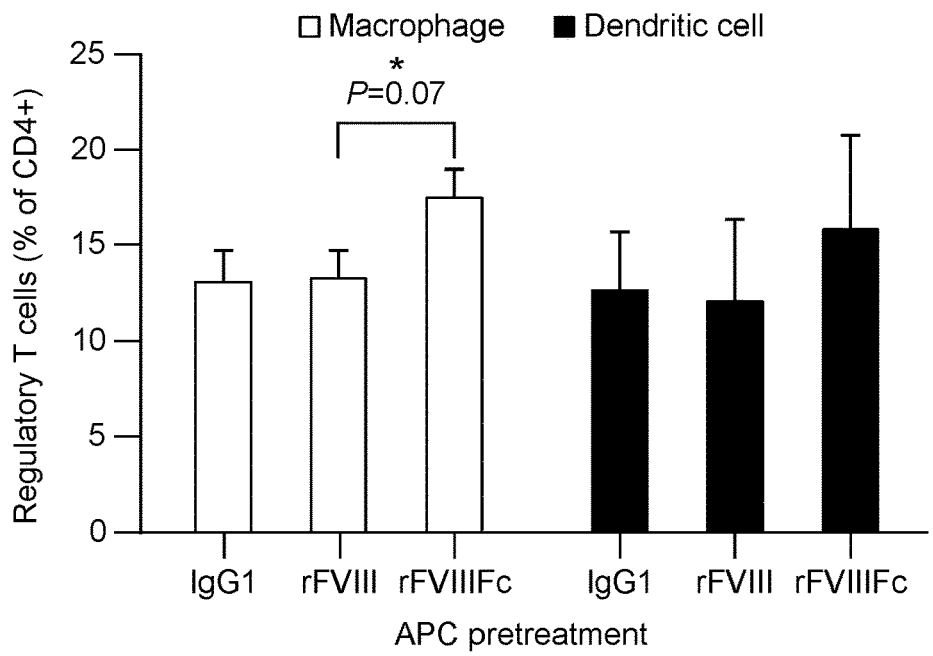
FIG. 21B is a graphical representation of the percent of regulatory T cells six days after macrophages or dendritic cells were treated with IgG1 (control), rFVIII, or rFVIIIFc for 24 hours, and then placed into co-culture with naïve CD4 positive T cells.
Figure 21C:
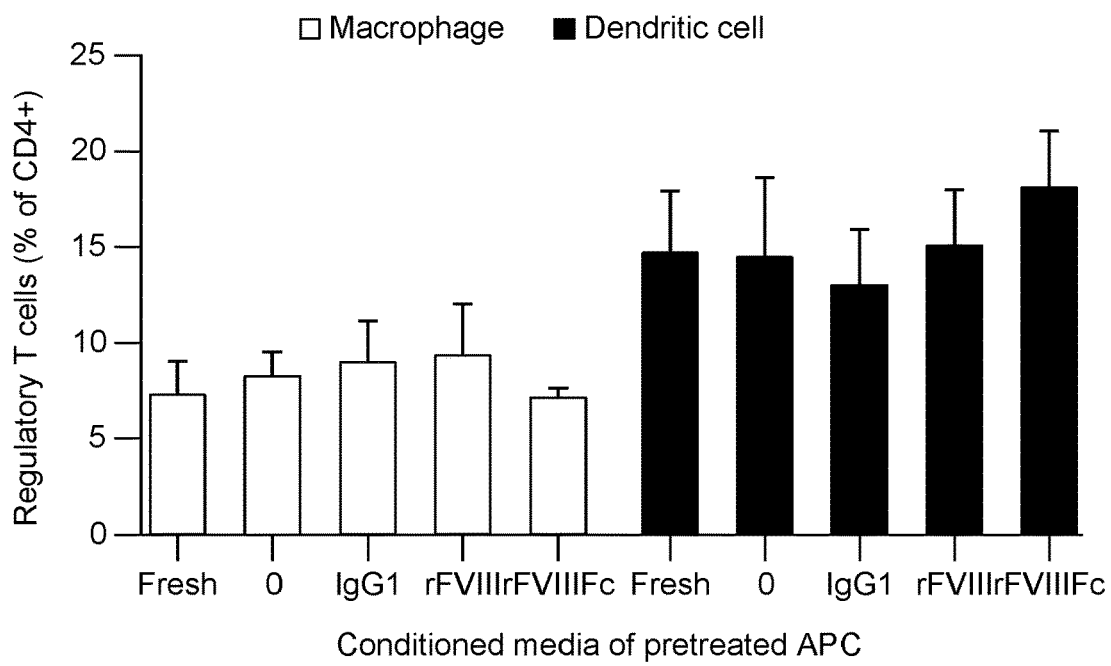
FIG. 21C is a graphical representation of the percent of regulatory T cells following culture of naïve CD4 positive T cells in the conditioned media of macrophages or dendritic cells pretreated with IgG1, rFVIII, or rFVIIIFc.

| Pathway Name | Set Size | Candidates Contained | P-value | q-value |
| --- | --- | --- | --- | --- |
| NRF2 pathway | 142 | 10 (7.0%) | 4.07e−06 | 0.000273 |
| Liproprotein metabolism | 68 | 7 (10.3%) | 1.01e−05 | 0.000338 |
| Lipid digestion, mobilization, and transport | 110 | 8 (7.3%) | 3.06e−05 | 0.000684 |
| Cysteine and methionine metabolism- Homo sapien (human) | 45 | 5 (11.1%) | 0.000137 | 0.00229 |
| C-MYB transcription factor network | 86 | 6 (7.0%) | 0.000389 | 0.00521 |
| Nuclear receptors meta-pathway | 316 | 11 (3.5%) | 0.000813 | 0.00908 | rFVIIIFc-treated antigen presenting cells influence regulatory T-cell differentiation that requires APC-T cell-cell contact (FIGS. 21A-21C). Peripheral blood monocyte-derived macrophages were treated with IgG1, rFVIII, or rFVIIIFc, then placed into co-culture with naïve CD4 positive T cells isolated from peripheral blood from the same donor. After six days in co-culture (FIG. 21A), the percent of regulatory T cells (CD4+CD25+ FoxP3+) was quantified using flow cytometry (n=4) (FIG. 21B). The percent of regulatory T cells were also quantified when naïve T cells were cultured in the conditioned media of APCs pretreated with IgG1, rFVIII, or rFVIIIFc (n=4) (FIG. 21C).

Figure 22:
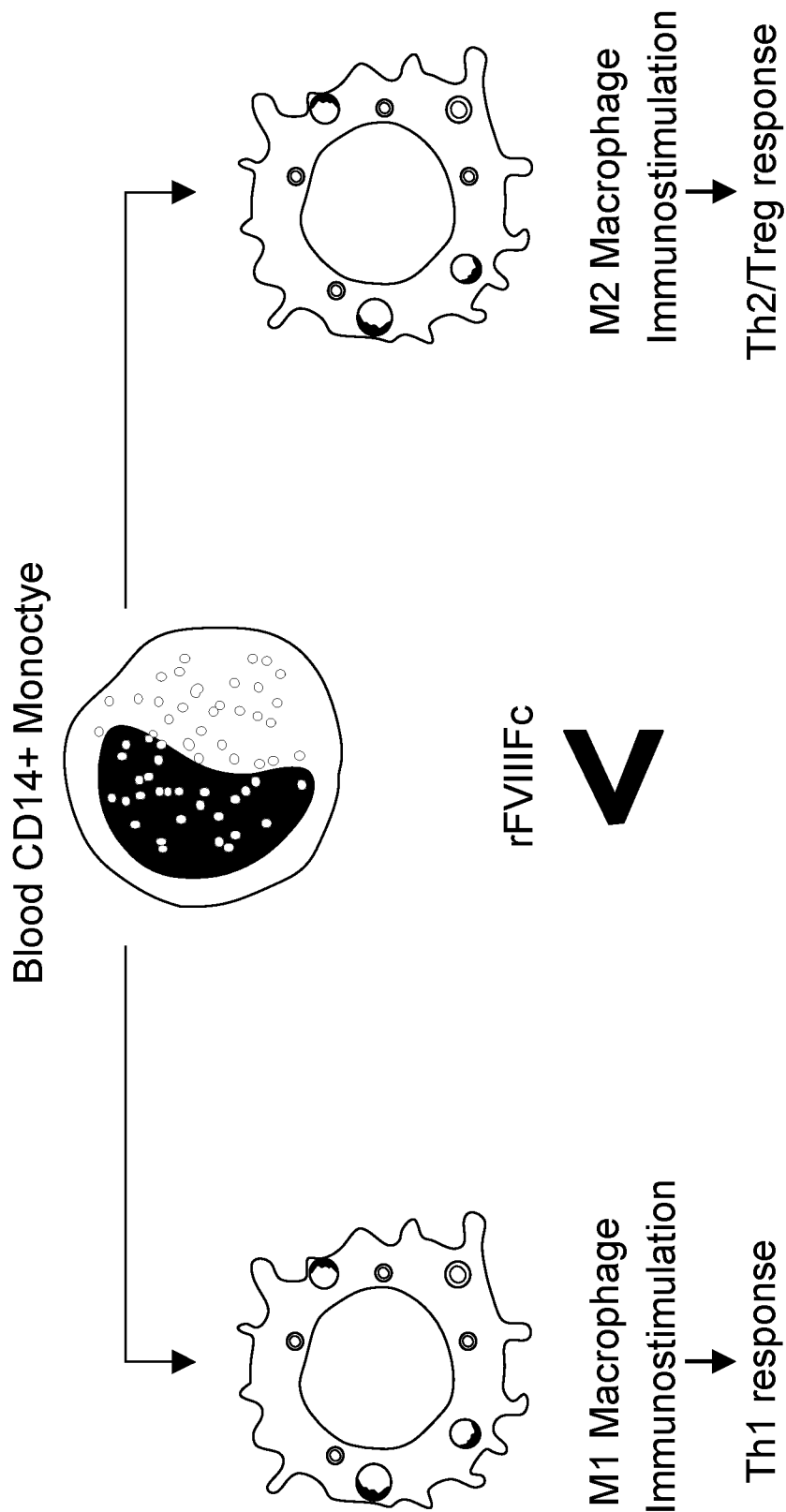
FIG. 22 is an illustration of the proposed mechanism of rFVIIIFc regulatory T-cell differentiation.
Figure 23:
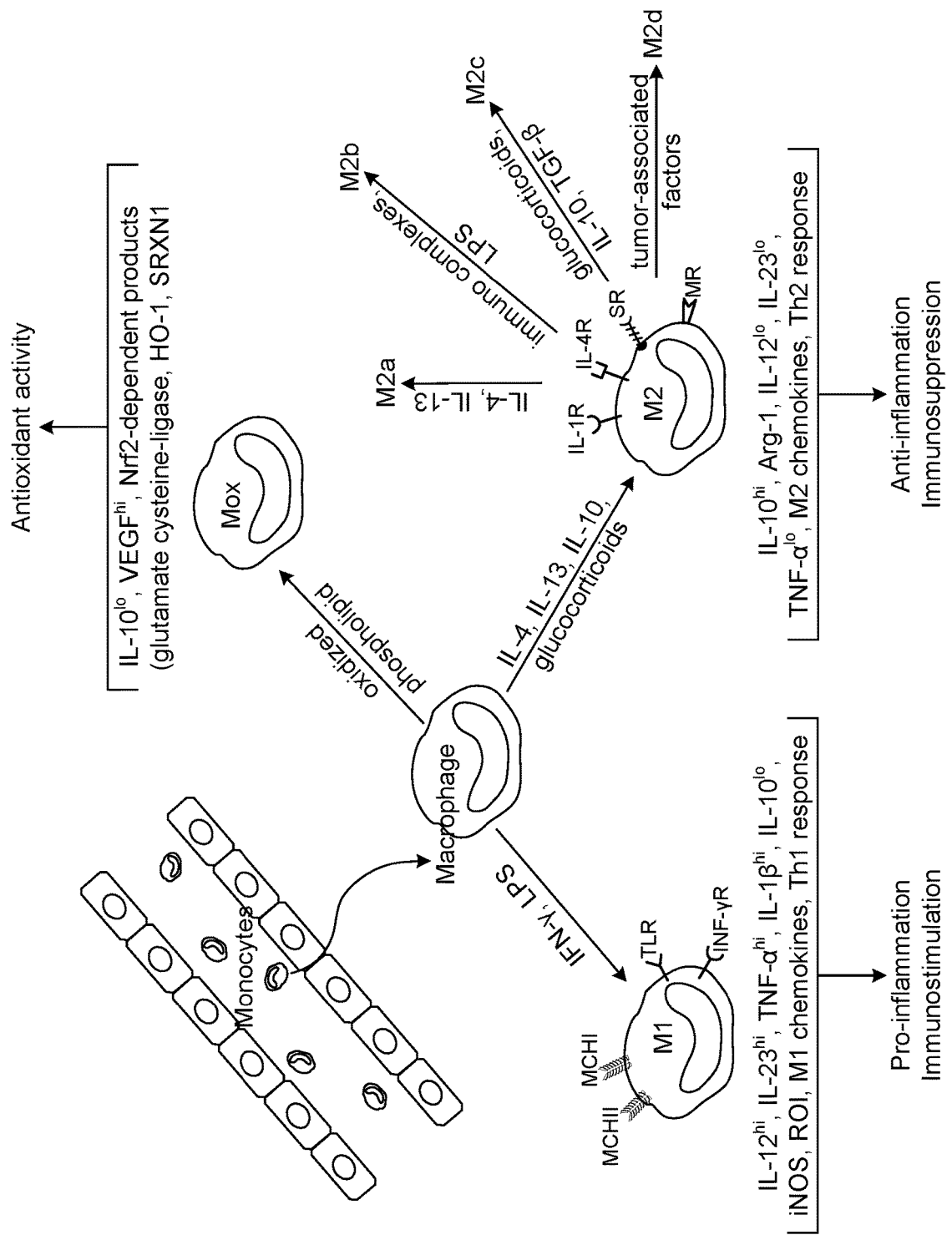
FIG. 23 is an illustration of the proposed effects of rFIXFc on macrophages.

Conclusion rFVIIIFc appears to bind and induce internalization and signaling through Fcγ receptors on APCs. This signaling does not translate to proinflammatory cytokine production and does not activate the APCs (data not shown). Immunomodulatory signaling events are initiated upon rFVIIIFc treatment. These events appear to drive macrophage differentiation towards an M2-like phenotype characterized by the upregulation of NRF2 and PPARγ pathways (FIG. 20H) as well as the upregulation of CD206 and arginase 1 molecules. Various other immunoregulators also showed increased expression, while at least guanylate cyclase 1 soluble subunit beta (2GUCY1B2), protoporphyrinogen oxidase (PPDX), and suppressor of cytokine signaling 3 (SOCS3) showed decreased expression in rFVIIIFc treated cells (FIG. 20H). These macrophages may execute the beneficial immunological effects previously reported, such as regulatory T-cell differentiation, FVIII tolerization, and anti-FVIII inhibitor reduction (FIGS. 22 and 23).

Example 7

The pharmacokinetic (PK) profile of factor IX (FIX) is consistent with a two-compartment model where FIX largely distributes to a space outside of the plasma compartment (extravascular space). We have previously shown using SPECT imaging that the rFIXFc and rFIX biodistribution profiles in hemophilia B mice are consistent with the hypothesis that FIX can distribute to tissues outside of the plasma compartment, while glycoPEGylated-rFIX remains mostly in the plasma compartment due to modifications imposed by the PEG moiety. In this study we evaluated the distribution of rFIX and rFIXFc in nonhuman primates (NHP)

rFIXFc and rFIX were labeled at lysine residues using an 124I-SIB (succinimidyl iodobenzoate). Cynomolgus monkeys received a single IV bolus injection of ~2 mCi tracer dose of 124I-SIB-rFIXFc (2 mg/kg) or 124I-SIB-rFIX (1 mg/kg). Reconstructed whole-body PET/CT scans were used for generating maximum-intensity projection (MIP) images and in vivo biodistribution was determined for regions of interest (ROIs) analysis.

PET imaging in NHP showed an early distribution of 124I-SIB-rFIXFc and 124I-SIB-rFIX in the blood pool, heart, liver and kidneys. At later time points both rFIXFc and rFIX showed distribution to shoulder joints as well as other bone joints (wrist, ankle and jaw) with rFIXFc displaying significantly higher distribution to these areas, even at time points when FIX plasma levels were below the detection level. Both in vivo and ex vivo data showed blood pool clearance of rFIXFc and rFIX. TCA precipitation data showed >95% radioactivity was associated with the FIX.

The rFIXFc and rFIX biodistribution profiles NHP are similar to those observed in hemophilia B mice and are consistent with the hypothesis that FIX can distribute to tissues outside of the plasma compartment. The significantly higher distribution of rFIXFc to joints areas compared to rFIX could potentially reflect retention at these tissues by an Fc-mediated mechanism or improved PK. While the role of extravascular distribution in prevention of bleeding and overall protection of joint health remains an area of investigation, this study is consistent with the observations in mice that demonstrated biodistribution differences for FIX variants suggesting plasma levels may not be comparable, or have the same meaning, across FIX variants.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All publications, patents, and patent applications disclosed herein are incorporated by reference to the same extent as if each individual publication, patent or patent application was specifically and individually indicated to be incorporated by reference.

What is claimed is:

1. A method for reversing hemophilic arthropathy of a target joint in a human subject who has hemophilia B, the method comprising:
   a) selecting a human subject with hemophilia B and stage I, II, or III hemophilic arthropathy with synovitis;
   b) prophylactically administering to the subject an effective amount of a chimeric protein comprising factor IX (FIX) and an Fc region (rFIXFc), such that the hemophilic arthropathy is reversed in the subject without surgical intervention.

2. The method of claim 1, wherein the hemophilic arthropathy comprises a microbleed.

3. The method of claim 1, wherein vascular remodeling in one or more target joints of the human subject is reduced.

4. The method of claim 1, wherein surrounding soft tissue of a joint of the human subject hemophilia is improved.

5. The method of claim 1, wherein the administering reduces joint pain in the human.

6. The method of claim 1, wherein the joint is selected from the group consisting of one or both elbows, one or both knees, one or both ankles, one or both shoulders, one or both hips, one or both wrists, one or more joints of the hand, one or more joints of the foot, and any combination thereof.

7. The method of claim 1, wherein the Fc region specifically binds to a low affinity immunoglobulin gamma Fc region receptor II-b (FcγRIB).

8. The method of claim 1, wherein the human has been identified as being in need of the treatment using an imaging modality selected from the group consisting of radiography, magnetic resonance imaging, ultrasonography, power Doppler sonography, and any combination thereof.

9. The method of claim 1, wherein the effective amount of the chimeric protein comprising the rFIXFc is from about 20 IU/kg to about 100 IU/kg.

10. The method of claim 1, wherein the chimeric protein comprising the rFIXFc is administered at a dosing interval of about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

11. The method of claim 9, wherein the chimeric protein comprising the rFIXFc is administered to the human subject in a dose of 50 IU/kg once a week.

12. The method of claim 9, wherein the chimeric protein comprising the rFIXFc is administered to the human subject in a dose of 100 IU/kg once every ten days.

13. The method of claim 1, wherein reversing hemophilic arthropathy comprises reversing hyperproliferation of the soft tissue of a joint.

14. The method of claim 1, wherein the synovitis comprises synovial hyperplasia.

15. The method of claim 1, wherein the subject is less than 6 years old.

16. The method of claim 1, wherein the subject is 6 years old to less than 12 years old.

17. The method of claim 1, wherein the subject is 12 years old or older.

* * * * *